(12) United States Patent
Fischer et al.

(10) Patent No.: US 8,802,821 B2
(45) Date of Patent: Aug. 12, 2014

(54) POLYPEPTIDES HAVING DNA DEMETHYLASE ACTIVITY

(75) Inventors: Robert Fischer, El Cerrito, CA (US); Jon Penterman, Berkeley, CA (US); Jin Hoe Huh, Davis, CA (US); Tzung-Fu Hsieh, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 1060 days.

(21) Appl. No.: 12/006,779

(22) Filed: Jan. 4, 2008

(65) Prior Publication Data

US 2009/0305241 A1  Dec. 10, 2009

Related U.S. Application Data

(60) Provisional application No. 60/878,997, filed on Jan. 5, 2007.

(51) Int. Cl.
*C07K 1/00* (2006.01)

(52) U.S. Cl.
USPC .......................................................... 530/350

(58) Field of Classification Search
None
See application file for complete search history.

(56) References Cited

U.S. PATENT DOCUMENTS

| 6,476,296 B1 * | 11/2002 | Fischer et al. | 800/290 |
| 7,109,394 B2 * | 9/2006 | Fischer et al. | 800/290 |
| 7,414,124 B2 * | 8/2008 | Fischer et al. | 536/24.1 |

OTHER PUBLICATIONS

Wells, Biochemistry, vol. 29, pp. 8509-8517, 1990.*
Seffernick et al. (J. Bacteriology, vol. 183, pp. 2405-2410, 2001).*
Choi et al. (PNAS, vol. 101, No. 19, pp. 7481-7486, May 11, 2004).*

* cited by examiner

*Primary Examiner* — Hope Robinson
(74) *Attorney, Agent, or Firm* — Kilpatrick Townsend & Stockton LLP

(57) ABSTRACT

Polypeptides with DNA demethylase activity as well as methods of their use are provided.

2 Claims, 23 Drawing Sheets

Fe-S Cluster Analysis

Random Mutagenesis To identify all amino acids necessary for DME activity

Triangles show position of essential amino acids for DME activity

```
MQSIMDSSAVNATEATEQNDGSRQDVLEFDLNKTPQQKPSKRKRKFMPKVVVEGKPKRKPRKPAELPKVVVEGKPKRKPRKAATQEKVKSKETGSAKKKN   100

LKESATKKPANVGDMSNKSPEVTLKSCRKALNFDLENPGDARQGDSESEIVQNSSGANSPSEIRDAIGGTNGSFLDSVSQIDKTNGLGAMNQPLEVSMGN   200

QFDKLSTGAKLARDQQPDLLTRNQQCQFPVATQNTQFPMENQQAWLQMKNQLIGFPFGNQQFRMTIRNQQPCLAMGNQQPMYLIGTPRPALVSGNQQLGG   300

PQGNKRPIFLNHQTCLPAGNQLYGSPTDMHQLVMSTGGQQHGLLIKNQQPGSLIRGQQPCVPLIDQQPATPKGFTHLNQMVATSMSSPGLRPHSQSQVPT   400

TYLHVESVSRILNGTTGTCQRSRAPAYDSLQQDIHQGNKYILSHEISNGNGCKKALPQNSSLPTPIMAKLEEARGSKRQYHRAMGQTEKHDLNLAQQIAQ   500

SQDVERHNSSTCVEYLDAAKKTKIQKVVQENLHGMPPEVIEIEDDPTDGARKGKNTASISKGASKGNSSPVKKTAEKEKCIVPKTPAKKGRAGRKKSVPP   600

PAHASEIQLWQPTPPKTPLSRSKPKGKGRKSIQDSGKARGPSGELLCQDSIAEIIYRMQNLYLGDKEREQEQNAMVLYKGDGALVPYESKKRKPRPKVDI   700

DDETTRIWNLLMGKGDEKEGDEEKDKKKEKWWEEERRVFRGRADSFIARMHLVQGDRRFSPWKGSVVDSVIGVFLTQNVSDHLSSSAFMSLAARFPPKLS   800

SSREDERNVRSVVVEDPEGCILNLNEIPSWQEKVQHPSDMEVSGVDSGSKEQLRDCSNSGIERFNFLEKSIQNLEEEVLSSQDSFDPAIFQSCGRVGSCS   900

CSKSDAEFPTTRCEBTKTVSGTSQSVQTGSPNLSDEICLQGNERPHLYEGSGDVQKQETTNVAQKKPDLEKTMNWKDSVCFGQPRNDTNWQTTPSSSYEQC   1000

ATRQPHVLDIEDFGMQGEGIGYSWMSISPRVDRVKNKNVPRRFFRQGGSVPREFTGQIIPSTPHELPGMGLSGSSSAVQEHQDDTQHNQQDEMNKASHLQ   1100

KTFLDLLNSSEBCLTRQSSTKQNITDGCLPRDRTAEDVVDPLSNNSSLQNILVESNSSNKEQTAVEYKETNATILREMKGTLADGKKPTSQWDSLRKDVE   1200

GNEGRQERNKNNMDSIDYEAIRRASISEISEAIKERGNNNNMLAVRIKDFLERIVKDHGGIDLEWLRESPPDKAKDYLLSIRGLGLKSVECVRLLTLHNLA   1300

FPVDTNVGRIAVRMGWVPLQPLPESLQLHLLELYPVLESIQKFLWPRLCKLDQRTLYELHYQLITFGKVFCTKSRPNCNACPMRGBCRHFASAYASARLA   1400

LPAPEERSLTSATIPVPPESFPPVAIPMIELPLPLEKSLASGAPSNRENCEPIIBEPASFGQECTEITESDIEDAYYNEDPDEIPTIKLNIEQFGMTLRE   1500

HMERNMELQEGDMSKALVALHPTTTSIPTPKLKNISRLRTEHQVYELPDSHRLLDGMDKREPDDPSPYLLAIWTPGETANSAQPPEQKCGGKASGKMCFD   1600

ETCSECNSLREANSQTVRGTLLIPCRTAMRGSFPLNGTYFQVNELFADHESSLKPIDVPRDWIWDLPRRTVYFGTSVTSIFRGLSTEQIQFCFWKGFVCV   1700

RGFEQKTRAPRPLMARLHFPASKLKNNKT   1729
```

Blue triangles obtained from site-directed mutagenesis, red triangles obtained by random mutagenesis.

*FIG. 13*

Summary of mutagenesis analysis in the DNA glycosylase domain

```
DME      DKAKDYLLSIRGLGLKSVECVRLLTLHNLAFPVDTNVGRIAVRMGWVPLOPLPESLQLHL 1330
MutY     PETFEEVAALPGVGRSTAGAILSLSLGKHFPILDGNVKRVLARCYAVSGWPGKKEVENKL 164
EndoIII  PEDRAALEALPGVGRKTANVVLNTAFGWPTIAVDTHIFRVCNRTQFAPGK-NVEQVEEKL 163
               :  :: *:* .:.  :  :: :  :* :: *: *  .  .::  :*

DME      LELYPVLESIQKFLWPRLCKLDQRTLYELHYQLITFGKVFCTKSRPNCNACPMRGECRHF 1390
MutY     WSLS-------------EQVTPAVGVERFNQAMMDLGAMICTRSKPKCSLCPLQNGCIAA 211
EndoIII  L----------------KVVPAEFKVDCHHWLILHGRYTCIARKPRCGSCIIEDLCEYK 216
                          :  ::  *   *   :*.*. *  :..  *

DME      ASAYASARLA 1400
MutY     ANNSWALYP- 220
EndoIII  EKVDI----- 221
```

*FIG. 14*

List of mutants with a single amino acid substitution that greatly decreases DME activity

| mutant | substitution | mutant | substitution |
|---|---|---|---|
| RM2-7 | I1216K | RM7-70 | A1300V |
| RM2-24 | G1185R | RM7-81 | M1238I |
| RM2-30 | C1381R | RM7-115 | K1286E |
| RM2-46 | L1277P | RM7-117 | L1293F |
| RM3-10 | S1230P | RM7-142 | L1277P |
| RM5-27 | Q1362P | RM7-147 | M1238T |
| RM5-31 | P1376L | RM7-153 | S1225I |
| RM7-16 | G1315R | RM7-155 | G1308E |
| RM7-18 | V1291E | RC1-8 | T1620A |
| RM7-28 | I1246S | RC1-9 | T1620A |
| RM7-32 | K1210T | RC1-28 | E1546K |
| RM7-38 | K1286N | RC1-29 | L1621H |
| RM7-54 | K1286R | | |
| RM7-68 | I1310M | | |

*FIG. 15*

List of mutants with double amino acid substitutions

| mutant | substitutions | mutant | substitutions | mutant | substitutions |
|---|---|---|---|---|---|
| RM2-22 | G1367E C1450S | RM6-11 | V1288D I1426V | RM7-154 | D1261Y G1315V |
| RM2-29 | P1302H I1364F | RM7-21 | E1228K V1288D | RM7-156 | Y1218H I1310K |
| RM2-34 | L1348H P1452N | RM7-27 | N1212S L1265S | RM7-159 | K1037Q G1308E |
| RM2-38 | R1052G R1313G | RM7-47 | M1241V V1307D | RC1-1 | C1598G D1648G |
| RM2-43 | P1130Q G1282S | RM7-49 | K1168R G1282C | RC1-2 | C1381S R1630S |
| RM2-44 | P1335L F1366L | RM7-53 | S1118P R1313M | RC1-3 | S1339P F1681Y |
| RM2-56 | A1224D Y1361H | RM7-60 | K1210E G1237E | RC1-6 | C1598G A1628T |
| RM2-57 | W1316G K1368T | RM7-61 | K1210E G1237E | RC1-10 | S1411R P1634S |
| RM3-20 | N1038T D1105V | RM7-62 | G1282D L1299P | RC1-25 | D1563A S1632G |
| RM4-10 | T1173I K1368T | RM7-69 | K1168N R1223P | | |
| RM4-13 | P1335L F1390L | RM7-86 | E1177V L1293P | | |
| RM4-34 | P1188H C1387Y | RM7-87 | S1287T L1331P | | |
| RM4-54 | D1248G R1309W | RM7-88 | Q1079L V1288F | | |
| RM5-62 | E1324K F1390V | RM7-102 | F1043S L1277P | | |

Amino acids in red font were shown by independent means to be essential for amino acid activity.

FIG. 16

DME family have introns in the same position within the conserved DNA Glycosylase Domain

Alignment of Domain A of DME family genes

```
DME   688 ESKKRKPRPKVDILDETTRIMNLLMGKGDEKEGDEEKLKKKEKWEEERRVERGRADSEI 747
ROS1  519 PVKKPRPRPKVDLEDETDRVAKLLLENINS-EGVDGSEEQKAKWEEERNVERGRADSEI 577
DML2  490 YSKKQKF--VQLLPFTSRVVKLIMSSIDC-DGVDGSEEKRKWEEERNMEHGRANSEI 546
DML3  400 KADKKLVTAKVNLLPETIKEKDVLMVNDSPSRSYD--KETEAKKKKEPEILQTRIDLEI 457
           .*      **::* ** : *.:*:  .   .  : *::.   *::**.:*: * : **

DME   748 ARMHLVQGDRRESPWKGSVVDSVIGVFLTQNVSDHLSSGAFMSLAARFEP 797
ROS1  578 ARMHLVQGDRRETPWKGSVVDSVVGVFLTQNVSDHLSSSAFMSLASQFPV 627
DML2  547 ARMRVVQGNRTESPWKGSVVDSVVGVFLTQNVADHSSSSRYMDLAAEFPV 596
DML3  458 NRMHRLQGNRKEKQWKGSVVDSVVGVFLTQNTTLYLSSNRFMSVAAKEPV 507
           **: ;**:* *. *********:******.:*: **.*:*.:*:.**
```

FIG. 21

Alignment of glycosylase domain of DME family genes

```
            ↓     ↓       ↓        ↓          ↓        ↓
DME   1204 GRQERNKNNMLSIDYEAIRRASISEISEAIKERGMNNMIAVRIKDFLERIVKDHGGIDLE 1263
ROS1   871 GIREKTRSTMITVDWKAILAADVKEVAETIKSRGMNHKLAERIQGFLDRLVNDHGSIDLE  930
DML2   803 RKRERTERTMITVDWDALRCTDVHKIANIIIKRGMNNMLAERIKAFLNRLQKKHGSIDLE  862
DML3   572 KEGSRPEMHMISVNWSDVFLSGQNVLETTIKKRGQFRILSERILKEINDEGNQNGNIDLE  631
            .: .    **::::.  :*  :.       :   *    .**    *:  **:   *:..:*.****
              ↓                ↓↓↓      ↓        ↓↓↓     ↓  ↓
DME   1264 WLRESFPDKAKDYLLSIRGLGLKSVECVRLITLHNLAFPVDTNVGRIAVRMGWVPLQFLP 1323
ROS1   931 WLRDVFPDKAKEYLLSFNGLGLKSVECVRLITLHHLAFPVDTNVGRIAVRLGWVPLQFLP  990
DML2   863 WLRDVFPDKAKEYLLSINGLGLKSVECVRLISLHQIAFPVDTNVGRIAVRLGWVPLQFLP  922
DML3   632 WLENAESHLVKRYLLEIESIGLKSAECVRLIGLKHHAFPVDTNVGRIAVRLGLVPLEPLP  691
           ***:  *.. .* ***.:.*:****.******  *:: **************:*  ***:***
                              ↓      ↓↓ ↓↓   ↓      ↓ ↓   ↓↓↓↓  ↓↓
DME   1324 ESLQLHLLELYPVLESIQKFLWPRLCKLDQRTLYELHYQLITFGKVFCTKSRPNCNACPM 1383
ROS1   991 ESLQLHLLEMYPMLESTQKYLWPRLCKLDQKTLYELHYQMITEGKVECTRSKPNCNACPM 1050
DML2   923 DELQMHLLELYPVLESVQKYLWPRLCKLDQKTLYELHYHMITEGKVECTIVKPNCNACPM  982
DML3   692 NGVQMHQLFEYPSMDSIQKYLWPRLCKLPQETLYELHYQMITEGKVECTIKTIPNCNACPM 751
           : :*:*  *    **  ::*:**.********  *.*******:::**********  ********
            ↓ ↓↓
DME   1384 RGECRHFASAYASARLALPAPE 1405
ROS1  1051 KGECRHFASAFASARLALPSTE 1072
DML2   983 KAECRHYSSARASARLALPEPE 1004
DML3   752 KSECKYFASAYVSSKVLLESPE  773
           :.**:::**  .*:::  *   .*
```

*FIG. 22*

Alignment of Domain B of DME family genes

```
DME  1513 MSKALVALHPTTTSIPT---PKLKNISRLRTEHQVYELFISHRLLDGMDKREPDLPSPYL 1569
ROS1 1174 MSSALVALTAETASLEM---PKLKNISQLRTEHPVYELPIELPLLAQLEKREPDLPCSYL 1230
DML2 1112 TSHDLVVLSTYAAAIER---RLLKIKEKLRTEHHVFELPIHESILEGFERREAELIVPYL 1168
DML3  882 ISKALVIPTPENACIEIKPPRKMKYYNRLRTEHVQYVLPLNLELPHDFERRKLDLPSPYL  941
           *  **   .  :..:*      *:*  .:***** *: *** * :*   ::*: :*  .**

DME  1570 LAIWTPGETANSAQEPEQKCG-GKASGKMQFDETCSEQNSLREANSQTVRGTLLIPCRTA 1628
ROS1 1231 LAIWTPGETADSIQESVSTCI-FQANGMLQDEETCFSQNSIKETRSQIVRGTLLIPCRTA 1289
DML2 1169 LAIWTPGETVNSIQEPKQRCALFESNNTLQNENKCFQGNKTREEESQTVRGTLLIPCRTA 1228
DML3  942 LAIWQPGETSSSFVEEKKKCS--SDGSKLGKIKNCSYGWTIREQNSNIFRGTILIPCRTA  999
           **** ****  * .*    *   . .:*  :.*   *   :*  .*: ***:*******

DME  1629 MRGSFPLNGTYFQVNELPADHESGLKETDVPRDWIWDLPRETVYFGTSVTSIFRGLSTEQ 1688
ROS1 1290 MRGSFPLNGTYFQVNEVPADHASSLNEINVPRELIWELPRETVYFETSVPTIFKGLSTEK 1349
DML2 1229 MRGGFPLNGTYFQTNEVPADHDSSINPIDVPTELIWDKPREVANLESSVSSICKGLSVEA 1288
DML3 1000 MRGAFPLNGTYFQTNEVPALHETSLNPIVFRRELCKGLEKEALVCESTVTSIFKLLDTRR 1059
           ***.********** :**:****  .: . . *  :*.  *   *:::*.:* :  *...

DME  1689 IQFCEWKGFVCVRGEEQKTLAERPLMARLFFPASKLKNNKT----- 1729
ROS1 1350 IQACEWKGYVCVRGEDRKTIGEKPLIARLFFPASKLKGQQANLA-- 1393
DML2 1289 IKYNQEGYVCVRGEDRENPKRSIVKRLFCSHVAIRTKEKTEE--  1332
DML3 1060 LELCEWTGFLGLRADRKQRDEREIVRRLFTPPDERGPKFMSDDDI 1105
           *:  *  *:*:*.*:::  * *: *: ***  .           :
```

*FIG. 23*

POLYPEPTIDES HAVING DNA DEMETHYLASE ACTIVITY

CROSS-REFERENCE TO RELATED PATENT APPLICATIONS

This patent application claims benefit of priority to U.S. Provisional Patent Application No. 60/878,997, filed Jan. 5, 2007, which is incorporated by reference.

STATEMENT AS TO RIGHTS TO INVENTIONS MADE UNDER FEDERALLY SPONSORED RESEARCH OR DEVELOPMENT

This invention was made with Government support under Grant No. GM069415, awarded by the National Institutes of Health and Grant No. 2005-02355, awarded by the U.S. Department of Agriculture. The Government has certain rights in this invention.

BACKGROUND OF THE INVENTION

Alleles of imprinted genes are expressed differently depending on whether they are inherited from the male or female parent. Imprinting regulates a number of genes essential for normal development in mammals and angiosperms. In mammals, imprinted genes contribute to the control of fetal growth and placental development (Constancia, M. et al., *Nature*, 432, 53-57 (2004)). Human diseases are linked to mutations in imprinted genes or aberrant regulation of their expression (Constancia, M. et al., *Nature*, 432, 53-57 (2004)). Mechanisms of distinguishing maternal and paternal alleles have been extensively characterized in mammals. Imprinted genes reside in chromosomal clusters and are regulated by differentially methylated imprinting control regions (ICRs) (Reik, W. and Walter, J., *Nat Rev Genet*, 2, 21-32 (2001)). Differential DNA methylation is established during oogenesis or spermatogenesis by de novo methyltransferases and maintained somatically by the CG maintenance methyltransferase Dnmt1 (Li, E. (2002). Nat Rev Genet 3, 662-673. ICRs are subject to differential histone modifications and in some instances can act as chromatin boundaries (Delaval, K. and Feil, R., *Curr Opin Genet Dev.*, 14, 188-195 (2004)). Other mechanisms to regulate allele-specific gene expression involve non-coding RNAs, including antisense transcripts and microRNAs (O'Neill, 2005). Polycomb group (PcG) proteins, which function in large complexes to methylate histones and modify chromatin (Cao, R. and Zang, Y., *Curr Opin Genet Dev.*, 14, 155-164 (2004)), maintain allele-specific silencing of some imprinted genes (Delaval, K. and Feil, R., *Curr Opin Genet Dev.*, 14, 188-195 (2004)).

The endosperm, one of the products of angiosperm double fertilization, is an important site of imprinting in plants (Gehring, M. et al., *Plant Cell*, 16, S203-S213 (2004)) and has functions analogous to the placenta. In flowering plants, meiosis followed by mitosis produces the female and male gametophytes. Two cells of the female gametophyte, the haploid egg and the diploid central cell, are fertilized by two haploid sperm from the male gametophyte to form the diploid embryo and triploid endosperm, respectively. The endosperm provides nutrients to the embryo during seed development and, in *Arabidopsis*, is almost entirely consumed by the time embryo maturation is completed.

Molecular events that take place in the female gametophyte before fertilization have an essential role in endosperm gene imprinting. The imprinting of two genes, MEA and FWA, is regulated by DEMETER (DME, also sometime abbreviated DMT), a helix-hairpin-helix DNA glycosylase (Choi, Y. et al., *Cell*, 110, 33-42 (2002); Kinoshita, T. et al., *Science*, 303, 521-523 (2004)). DME has also been referred to in the literature as Atropos (ATR). The DME plant gene product has been described to control plant phenotypes and affect DNA methylation. The DME gene product is described in, e.g., U.S. Pat. Nos. 6,476,296 and 7,109,394 as well as Choi, Y. et al., *Cell*, 110:33-42 (2002); Gehring, M. et al., *Cell*, 124:495-506 (2006).

DNA glycosylases function in the base excision repair pathway by removing damaged or mismatched bases from DNA (Scharer, O. D. and Jiricny, J., *BioEssays*, 23, 270-281 (2001)). Bifunctional helix-hairpin-helix DNA glycosylases have both DNA glycosylase and apurinic/apyrimidinic (AP) lyase activities. The DNA glycosylase activity removes the damaged or mispaired base by cleaving the N-glycosylic bond, creating an abasic site, whereas the lyase activity nicks the DNA. An AP endonuclease generates a 3'-hydroxyl used by a DNA repair polymerase that inserts the proper nucleotide. A DNA ligase seals the nick to complete the repair process. DNA glycosylase/lyases have not been implicated in mammalian imprinting mechanisms.

Both MEA and FWA are expressed in the central cell before fertilization and in the endosperm, from the maternal allele, after fertilization (Kinoshita, T. et al., *Science*, 303, 521-523 (2004); Kinoshita, T. et al., *Plant Cell*, 11, 1945-1952 (2004); Vielle-Calzada, J. P. et al., *Genes Dev*, 13, 2971-2982 (1999)). In contrast, DME is expressed in the central cell of the female gametophyte but not in the endosperm (Choi, Y. et al., *Cell*, 110, 33-42 (2002)). Expression of MEA and FWA in the central cell and early endosperm is dependent on DME (Choi, Y. et al., *Cell*, 110, 33-42 (2002); Kinoshita, T. et al., *Science*, 303, 521-523 (2004)).

Though maternal expression of MEA and FWA is controlled by DME, there are important distinctions regarding the regulation of expression of these genes. FWA is silent in all vegetative and reproductive tissues except for expression of the maternal allele in the female gametophyte and endosperm (Kinoshita, T. et al., *Science*, 303, 521-523 (2004); Soppe, W. J. J. et al., *Mol Cell*, 6, 791-802 (2000)). MEA is imprinted in the endosperm, but is biallelically expressed in the embryo and in other sporophytic tissues (Kinoshita, T. et al., *Science*, 303, 521-523 (2004)). Expression of MEA in the embryo is likely not under DME control, as DME expression is not detected in the egg cell or embryo (Choi, Y. et al., *Cell*, 110, 33-42 (2002)). Expression of FWA in the endosperm, and elsewhere in the plant, is associated with hypomethylation of repeats in the 5' region of the gene (Kinoshita, T. et al., *Science*, 303, 521-523 (2004); Soppe, W. J. J. et al., *Mol Cell*, 6, 791-802 (2000)). Paternal inheritance of met1 releases FWA paternal allele silencing in the endosperm and embryo (Kinoshita, T. et al., *Science*, 303, 521-523 (2004)). MET1 is the homolog of Dnmt1 (Bender, J., *Ann Rev Plant Biology*, 55, 41-68 (2004)).

DME, MEA, and MET1 genetically interact in the female gametophyte. MEA is an E(z) homologue that functions in a PcG complex along with FIE (Kohler, C. et al., *EMBO J*, 22, 4804-4814 (2003)), a homologue of Eed, to repress endosperm growth. Inheritance of mutant maternal dme or mea alleles causes endosperm overproliferation, embryo arrest, and seed abortion (Choi, Y. et al., *Cell*, 110, 33-42 (2002); Grossniklaus, U. et al., *Science*, 280, 446-450 (1998); Kiyosue, T. et al., *Proc Natl Acad Sci USA*, 96, 4186-4191 (1999); Luo, M. et al., *Proc Natl Acad Sci USA*, 96, 296-301 (1999)). Seed abortion caused by dme is suppressed by maternally inherited met1 if a wild type maternal MEA allele is present (Xiao, W. et al., *Developmental Cell*, 5, 891-901

(2003)). Moreover, met1 can restore MEA expression in dme mutants (Xiao, W. et al., *Developmental Cell*, 5, 891-901 (2003)). It is known that the glycosylase activity of DME is necessary for seed viability and activation of MEA transcription (Choi, Y. et al., *Proc Natl Acad Sci USA*, 101, 7481-7486 (2004)). DME antagonizes MET1 by specifically removing 5'-methylcytosine from MEA in the central cell, allowing the maternal MEA allele to be expressed there before fertilization and in the endosperm after fertilization.

As mentioned above, genetic information is stored not only in the sequential arrangement of four nucleotide bases, but also in covalent modification of selected bases (see, e.g., Robertson et al., Nature Rev. Genet. 1:11-19 (2000)). One of these covalent modifications is methylation of cytosine nucleotides, particularly cytosines adjacent to guanine nucleotides in "CpG" dinucleotides. Covalent addition of methyl groups to cytosine within CpG dinucleotides is catalyzed by proteins from the DNA methyltransferase (DNMT) family (Amir et al., Nature Genet. 23:185-88 (1999); Okano et al., Cell 99:247-57 (1999)). In the human genome, CpG dinucleotides are generally under represented, and many of the CpG dinucleotides occur in distinct areas called CpG islands. A large proportion of these CpG islands can be found in promoter regions of genes. The conversion of cytosine to 5'-methylcytosine in promoter associated CpG islands has been linked to changes in chromatin structure and often results in transcriptional silencing of the associated gene. Transcriptional silencing by DNA methylation has been linked to mammalian development, imprinting and X-Chromosome inactivation, suppression of parasitic DNA and numerous cancer types (see, e.g., Li et al., Cell 69:915-26 (1992); Okano et al., Cell 99:247-57 (1999)). Detected changes in the methylation status of DNA can serve as markers in the early detection of neoplastic events (Costello et al., Nature Genet. 24:132-38 (2000)).

BRIEF SUMMARY OF THE INVENTION

The present invention provides isolated demethylase polypeptides. In some embodiments, the polypeptides comprise an amino acid sequence substantially identical (e.g., at least 95% identical) to SEQ ID NO:3, wherein the polypeptide excises methylated cytosines in DNA when contacted to DNA comprising methylated cytosines, and wherein the polypeptide does not comprise the entire sequence in SEQ ID NO:2. In some embodiments, the sequence comprises SEQ ID NO:4. In some embodiments, the sequence comprises no more of SEQ ID NO:2 than the portion of SEQ ID NO:2 displayed in SEQ ID NO:4.

In some embodiments, the demethylase is an isolated polypeptide that excises methylated cytosines in DNA when contacted to DNA comprising methylated cytosines, wherein the polypeptide comprises portions of two different DNA demethylases, wherein the polypeptide comprises a glycosylase domain from SEQ ID NO:2, SEQ ID NO:6, SEQ ID NO:8, or SEQ ID NO: 10 and a fragment of a DNA demethylase selected from SEQ ID NO:2, SEQ ID NO:6, SEQ ID NO:8, or SEQ ID NO:10, wherein the fragment does not comprise a glycosylase domain, wherein the glycosylase domain and the fragment do not occur in the same DNA demethylase (i.e., does not occur in the same naturally-occurring DNA demethylase, for example, the demethylase of the invention is a chimera formed from portions of at least two different DNA demethylases). In some embodiments, the polypeptide a sequence substantially identical (e.g., at least 95% identical) to SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In some embodiments, the polypeptide comprises SEQ ID NO:12, SEQ ID NO:14, SEQ ID NO:16, SEQ ID NO:18, SEQ ID NO:20, SEQ ID NO:22, SEQ ID NO:24, or SEQ ID NO:26.

The present invention also provides isolated nucleic acids encoding demethylases. In some embodiments, the nucleic acids comprise a polynucleotide encoding a polypeptide comprising an amino acid sequence substantially identical (e.g., at least 95% identical) to SEQ ID NO:3, wherein the polypeptide excises methylated cytosines in DNA when contacted to DNA comprising methylated cytosines, and wherein the polypeptide does not comprise the entire sequence in SEQ ID NO:2. In some embodiments, the sequence comprises SEQ ID NO:4. In some embodiments, the sequence comprises no more of SEQ ID NO:2 than the portion of SEQ ID NO:2 displayed in SEQ ID NO:4.

The present invention also provides isolated nucleic acids comprising a polypeptide that excises methylated cytosines in DNA when contacted to DNA comprising methylated cytosines, wherein the polypeptide comprises portions of two different DNA demethylases, wherein the polypeptide comprises a glycosylase domain from SEQ ID NO:2, SEQ ID NO:6, SEQ ID NO:8, or SEQ ID NO: 10 and a fragment of a DNA demethylase selected from SEQ ID NO:2, SEQ ID NO:6, SEQ ID NO:8, or SEQ ID NO:10, wherein the fragment does not comprise a glycosylase domain, wherein the glycosylase domain and the fragment do not occur in the same DNA demethylase. In some embodiments, the polypeptide comprises a sequence substantially identical (e.g., at least 95% identical) to SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In some embodiments, the polypeptide comprises SEQ ID NO: 12, SEQ ID NO:14, SEQ ID NO:16, SEQ ID NO:18, SEQ ID NO:20, SEQ ID NO:22, SEQ ID NO:24, or SEQ ID NO:26.

The present invention also provides host cells comprising a heterologous expression cassette, the expression cassette comprising a promoter operably linked to a polynucleotide encoding a polypeptide, the polypeptide comprising an amino acid sequence substantially identical (e.g., at least 95% identical) to SEQ ID NO:3, wherein the polypeptide excises methylated cytosines in DNA when contacted to DNA comprising methylated cytosines, and wherein the polypeptide does not comprise the entire sequence in SEQ ID NO:2. In some embodiments, the sequence comprises SEQ ID NO:4. In some embodiments, the sequence comprises no more of SEQ ID NO:2 than the portion of SEQ ID NO:2 displayed in SEQ ID NO:4.

The present invention also provides host cells comprising a heterologous expression cassette, the expression cassette comprising a promoter operably linked to a polynucleotide encoding a polypeptide, the polypeptide comprising polypeptide that excises methylated cytosines in DNA when contacted to DNA comprising methylated cytosines, wherein the polypeptide comprises portions of two different DNA demethylases, wherein the polypeptide comprises a glycosylase domain from SEQ ID NO: 2, SEQ ID NO:6, SEQ ID NO:8, or SEQ ID NO:10 and a fragment of a DNA demethylase selected from SEQ ID NO: 2, SEQ ID NO:6, SEQ ID NO:8, or SEQ ID NO:10, wherein the fragment does not comprise a glycosylase domain, wherein the glycosylase domain and the fragment do not occur in the same DNA demethylase. In some embodiments, the polypeptide comprises a sequence substantially identical (e.g., at least 95% identical) to SEQ ID NO: 12, SEQ ID NO: 14, SEQ ID NO:16, SEQ ID NO:18, SEQ ID NO:20, SEQ ID NO:22, SEQ ID NO:24, or SEQ ID NO:26. In some embodiments, the polypeptide comprises SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In some embodiments, the host cell DNA is demethylated compared to a host cell not expressing the demethylase.

In some embodiments, the cell is a plant cell. In some embodiments, the cell is an animal (e.g., a mammalian) cell. In some embodiments, the cell is a prokaryotic cell.

The present invention also provides plants or plant cells comprising a heterologous expression cassette, the expression cassette comprising a promoter operably linked to a polynucleotide encoding a demethylase polypeptide. In some embodiments, the polypeptide comprises an amino acid sequence substantially identical (e.g., at least 95% identical) to SEQ ID NO:3, wherein the polypeptide excises methylated cytosines in DNA when contacted to DNA comprising methylated cytosines, and wherein the polypeptide does not comprise the entire sequence in SEQ ID NO:2. In some embodiments, the sequence comprises SEQ ID NO:4. In some embodiments, the sequence comprises no more of SEQ ID NO:2 than the portion of SEQ ID NO:2 displayed in SEQ ID NO:4.

In some embodiments, the plant or plant cells comprises a heterologous expression cassette, the expression cassette comprising a promoter operably linked to a polynucleotide encoding a polypeptide, the polypeptide comprising polypeptide that excises methylated cytosines in DNA when contacted to DNA comprising methylated cytosines, wherein the polypeptide comprises portions of two different DNA demethylases, wherein the polypeptide comprises a glycosylase domain from SEQ ID NO:2, SEQ ID NO:6, SEQ ID NO:8, or SEQ ID NO:10 and a fragment of a DNA demethylase selected from SEQ ID NO:2, SEQ ID NO:6, SEQ ID NO:8, or SEQ ID NO:10, wherein the fragment does not comprise a glycosylase domain, wherein the glycosylase domain and the fragment do not occur in the same DNA demethylase. In some embodiments, the polypeptide a sequence substantially identical (e.g., at least 95% identical) to SEQ ID NO:12, SEQ ID NO:14, SEQ ID NO:16, SEQ ID NO:18, SEQ ID NO:20, SEQ ID NO:22, SEQ ID NO:24, or SEQ ID NO:26. In some embodiments, the polypeptide comprises SEQ ID NO: 12, SEQ ID NO: 14, SEQ ID NO:16, SEQ ID NO:18, SEQ ID NO:20, SEQ ID NO:22, SEQ ID NO:24, or SEQ ID NO:26.

The present invention also provides methods of modulating transcription of a demethylase polynucleotide. In some embodiments, the method comprise introducing into a host cell an expression cassette comprising a promoter operably linked to a polynucleotide encoding a demethylase, wherein the demethylase comprises an amino acid sequence substantially identical (e.g., at least 95% identical) to SEQ ID NO:3 and the demethylase does not comprise the entire sequence in SEQ ID NO:2; or is a polypeptide comprising portions of two different DNA demethylases, wherein the polypeptide comprises a glycosylase domain from SEQ ID NO:2, SEQ ID NO:6, SEQ ID NO:8, or SEQ ID NO:10 and a fragment of a DNA demethylase selected from SEQ ID NO:2, SEQ ID NO:6, SEQ ID NO:8, or SEQ ID NO: 10, wherein the fragment does not comprise a glycosylase domain, wherein the glycosylase domain and the fragment do not occur in the same DNA demethylase.

In some embodiments, the polynucleotide is linked to the promoter in the sense orientation. In some embodiments, the polynucleotide is linked to the promoter in the antisense orientation. In some embodiments, the expression cassette is introduced into a plant and expression of the demethylase is increased, thereby delaying flowering in the plant compared to a plant lacking the expression cassette.

In some embodiments, the host cell is a plant cell. In some embodiments, the plant cell is regenerated into a plant and the plant has delayed flowering in the plant compared to a plant lacking the expression cassette.

The present invention also provides methods of detecting cytosine methylation in a DNA sample. In some embodiments, the method comprises contacting DNA with a demethylase polypeptide such that the polypeptide excises methylated cytosines, if present, from the DNA, thereby cleaving the DNA strand having the methylated cytosine to cause a nick in the DNA; extending a primer that is complementary to a sequence in the DNA up to the nick, thereby producing an extension product; and detecting the extension product, wherein the quantity or length of the extension product indicates cytosine methylation in the DNA sample, wherein the method does not involve adding nucleotides to the extension product with a terminal transferase. In some embodiments, the primer extension comprises a nucleic acid amplification. In some embodiments, the amplification is PCR comprise an amino acid sequence substantially identical (e.g., at least 95% identical) to SEQ ID NO:3, wherein the polypeptide excises methylated cytosines in DNA when contacted to DNA comprising methylated cytosines, and wherein the polypeptide does not comprise the entire sequence in SEQ ID NO:2. In some embodiments, the sequence comprises SEQ ID NO:4. In some embodiments, the sequence comprises no more of SEQ ID NO:2 than the portion of SEQ ID NO:2 displayed in SEQ ID NO:4.

In some embodiments, the method comprises contacting DNA with a DNA demethylase under conditions such that the demethylase excises methylated cytosines, if present, from the DNA, thereby cleaving the DNA strand having the methylated cytosine to cause a nick in the DNA; extending a detectably-labeled primer that is complementary to a sequence in the DNA up to the nick, thereby producing an extension product; and detecting the length of the extension product, thereby detecting methylation of the DNA in the DNA sample. In some embodiments, the DNA demethylase comprises a polypeptide substantially identical (e.g., at least 95% identical) to SEQ ID NO:2, 3, 4, 6, 8, 10, 12, 14, 16, 18, 20, 22, 24, 26, or 28. In some embodiments, the DNA demethylase comprises SEQ ID NO:2, 3, 4, 6, 8, 10, 12, 14, 16, 18, 20, 22, 24, or 26.

In some embodiments, the method comprises contacting DNA with a DNA demethylase under conditions such that the demethylase becomes covalently linked to the DNA at the site of methylated cytosines, if present, thereby cleaving the DNA strand having the methylated cytosine to cause a nick in the DNA; separating double stranded DNA covalently bound to the DNA demethylase from DNA not bound to the demethylase, wherein the double stranded DNA covalently bound to the DNA demethylase comprises a first strand covalently linked to the demethylase and a complementary strand not linked to the demethylase; and amplifying DNA on the complementary strand and detecting an amplification product, thereby detecting DNA methylation in a DNA sample. In some embodiments, the conditions comprise the presence of a reducing agent in sufficient quantity to result in covalent linkage of the demethylase to the DNA. In some embodiments, the reducing agent is sodium borohydride. In some embodiments, the separating step comprises contacting the demethylase with an agent that specifically binds to the demethylase to form a complex between the agent and the demethylase bound to the DNA; and isolating the complex from other non-bound DNA. In some embodiments, the agent is an antibody. IN some cases, the demethylase comprises an epitope tag and the agent binds to the tag. In some embodiments, the DNA demethylase comprises a polypeptide substantially identical (e.g., at least 95% identical) to SEQ ID NO:2, 3, 4, 6, 8, 10, 12, 14, 16, 18, 20, 22, 24, 26, or 28. In some embodiments, the DNA demethylase comprises SEQ ID NO:2, 3, 4, 6, 8, 10, 12, 14, 16, 18, 20, 22, 24, or 26.

In some embodiments, the method comprises contacting DNA with a DNA demethylase under conditions such that the demethylase excises methylated cytosines, if present, from the DNA, thereby cleaving the DNA strand having the methylated cytosine to cause a nick in the DNA; amplifying a region of DNA between two primers that are complementary to chromosomal DNA; and detecting the quantity of an amplification product, wherein the presence, absence and/or quantity of the amplification product is indicative of methylation of the DNA in the DNA sample. In some embodiments, the DNA demethylase comprises a polypeptide substantially identical (e.g., at least 95% identical) to SEQ ID NO:2, 3, 4, 6, 8, 10, 12, 14, 16, 18, 20, 22, 24, 26, or 28. In some embodiments, the DNA demethylase comprises SEQ ID NO:2, 3, 4, 6, 8, 10, 12, 14, 16, 18, 20, 22, 24, or 26.

In some embodiments, the DNA demethlases in the DNA methylation detection methods described above are fused to a second polypeptide. In some embodiments, the second polypeptide is maltose binding protein.

BRIEF DESCRIPTION OF THE DRAWINGS

FIG. 13 illustrates a summary of results of DME (SEQ ID NO:2) mutagenesis.

FIG. 14 illustrates a summary of results of mutagenesis of the DME glycosylase domain. DME=SEQ ID NO:29; MutY=SEQ ID NO:30; EndoIII=SEQ ID NO:31.

FIG. 15 illustrates single amino acid substitutions that decrease DME activity.

FIG. 16 illustrates double amino acid substitutions that decrease DME activity.

FIG. 21 illustrates an alignment of "Domain A" of demethylases. DME=SEQ ID NO:37; ROS1=SEQ ID NO:38; DML2=SEQ ID NO:39; DML3=SEQ ID NO:40.

FIG. 22 illustrates an alignment of glycosylase domains of demethylases. DME=SEQ ID NO:41; ROS1=SEQ ID NO:42; DML2=SEQ ID NO:43; DML3=SEQ ID NO:44.

FIG. 23 illustrates an alignment of "Domain B" of demethylases. DME=SEQ ID NO:45; ROS1=SEQ ID NO:46; DML2=SEQ ID NO:47; DML3=SEQ ID NO:48.

DEFINITIONS

Figure 1:
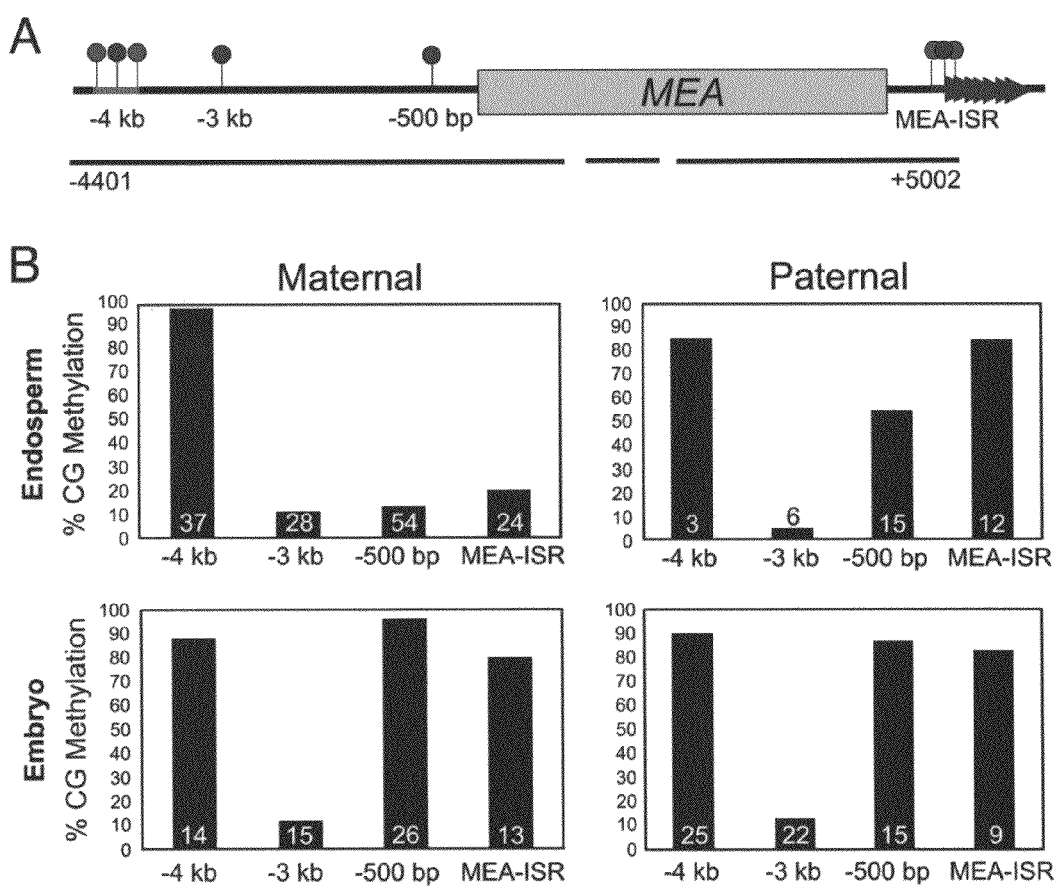
FIG. 1. MEA Methylation in Dissected Seeds. (A) MEA is methylated in four regions. Numbers are relative to the transcription start site. (B) CG methylation of maternal and paternal embryo and endosperm alleles from a Co1-gl female crossed to a RLD male. The number of clones sequenced is given at the base of each column. Black lines, sequences assayed by bisulfite sequencing; blue bar, Helitron transposon element; red arrowheads, 182 bp direct repeats; lollipops, sites of DNA methylation (red, CG; blue, CNG; gray, CNN).

The term "a" refers to at least one of something.

The terms "DME", "DMT" and "ATR" are used interchangeably to refer to the same gene and gene product.

"Cytosine methylation" refers to 5-methyl cytosine.

"Methylated DNA" refers to DNA comprising 5-methyl cytosine.

The term "nucleic acid" or "polynucleotide" as used herein refers to a deoxyribonucleotide or ribonucleotide in either single- or double-stranded form. The term encompasses nucleic acids containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189-197. Other synthetic backbones encompassed by the term include methyl-phosphonate linkages or alternating methylphosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156).

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds, embryos, endosperm, ovules, male and female gametophytes, and plant cells and progeny of same. The class of plants which can be used in the method of the invention is generally as broad as the class of flowering plants amenable to transformation techniques, including angiosperms (monocotyledonous and dicotyledonous plants), as well as gymnosperms. It includes plants and plant cells of a variety of ploidy levels, including polyploid, diploid, haploid, aneuploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like. "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a TO for the primary transgenic plant and TI for the first generation. The term "exogenous" as used herein is also intended to encompass inserting a naturally found element into a non-naturally found location.

The phrase "host cell" refers to a cell from any organism. Exemplary host cells are derived from plants, bacteria, yeast, fingi, insects or animals, including humans. Methods for introducing polynucleotide sequences into various types of host cells are well known in the art. Host cells can be isolated from an organism rather than as part of an organism.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

"Demethylase activity" refers to the ability of a polypeptide to excise a methylated nucleotide (e.g., 5-methyl cytosine) from a DNA sequence. Demethylation activity can be assayed in vivo by expressing a candidate polypeptide in the nucleus of a cell and then assaying for a change in methylation of the cell's DNA. See, e.g., Vong, et al., *Science* 260:1926-1928 (1993). Changes in chromosomal methylation can be measured by comparing the ability of methylation sensitive and insensitive endonucleases to cleave DNA from a cell expressing a polypeptide suspected of having demethylase or methylase activity. Alternatively, bisulfate sequencing can be used to identify which base pairs are methylated in a DNA sequence. For a discussion of both methods, see Soppe, W. J. J. et al., *Mol Cell*, 6, 791-802 (2000). In vitro assays to measure demethylase activity using labeled substrates are also known to those of skill in the art. See, e.g., Vhu et al., *Proc. Natl. Acad. Sci. USA* 97:5135-5139 (2000). Further methods for measuring demethylase activity are provided in the Examples.

The phrase "substantially identical," in the context of two nucleic acids or polypeptides, refers to a sequence or subsequence that has at least 40% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 95%, or 99% compared to a reference sequence using the programs described herein; preferably BLAST using standard parameters, as described below. The present invention provides sequences substantially identical to SEQ ID NOS: 1, 2, 3, 4, 5, 6, 7, 8, 9, 10, 11, 12, 13, 14, 15, 16, 17, 18, 19, 20, 21, 22, 23, 24, 25, or 26. In view of the extensive mutation analysis provided in the examples, it will be clear to those of skill in the art what residues can or cannot be altered while retaining demethylase activity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. If no range is provided, the comparison window is the entire length of the reference sequence. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

An example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 55° C., sometimes 60° C., and sometimes 65° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4:72

(1983); Cole et al., pp. 77-96 in *Monoclonal Antibodies and Cancer Therapy* (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946, 778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

DETAILED DESCRIPTION OF THE INVENTION

I. Introduction

The present invention provides for novel polypeptides with DNA demethylase activity and methods for their use. The DNA demethylases are useful for various in vitro assays, including DNA methylation detection, as well as in vivo uses, such as altering plant phenotypes such a timing of flowering, or modulating DNA methylation and gene transcription in plant or non-plant (including but not limited to, mammalian) cells.

II. Demethylases

The present invention provides for novel DME fragments that retain demethylase activity. The data provided herein demonstrates that as many as 677 amino acids can be deleted from the amino terminus of DME while retaining demethylase activity. Accordingly, the present application provides demethylase polypeptides comprising less than the full length DME amino acid sequence, but at least a polypeptide identical or substantially identical to SEQ ID NO:3. In some embodiments, the demethylase polypeptides comprise a sequence substantially identical or identical to SEQ ID NO:4 (corresponding to a Δ538 deletion of the full length DME amino acid sequence), but does not include all of SEQ ID NO:2. In some embodiments, the demethylase polypeptide comprise a polypeptide substantially identical to SEQ ID NO:3, but comprises no more of SEQ ID NO:2 (the full length DME amino acid sequence) than is in SEQ ID NO:4. Accordingly, in some embodiments, the demethylases of the invention comprise a polypeptide represented by SEQ ID NO:2, but wherein at least 1, 2, 3, 4, 5, 6, 7, 8, 9, 10, 50, 100, 200, 300, 400, 500, 530, 536, 537, 538, 540, 550, 600, 650 or more amino terminal amino acids of SEQ ID NO:2 are absent and the polypeptide comprises a sequence identical or substantially identical to the entire sequence of SEQ ID NO:3. Similarly, in some embodiments, the demethylases of the invention comprise a polypeptide represented by SEQ ID NO:6, but wherein at least 1, 2, 3, 4, 5, 6, 7, 8, 9, 10, 50, 100, 200, 300, 400, 500, 530, 536, 537, 538, 540, 550, 600, 650 or more amino terminal amino acids of SEQ ID NO:6 are absent. In some embodiments, the demethylases of the invention comprise a polypeptide represented by SEQ ID NO:8, but wherein at least 1, 2, 3, 4, 5, 6, 7, 8, 9, 10, 50, 100, 200, 300, 400, 500, 530, 536, 537, 538, 540, 550, 600, 650 or more amino terminal amino acids of SEQ ID NO:8 are absent. In some embodiments, the demethylases of the invention comprise a polypeptide represented by SEQ ID NO:10, but wherein at least 1, 2, 3, 4, 5, 6, 7, 8, 9, 10, 50, 100, 200, 300, 400, 500, 530, 536, 537, 538, 540, 550, 600, 650 or more amino terminal amino acids of SEQ ID NO:10 are absent.

The present invention further provides numerous chimeric polypeptides with demethylase activity, the chimeric polypeptides comprising the fusion of portions of at least two different demethylases. The chimeric polypeptides comprise the glycosylase domain from a first demethylase and a portion of a second demethylase, wherein the portion is other than the glycosylase domain. Exemplary demethylases from which chimeras can be constructed include, e.g., DME (SEQ ID NO:2), ROS1(SEQ ID NO:6), DML2 (SEQ ID NO:8), or DML3 (SEQ ID NO:10). Exemplary chimeric polypeptides include, but are not limited to, a chimera comprising portions from any two or more of the above-listed demethylases. Some exemplary chimeric polypeptides of the invention include, e.g., proteins comprising polypeptides substantially identical to the following ROS1-DME chimeras: SEQ ID NO:12, SEQ ID NO:14, SEQ ID NO:16, SEQ ID NO:18, SEQ ID NO:20, SEQ ID NO:22, SEQ ID NO:24, SEQ ID NO:26. Functional chimeras can also be formed, for example, by replacing the DME or ROS1 portions in the above chimeras with a corresponding sequence from, e.g., DML2 or DML3. Generally, the chimeras will comprise a polypeptide sequence with domains at least corresponding to those in the Δ677 truncation of DME (SEQ ID NO:3).

Chimeras can be formed, e.g., by fusing the Domain A region of a first demethylase with the glycosylase domain and Domain B portions of a second demethylase. Alternatively, a fusion can be made with the Domain A region and glycosylase domain of a first demethylase and the Domain B portion of a second demethylase. In other embodiments, fusions are made within the Domain A, Domain B and/or glycosylase domains. It is noted that the Domain A, Domain B and glycosylase domain are most conserved between demethylases and therefore it is likely that the amino acid sequences between the above-listed domains are most tolerant of mutation or fusion without significantly affecting demethylase activity. Domain A, Domain B and glycosylase domain are depicted in FIGS. 17, 21-23.

Optionally, the demethylases of the invention are fused with a further polypeptide sequence that can be used, e.g., to assist in purification of the demethylase and/or assist in rendering the demethylases more soluble. Examples of further polypeptides to which the demethylases can be fused include, e.g., maltose binding protein (MBP), glutathione (GST), etc.

The chimeras of the present invention can be made by any method known in the art. Chimeras are readily constructed using recombinant DNA technology, fusing polynucleotide coding sequences of different demethylases to construct a synthetic coding sequence encoding the desired chimera. Once constructed, the recombinant polynucleotide can be used in expression systems to generate the desired demethylase polypeptide.

The present invention also provides polynucleotides encoding any of the demethylase polypeptides described herein. In some embodiments, the polynucleotides of the invention comprise an expression cassette, the expression cassette comprising a promoter operably linked to a polynucleotide encoding a demethylase described herein. The promoter can be a promoter that initiates and/or controls transcription in prokaryotic and/or eukaryotic cells. The promoter can initiate and/or control transcription in plant, animal, insect or other eukaryotic cells.

III. Transgenic Plants and Uses Thereof

Time to flowering and DNA methylation can be modulated by increasing demethylase activity in a plant. For example, enhanced expression of demethylases can result in delayed time to flowering in plants compared to plants not having enhanced expression. Demethylases can also be used to modulate the amount of methylated DNA in a cell. Indeed, since expression of many genes is dependent on their methylation state, modulation of demethylase activity modulates gene expression in a cell. Examples of genes whose expression is modulated by DME include MEDEA. Further, the polynucleotide sequences described herein can be used as antisense or RNAi molecules to suppress endogenous demethylase expression.

Isolated sequences prepared as described herein can also be introduced into a host cell, thereby modulating expression of a particular demethylase nucleic acid (encoding a demethylase) to enhance or increase endogenous gene expression. Enhanced expression can therefore be used to control plant morphology by controlling expression of genes under DME's control, such as MEDEA, in desired tissues or cells. Enhanced expression can also be used, for instance, to increase vegetative growth by preventing the plant from setting seed. Where overexpression of a gene is desired, the desired gene from a different species may be used to decrease potential sense suppression effects.

Preparation of Recombinant Vectors

In some embodiments, to use isolated sequences in the above techniques, recombinant DNA vectors suitable for transformation of plant cells are prepared. Techniques for transforming a wide variety of flowering plant species are well known and described in the technical and scientific literature. See, for example, Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, a plant promoter can be employed which will direct expression of a demethylase in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251: 196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol.* 208:551-565 (1989)), and Gpc2 from maize (GenBank No. U45855, Manjunath et al., *Plant Mol. Biol.* 33:97-112 (1997)).

Alternatively, the plant promoter may direct expression of the demethylase nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include a promoter from the ovule-specific BEL1 gene described in Reiser et al. *Cell* 83:735-742 (1995) (GenBank No. U39944). Other suitable seed specific promoters are derived from the following genes: MAC1 from maize (Sheridan et al. *Genetics* 142: 1009-1020 (1996), Cat3 from maize (GenBank No. L05934, Abler et al. *Plant Mol. Biol.* 22:10131-1038 (1993), the gene encoding oleosin 18 kD from maize (GenBank No. J05212, Lee et al. *Plant Mol. Biol.* 26:1981-1987 (1994)), vivparous-1 from *Arabidopsis* (Genbank No. U93215), the gene encoding oleosin from *Arabidopsis* (Genbank No. Z17657), Atmyc1 from *Arabidopsis* (Urao et al *Plant Mol. Biol.* 32:571-576 (1996), the 2s seed storage protein gene family from *Arabidopsis* (Conceicao et al. Plant 5:493-505 (1994)) the gene encoding oleosin 20 kD from *Brassica napus* (GenBank No. M63985), napA from *Brassica napus* (GenBank No. J02798, Josefsson et al. *JBL* 26:12196-1301 (1987), the napin gene family from *Brassica napus* (Sjodahl et al. *Planta* 197:264-271 (1995), the gene encoding the 2S storage protein from *Brassica napus* (Dasgupta et al. *Gene* 133:301-302 (1993)), the genes encoding oleosin A (Genbank No. U09118) and oleosin B (Genbank No. U09119) from soybean and the gene encoding low molecular weight sulphur rich protein from soybean (Choi, Y. et al., *Mol Gen Genet.,* 246:266-268 (1995)).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention can comprise a marker gene which confers a selectable phenotype on plant cells. For example, the marker can encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. These procedures will depend, part on the particular plant species being used, but will be carried out according to methods well known to those of skill.

Other non-plant host cells can also be used to express the demethylases of the invention. Exemplary host cells include, e.g., prokaryotic cells such as *E. coli* or other bacteria, insect cells, or animal cells, including mammalian cells including human cells. Cells can be isolated cells in culture (e.g., CHO or HELA cells, for example) or can be cells in vivo.

IV. Detection of Methylation

As the demethylases of the invention bind to methylated DNA sequences and modify such sequences, demethylases are useful for detecting the presence or absence and/or the location (i.e., specific sequence) of cytosine methylation in DNA. Cytosine methylation is known to regulate transcription, thereby affecting biological processes in cells and organisms. Accordingly, detection of DNA methylation has numerous uses in biological research. Moreover, aberrant methylation can be a marker for aging and disease, including various cancers. See, e.g., Jones, *Oncogene*, 21(35):5358-5360 (2002); Esteller, *Annual Review of Pharmacology and Toxicology*, 45: 629-656 (2005); Li, *Biochim Biophys Acta.*, 21704(2):87-102 (2004); Szyf, *Biochem Pharmacol.*, 68(6): 1187-97 (2004). Exemplary human genes whose methylation status is implicated in cancer and/or aging and can be detected according to the methods of the present invention include, but are not limited to, e.g., 14-3-3 Sigma, ABL1 (P1), ABO, APC, AR (Androgen Receptor), BLT1 (Leukotriene B4 Receptor), BRCA1, CALCA (Calcitonin), CASP8 (CASPASE 8), Caveolin 1, CD44, CFTR, COX2, CSPG2 (Versican), CX26 (Connexin 26), Cyclin A1, DBCCR1, ECAD (E-cadherin), Endothelin Receptor B, EPHA3, EPO (Erythropoietin), ER (Estrogen Receptor), FHIT, GPC3 (Glypican 3), GST-pi, H19, H-Cadherin (CDH13), HIC1, hMLH1, HOXA5, IGF2 (Insulin-Like Growth Factor II), IGFBP7, IRF7, LKB1, LRP-2 (Megalin), MDGI (Mammary-derived growth inhibitor), MDR1, MDR3 (PGY3), MGMT (O6 methyl guanine methyl transferase), MT1a (metallothionein 1), MUC2, MYOD1, N33, NEP (Neutral Endopeptidase 24.1)/CALLA, NF-L (light-neurofilament-encoding gene), NIS (sodium-iodide symporter gene), p14/ARF, p15 (CDKN2B), p16 (CDKN2A), p27KIP1, p57 KIP2, PAX6, PgR (Progesterone Receptor), RAR-Beta2, RASSF1, RB1 (Retinoblastoma), TERT, TESTIN, TGFBRI, THBS1 (Thrombospondin-1), TIMP3, TLS3 (T-Plastin), Urokinase (uPA), VHL (Von-Hippel Lindau), WT1, ZO2 (Zona Occludens 2). Accordingly, the present invention provides for detecting methylation of these or other mammalian (e.g., human) gene sequences, including, e.g., promoters thereof), by any methylation detection method provided herein. The DNA samples can be obtained from any mammal, including humans, and can be any biological sample that contains DNA, include, but not limited to, tissue biopsies (e.g., solid tumors or tissues suspect of having cancer or pre-cancerous tissue), blood samples, stool samples, etc.

The DNA methylation detection methods of the present invention can be used to detect DNA methylation, including for use in determining a diagnosis or prognosis, or, e.g., for monitoring progress of a disease or drug therapy.

Demethylases useful for the DNA methylation detection methods described herein include any demethylase that causes a nick when excising a methylated cytosine. Such demethylases include, but are not limited to, full length DME, ROS1, DML2, DML3, truncations thereof (for example as discussed herein, including in the "Demethylases" section above) and chimeras as described herein.

A. Methods Involving Primer Extension

Numerous methods of DNA methylation detection are provided herein. In some embodiments, the methods take advantage of the DNA "nicking" activity of the demethylases of the present invention. "Nicking" refers to an activity of demethylases in which at least one strand of the DNA double helix is cleaved at or adjacent to a methylated nucleotide (e.g., a methylated cytosine) on the phosphodiester backbone of the DNA. See, e.g., Gehring, M. et al., *Cell*, 124:495-506 (2006).

In some embodiments, the methods comprise nicking DNA with a demethylase of the invention and using primer extension from a DNA sequence adjacent to a DNA region of interest to detect the nick and thus the methylated nucleotide. In these embodiments, the primer extension continues until it is stopped by the nick. Determination of the length of the extension product, with knowledge of the chromosomal sequence and the sequence to which the primer hybridizes on the chromosomal sequence, allows one to determine where the methylation occurs in the chromosome. For example, if the extension product is 100 nucleotides long, then the methylated nucleotide is approximately 100 nucleotides from the site to which the primer hybridizes. Determination of the quantity of the primer extension product is indicative of the amount of methylated DNA. For example, if only 50% of the chromosomal copies are methylated (or if 50% of the cells in a sample from which DNA is obtain have methylated copies) then there will be a long extension product at the limits of primer extension and a shorter extension product which results from the nick stopping the extension, each in approximately equal amounts. In some embodiments, multiple different length extension products of different quantity are detected, thereby detecting a complicated heterogeneous methylation pattern of a sample, thereby detecting methylation at multiple sites on the DNA.

Primer extension can be performed by any method that allow for polymerase-based extension of a primer hybridized to genomic DNA. In some embodiments, simple primer extension involves addition of a primer and DNA polymerase to genomic DNA under conditions to allow for primer hybridization and primer extension by the polymerase. Of course, such a reaction includes the necessary nucleotides, buffers, and other reagents known in the art for primer extension.

In some embodiments, primer extension occurs during a nucleic acid amplification reaction. A non-limiting example of nucleic acid amplification is the polymerase chain reaction (PCR). Additional examples of amplification reactions include the ligase chain reaction (LCR), strand displacement amplification (SDA) (Walker, et al. *Nucleic Acids Res.* 20(7): 1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313): 91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell. Probes* 13(4):315-320 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS. In embodiments involving amplification, one or more primers are extended by amplification following nicking of the genomic DNA template with a demethylase of the invention, and the amplification product quantity or length is determined. Any number of methods are known for detecting amplification products, including, e.g., real-time amplification techniques, including those involving probes that specifically detect amplification products in real time, such as TaqMan® probes, Molecular Beacons and the like.

In some embodiments, the primer is detectably labeled (e.g., at its 5' end or otherwise located to not interfere with 3' extension of the primer) and following primer extension, the length and/or quantity of the labeled extension product is detected by detecting the label.

In some embodiments, the primer extension products are detected by adding a nucleotide sequence to the 3' end of the extension product. A non-limiting example of this process includes "tailing" with a single nucleotide (e.g., one of A, C, T, or G) using terminal tranferase and subsequent amplification using a primer that hybridizes to the tailed homopolymeric sequence. An example of such a method is described in Choi, Y. et al., *Cell*, 110:33-42 (2002). In some embodiments, this method is performed using demethylases comprising less than the full length DME protein sequences (or substantially identical sequences thereof) as disclosed herein or using chimeric demethylases (or substantially identical sequences thereof) as described herein. In some embodiments, the primer extension methods of the invention do not involving adding nucleotides to the extension product with a terminal transferase.

B. Methods Involving Covalent Bonding of Demethylase to DNA

The present invention also provides methods of detecting DNA methylation by taking advantage of the ability of the demethylases of the invention to bind to methylated DNA. The demethylases of the invention temporarily bind to methylated DNA in the process of introducing a nick by cleavage of the phosphodiester backbone of DNA. This temporary binding of the DNA can be converted to a covalent bond if the demethylase and DNA are contacted together in the presence of a reducing agent. The presence of the reducing agent results ins a chemical reduction reaction resulting in covalent linkage of the demethylase to the DNA at the site of the methylated nucleotide. Exemplary non-limited reducing agents include $NaBH_4$.

Once the demethylase is covalently bound to the DNA, the DNA/demethylase complex can be separated from other DNA (and, e.g., protein, carbohydrates and other cellular constituents) in the sample using any agent that has affinity for the demethylase. For example, a reagent that specifically binds to the demethylase can be bound to a solid surface, the demethylase/DNA mixture can be contacted to the agent under conditions in which the agent binds to the demethylase and then washed, thereby removing any DNA not bound to the demethylase. Exemplary agents that bind the demethylases of the invention include, but are not limited to antibodies that bind the demethylases. In alternate embodiments, the demethylase can be engineered to include an epitope or other tag that is recognized by an affinity agent. For example, a poly-His sequence can be genetically engineered to either end of the demethylase. Nickel can then be used as an affinity agent to bind the poly-His demethylase bound to DNA. In another non-limiting embodiment, the demethylase is biotinylated and the affinity agent is streptavidin or another molecule with affinity for biotin. In yet another embodiment, an epitope tag is genetically engineered into the demethylase and an antibody that binds to the epitope is used to bind to the demethylase.

Once the demethylase/DNA complex is separated from non-bound DNA, the double stranded DNA strand bound to the demethylase is detected directly. Alternatively, the DNA bound to the demethylase is double stranded and the doubles-stranded DNA is denatured after the demethylase/DNA complex is separated from non-bound DNA, and the resulting intact strand of DNA is detected. Detection can include any nucleic acid detection method known in the art, e.g., nucleic acid amplification techniques such as those relying on PCR.

V. Kits

For use in diagnostic, prognostic, research applications and other uses described herein, kits are also provided by the invention. The kits of the invention may comprise any or all of the reagents to perform the methods described herein. Such kits may include any or all of the following: at least one demethylase of the invention, or nucleic acid encoding a demethylase, primers for primer extension (optionally detectably labeled), a DNA polyermerase (optionally a thermostable polymerase capable of carrying out PCR under standard conditions), a terminal transferase, hybridization probes (optionally labeled) for detecting extension products, etc.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

V. Therapeutic Use of Demethylases

The present invention also provides for use of the demethylases of the invention to reduce methylation in cells, including cells in vivo as well as ex vivo (e.g., cells extracted from an individual, treated with a demethylase and then returned to an individual). Thus, demethylases of the invention can be used for the purpose of modulating the activity of target genes through chromatin architecture in animal cells as well as plant cells. For example, in some embodiments, a demethylase of the invention is used to catalytically remove 5-MeC from target gene DNA in several ways: e.g., (1) by fusing the demethylase to a sequence specific DNA binding protein, or (2) by fusing the demethylase to a subunit of the target repressor complex such as MeCP2 or Sin3. When combined with cell, tissue, or developmentally specific promoters, a demethylase of the invention can be used to modulate specific sets of target genes.

In addition, reactive oxygen species, partially reduced species that are produced as intermediates of aerobic respiration, are powerful oxidizing agents that escape the mitochondria and attach via cellular components. Ionizing radiation and other agents that generate free radicals also produce reactive oxygen species that can attack the genome and cause lesions that are thought to have a key role in causing cancer and ageing. For example, 7,8-dihydro-8-oxoguanine (oxoG) is a very deleterious adduct generated by oxidation of the guanine base in DNA. The oxoG protein can pair with either cytosine or adenine during DNA replication. Thus, oxoG residues in DNA give rise to G/C to T/A transversion mutations. These transversions are common somatic mutations found in human cancers. Demethylases of the invention, such as those described herein, represent a defense against oxoG by catalysing the expulsion of the oxoG. Thus, in some embodiments, enhancing demethylase activity is a method to reduce the incidence of mutations in animal cells. Also, a demethylase of the invention can be used to catalytically remove oxoG from a target gene by fusing a demethylase of the invention to a sequence specific DNA binding protein. When combined with a cell, tissue, or developmentally specific promoters a demethylase of the invention can be used to modulate repair of target genes.

As described above, the polypeptides of the invention can be targeted to chromosomal regions of interest by linking the polypeptides of the invention, including fragments with demethylase activity, to a DNA-binding domain that binds a target sequence. For example, it is known that an enzyme that methylates DNA (Dam methylase) can be targeted to specific sites in the genome (B. V. Steensel and S. Henikoff, *Nature Biotechnology* 18:424-428 (2000)). Specifically, the methylase was tethered to the DNA-binding domain of GAL4. When recombinant GAL4-methylase protein was expressed in transgenic *Drosophila*, targeted methylation occurred in a region of a few kilobases surrounding the GAL4 DNA binding sequence. In a analogous fashion, a demethylase of the invention can be tethered (e.g., as a translational fusion or chemically linked) to proteins that interact at specific sites in the genome). As a result, specific targeted regions of the genome are hypomethylated by a demethylase of the invention. As discussed above, typically hypomethylation promotes transcription of genes (S. E. Jacobsen, *Current Biology* 9, 617 (1999). The invention provides compositions and methods for demethylation of a desired area of the chromosome by targeting a demethylase of the invention to those regions. Thus, these embodiments provide additional ways to activate transcription of a desired gene in a targeted chromosomal region.

EXAMPLES

Example 1

MEDEA (MEA) is an *Arabidopsis* Polycomb group gene that is imprinted in the endosperm. The maternal allele is expressed and the paternal allele is silent. MEA is controlled by DEMETER (DME), a DNA glycosylase required to activate MEA expression, and METHYLTRANSFERASE I (MET1), which maintains CG methylation at the MEA locus. Here we show that DME is responsible for endosperm maternal allele-specific hypomethylation at the MEA gene. DME can excise 5-methylcytosine in vitro and when expressed in *E. coli*. Abasic sites opposite 5-methylcytosine inhibit DME activity and might prevent DME from generating double-stranded DNA breaks. Unexpectedly, paternal allele silencing is not controlled by DNA methylation. Rather, Polycomb group proteins that are expressed from the maternal genome, including MEA, control paternal MEA silencing. Thus, DME establishes MEA imprinting by removing 5-methylcytosine to activate the maternal allele. MEA imprinting is subsequently maintained in the endosperm by maternal MEA silencing the paternal allele.

Results

Maternal MEA Allele is Hypomethylated in Wild Type Endosperm

Four regions around the MEA locus were previously shown to be methylated; a Helitron DNA transposon element (Kapitonov, V. V. and Jurka, J., *Proc Natl Acad Sci USA*, 98, 8714-8719 (2001)), AtREP2, about 4 kb 5' of the start site (Xiao, W. et al., *Developmental Cell*, 5, 891-901 (2003)), CG sites 3 kb and 500 bp upstream (Xiao, W. et al., *Developmental Cell*, 5, 891-901 (2003)), and seven ~182 bp direct repeats 3' of the gene, termed MEA-ISR (Cao, X. and Jacobsen, S. E., *Proc Natl Acad Sci USA*, 99, 16491-16498 (2002)). Here we show that bisulfite sequencing covering 91% of the CG sites in the MEA coding region did not reveal any additional methylated cytosines (FIG. 1A). To see if DME antagonizes MET1 by removing MEA DNA methylation in the central cell, we compared the methylation of maternal and paternal alleles in the embryo and endosperm of seeds dissected between 7 and 8 days after pollination (DAP). Allele-specific methylation was determined in reciprocal crosses between the accessions Co1-gl and RLD. This allowed us to discount any methylation effects due to natural variation or the direction of the cross. Maternal and paternal alleles could be distinguished after sequencing because of polymorphisms between RLD and Col-gl near the regions of methylation. The two accessions used in this study have similar levels of MEA methylation in leaves.

In a cross between a Col-gl female and a RLD male, the −4 kb transposon element was highly methylated on both maternal and paternal embryo and endosperm alleles (FIG. 1B). The −3 kb region exhibited low levels of methylation on all alleles (FIG. 1B). However, the maternal endosperm allele was hypomethylated at the −500 bp (13% CG) region compared to the paternal endosperm allele (54%) and the maternal (96%) and paternal (87%) embryo alleles (FIG. 1B). The same relationship was observed at the MEA-ISR. The maternal endosperm allele had 20% CG methylation compared to the paternal endosperm allele, which had 83%, and maternal and paternal embryo alleles, with 80% and 85% CG methylation, respectively (FIG. 1B). The −500 bp region and MEA-ISR were also maternally hypomethylated in the endosperm of the reciprocal cross with RLD as the female and Col-gl as the male.

Maternal MEA is not Hypomethylated in DME Endosperm

If DME is responsible for hypomethylation of MEA in the female gametophyte, then dme mutant endosperm should, in comparison, inherit hypermethylated maternal MEA alleles from dme central cells. We crossed dme-2 heterozygous mutant females in both the Col-gl and Ler backgrounds to wild type RLD males and analyzed methylation of maternal and paternal alleles from dme mutant endosperm 9 or 10 DAP. Compared to maternal allele methylation in wild type endosperm, we found a substantial increase in maternal allele CG methylation in both the −500 bp (76% vs. 13% for wild type) and MEA-ISR (89% vs. 20% for wild type) regions in crosses with dme in a Col-gl background (FIG. 2A). In crosses with dme in a Ler background, methylation on the maternal allele increased at the MEA-ISR (84% vs. 18% for wild type), but not in the −500 bp region (1% vs. 22% for wild type) (FIG. 2B). We expected no change for the −500 bp region in the dme Ler mutant because there is very little methylation there for DME to act on in wild. We conclude that, in wild type, DME DNA glycosylase is responsible for hypomethylation of the maternal endosperm allele observed at the MEA-ISR in the Col-gl, Ler, and RLD backgrounds and for hypomethylation of the −500 bp region in Col-gl and RLD.

Figure 3:
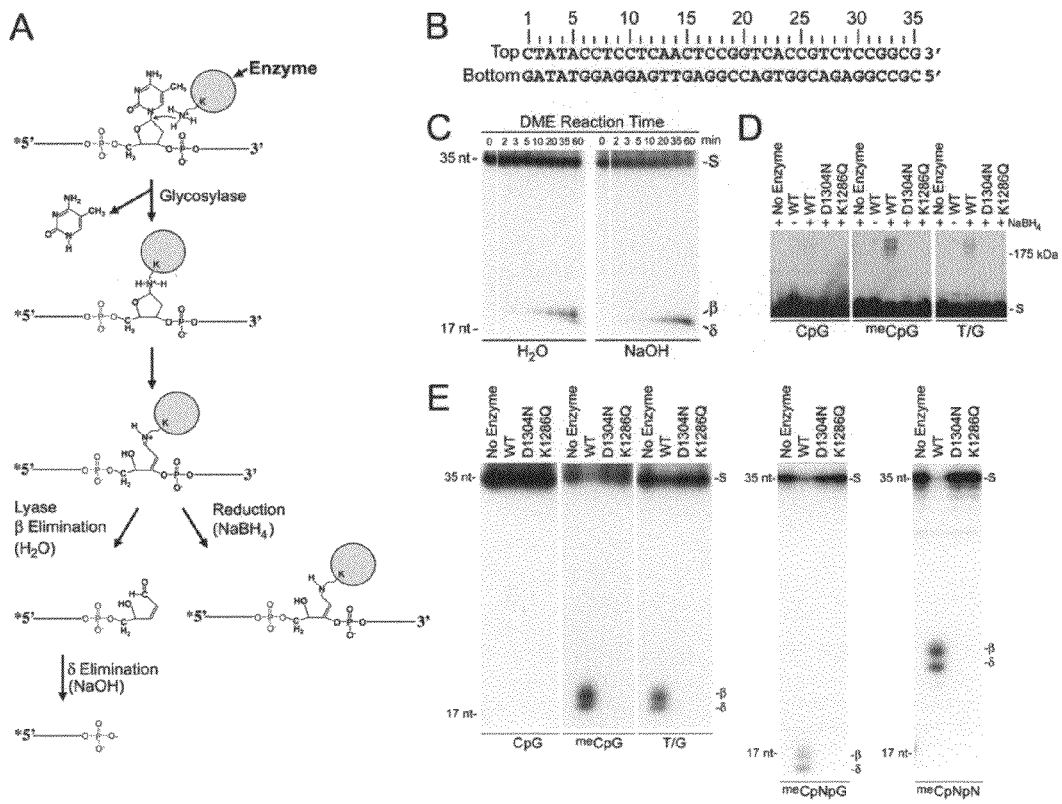
FIG. 3. DME in vitro Activity. (A) Schematic mechanism of bifunctional DNA glycosylases. (B) DNA substrate sequence (SEQ ID NO:27). Base pair positions relative to the 5'-end of the top DNA strand are shown. Double-stranded DNA oligonucleotide substrates in panels C to E were labeled at the 5'-end of the top strand. DNAs in panel C had 5-methylcytosine at position 18 in the top strand. The top strand for panels D and E has: CpG, C at position 18; $^{me}$CpG, 5-methylcytosine at position 18; T/G, T at position 18; $^{me}$CpNpG, 5-methylcytosine at position 17; $^{me}$CpNpN, 5-methylcytosine at position 22. All reactions were for 1 hr. (C) Reaction products of DME. Products were treated with either water or NaOH as indicated, denatured and analyzed on 15% polyacrylamide gels with 7.5 M urea. (D) Covalent cross-linking of DME to DNA. Reaction products were treated with NaBH$_4$, denatured, and analyzed on a 10% SDS-polyacrylamide gel. (E) Substrate specificity of DME. Reaction products were denatured and analyzed on 15% polyacrylamide gels with 7.5 M urea. Both β- and α-elimination products are observed because reactions were not treated with NaOH before gel electrophoresis. S, uncleaved substrate; β, predicted β-elimination product; δ, predicted δ-elimination product; 35 nt, 35 nucleotide size marker; 17 nt, 17 nucleotide size marker.

DME with a Wild Type DNA Glycosylase/Lyase Domain Excises 5 Methylcytosine In Vitro DME is related to DNA glycosylases (Choi, Y. et al., *Cell,* 110, 33-42 (2002)) that catalyze the first steps in the base excision DNA repair pathway (Scharer, O. D. and Jiricny, J., *BioEssays,* 23, 270-281 (2001)). The reaction mechanism of bifunctional DNA glycosylases is well known (Scharer, O. D. and Jiricny, J., *BioEssays,* 23, 270-281 (2001)). A conserved aspartic acid acquires a proton from a conserved lysine residue that attacks the C1' carbon of the deoxyribose ring creating a covalent DNA-enzyme intermediate (FIG. 3A). β- or δ-elimination reactions release the enzyme from the DNA and cleave one of the phosphodiester bonds (FIG. 3A). Cleavage 5' to the abasic site of the β- or δ-elimination produced by an AP endonuclease generates a 3'-hydroxyl used by a DNA repair polymerase that inserts the proper nucleotide and a DNA ligase seals the nick.

We expressed in *E. coli* an 1192 amino acid portion of DME that lacks 537 amino-terminal amino acids (Δ537DME), but includes the predicted DNA glycosylase domain. Δ537DME was fused to the maltose binding protein (MBP). MBP-Δ537DME was purified over an amylose column and is referred to as wild type DME. For control experiments, we expressed and purified mutant forms of DME where the invariant aspartic acid at position 1304 was converted to asparagine (D1304N) or the lysine at position 1286 was converted to glutamine (K1286Q). Both mutations reduce DNA glycosylase activity while preserving enzyme structure and stability (Fromme, J. C. et al., *Nature,* 427, 652-656 (2004); Norman, D. P., *Hum Mol Genet,* 14, R113-R120 (2003)).

We incubated DME with various double-strand oligonucleotides (FIG. 3B) to understand its biochemical mechanism. DME breaks the phosophodiester linkage on the 3'-side of a 5-methylcytosine residue (hemimethylated substrate) and generates end-labeled DNAs that migrate on denaturing polyacrylamide gels at the predicted position for β-elimination products (FIG. 3C). The subsequent cleavage of the phosphodiester linkage on the 5'-side yields δ-elimination products through the same mechanism found in related DNA glycosylases (Bhagwat, M. and Gerlt, J. A., *Biochemistry,* 35, 659-665 (1996)). Treatment of products with strong base (NaOH) prior to gel electrophoresis confirmed the δ-elimination process at the predicted position (FIG. 3C). Consistent with the reaction mechanism for a bifunctional DNA glycosylase/lyase (FIG. 3A), products treated with a reducing agent (NaBH$_4$) migrated in the predicted region for trapped enzyme-DNA complexes (~200 kd), suggesting that the Schiff base intermediate between DME and a ring-opened sugar is covalently reduced (FIG. 3D). No lyase activity (FIG. 3E) or covalent trapping (FIG. 3D) was detected when DME was incubated with non-methylated oligonucleotides, or when hemimethylated substrate was incubated with no enzyme or mutant enzymes (D1304N or K1286Q). Plants have 5-methylcytosine in the three sequence contexts; CpG, CpNpG, and CpNpN (Bender, J., *Ann Rev Plant Biology,* 55, 41-68 (2004)). DME has activity on 5-methylcytosine in each of these sequence contexts (FIG. 3E). We detected no DME activity when single-stranded oligonucleotides with 5-methylcytosine were used in the reaction (data not shown). These results show that DME is a bifunctional DNA glycosylase/lyase with activity on 5-methylcytosine substrates. It is notable that DME does not display DNA sequence specificity when excising methylated cytosines.

DME Excises Thymine from a T/G Mismatch 5-methylcytosine is mutagenic because it spontaneously deaminates to form thymine, generating a T/G mismatch. Deamination can also occur enzymatically by cytosine deaminase, a process that may play a role in mammalian epigenetic reprogramming and cell plasticity (Morgan, H. D. et al., *J Biol Chem,* 279, 52353-52360 (2004)). Specific DNA glycosylases initiate DNA repair by excising T from T/G mispairs (Scharer, O. D. and Jiricny, J., *BioEssays,* 23, 270-281 (2001)). We found that DME also is a thymine DNA glycosylase. DME activity on T/G mispairs is somewhat less than its activity on $^{me}$C/G base pairs (FIG. 3E and data not shown). DME also forms a trapped enzyme-DNA complex with DNA containing a T/G base pair (FIG. 3D).

Figure 2:
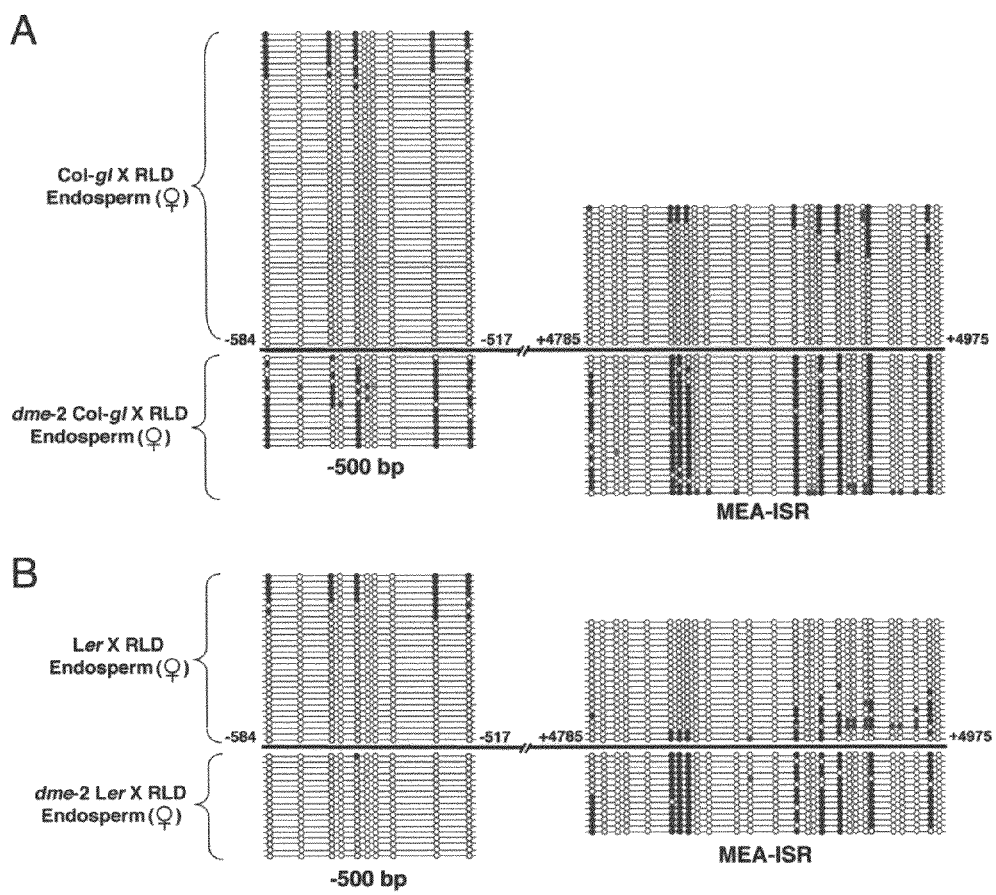
FIG. 2. Hypermethylation of Maternal MEA in dme Mutant Endosperm. Maternal allele methylation in the −500 bp and MEA-ISR regions in endosperm from crosses between dme-2 heterozygous females and RLD males compared to maternal endosperm allele methylation from crosses between wild type females and RLD males. (A) dme-2 heterozygous Co1-gl crossed to RLD. (B) dme-2 heterozygous Ler crossed to RLD. Mutant endosperm was collected at 9 DAP from seeds with the dme endosperm overproliferation phenotype. Numbers are from the translation start site. To determine the pattern of DNA methylation, DNA was treated with bisulfite, PCR-amplified, cloned, and sequenced. Circles connected by lines represent the results from determining the DNA sequence of one clone. Filled circle, methylated cytosine; open circle, unmethylated cytosine; Red circle, CG site; blue circle, CNG site; gray circle, CNN site.

DME could cause hypomethylation of the maternal MEA alleles in the endosperm using two different mechanisms. DME might excise 5-methylcytosine, leading to its replacement with unmethylated cytosine. Or, DME might excise thymine from a T/G mismatch formed from deamination of 5-methylcytosine. To distinguish between these two mechanisms, we sequenced DNA from dme mutant endosperm. If DME excised thymine instead of 5-methylcytosine, we expected to find numerous C→T transitions at CG sites in the −500 bp region and MEA-ISR, which are hypomethylated in wild type endosperm (FIGS. 1 and 2). However, no C→T transitions were found (Supplementary FIG. 2). Thus, the thymine DNA glycosylase activity of DME is likely not responsible for maternal MEA allele hypomethylation.

DME is Toxic in *E. Coli* with 5-Methylcytosines

When expressing DME from an IPTG-inducible promoter, we found that DME was toxic to *E. coli* K-12 strains in an IPTG-concentration dependent manner (FIGS. 4A and 4C). The toxicity of DME expression was significantly increased in a strain bearing mutations in two AP endonuclease genes (xth and nfo) (Cunningham, R. P. et al., *Endonuclease IV (nfo) mutant of Escherichia coli,* 168, 1120-1127 (1986)), which remove abasic sites and trim the 3'-structure of nicks. This result suggests that DME DNA glycosylase and/or lyase activity is toxic, perhaps due to the formation of mutagenic abasic sites and/or nicks in the *E. coli* genome. Indeed, expression of inactive DME(D1304N) was nontoxic in xth nfo mutants or the isogenic wild type background (FIG. 4B). DME has in vitro 5-methylcytosine activity (FIGS. 3C-3E) and *E. coli* K-12 strains have 5-methylcytosine in their genomes. Perhaps DME produces deleterious abasic sites in *E. coli* by excising 5-methylcytosine at a genome-wide level. We tested this hypothesis by expressing DME in a dcm mutant strain (Palmer, B. R. and Marinus, M. G., *Gene,* 143, 1-12 (1994)), which has no 5-methylcytosine in its genomes. DME expression was not toxic to dcm bacteria compared to expression in the isogenic wild type strain (FIG. 4C). Expression of inactive DME(D1304N) had no effect on either strain (FIG. 4D). This suggests that 5-methylcytosine is a substrate for DME in *E. coli* K-12 bacteria.

Base Excision Inhibits Further Excision by DME on the Opposite DNA Strand

Excision of 5-methylcytosine from fully methylated $^{me}$CpG/Gp$^{me}$C sequences by DME would generate nicks 1-nucleotide apart on opposing DNA strands, which could lead to deleterious double-stranded breaks in the DNA (Hanai, R. et al., *Int J Radiat Biol,* 73, 475-479 (1998)). A similar problem occurs when DNA glycosylases encounter clustered lesions on opposing DNA strands, where it has been shown that abasic sites and/or nicks on one DNA strand inhibit glycosylase-mediated excision of nearby lesions on the opposing strand (David-Cordonnier et al., *Biochemistry,* 40, 11811-11818 (2001); Weinfeld, M. et al., *Radiation Res,* 156, 584-589 (2001)). Consistent with this mechanism, we found that DME is more active on a specific 5-methylcytosine when it is in the hemi-methylated state compared to the fully-methylated state (FIG. 5A). Moreover, an abasic site on the opposite strand (~pG/Gp$^{me}$C, where ~represents the abasic site) reduced the reaction rate approximately 10-fold compared to DME activity on hemi-methylated DNA (FIGS. 5A and 5B, lane 2). A similar inhibitory effect was observed when an abasic was in a hemimethylated CpNpG context (~pNpG/GpNp$^{me}$C) (FIG. 5B, lane 3). By contrast, there is significantly less inhibition of DME activity when the abasic site is shifted 4-(FIG. 5B, lane 4) or 7-nucleotides (FIG. 5B, lane 5) away from the 5-methylcytosine. These results indicate that the abasic site created by excision of 5-methylcytosine from fully methylated CpG or CpNpG DNA specifically inhibits subsequent excision of 5-methylcytosine on the opposite strand. This would allow AP endonuclease, DNA polymerase, and ligase to complete the base-excision DNA repair pathway on one DNA strand before excising 5'-methylcytosine on the opposite strand, thereby avoiding a double strand break.

Hypomethylated Paternal Genome does not Release Paternal MEA Silencing

Figure 6:
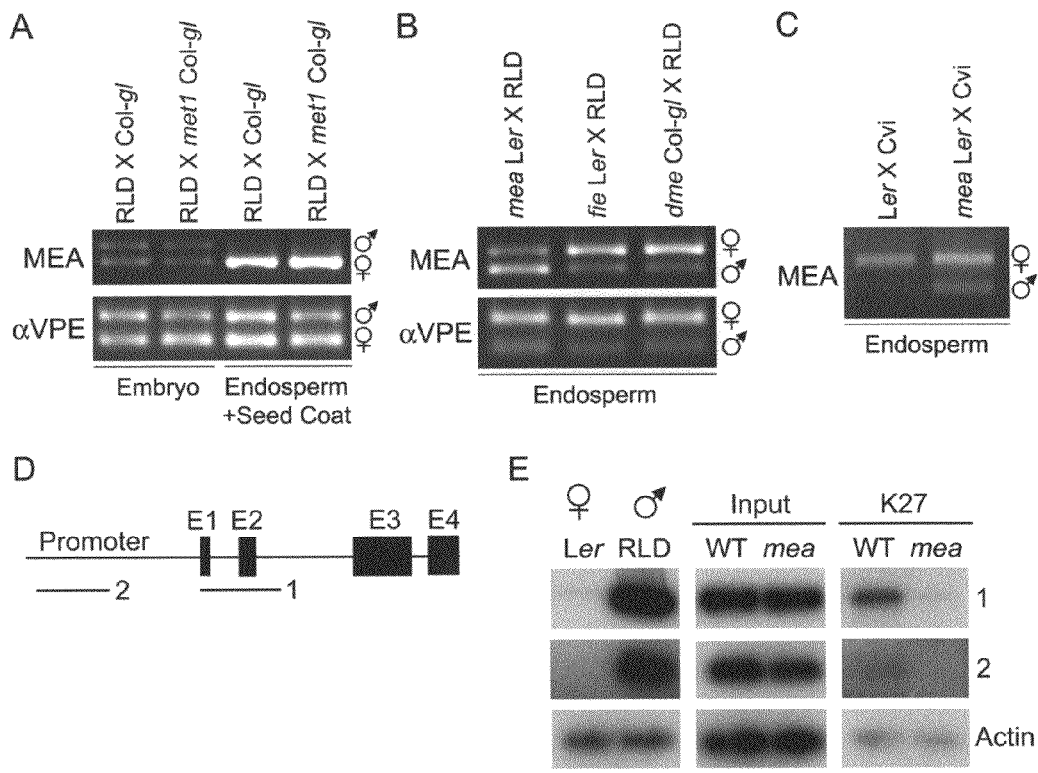
FIG. 6. Regulation of MEA Paternal Allele Silencing. (A) Paternal MEA silencing is not affected by a hypomethylated paternal genome. Expression of MEA in the embryo and endosperm/seed coat of crosses between a RLD female and Co1-gl male and a RLD female and a met1-6-/-Co1-gl male. Seeds were dissected 7 DAP. (B) MEA expression in endosperm of crosses between mea-3-/- Ler, fie-1+/-Ler, and dme-2+/-Co1-gl females and RLD males, dissected 9 DAP. (C) MEA expression in endosperm of crosses between Ler and mea-3-/- Ler females and Cvi males, dissected 7 and 8 DAP, respectively, at the torpedo stage of embryogenesis. VPE is a control for biallelic expression. (D) Genomic structure of Arabidopsis MEA and regions examined by ChIP. E1 through E4; exons 1 through 4. Regions amplified are shown by bars labeled 1 and 2. (E) ChIP with anti-dimethyl H3K27 comparing amplification of MEA in WT Ler X RLD and mutant Ler mea X RLD siliques 7 DAP. LNA primers were used to amplify regions 1 and 2, and not the actin control DNA.

The silent paternal endosperm allele is hypermethylated compared to the expressed maternal allele (FIG. 1B). Would inheritance of a hypomethylated paternal genome release silencing of the paternal allele in the endosperm? We crossed a wild type female to a met1-6 homozygous mutant male and analyzed allele specific expression in embryo and endosperm plus seed coat fractions by RT-PCR. Expression was indistinguishable from wild type crosses, indicating no change in MEA paternal allele silencing (FIG. 6A). We tested a variety of other mutations (Bender, J., *Ann Rev Plant Biology,* 55, 41-68 (2004)) that affect DNA methylation in various sequence contexts for their ability to alter imprinting in the endosperm. Paternal inheritance of ddm1-2, drm1 drm2 cmt3-7, ago4-1, rdr2-1, or dcl3-1 did not result in paternal allele expression in the endosperm (data not shown).

Polycomb Group Proteins Maintain Paternal Allele Silencing

What, then, is the mechanism for maintaining silencing of the paternal allele in the endosperm? In insects, mammals, and plants, Polycomb group (PcG) proteins maintain repressed states of gene transcription. PcG proteins are involved in a variety of epigenetic processes, including maintenance of X-inactivation and of allele-specific silencing of a subset of imprinted genes in mammals (Cao, R. and Zang, Y., *Curr Opin Genet Dev.,* 14, 155-164 (2004)). We tested whether PcG genes are involved in MEA imprinting and found that endosperm paternal allele silencing is lost when mutations in Polycomb group genes are inherited maternally. In a cross between Ler mea-3 (Kiyosue, T. et al., *Proc Natl Acad Sci USA,* 96, 4186-4191 (1999)) homozygous mutant females and wild type RLD males, almost all seeds undergo endosperm overproliferation, embryo arrest, and seed abortion. We collected the mutant endosperm before seed abortion and analyzed allele specific expression. Expression from both maternally and paternally inherited alleles was detected, indicating a loss of imprinting (FIG. 6B).

Paternal allele expression was also observed in endosperm from seeds that lack maternal MEA but do not abort. When Ler mea/mea plants are pollinated by the Cvi accession, the seed abortion phenotype is suppressed and 95% viable seeds are produced. Endosperm allele-specific gene expression in seeds dissected at the torpedo stage of embryogenesis was compared in crosses between Ler and Cvi and Ler mea/mea and Cvi. In the wild type cross, only maternal allele expression was detected in the endosperm. When Ler mea/mea was the female in the cross, expression from both maternal and paternal alleles was observed (FIG. 6C). Thus, MEA paternal allele silencing is lost in both viable (FIG. 6C) and aborting (FIG. 6B) seeds when maternal MEA is not made.

FIE is a PcG gene homologue of *Drosophila* Esc and mammalian Eed, and fie mutants have a seed abortion phenotype like mea (Ohad, N. et al., *Plant Cell,* 11, 407-415 (1999)). FIE and MEA interact in a PcG complex (Kohler, C. et al., *EMBO J,* 22, 4804-4814 (2003)). Loss of imprinting was also observed when fie-1 heterozygous females were crossed to wild type males (FIG. 6B). These results suggest that silencing of the paternal allele in the endosperm is maintained by maternally-expressed Polycomb group proteins that likely act at the paternal MEA locus.

Paternal MEA is Enriched in H3K27 Methylation

Polycomb group complexes modify histones. In *Drosophila* and mammals, ESC-E(Z) and EED-EZH2 PcG complexes methylate histone H3 at K27 (Czermin, B. et al., *Cell*, 111, 185-196 (2002); Muller, J. et al., *Cell*, 111, 197-208 (2002)). H3K27 methylation is also a likely Polycomb mark in *Arabidopsis*. Expression of the FLC gene is regulated by vernalization (exposure to cold), which causes an increase in H3K27 dimethylation at the locus (Bastow, R. et al., *Nature*, 427, 164-167 (2004); Sung, S. and Amasino, R. M., *Nature*, 427, 159-164 (2004)). This change is dependent on VRN2, a Polycomb group gene that maintains vernalization-induced down regulation of FLC expression (Bastow, R. et al., *Nature*, 427, 164-167 (2004); Sung, S. and Amasino, R. M., *Nature*, 427, 159-164 (2004)).

We hypothesized that the maternal MEA-FIE complex methylates H3K27 at the paternal MEA allele in the endosperm. By a chromatin immunoprecipation assay, we compared paternal allele H3K27 dimethylation patterns in siliques from crosses between Ler females and RLD males, and Ler mea/mea females with RLD males. We took advantage of MEA sequence polymorphisms between Ler and RLD to specifically amplify paternal DNA by using PCR primers containing high affinity DNA analogs known as Locked Nucleic Acids (LNA) (Koshkin, A. A. et al., *TETRAHEDRON*, 54, 3607-3630 (1998)). The last base of each primer contains a LNA base analogue that will pair with the RLD base at a much higher affinity than the Ler base. Primer sets for the MEA promoter and coding region (FIG. 6D) amplified RLD (male parent) genomic DNA well, but Ler (female parent) very poorly (FIG. 6E).

The vast majority of silique DNA is of maternal origin, from the maternal silique and seed coat tissue and the contributions of the maternal genome to the embryo and endosperm. The only paternal DNA in siliques is from the embryo and endosperm. Since paternal DNA is a small fraction of the total DNA, radioactive nucleotides were used to increase the sensitivity of the assay. As shown in FIG. 6E, we found that after ChIP with antibodies specific to H3 dimethyl K27, paternal MEA DNA was enriched in wild type siliques compared to maternal mea siliques for the coding region from −5 to +440 (region 1). By contrast, little if any paternal MEA DNA was detected in MEA 5' sequences from −947 to −547 (region 2). We cloned the −5 to +440 wild type and mea PCR products, sequenced across an internal Ler/RLD polymorphism, and verified that almost all of the clones were from paternal RLD DNA (21 of 22 wild type clones and 22 of 22 mea clones). Although paternal embryo and endosperm alleles cannot be distinguished, these results indicate that wild type maternal MEA is required for paternal MEA H3 K27 dimethylation.

Paternal Silencing is Lost in DME Mutants

Because dme mutants lack MEA expression in the female gametophyte (Choi, Y. et al., *Cell*, 110, 33-42 (2002)), we looked at the effect of dme on paternal MEA expression in the endosperm. Paternal allele expression was detected when dme-2 heterozygous plants were crossed as females to wild type males (FIG. 6B). This is consistent with our finding that maternal MEA expression in the female gametophyte, activated by DME, is required for paternal allele silencing.

The expressed paternal allele in dme endosperm is as highly methylated as the silent paternal allele from wild type endosperm (FIG. 1B). In a cross between dme-2 Col-gl females and RLD males, expressed paternal endosperm alleles had 100% and 94% CG methylation in the −500 bp region and MEA-ISR, respectively (3 and 11 clones sequenced). In a cross between dme-2 Ler females and RLD males, expressed paternal endosperm alleles had 54% and 93% CG methylation in the −500 bp region and MEA-ISR (7 and 5 clones sequenced). This suggests, in agreement with results presented in FIG. 6A, that the presence or absence of DNA methylation is not relevant to MEA paternal allele silencing in the endosperm.

We also detected expression of the highly methylated maternal MEA allele (FIG. 2A) in dme endosperm (FIG. 6B). Previously, we showed that DME is required for MEA expression before fertilization (Choi, Y. et al., *Cell*, 110, 33-42 (2002)). These results suggest that although hypomethylation via DME is required for MEA expression in the central cell before fertilization and possibly during early endosperm development (Choi, Y. et al., *Cell*, 110, 33-42 (2002)), it is not required for maternal MEA expression in the endosperm by 9 DAP.

Discussion

Activation of Maternal MEA Allele Expression by DME

Figure 4:
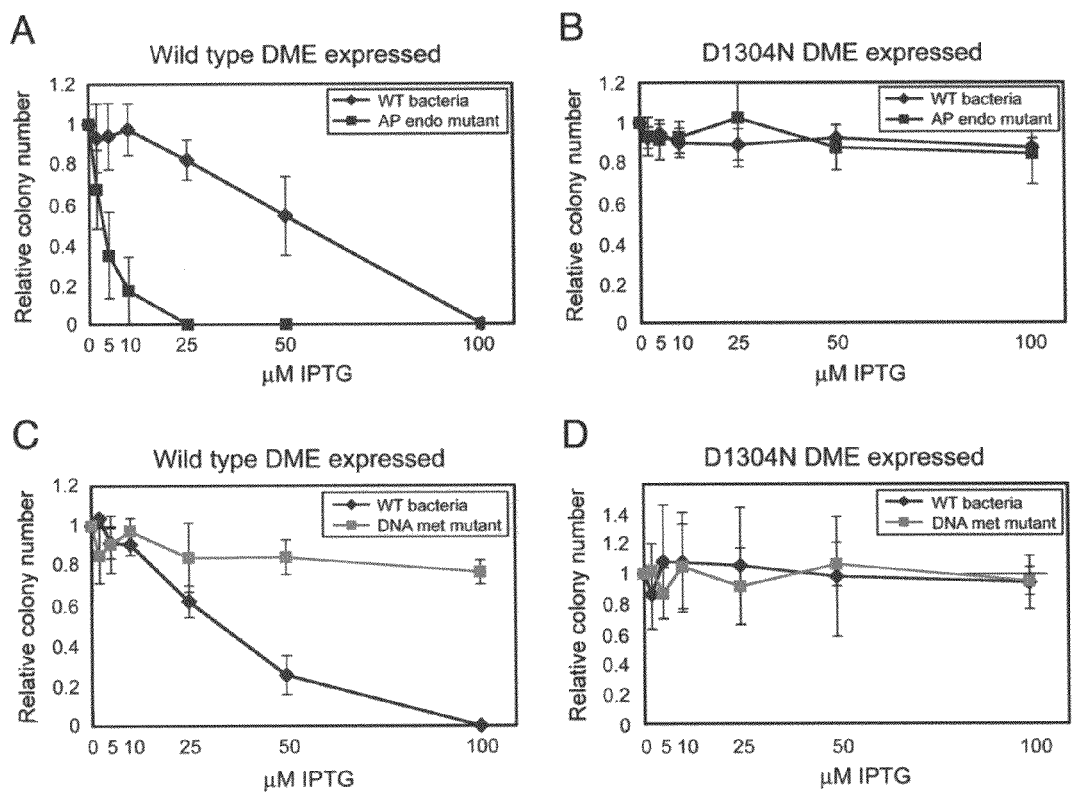
FIG. 4. DME Functions as a 5-methylcytosine DNA Glycosylase in E. coli. Relative colony number; number of colonies on plate divided by the number of colonies obtained when plate has no IPTG inducer. (A and B) WT bacteria, AB1157; AP Endo Mutant, RPC501 (Cunningham, R. P. et al., Endonuclease IV (nfo) mutant of Escherichia coli, 168, 1120-1127 (1986)) isogenic to AB1157 with mutations in two AP endonuclease genes (xth, nfo). (C and D) WT bacteria, GM30; DNA Met Mutant, GM31 (Palmer, B. R. and Marinus, M. G., Gene, 143, 1-12 (1994)) isogenic to GM30 with a mutation in the dcm DNA methyltransferase.

We have found that the expressed maternal endosperm allele of the imprinted MEA gene is hypomethylated in specific 5' and 3' regions (FIG. 1). DME is required for MEA expression in the central cell (Choi, Y. et al., *Cell*, 110, 33-42 (2002)) and for hypomethylation of the maternal MEA allele inherited from the central cell (FIGS. 1 and 2). Thus, expression of the maternal MEA allele is associated with removal of DNA methylation by a DNA glycosylase. This in vivo data suggests that one DNA repair function of DME is to excise 5-methylcytosine from CG contexts, leading to its replacement with cytosine. This is supported by DME excision of 5-methylcytosine in vitro (FIG. 3), as well as DME activity on 5-methylcytosine in the base excision repair pathway in *E. coli* (FIG. 4). Another DME family member, ROS1, also has activity on 5-methylcytosine in vitro (Gong, Z. et al., *Cell*, 111, 803-814 (2002)).

Figure 5:
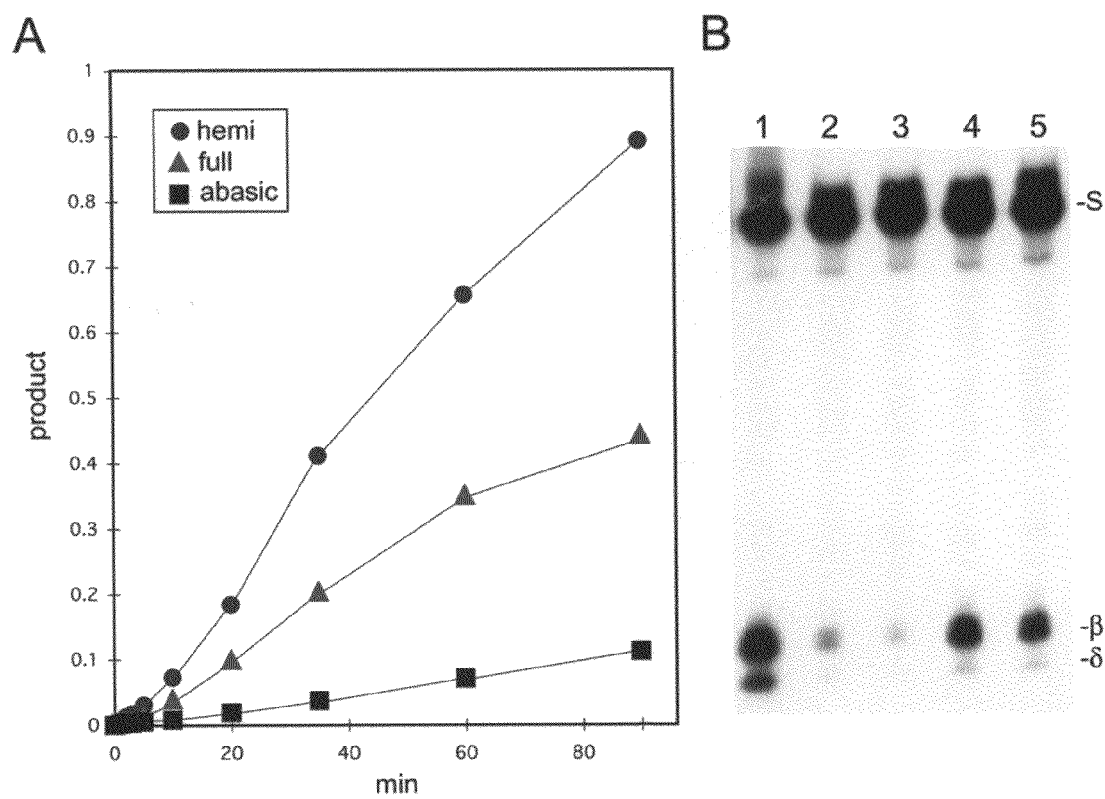
FIG. 5. Inhibition of DME Activity by Abasic Sites. (A) Rate of DME activity. Labeled (5'-end of the bottom strand) double-stranded oligonucleotides (FIG. 3B) were used with the following sequences: hemi, 5-methylcytosine at position 19 (bottom strand); full, 5-methylcytosine at positions 19 (bottom strand) and 18 (top strand); abasic, 5-methylcytosine at position 19 (bottom strand) and an abasic site at 18 (top strand). Reactions were performed, terminated by addition of NaOH, boiled, and subjected to electrophoresis. Gels were exposed to a phosphor imager screen to determine the amount of product. (B) Effect of abasic site position on DME activity. Double-stranded oligonucleotides (FIG. 3B) were labeled at the 5'-end of the bottom strand and had 5-methylcytosine at position 19 of the bottom strand (lane 1). In addition, abasic sites were in the top strand at position 18 (lane 2), position 17 (lane 3), position 15 (lane 4), position 12 (lane 5).

Excision of symmetric 5-methylcytosine is predicted to cause deleterious double-strand DNA breaks. However, this might be mitigated by the inhibition of DME activity by abasic sites (FIG. 5). The mechanism for the inhibition is not known. DME has little lyase activity on abasic sites (data not shown), so it is likely to be the abasic site, not a nick in the DNA, which inhibits DME. One possibility is that DME binds to the abasic site and physically hinders other DME molecules from excising 5-methylcytosine on the opposite strand. Alternatively, an abasic site near the active site of a DME enzyme may inhibit an essential step of the base excision reaction mechanism for the 5-methylcytosine on the opposing strand.

Several aspects of the activation of MEA by DME remain unclear. Do reduced levels of DNA methylation directly lead to expression of MEA in the central cell? Or, does an accompanied change induced by the act of DNA repair render the locus transcriptionally competent? Unlike the maternal MEA allele in the central cell, paternal allele expression in the endosperm is not affected by changes in DNA methylation (FIG. 6A). Instead, paternal silencing is lost when the function of maternal MEA-FIE PcG complexes is perturbed (FIG. 6B). This is associated with decreased H3K27 methylation on the paternal allele (FIG. 6E).

Central Cell Specific Interpretation of Mea DNA Methylation

Our data show that removal of CG methylation is required for MEA expression in the central cell, but not in the embryo or during later stages of endosperm development. A hypomethylated paternal genome does not affect MEA imprinting (FIG. 6A). Furthermore, in dme endosperm the expressed maternal and paternal alleles are highly methylated in the −500 bp region and MEA-ISR. Hypomethylation of MEA is only required for expression in the central cell, and perhaps during early endosperm development at a stage prior to dme seed dissection. This conclusion is supported by embryo methylation data from wild type crosses (FIG. 1). MEA is expressed biallelically in the embryo (FIG. 3; (Kinoshita, T. et al., *Plant Cell*, 11, 1945-1952 (2004)). Yet, we found that the expressed embryo alleles are as highly methylated as the silent paternal endosperm allele, and hypermethylated compared to the expressed maternal endosperm allele (FIG. 1). Differences in methylation between the maternal embryo and maternal endosperm alleles hearken back to the distinct origins of these alleles in the female gametophyte, which arise from the egg and central cell, respectively. Due to the exclusive expression of DME in the central cell, only the maternal endosperm allele, and not the maternal embryo allele, has been exposed to DME. Removal of DNA methylation at the maternal MEA allele in the central cell represents the first case in angiosperms in which changing the methylation status of a gene is an integral part of an essential developmental program, the formation of viable seeds.

The limited regulation of MEA expression by the removal of DNA methylation is in contrast to the imprinted gene FWA, where there is a strong correlation between DNA methylation and gene expression not only in the endosperm but also in the embryo and throughout the entire plant (Kinoshita, T. et al., *Science*, 303, 521-523 (2004); Soppe, W. J. J. et al., *Mol Cell*, 6, 791-802 (2000)). FWA is not expressed vegetatively and is highly methylated on promoter repeats. These repeats are hypomethylated in mutants that ectopically express the gene (Soppe, W. J. J. et al., *Mol Cell*, 6, 791-802 (2000)). Additionally, endosperm imprinting is lost when FWA is inherited from a met1 pollen parent (Kinoshita, T. et al., *Science*, 303, 521-523 (2004)). Our results (FIGS. 1, 6A) suggest that for MEA there is a high degree of specificity in the interpretation of DNA methylation. Methylation status is only relevant in the central cell. Thus, while both maternal expression of MEA and FWA are regulated by DNA methylation and DME in the central cell, additional distinct mechanisms, discussed below, control silencing of the paternal MEA allele.

Maternally and Paternally Silent Alleles of Imprinted Genes are Maintained by Polycombs The mouse Polycomb group protein EED, a homolog of FIE, is required to maintain silencing of some imprinted autosomal genes (Delaval, K. and Feil, R., *Curr Opin Genet Dev.*, 14, 188-195 (2004)); Lewis, A. et al., *Nat Genet*, 36, 1291-1295 (2004); Umlauf, D. et al., *Nat Genet*, 36 (2004)]. Certain paternally silent alleles in the placenta are associated with repressive histone H3K27 methylation regulated by the Polycomb complex EED-EZH2 (Lewis, A. et al., *Nat Genet*, 36, 1291-1295 (2004); Umlauf, D. et al., *Nat Genet*, 36 (2004)). Some of these genes are also imprinted in the embryo. However, unlike in the embryo, placental repression takes places in the absence of the promoter DNA methylation (Lewis, A. et al., *Nat Genet*, 36, 1291-1295 (2004); Umlauf, D. et al., *Nat Genet*, 36 (2004)). Köhler et al. (Kohler, C. et al., *Genes and Development*, 17, 1540-1553 (2003); Kohler, C. et al., *Nat Genet*, 37, 28-30 (2005)) showed that maternal MEA PcG complexes repress maternal expression of the MADS-box gene PHERES1 (PHE1). PHE1 is an example of a gene oppositely imprinted to MEA and FWA, such that the maternal allele is largely silent and the paternal allele is expressed in the endosperm (Kohler, C. et al., *Nat Genet*, 37, 28-30 (2005)). MEA PcG complexes likely assemble at the maternal PHE1 allele in the central cell before fertilization (Kohler, C. et al., *Nat Genet*, 37, 28-30 (2005)). We found that maternal MEA PcG complexes maintain silencing of the paternal MEA allele (FIGS. 6B, C and E). The paternal MEA allele is enriched in H3K27 dimethylation when the maternal MEA allele is wild type compared to when the maternal mea allele is mutant (FIG. 6E). This suggests maternal MEA Polycomb group complexes play a direct role in regulating the chromatin structure at the paternal MEA allele. Paternal allele silencing is maintained even if the paternal genome is hypomethylated (FIG. 6A). Thus, maternal MEA functions in maintaining both maternally (e.g. PHE1) and paternally (e.g. MEA) silenced alleles of imprinted genes. It remains unknown how PcG complexes are directed to the paternal MEA locus, or how the silent state is initially established. Our data indicate that the PcG complex is one means by which the maternal genome modifies the activity of the paternal genome. This emphasizes the prominent role the maternal genome has in controlling endosperm imprinting and development.

Model for the Regulation of MEA Imprinting

Figure 7:
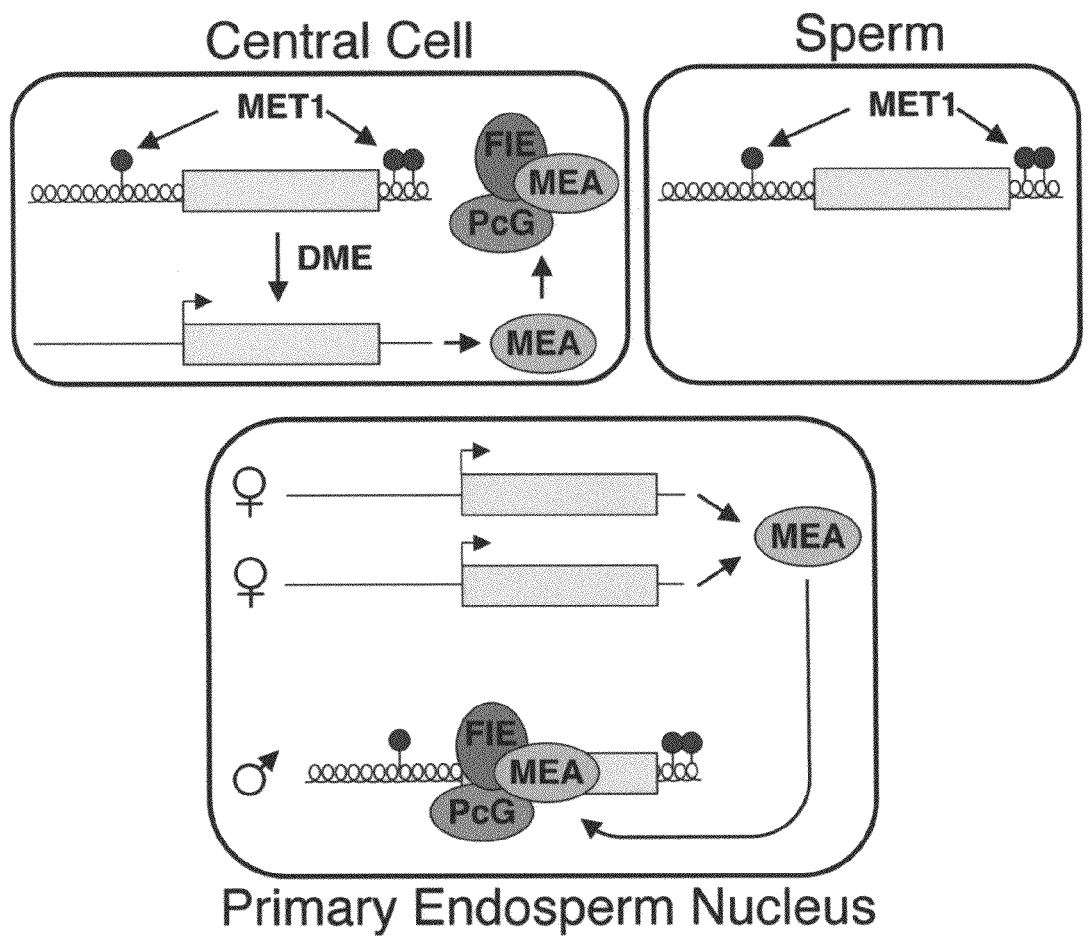
FIG. 7. Model for Regulation of MEA Imprinting. MEA methylation is maintained by MET 1. In the central cell, DME removes methylation at the −500 bp region and MEA-ISR. MEA protein is produced and forms PcG complexes. After fertilization, MEA-FIE PcG complexes target the paternal allele to maintain its silent state. Maternal MEA continues to be expressed in the endosperm. Gray box, MEA gene; red circles, DNA methylation; helical line, non-transcribed compacted chromatin; straight line, transcribed open chromatin.
Figure 8:
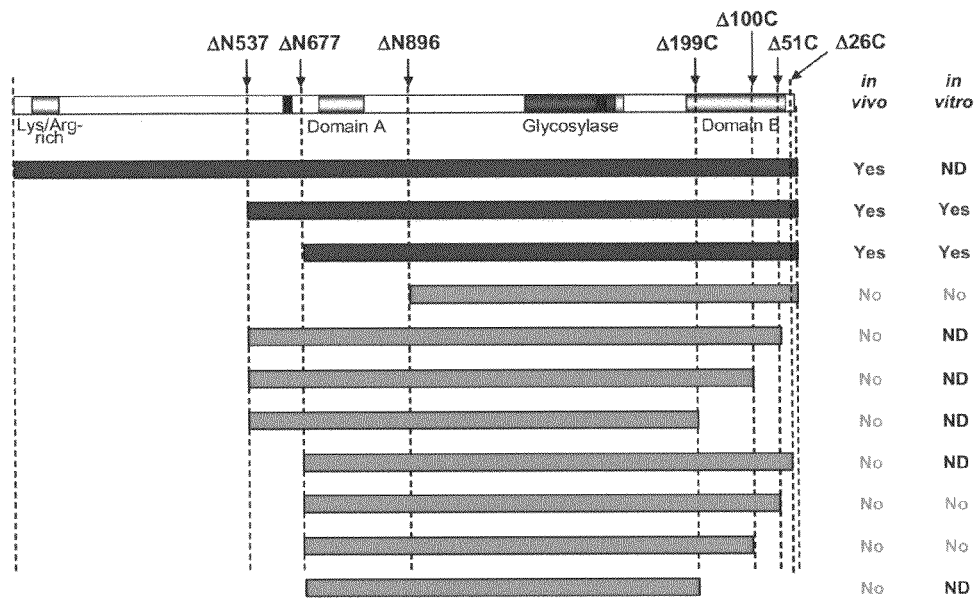
FIG. 8 illustrates results of deletion experiments of DME.
Figure 9:
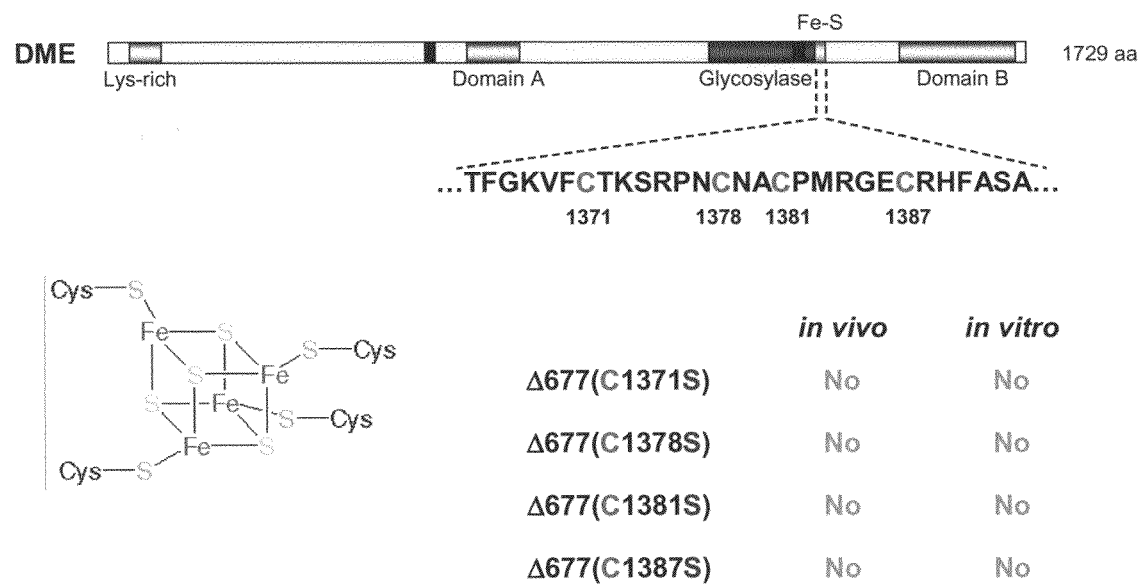
FIG. 9 illustrates mutation analysis of cysteines that form the Fe—S cluster in DME. TFGKVFCTKSRPNCNACPMRGECRHFASA=SEQ ID NO:28.
Figure 10:
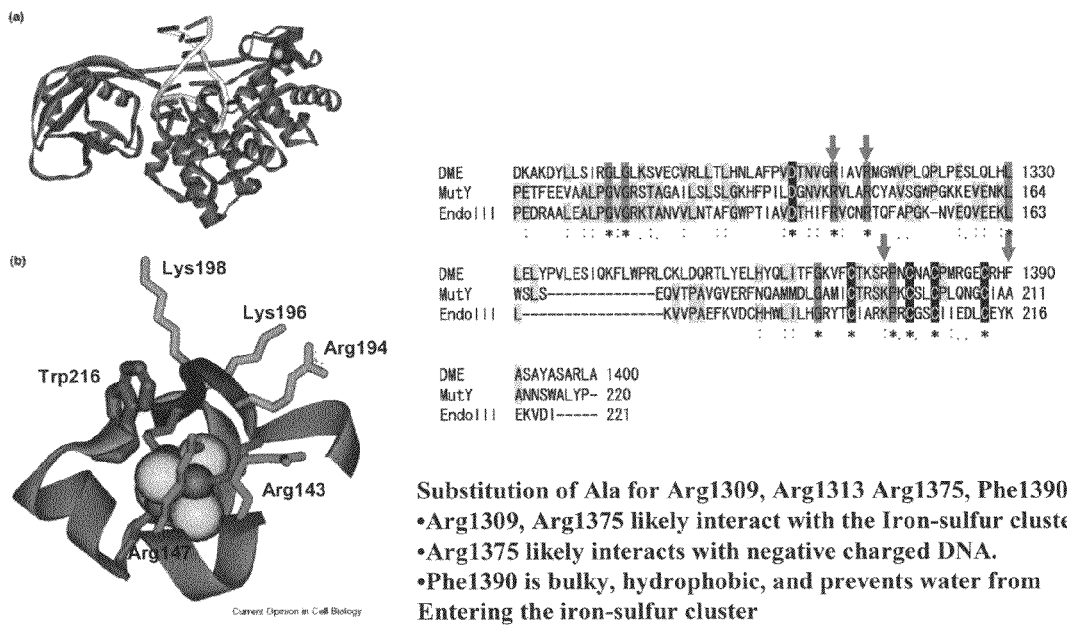
FIG. 10 illustrates amino acids in DME that undergo site-directed mutagenesis. DME=SEQ ID NO:29; MutY=SEQ ID NO:30; EndoIII=SEQ ID NO:31.
Figure 11:
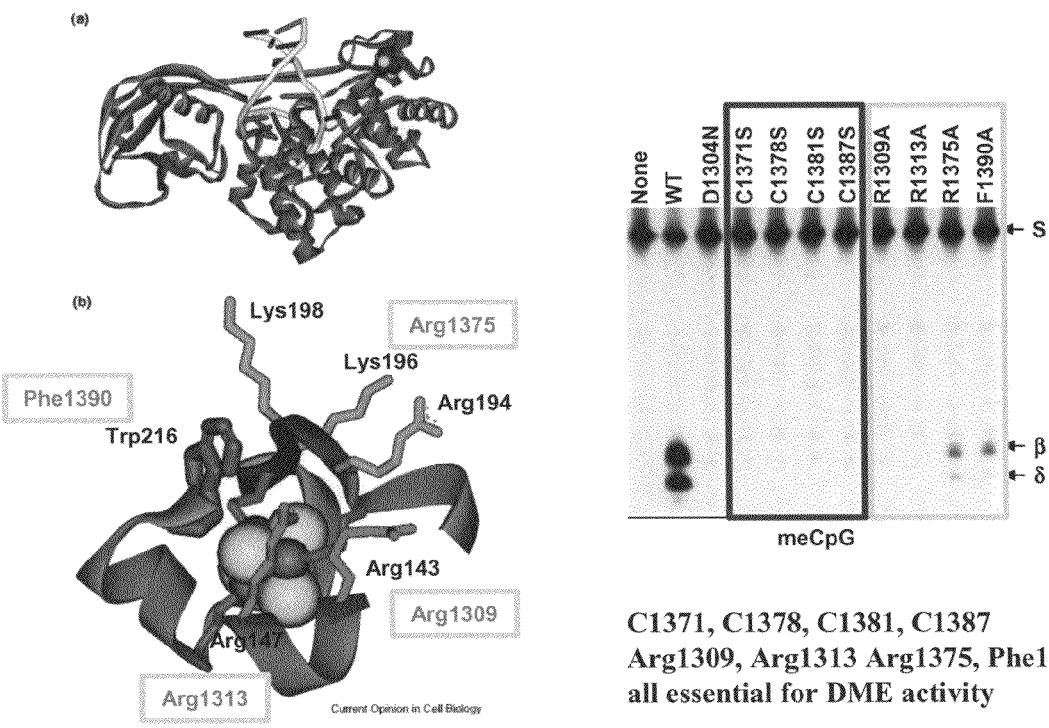
FIG. 11 illustrates results of site-directed mutagenesis of DME.
Figure 12:
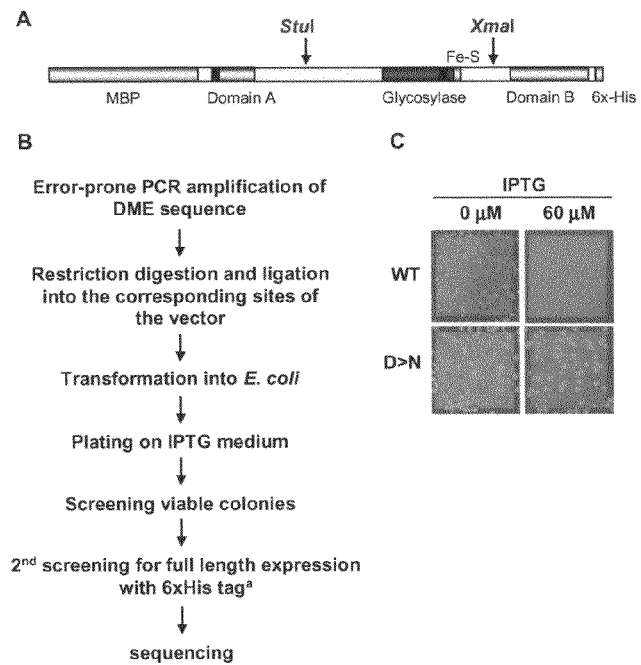
FIG. 12A provides a schematic of the *Arabidopsis* DME gene.
FIG. 12B illustrates a random mutagenesis and screening method to identify amino acid residues involved in DME activity.
FIG. 12C shows that wildtype DME is toxic to *E. coli* cells in the presence of IPTG, whereas *E. coli* cells are resistant to mutant (D>N) DME expression.
Figure 17:
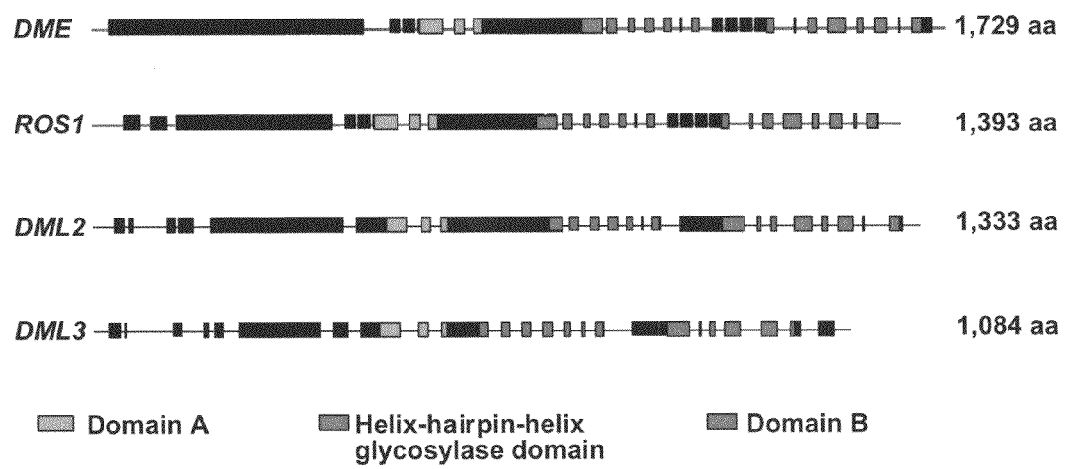
FIG. 17 illustrates and compares gene structure of various demethylases from *Arabidopsis*.
Figure 18:
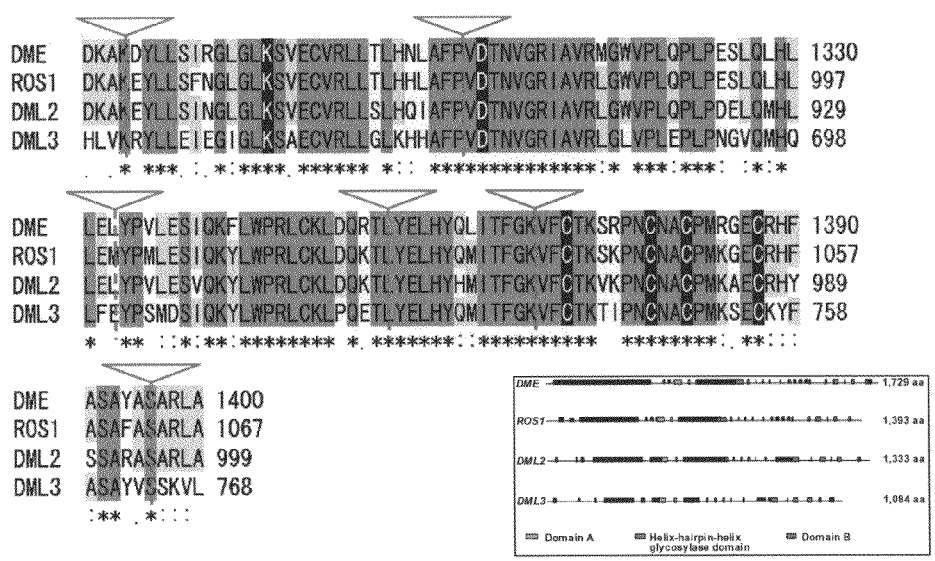
FIG. 18 illustrates intron location of various demethylases from *Arabidopsis*. DME=SEQ ID NO:29; ROS1=SEQ ID NO:32; DML2=SEQ ID NO:33; DML3=SEQ ID NO:34.
Figure 19:
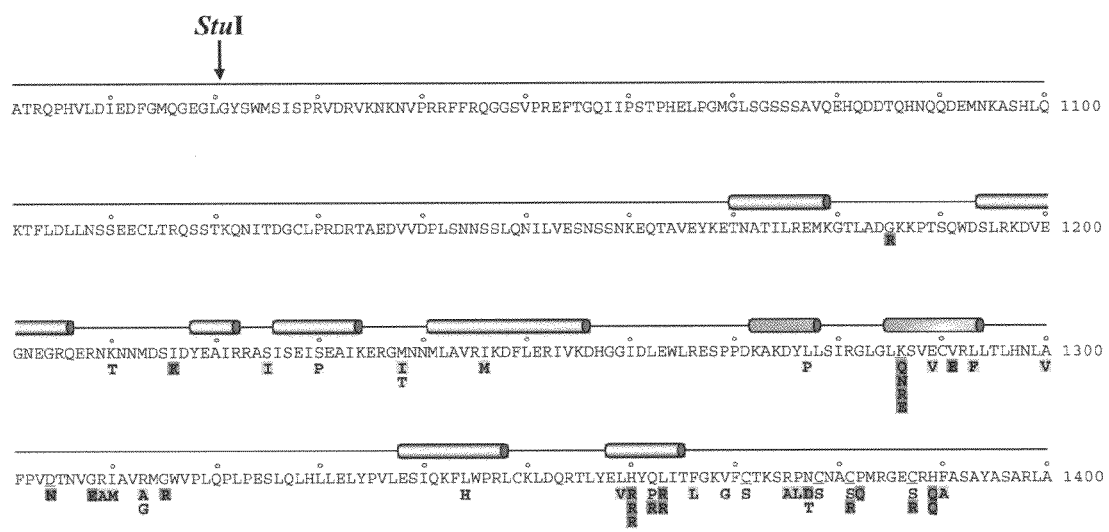
FIG. 19 illustrates a summary of mutations in the DME glycosylase domain (SEQ ID NO:35).
Figure 20:
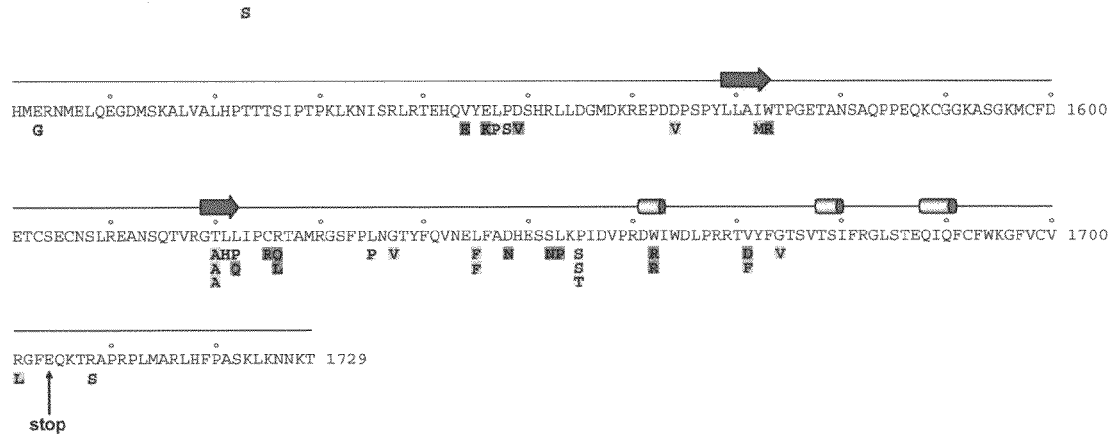
FIG. 20 illustrates a summary of mutations in the C-terminus of DME (SEQ ID NO:36).

We propose the following model for MEA imprinting (FIG. 7). DME is expressed in the central cell of the female gametophyte and removes MEA DNA methylation by excising 5'-methylcytosine. The hypomethylated maternal MEA allele is expressed, producing MEA protein. Shortly after fertilization, FIE-MEA PcG complexes assemble at the paternal MEA allele, maintaining its previously established silent state. Thus, DME-mediated methylation changes that take place in the central cell before fertilization control both aspects of MEA imprinting—maternal allele expression and subsequent paternal allele silencing. Imprinting is lost in maternal mea and dme mutant endosperm because maternal MEA protein is not present at the time of fertilization. Methylation does not inhibit maternal MEA expression in dme endosperm during later stages of endosperm development (by 9 DAP) but by this time the paternal MEA allele has already lost its silent state. Maintenance of MEA silencing by MEA represents a unique instance of a Polycomb group gene regulating its own imprinting.

Experimental Procedures

Plant Material

Seeds were plated on 0.5× Murashige and Skoog salts (Caisson Laboratories, Inc.), 1× Gamborg's Vitamins (Sigma), and 2% sucrose, stratified at 4° C. for two days, grown in continuous light in a growth chamber for 10 days, and then transplanted to soil and grown in greenhouse conditions (16 h light). For crosses, flowers were emasculated two days before pollination. met1-6 homozygous plants were obtained from a self-pollinated met1-6 heterozygote that had never been homozygous. Ler mea/mea plants were the F3 generation.

Bisulfite DNA Sequencing

Seeds at the mid- to late-torpedo stage of embryogenesis (7 to 8 DAP) were dissected into embryo, endosperm, and seed coat fractions in 0.3 M sorbitol, 5 mM MES pH 5.7 on a slide under a dissecting microscope. Endosperm tissue was ground in CTAB to isolate DNA. Embryos were washed to remove contaminating endosperm. Bisulfite treatment and sequencing were performed as described (Xiao, W. et al., *Developmental Cell*, 5, 891-901 (2003)). Primer sequences for PCR-amplification are in the Supplemental Experimental Procedures.

DME Activity

5'-labeled oligonucleotide substrates (13.3 nM) were incubated with DME protein (250 nM) in a 15 µl reaction with 40 mM HEPES-KOH (pH 8.0), 0.1 M KCl, 0.1 mM EDTA, 0.5 mM dithiothreitol, and 200 µg/mL BSA at 37° for 1 hr. The reaction was terminated with 15 µl of 95% formamide, 20 mM EDTA, 0.05% bromophenol blue, 0.05% xylene cyanol FF and boiled for 5 min. To induce 6-elimination, NaOH was added at a final concentration of 0.1 M and the reaction was boiled for 7 min. Products were fractionated on a 15% polyacrylamide gel containing 7.5 M urea and 1×TBE. Electrophoresis was done at 1000V for 4 hrs with a Hoefer SQ3 gel apparatus. The gel was exposed to Kodak BioMax MR film at −80°. Methods for purification of recombinant DME, oligonucleotide substrates, $NaBH_4$ trapping, and toxicity in *E. coli* are in the Supplemental Experimental Procedures.

Protein Gel Analysis

Protein purity was determined by staining gels with Code Blue Reagent (Pierce). Gels were blotted on nitrocellulose membranes (BioRad) and reacted with anti-MBP monoclonal antibody (New England Biolabs) as described by the manufacturer. Goat anti-mouse IgG-AP conjugated antibody (BioRad) and the AP Conjugate Substrate Kit (BioRad) were used for colorimetric detection. Goat anti-mouse IgG-HRP conjugated antibody (BioRad) and SuperSignal Substrate (Pierce) were used for chemiluminescent detection. Reacted membranes were exposed to Kodak BioMax MS film for 5 to 10 min.

Expression Analysis

RNA was isolated using an RNAqueous Kit with Plant RNA Isolation Aid (Ambion, Inc.), and treated with DNase I (Invitrogen) before reverse transcription. For FIGS. 6A and 6B, the 72° C. amplification step for PCR was 10 sec. For FIG. 6C, 533 bp of MEA RNA from exons 3 to 6 was amplified with primers SR12 (5'-CAGAGGATGATAATGGAG-GAGA-3'; SEQ ID NO:49) and UCB3SR8 (5'-GCTTGAGT-TCATTGTATCTTTCC-3'; SEQ ID NO:50) for 40 cycles with a 40 sec amplification step. An XbaI site is present in exon 3 in Cvi and not in Ler. After XbaI digestion, Cvi is cut into 395 and 138 bp pieces. For αVPE, primers for first amplification were VPE2912 (5-ACAACTTTCCCACTTC-CTCCT-3'; SEQ ID NO:51) and VPEdSal (5'-TCGCCG-GATCCAGCGGATACTGGAATTGTCG-3'; SEQ ID NO:52). Primers for a second amplification were VPE2679 (5'-GATTCTCCTCGTTCTCCGCA-3'; SEQ ID NO:53) and VPEdSal. Digestion of VPE with Sal I restriction endonuclease cut the RLD allele.

Chip Assay

Siliques were collected 7-8 DAP, slit, and fixed in 1% formaldehyde. Tissue (0.4 g) was used for chromatin immunoprecipitation (ChIP) with anti-dimethyl histone H3 (Lys27) (Upstate Biotechnology). After immunoprecipitation, protein A bound immunocomplexes were washed as described (Johnson, L. M. et al., *Curr Biol*, 12, 1360-1367 (2002)). ChIP PCR reactions (25 µl) were performed with 35 or 45 amplification cycles for Actin and MEA, respectively. The amount of immunoprecipitate was quantified so that equal amounts of ACTIN were amplified from WT and mea. The annealing temperature was 61° C. for Actin, 58° C. for MEA region 1 and 60° C. for MEA region 2. LNA primer sequences are in the Supplementary Experimental Procedures.

Supplemental Experimental Procedures

Primers for Bisulfite Sequencing

Primers for the −4 kb region were MEA3904 (5'-AACTT-TATTCATRTAATRRTCRAACACT-3'; SEQ ID NO:54) or MEA3979 and MEA4510. The −3 kb region was amplified with MEA5187BFc (5'-CAAAATACTCTATTCTACATTC-CCATCTAT-3'; SEQ ID NO:55) and MEA5810BRc (5-TAAATAAATTAAATGAGTTTGAGTATAAAATG-3'; SEQ ID NO:56), followed by a nested amplification with MEA5212 and MEA5810BRc. The −500 bp region was amplified with MEA7671 (5'-TAACCATTAAACATTAATT-TAAATCTT-3'; SEQ ID NO:57) or MEA7529 and MEA7935. MEA-ISR was amplified from Ler and Col-gl backgrounds using JP1026 and JP1027 (Cao, X. and Jacobsen, S. E., *Proc Natl Acad Sci USA*, 99, 16491-16498 (2002)). A large deletion and extensive polymorphisms prevented the use of these primers in RLD. Instead, the first repeat was amplified with RLDBi (5'-TAATTTAAAATAATGGTGAT-GTTGTTAGTTTG-3'; SEQ ID NO:58) and RLDBi4 (5'-AAAAARRTTTTATAAATATTAAATTAATATRA-3'; SEQ ID NO:59). For MEA coding region bisulfite sequencing, Col-gl rosette leaf DNA was bisulfite treated as previously (Xiao, W. et al., *Developmental Cell*, 5, 891-901 (2003)) and methylation on the bottom strand determined. We sequenced 7 clones from MEA8355F (5'-TTTCACTCCAAA-CATATATAAATTAAC-3'; SEQ ID NO:60) to MEA8755R (5'-GAYTAATGTATAAYTGTTTATTAGATGTAT-3'; SEQ ID NO:61), 5 clones each from MEA8646F (5'-CTCTTCTR-TATRTTTTTCTRAAAATTAARRA-3'; SEQ ID NO:62) to MEA9066R (5'-TGYATYAATYTTGGYTTTTTTGGYT-GAATG-3'; SEQ ID NO:63) and from MEA9294F (5'-CACTTTTRTCRARAATRCAAAACCCACTT-3'; SEQ ID NO:64) to MEA9801R (5'-TAATGYAAAAAY-TAAYYATATAAATYGGTY-3'; SEQ ID NO:65), 8 clones from MEA9810F (5'-CTTRATTATTAATTTRTARTC-CATATTTAATAAACTR-3'; SEQ ID NO:66) to MEA10221R (5'-GTGGYTAAATTAAAAAAGAAAGAT-TYAAAGTTAYYATG-3'; SEQ ID NO:67), 10 clones from MEA10310F (5'-CCCRARTCTARATCCRTAARCAT-TAAATC-3'; SEQ ID NO:68) to MEA10650R (5'-GGATYT-GAGAYYAYAATYTTGTTTGATATAGAG-3'; SEQ ID NO:69), 8 clones each from MEA10528F (5'-CTATTCCT-TAATTACRTTTATTARTTACTRRT-3'; SEQ ID NO:70) to MEA10905R (5'-GTTTTGTTAAGGTYTAATGAYATAG- TAYATTG-3'; SEQ ID NO:71) and MEA10761F (5'-TACT-TACACTRTATTCCTTRATTATRC-3'; SEQ ID NO:72) to MEA11285R (5'-TAYAAAYTYATGTTYAAAT-TAAATYTYATGG-3'; SEQ ID NO:73), 6 clones from MEA11131F (5'-ATAARCACTACACACCATRCACTTR-CAART-3'; SEQ ID NO:74) to MEA11460R (5'-CAAATTC-TATAATCAAARTAATTCAAACC-3'; SEQ ID NO:75), 7 clones from MEA11571F (5'-CATACAATTCCTCCT-TCAAACCAATAA-3'; SEQ ID NO:76) to MEA 1987R (5'-GATYATTYAAGGTAAAGAGGTAGGAAGAAYYAA-3'; SEQ ID NO:77), 8 clones each from MEA11906F (5'-CTRATCACTCATRATRAARCTAATRARCRT-3'; SEQ ID NO:78) to MEA12300R (5'-GAGTTTGAGTTTYTTG-GAATATYTTYAATATG-3'; SEQ ID NO:79) and MEA12234F (5'-TCRTRTATCAACTTTACTCRTCRT-TRATTRR-3'; SEQ ID NO:80) to MEA12647R (5'-GTTTTGGTTTAGTAAYAYAAAATAGYATTA-3'; SEQ ID NO:81), and 9 clones from MEA12740F (5'-CAATRTT-TATRTTRTTARTTTRCATARACC-3'; SEQ ID NO:82) to MEA13093R (5'-GTTTAGATAYTAAATGTTAGAT-GYATYAAAT-3'; SEQ ID NO: 83). This covers 91 of the 99 CG sites present from the MEA transcription start site to the beginning of the 3' repeats.

Amplification and Cloning of the Mea Allele in DME-2 Mutant Endosperm

The −500 bp region and MEA-ISR were amplified with Pfu Turbo DNA polymerase (Stratagene) from the same dme-2 DNA used for the experiment in FIG. 2. PCR products were cloned into the pCR-Blunt II-TOPO vector (Invitrogen) and sequenced. The primers for amplifying the −500 bp region were MEA8323Xba (5'-ATATTCTA-GACTTTTTTTCTCGTCTTCTCTGATGTTGGT-3'; SEQ ID NO:84) and UCB3SR12R-sac1 (5'-GGGAGCTCGT-TAAGCCTGTGGTTGACAAC-3'; SEQ ID NO:85). The primers for amplifying the MEA-ISR were B5-7RR (5'-TTAGGTATTAGCTCGTTTGGTTTTA-3'; SEQ ID NO:86) and MEA 3 REP (5'-CTTAAAAGATTTTCAACT-CATTTTTTTAAAAGG-3'; SEQ ID NO:87).

Cloning, Expression and Purification of DME in *E. Coli*

A full-length DME cDNA (Choi, Y. et al., *Cell*, 110, 33-42 (2002)) was used as template in a PCR reaction with oligonucleotides JH021 (5'-TTAA TCTAGAATGCAGAGCATTATGGACTCG-3'; SEQ ID NO:88) and JH017 (5'-CG GTCGACTTAGGTTTTGTTGTTCTTCAATTTGC-3'; SEQ ID NO:89), which add XbaI and SalI restriction sites (underlined), respectively. The 5.2 kb PCR product was digested with XbaI and SalI and cloned into the pMAL-c2x vector (NEB) to create c2x-DME. To generate a N-terminal 537 amino acid deletion, c2x-DME was digested with XbaI and Bsu36I. The 3' overhangs were filled in with T4 DNA polymerase and self-ligated, creating the c2x-DMEΔN537 clone. The construct with an D1304N point mutation was generated using the full-length DME(D1304N) cDNA clone (Choi, Y. et al., *Proc Natl Acad Sci USA*, 101, 7481-7486 (2004)), following the same procedure as above. This fuses DME in frame downstream of maltose-binding protein (MBP). The c2x-DMEΔN537 or c2x-DMEΔN537(D1304N) clones were transformed into *E. coli* Rosetta cells (Novagen). Transformed cells were grown at 28° C. in LB supplemented with 0.2% glucose, 100 μg/mL of ampicillin, and 50 μg/mL of chloramphenicol until the $OD_{600}$ reached 0.4. Protein expression was induced with 10 μM of IPTG at 18° C. for 1 hr. The culture was centrifuged at 6,500 rpm for 15 min at 4° C. and the pellet was resuspended in 30 mL of 4° C. column buffer (20 mM Tris-HCl, pH 7.4, 200 mM NaCl, 1 mM EDTA). Cells were sonicated for 2 min on ice (output power 4; duty cycle 50%; Branson Sonifer 250). The lysate was centrifuged at 9,000 rpm for 25 min at 4° C. and the supernatant was collected and subjected to gravity column purification. The MBP-DMEΔN537 and MBP-DMEΔN537(D1304N) fusion proteins were purified following the manufacturer's protocol through amylose resin (New England Biolabs). Eluted protein was dialyzed in the Slide-A-Lyzer dialysis cassette (10,000 MWCO; Pierce) against 50% glycerol at 4° C. overnight. Protein concentration was determined by the Bradford method using the Protein Assay kit (Bio-Rad Laboratories) and stored at −20° C. until use.

Substrate Preparation for DNA Glycosylase Activity Assays

Synthetic oligonucleotides were purchased either from Operon or Midland Certified. All oligonucleotides were 35-nucleotides in length with modifications denoted within parentheses as shown below:

MEA-1.6F
(SEQ ID NO: 90)
5'-CTATACCTCCTCAACTCCGGTCACCGTCTCCGGCG,

MEA-1.6F18meC
(SEQ ID NO: 91)
5'-CTATACCTCCTCAACTC(5-meC)GGTCACCGTCTCCGGCG,

MEA-1.6F17meC
(SEQ ID NO: 92)
5'-CTATACCTCCTCAACT(5-meC)CGGTCACCGTCTCCGGCG,

MEA-1.6F22meC
(SEQ ID NO: 93)
5'-CTATACCTCCTCAACTCCGGT(5-meC)ACCGTCTCCGGCG,

MEA-1.6F18AP
(SEQ ID NOS: 94 and 95)
5'-CTATACCTCCTCAACTC(abasic)GGTCACCGTCTCCGGCG, MEA-1.6F17AP
(SEQ ID NOS: 96 and 97)
5'-CTATACCTCCTCAACT(abasic)CGGTCACCGTCTCCGGCG, MEA-1.6F15AP
(SEQ ID NOS: 98 and 99)
5'-CTATACCTCCTCAA(abasic)TCCGGTCACCGTCTCCGGCG MEA-1;6F12AP
(SEQ ID NOS: 100 and 101)
5'-CTATACCTCCT(abasic)AACTCCGGTCACCGTCTCCGGCG,

MEA-1.6F18T
(SEQ ID NO: 102)
5'-CTATACCTCCTCAACTCTGGTCACCGTCTCCGGCG,

MEA-1.6R
(SEQ ID NO: 103)
5'-CGCCGGAGACGGTGACCGGAGTTGAGGAGGTATAG,

MEA-1.6R17meC
(SEQ ID NO: 104)
5'-CGCCGGAGACGGTGAC(5-meC)GGAGTTGAGGAGGTATAG,

Twenty pmol of oligonucleotide were end-labeled in a 50 μL reaction using 20 units of T4 polynucleotide kinase in the presence of 30 μCi of (γ-$^{32}$P)ATP (6000 Ci/mmol, Perkin Elmer Life Sciences) at 37° C. for 1 hr. The labeled oligonucleotide was purified using a Qiaquick Nucleotide Removal Kit (Qiagen) as described by the manufacturer.

Labeled oligonucleotides were annealed to the appropriate complementary oligonucleotides in 10 mM Tris-HCl (pH 8.0), 1 mM EDTA and 0.1 M NaCl. The mixture was boiled in water for 10 min and then slowly cooled to room temperature overnight. MspI or HpaII restriction endonuclease digestion followed by gel electrophoresis was used to determine the efficiency of annealing. Only substrates that were greater than 90% double-stranded were used in glycosylase activity assays.

NaBH4 Trapping Assays

5'-labeled oligonucleotide substrates (13.3 nM) were incubated with DME protein (250 nM) in a 15 μl reaction with 40 mM HEPES-KOH (pH 8.0), 0.1 M KCl, 0.1 mM EDTA, 0.5 mM dithiothreitol, and 200 μg/mL BSA at 37°. After 1 hr of incubation, 1 M NaBH$_4$ was added to a final concentration of 100 mM and the reaction tubes were placed at 37° for an additional 10 min. An equal volume of 2×SDS-PAGE loading buffer (90 mM Tris-HCl, pH 6.8, 20% glycerol, 2% SDS, 0.02% bromophenol blue, 100 mM dithiothreitol) was added to terminate the trapping reaction. Products were boiled for 10 min before loading onto a 10% SDS-PAGE gel. The wet gel was exposed to Kodak Biomax MS film for 12-18 h at −80°.

Bacterial Cell Toxicity Assays

Bacterial strains AB1157 (F-thr-1 ara-14 leuB6(Am) lacY1 (gpt-proA2)62 tsx-33 supE44(Am) galK2 rac hisG4 (Oc) rfbD1 mgl-51 rpsL31 kdgK51 xyl-5 mtl-1 argE3(Oc) thi-1) and its isogeneic AP endonuclease mutant RPC501 (xth nfo) were kindly provided by R. P. Cunningham (Cunningham, R. P. et al., *Endonuclease IV (nfo) mutant of Escherichia coli*, 168, 1120-1127 (1986)). Strains GM30 (F thr-1 ara-14 leuB6 tonA31 lacY1 tsx-78 supE44 galK2 galT22 hisG4 rpsL136 xyl-5 mtl-1 thi-1) and its isogenic dcm-6 derivative, GM31, were kindly provided by Martin G. Marinus (Palmer, B. R. and Marinus, M. G., *Gene*, 143, 1-12 (1994)).

The c2x-DMEΔN537 and c2x-DMEΔN537(D1304N) plasmids were individually transformed into the strains above by electroporation and cells were grown on LB/Glu/Amp plates (LB supplemented with 0.2% glucose and 100 μg/mL of ampicillin) at 37° overnight. Fresh colonies were picked and resuspended in 5 mL of LB/Glu/Amp liquid medium. After 12-14 h incubation at 37°, the culture was diluted 100,000-fold in LB medium and 100 μL was plated on the LB/Glu/Amp plates with 0, 2, 5, 10, 25, 50, and 100 μM of IPTG (isopropyl-β-D-thiogalactopyranoside; Sigma). The plates were incubated at 28° for 20 to 28 hr and the number of colonies was counted.

Chromatin Immunoprecipitation (Chip) Procedures

LNA nucleotide analogues (Promega) contain a 2'-O, 4'-C methylene bridge that locks the ribose moiety into a C3'-endo conformation (Koshkin, A. A. et al., *TETRAHEDRON*, 54, 3607-3630 (1998); Obika, S. et al., *Tetrahedron Lett*, 39, 5401-5404 (1998); Singh, H. et al., *Biotechniques*, 7, 252-261 (1989)). Region one (−4 to +440) of MEA was amplified with MEA-LNA006 (5'-CACCAACATCAGAGAAGAC-GAGAAAA<u>G</u>-3'; SEQ ID NO:105) and MEA-LNA004 (5'-GATTATGACTAATGTATAACTGTTTA<u>C</u>-3'; SEQ ID NO: 106). Region 2 (−947 to −547) of MEA was amplified with MEA-LNA002 (5'-GGGTCTCAATTTTGTGAACTG-GTGT<u>G</u>-3'; SEQ ID NO:107) and MEA-LNA003 (5'-CCGA<u>T</u>ATTTTTTACTATTTATAACGTTAATTA<u>C</u>-3'; SEQ ID NO:108). LNA nucleotides are underlined and are complementary to the RLD template sequence but have a mismatch with the Ler template due to a polymorphism. To demonstrate the specificity of LNA-containing primers, approximately 50 pg of Ler and RLD genomic DNA were used as a control. To increase the sensitivity of the LNA PCR reaction, 1 μCi of α-dATP-P$^{32}$ was added to each PCR reaction. A polymorphism within region 1 (+60, T in RLD, C in Ler) was used to check the parental origin of PCR products by sequencing. PCR products from region 1 from wild type (Ler crossed to RLD) and mea (Ler mea/mea crossed to RLD) were cloned into TOPO TA-cloning vector (Invitrogen, CA). 22 clones each were sequenced to determine the origin of amplification templates. Primer sequences and reaction conditions for Actin gene amplification were as described (Johnson, L. M. et al., *Curr Biol*, 12, 1360-1367 (2002)).

Example 2

FIGS. 8-16, 19, 20, 22, and 23 summarize data from mutagenesis studies of the DME demethylase. The data indicates a number of amino acid residues whose mutation affects demethylase activity in vitro (i.e., in a in vitro demethylase activity assay) or in vivo (i.e., having the ability to complement an *Arabidopsis* dme mutant, or by expression in *E. coli*, where expression of active demethylases is toxic to *E. coli* (e.g., FIGS. 4, 8, 9, and 12)).

Example 3

The following constructs were constructed and transformed into a dme-2 heterozygous background. Transformants were selected using the selectable marker (KAN$^r$) and were then genotyped to find dme-2 heterozygotes with the transgene. The dme-2 heterozygotes with the transgene were then crossed as females to wild type males. Normally in this cross dme-2 heterozygotes produce 50% aborted seeds. If the transgene complements the dme-2 mutation, the seed abortion rate will fall to around 25% or less.

| Construct | Line | Percent seed abortion in dme-2 heterozygotes | Complements dme-2 |
|---|---|---|---|
| pDME::DME$^{1,192-1,402\ aa\ DME\ deleted,}$ inserted is ROS1 859-1,069 aa. | 1-1 | 23% | Yes |
| | 1-2 | 22% | Yes |
| DNA Sequence: SEQ ID NO: 11 | 1-3 | 23% | Yes |
| Encoded polypeptide: SEQ ID NO: 12 | 1-4 | 26% | Yes |
| | 1-5 | 24% | Yes |
| pDME::ROS1$^{859-1069\ aa\ ROS1\ deleted,}$ inserted is DME 1,192-1,402 aa. | 2-1 | 20% | Yes |
| | 2-2 | 26% | Yes |
| DNA Sequence: SEQ ID NO: 13 | 2-3 | 28% | Yes |
| Encoded polypeptide: SEQ ID NO: 14 | 2-4 | 27% | Yes |
| | 2-5 | 22% | Yes |

-continued

| Construct | Line | Percent seed abortion in dme-2 heterozygotes | Complements dme-2 |
|---|---|---|---|
| pDME::ROS1$^{859-1,394\ aa\ ROS1\ deleted,}$ inserted is DME 1,192-1,730 aa | 3-1 | 15% | Yes |
|  | 3-2 | 20% | Yes |
| DNA Sequence: SEQ ID NO: 15 | 3-3 | 25% | Yes |
| Encoded polypeptide: SEQ ID NO: 16 | 3-4 | 19% | Yes |
| pDME::DME$^{1,192-1,730\ aa\ DME\ deleted,}$ inserted is ROS1 859-1,394 aa | 4-1 | 26% | Yes |
|  | 4-2 | 26% | Yes |
| DNA Sequence: SEQ ID NO: 17 | 4-3 | 34% | Yes |
| Encoded polypeptide: SEQ ID NO: 18 |  |  |  |
| pDME::DME$^{690-797\ aa\ DME\ deleted,}$ inserted is ROS1 521-627 aa | 5-1 | 24.5% | Yes |
|  | 5-2 | 24.5% | Yes |
| DNA Sequence: SEQ ID NO: 19 | 5-3 | 23% | Yes |
| Encoded polypeptide: SEQ ID NO: 20 | 5-4 | 20% | Yes |
|  | 5-5 | 21% | Yes |
| pDME::ROS1$^{521-627\ aa\ ROS1\ deleted,}$ inserted is DME 690-797 aa | 6-1 | 16% | Yes |
|  | 6-2 | 21% | Yes |
| DNA Sequence: SEQ ID NO: 21 | 6-3 | 13% | Yes |
| Encoded polypeptide: SEQ ID NO: 22 | 6-4 | 15% | Yes |
|  | 6-5 | 28% | Yes |
| pDME::DME$^{1-689\ aa\ DME\ deleted,}$ inserted is ROS1 1-520 aa | 7-1 | 22% | Yes |
|  | 7-2 | 31% | Yes |
| DNA Sequence: SEQ ID NO: 23 | 7-3 | 21% | Yes |
| Encoded polypeptide: SEQ ID NO: 24 | 7-4 | 20% | Yes |
|  | 7-5 | 21% | Yes |
| pDME::DME$^{1,403-1,730\ aa\ DME\ deleted,}$ inserted is ROS1 1,070-1,394 aa | 8-1 | 29% | Yes |
|  | 8-2 | 28.5% | Yes |
| DNA Sequence: SEQ ID NO: 25 | 8-3 | 20% | Yes |
| Encoded polypeptide: SEQ ID NO: 26 | 8-4 | 25% | Yes |
|  | 8-5 | 26% | Yes |
| pDME::ROS1 (1-1,394 aa) | 9-1 | 22% | Yes |
| DNA Sequence: SEQ ID NO: 5 | 9-2 | 31% | Yes |
| Encoded polypeptide: SEQ ID NO: 6 | 9-3 | 31% | Yes |
|  | 9-4 | 16% | Yes |
|  | 9-5 | 15% | Yes |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated polypeptide comprising an amino acid sequence that is at least 95% identical to the amino acid sequence of SEQ ID NO:3, wherein the amino acid corresponding to position 627 in SEQ ID NO:3 is an aspartic acid, wherein the isolated polypeptide excises methylated cytosines in DNA when contacted with DNA comprising methylated cytosines, and wherein the isolated polypeptide does not comprise the amino acid sequence of SEQ ID NO:2.

2. The method of claim 1, wherein the isolated polypeptide comprises a glycosylase domain of SEQ ID NO:3.

* * * * *

UNITED STATES PATENT AND TRADEMARK OFFICE
CERTIFICATE OF CORRECTION

| | |
|---|---|
| PATENT NO. | : 8,802,821 B2 |
| APPLICATION NO. | : 12/006779 |
| DATED | : August 12, 2014 |
| INVENTOR(S) | : Fischer et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1273 days.

Signed and Sealed this
Twenty-first Day of July, 2015

Michelle K. Lee
*Director of the United States Patent and Trademark Office*

```
                        SEQUENCE LISTING

<160> NUMBER OF SEQ ID NOS: 108

<210> SEQ ID NO 1
<211> LENGTH: 5190
<212> TYPE: DNA
<213> ORGANISM: Arabidopsis sp.
<220> FEATURE:
<223> OTHER INFORMATION: DNA demethylase DEMETER (DME, DMT),
      helix-hairpin-helix DNA glycosylase, Atropos
      (ATR), apurinic/apyrimidinic (AP) lyase coding
      sequence

<400> SEQUENCE: 1
atgcagagca ttatggactc gtctgctgtt aatgcgacgg aagctactga acaaaatgat       60
ggcagcagac aagatgttct ggagttcgac cttaacaaaa ctcctcagca gaaaccctcc      120
aaaaggaaaa ggaagttcat gcccaaggtg gtcgtggaag gcaaacctaa agaaagcca       180 cgcaaacctg cagaacttcc caagtggtc gtggaaggca aacctaaaag gaagccacgc      240
aaagctgcaa ctcaggaaaa agtgaaatct aaagaaaccg ggagtgccaa aagagaaaat      300
ttgaaagaat cagcaactaa aaagccagcc aatgttggag atatgagcaa caaagcccct      360
gaagtcacac tcaaaagttg cagaaaagct ttgaatttg acttggagaa tcctggagat      420
gcgaggcaag gtgactctga gtctgaaatt gtccagaaca gtagtggcgc aaactcgttt      480
```

```
tctgagatca gagatgccat tggtggaact aatggtagtt tcctggattc agtgtcacaa    540
atagacaaga ccaatggatt gggggctatg aaccagccac ttgaagtgtc aatgggaaac    600
cagccagata aactatctac aggagcgaaa ctggccagag accaacaacc tgatttattg    660
actagaaacc agcaatgcca gttcccagtg caacccagaa acacccagtt cccaatggaa    720
aaccaacaag cttggcttca gatgaaaaac caacttattg gctttccatt tggtaaccag    780
caacctcgca tgaccataag aaaccagcag ccttgcttgg ccatgggtaa tcaacaacct    840
atgtatctga taggaactcc acggcctgca ttagtaagtg aaaccagca actaggaggt     900 ccccaaggaa acaagcggcc tatattttg aatcaccaga cttgtttacc tgctggaaat     960
cagctatatg gatcacctac agacatgcat caacttgtta tgtcaaccgg agggcaacaa   1020
catggactac tgataaaaaa ccagcaacct ggatcattaa taagaggcca gcagccttgc   1080
gtacctttga ttgaccagca acctgcaact ccaaaaggtt ttactcactt gaatcagatg   1140
gtagctacca gcatgtcatc gcctgggctt cgacctcatt ctcagtcaca agttcctaca   1200
acatatctac atgtggaatc tgtttccagg attttgaatg ggactacagg tacatgccag   1260
agaagcaggg ctcctgcata cgattcttta cagcaagata ccatcaagg aaataagtac    1320 atactttctc atgagatatc caatggtaat gggtgcaaga aagcgttacc tcaaaactct   1380
tctctgccaa ctccaattat ggctaaactt gaggaagcca ggggctcgaa gagacagtat   1440
catcgtgcaa tgggacagac ggaaaagcat gatctaaact tagctcaaca gattgctcaa   1500
tcacaagatg tggagagaca taacagcagc acgtgtgtgg aatatttaga tgctgcaaag   1560
aaaacgaaaa tccagaaagt agtccaagaa aatttgcatg gcatgccacc tgaggttata   1620
gaaatcgagg atgatccaac tgatggggca agaaaaggta aaaatactgc cagcatcagt   1680
aaaggtgcat ctaaaggaaa ctcgtctcca gttaaaaaga cagcagaaaa ggagaaatgt   1740
attgtcccaa aaacgcctgc aaaaagggt cgagcaggta gaaaaaaatc agtacctccg   1800
cctgctcatg cctcagagat ccagcttttg caacctactc ctccaaagac acctttatca   1860
agaagcaagc ctaaaggaaa agggagaaag tccatacaag attcaggaaa agcaagaggt   1920
ccatcaggag aacttctgtg tcaggattct attgcggaaa taatttacag gatgcaaaat   1980
ctgtatctag gagacaaaga aagagaacaa gagcaaaatg caatggtctt gtacaaagga   2040
gatggtgcac ttgttcccta tgagagcaag aagcgaaaac caagacccaa agttgacatt   2100
gacgatgaaa caactcgcat atggaactta ctgatgggga aggagatga aaagaaggg    2160 gatgaagaga aggataaaaa gaaagagaag tggtgggaag aagaaagaag agtcttccga   2220
ggaagggctg attccttcat cgctcgcatg cacctggtac aaggagatag acgttttcg    2280 ccatggaagg gatcggtggt tgattcggtc attggagttt tccttacaca gaatgtctcg   2340
gatcaccttt caagctctgc gttcatgtct ctagctgctc gattccctcc aaaattaagc   2400
agcagccgag aagatgaaag gaatgttaga agcgtagttg ttgaagatcc agaaggatgc   2460
attctgaact aaatgaaat tccttcgtgg caggaaaagg ttcaacatcc atctgacatg   2520
gaagtttctg ggttgatag tggatcaaaa gagcagctaa gggactgttc aaactctgga   2580
attgaaagat ttaatttctt agagaagagt attcaaaatt tagaagagga agtattatca   2640
tcacaagatt cttttgatcc ggcgatattt cagtcgtgtg ggagagttgg atcctgttca   2700
tgttccaaat cagacgcaga gtttcctaca accaggtgtg aaacaaaaac tgtcagtgga   2760
acatcacaat cagtgcaaac tgggagccca aacttgtctg atgaaatttg tcttcaaggg   2820
aatgagagac cgcatctata tgaaggatct ggtgatgttc agaaacaaga aactacaaat   2880
```

```
gtcgctcaga agaaacctga tcttgaaaaa acaatgaatt ggaaagactc tgtctgtttt      2940
ggtcagccaa gaaatgatac taattggcaa acaactcctt ccagcagcta tgagcagtgt      3000
gcgactcgac agccacatgt actagacata gaggattttg gaatgcaagg tgaaggcctt      3060
ggttattctt ggatgtccat ctcaccaaga gttgacagag taaagaacaa aaatgtacca      3120
cgcaggtttt tcagacaagg tggaagtgtt ccaagagaat tcacaggtca gatcatacca      3180
tcaacgcctc atgaattacc aggaatggga ttgtccggtt cctcaagcgc cgtccaagaa      3240
caccaggacg atacccaaca taatcaacaa gatgagatga ataaagcatc ccatttacaa      3300
aaaacatttt tggatctgct caactcctct gaagaatgcc ttacaagaca gtccagtacc      3360
aaacagaaca tcacggatgg ctgtctaccg agagatagaa ctgctgaaga cgtggttgat      3420
ccgctcagta acaattcaag cttacagaac atattggtcg aatcaaattc cagcaataaa      3480
gagcagacgg cagttgaata caaggagaca atgccacta ttttacgaga gatgaaaggg       3540
acgcttgctg atgggaaaaa gcctacaagc cagtgggata gtctcagaaa agatgtggag      3600
gggaatgaag ggagacagga acgaaacaaa acaatatgg attccataga ctatgaagca       3660
ataagacgtg ctagtatcag cgagatttct gaggctatca aggaaagagg gatgaataac      3720
atgttggccg tacgaattaa ggatttccta gaacggatag ttaaagatca tggtggtatc      3780
gaccttgaat ggttgagaga atctcctcct gataaagcca aggactatct cttgagcata      3840
agaggtctgg gtttgaaaag tgttaatgc gtgcgactct taacactcca caatcttgct       3900
ttccctgttg acacgaatgt tggaaggata gcagttagga tgggatgggt gcctctacaa      3960
cccctacctg aatcacttca gttacacctc ctggagctat acccagtgct cgagtccatc      4020
caaaaatttc tttggccaag actttgcaaa ctcgatcaac gaacactgta tgaattacac      4080
taccaactga ttacgtttgg aaaggtattt tgcacaaaga gtagaccaaa ttgtaatgca      4140
tgtccaatga gaggagagtg cagacacttt gccagtgctt atgctagtgc aagacttgct      4200
ttaccggcac cagaggagag gagcttaaca agtgcaacta ttccggtccc tcccgagtcc      4260
tttcctcctg tagccatccc gatgatagaa ctacctcttc cgttggagaa atccctagca      4320
agtggagcac catcgaatag agaaaactgt gaaccaataa ttgaagagcc ggcctcgccc      4380
gggcaagagt gcactgaaat aaccgagagt gatattgaag atgcttacta caatgaggac      4440
cctgacgaga tcccaacaat aaaactcaac attgaacagt ttggaatgac tctacgggaa      4500
cacatggaaa gaaacatgga gctccaagaa ggtgacatgt ccaaggcttt ggttgctttg      4560
catccaacaa ctacttctat tccaactccc aaactaaaga acattagccg tctcaggaca      4620
gagcaccaag tgtacgagct cccagattca catcgtctcc ttgatggtat ggataaaaga      4680
gaaccagatg atccaagtcc ttatctctta gctatatgga caccaggtga acagcgaat       4740 tcggcacaac cgcctgaaca gaagtgtgga gggaaagcgt ctggcaaaat gtgctttgac      4800
gagacttgtt ctgagtgtaa cagtctgagg gaagcaaact cacagacagt tcgaggaact      4860
cttctgatac cttgtcggac tgccatgaga ggaagttttc cgctcaacgg gacatatttc      4920
caagtcaacg agttatttgc agaccacgag tccagtctca aacccatcga tgttcctaga      4980
gattggatat gggatctccc aagaaggact gtttacttcg gaacatcagt aacatcaata      5040
ttcagaggtc tttcaacgga gcagatacag ttctgctttt ggaaaggatt cgtatgtgtc      5100
cgtggattcg aacagaagac aagagcaccg cgtccattaa tggcaaggtt gcattttcct      5160
gcgagcaaat tgaagaacaa caaaacctaa                                       5190
```

```
<210> SEQ ID NO 2
<211> LENGTH: 1729
<212> TYPE: PRT
<213> ORGANISM: Arabidopsis sp.
<220> FEATURE:
<223> OTHER INFORMATION: DNA demethylase DEMETER (DME, DMT),
      helix-hairpin-helix DNA glycosylase, Atropos
      (ATR), apurinic/apyrimidinic (AP) lyase

<400> SEQUENCE: 2

Met Gln Ser Ile Met Asp Ser Ser Ala Val Asn Ala Thr Glu Ala Thr
 1               5                  10                  15

Glu Gln Asn Asp Gly Ser Arg Gln Asp Val Leu Glu Phe Asp Leu Asn
                20                  25                  30

Lys Thr Pro Gln Gln Lys Pro Ser Lys Arg Lys Arg Lys Phe Met Pro
            35                  40                  45

Lys Val Val Val Glu Gly Lys Pro Lys Arg Lys Pro Arg Lys Pro Ala
        50                  55                  60

Glu Leu Pro Lys Val Val Val Glu Gly Lys Pro Lys Arg Lys Pro Arg
65                  70                  75                  80

Lys Ala Ala Thr Gln Glu Lys Val Lys Ser Lys Glu Thr Gly Ser Ala
                85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
    130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190

Pro Leu Glu Val Ser Met Gly Asn Gln Pro Asp Lys Leu Ser Thr Gly
        195                 200                 205

Ala Lys Leu Ala Arg Asp Gln Gln Pro Asp Leu Leu Thr Arg Asn Gln
    210                 215                 220

Gln Cys Gln Phe Pro Val Ala Thr Gln Asn Thr Gln Phe Pro Met Glu
225                 230                 235                 240

Asn Gln Gln Ala Trp Leu Gln Met Lys Asn Gln Leu Ile Gly Phe Pro
                245                 250                 255

Phe Gly Asn Gln Gln Pro Arg Met Thr Ile Arg Asn Gln Gln Pro Cys
            260                 265                 270

Leu Ala Met Gly Asn Gln Gln Pro Met Tyr Leu Ile Gly Thr Pro Arg
        275                 280                 285

Pro Ala Leu Val Ser Gly Asn Gln Gln Leu Gly Gly Pro Gln Gly Asn
    290                 295                 300

Lys Arg Pro Ile Phe Leu Asn His Gln Thr Cys Leu Pro Ala Gly Asn
305                 310                 315                 320

Gln Leu Tyr Gly Ser Pro Thr Asp Met His Gln Leu Val Met Ser Thr
                325                 330                 335

Gly Gly Gln Gln His Gly Leu Leu Ile Lys Asn Gln Gln Pro Gly Ser
            340                 345                 350

Leu Ile Arg Gly Gln Gln Pro Cys Val Pro Leu Ile Asp Gln Gln Pro
        355                 360                 365
```

```
Ala Thr Pro Lys Gly Phe Thr His Leu Asn Gln Met Val Ala Thr Ser
    370                 375                 380
Met Ser Ser Pro Gly Leu Arg Pro His Ser Gln Ser Gln Val Pro Thr
385                 390                 395                 400
Thr Tyr Leu His Val Glu Ser Val Ser Arg Ile Leu Asn Gly Thr Thr
                405                 410                 415
Gly Thr Cys Gln Arg Ser Arg Ala Pro Ala Tyr Asp Ser Leu Gln Gln
            420                 425                 430
Asp Ile His Gln Gly Asn Lys Tyr Ile Leu Ser His Glu Ile Ser Asn
        435                 440                 445
Gly Asn Gly Cys Lys Lys Ala Leu Pro Gln Asn Ser Ser Leu Pro Thr
    450                 455                 460
Pro Ile Met Ala Lys Leu Glu Glu Ala Arg Gly Ser Lys Arg Gln Tyr
465                 470                 475                 480
His Arg Ala Met Gly Gln Thr Glu Lys His Asp Leu Asn Leu Ala Gln
                485                 490                 495
Gln Ile Ala Gln Ser Gln Asp Val Glu Arg His Asn Ser Ser Thr Cys
            500                 505                 510
Val Glu Tyr Leu Asp Ala Ala Lys Lys Thr Lys Ile Gln Lys Val Val
        515                 520                 525
Gln Glu Asn Leu His Gly Met Pro Pro Glu Val Ile Glu Ile Glu Asp
    530                 535                 540
Asp Pro Thr Asp Gly Ala Arg Lys Gly Lys Asn Thr Ala Ser Ile Ser
545                 550                 555                 560
Lys Gly Ala Ser Lys Gly Asn Ser Ser Pro Val Lys Lys Thr Ala Glu
                565                 570                 575
Lys Glu Lys Cys Ile Val Pro Lys Thr Pro Ala Lys Lys Gly Arg Ala
            580                 585                 590
Gly Arg Lys Lys Ser Val Pro Pro Ala His Ala Ser Glu Ile Gln
        595                 600                 605
Leu Trp Gln Pro Thr Pro Pro Lys Thr Pro Leu Ser Arg Ser Lys Pro
    610                 615                 620
Lys Gly Lys Gly Arg Lys Ser Ile Gln Asp Ser Gly Lys Ala Arg Gly
625                 630                 635                 640
Pro Ser Gly Glu Leu Leu Cys Gln Asp Ser Ile Ala Glu Ile Ile Tyr
                645                 650                 655
Arg Met Gln Asn Leu Tyr Leu Gly Asp Lys Glu Arg Glu Gln Glu Gln
            660                 665                 670
Asn Ala Met Val Leu Tyr Lys Gly Asp Gly Ala Leu Val Pro Tyr Glu
        675                 680                 685
Ser Lys Lys Arg Lys Pro Arg Pro Lys Val Asp Ile Asp Asp Glu Thr
    690                 695                 700
Thr Arg Ile Trp Asn Leu Leu Met Gly Lys Gly Asp Glu Lys Glu Gly
705                 710                 715                 720
Asp Glu Glu Lys Asp Lys Lys Glu Lys Trp Trp Glu Glu Arg
                725                 730                 735
Arg Val Phe Arg Gly Arg Ala Asp Ser Phe Ile Ala Arg Met His Leu
            740                 745                 750
Val Gln Gly Asp Arg Arg Phe Ser Pro Trp Lys Gly Ser Val Val Asp
        755                 760                 765
Ser Val Ile Gly Val Phe Leu Thr Gln Asn Val Ser Asp His Leu Ser
    770                 775                 780
```

```
Ser Ser Ala Phe Met Ser Leu Ala Ala Arg Phe Pro Pro Lys Leu Ser
785                 790                 795                 800

Ser Ser Arg Glu Asp Glu Arg Asn Val Arg Ser Val Val Glu Asp
            805                 810                 815

Pro Glu Gly Cys Ile Leu Asn Leu Asn Glu Ile Pro Ser Trp Gln Glu
                820                 825                 830

Lys Val Gln His Pro Ser Asp Met Glu Val Ser Gly Val Asp Ser Gly
            835                 840                 845

Ser Lys Glu Gln Leu Arg Asp Cys Ser Asn Ser Gly Ile Glu Arg Phe
    850                 855                 860

Asn Phe Leu Glu Lys Ser Ile Gln Asn Leu Glu Glu Val Leu Ser
865                 870                 875                 880

Ser Gln Asp Ser Phe Asp Pro Ala Ile Phe Gln Ser Cys Gly Arg Val
                885                 890                 895

Gly Ser Cys Ser Cys Ser Lys Ser Asp Ala Glu Phe Pro Thr Thr Arg
            900                 905                 910

Cys Glu Thr Lys Thr Val Ser Gly Thr Ser Gln Ser Val Gln Thr Gly
            915                 920                 925

Ser Pro Asn Leu Ser Asp Glu Ile Cys Leu Gln Gly Asn Glu Arg Pro
    930                 935                 940

His Leu Tyr Glu Gly Ser Gly Asp Val Gln Lys Gln Glu Thr Thr Asn
945                 950                 955                 960

Val Ala Gln Lys Lys Pro Asp Leu Glu Lys Thr Met Asn Trp Lys Asp
                965                 970                 975

Ser Val Cys Phe Gly Gln Pro Arg Asn Asp Thr Asn Trp Gln Thr Thr
            980                 985                 990

Pro Ser Ser Ser Tyr Glu Gln Cys Ala Thr Arg Gln Pro His Val Leu
            995                 1000                1005

Asp Ile Glu Asp Phe Gly Met Gln Gly Glu Gly Leu Gly Tyr Ser Trp
    1010                1015                1020

Met Ser Ile Ser Pro Arg Val Asp Arg Val Lys Asn Lys Asn Val Pro
1025                1030                1035                1040

Arg Arg Phe Phe Arg Gln Gly Gly Ser Val Pro Arg Glu Phe Thr Gly
                1045                1050                1055

Gln Ile Ile Pro Ser Thr Pro His Glu Leu Pro Gly Met Gly Leu Ser
            1060                1065                1070

Gly Ser Ser Ser Ala Val Gln Glu His Gln Asp Asp Thr Gln His Asn
            1075                1080                1085

Gln Gln Asp Glu Met Asn Lys Ala Ser His Leu Gln Lys Thr Phe Leu
    1090                1095                1100

Asp Leu Leu Asn Ser Ser Glu Glu Cys Leu Thr Arg Gln Ser Ser Thr
1105                1110                1115                1120

Lys Gln Asn Ile Thr Asp Gly Cys Leu Pro Arg Asp Arg Thr Ala Glu
                1125                1130                1135

Asp Val Asp Pro Leu Ser Asn Asn Ser Ser Leu Gly Asn Ile Leu
        1140                1145                1150

Val Glu Ser Asn Ser Ser Asn Lys Glu Gln Thr Ala Val Glu Tyr Lys
            1155                1160                1165

Glu Thr Asn Ala Thr Ile Leu Arg Glu Met Lys Gly Thr Leu Ala Asp
        1170                1175                1180

Gly Lys Lys Pro Thr Ser Gln Trp Asp Ser Leu Arg Lys Asp Val Glu
1185                1190                1195                1200

Gly Asn Glu Gly Arg Gln Glu Arg Asn Lys Asn Asn Met Asp Ser Ile
```

```
                1205                1210                1215
Asp Tyr Glu Ala Ile Arg Arg Ala Ser Ile Ser Glu Ile Ser Glu Ala
            1220                1225                1230
Ile Lys Glu Arg Gly Met Asn Asn Met Leu Ala Val Arg Ile Lys Asp
            1235                1240                1245
Phe Leu Glu Arg Ile Val Lys Asp His Gly Gly Ile Asp Leu Glu Trp
            1250                1255                1260
Leu Arg Glu Ser Pro Pro Asp Lys Ala Lys Asp Tyr Leu Leu Ser Ile
1265                1270                1275                1280
Arg Gly Leu Gly Leu Lys Ser Val Glu Cys Val Arg Leu Leu Thr Leu
            1285                1290                1295
His Asn Leu Ala Phe Pro Val Asp Thr Asn Val Gly Arg Ile Ala Val
            1300                1305                1310
Arg Met Gly Trp Val Pro Leu Gln Pro Leu Pro Glu Ser Leu Gln Leu
            1315                1320                1325
His Leu Leu Glu Leu Tyr Pro Val Leu Glu Ser Ile Gln Lys Phe Leu
            1330                1335                1340
Trp Pro Arg Leu Cys Lys Leu Asp Gln Arg Thr Leu Tyr Glu Leu His
1345                1350                1355                1360
Tyr Gln Leu Ile Thr Phe Gly Lys Val Phe Cys Thr Lys Ser Arg Pro
            1365                1370                1375
Asn Cys Asn Ala Cys Pro Met Arg Gly Glu Cys Arg His Phe Ala Ser
            1380                1385                1390
Ala Tyr Ala Ser Ala Arg Leu Ala Leu Pro Ala Pro Glu Glu Arg Ser
            1395                1400                1405
Leu Thr Ser Ala Thr Ile Pro Val Pro Pro Glu Ser Phe Pro Pro Val
            1410                1415                1420
Ala Ile Pro Met Ile Glu Leu Pro Leu Pro Leu Glu Lys Ser Leu Ala
1425                1430                1435                1440
Ser Gly Ala Pro Ser Asn Arg Glu Asn Cys Glu Pro Ile Ile Glu Glu
            1445                1450                1455
Pro Ala Ser Pro Gly Gln Glu Cys Thr Glu Ile Thr Glu Ser Asp Ile
            1460                1465                1470
Glu Asp Ala Tyr Tyr Asn Glu Asp Pro Asp Glu Ile Pro Thr Ile Lys
            1475                1480                1485
Leu Asn Ile Glu Gln Phe Gly Met Thr Leu Arg Glu His Met Glu Arg
            1490                1495                1500
Asn Met Glu Leu Gln Glu Gly Asp Met Ser Lys Ala Leu Val Ala Leu
1505                1510                1515                1520
His Pro Thr Thr Thr Ser Ile Pro Thr Pro Lys Leu Lys Asn Ile Ser
            1525                1530                1535
Arg Leu Arg Thr Glu His Gln Val Tyr Glu Leu Pro Asp Ser His Arg
            1540                1545                1550
Leu Leu Asp Gly Met Asp Lys Arg Glu Pro Asp Asp Pro Ser Pro Tyr
            1555                1560                1565
Leu Leu Ala Ile Trp Thr Pro Gly Glu Thr Ala Asn Ser Ala Gln Pro
            1570                1575                1580
Pro Glu Gln Lys Cys Gly Gly Lys Ala Ser Gly Lys Met Cys Phe Asp
1585                1590                1595                1600
Glu Thr Cys Ser Glu Cys Asn Ser Leu Arg Glu Ala Asn Ser Gln Thr
            1605                1610                1615
Val Arg Gly Thr Leu Leu Ile Pro Cys Arg Thr Ala Met Arg Gly Ser
            1620                1625                1630
```

-continued

```
Phe Pro Leu Asn Gly Thr Tyr Phe Gln Val Asn Glu Leu Phe Ala Asp
        1635                1640                1645

His Glu Ser Ser Leu Lys Pro Ile Asp Val Pro Arg Asp Trp Ile Trp
    1650                1655                1660

Asp Leu Pro Arg Arg Thr Val Tyr Phe Gly Thr Ser Val Thr Ser Ile
1665                1670                1675                1680

Phe Arg Gly Leu Ser Thr Glu Gln Ile Gln Phe Cys Phe Trp Lys Gly
        1685                1690                1695

Phe Val Cys Val Arg Gly Phe Glu Gln Lys Thr Arg Ala Pro Arg Pro
        1700                1705                1710

Leu Met Ala Arg Leu His Phe Pro Ala Ser Lys Leu Lys Asn Asn Lys
        1715                1720                1725

Thr

<210> SEQ ID NO 3
<211> LENGTH: 1052
<212> TYPE: PRT
<213> ORGANISM: Artificial Sequence
<220> FEATURE:
<223> OTHER INFORMATION: Description of Artificial Sequence:amino
      terminus deletion DME delta677, DME delta677 truncation

<400> SEQUENCE: 3

Tyr Lys Gly Asp Gly Ala Leu Val Pro Tyr Glu Ser Lys Lys Arg Lys
  1               5                  10                  15

Pro Arg Pro Lys Val Asp Ile Asp Asp Glu Thr Thr Arg Ile Trp Asn
                20                  25                  30

Leu Leu Met Gly Lys Gly Asp Glu Lys Glu Gly Asp Glu Glu Lys Asp
            35                  40                  45

Lys Lys Lys Glu Lys Trp Trp Glu Glu Glu Arg Arg Val Phe Arg Gly
        50                  55                  60

Arg Ala Asp Ser Phe Ile Ala Arg Met His Leu Val Gln Gly Asp Arg
 65                  70                  75                  80

Arg Phe Ser Pro Trp Lys Gly Ser Val Val Asp Ser Val Ile Gly Val
                85                  90                  95

Phe Leu Thr Gln Asn Val Ser Asp His Leu Ser Ser Ser Ala Phe Met
                100                 105                 110

Ser Leu Ala Ala Arg Phe Pro Pro Lys Leu Ser Ser Arg Glu Asp
            115                 120                 125

Glu Arg Asn Val Arg Ser Val Val Glu Asp Pro Glu Gly Cys Ile
        130                 135                 140

Leu Asn Leu Asn Glu Ile Pro Ser Trp Gln Glu Lys Val Gln His Pro
145                 150                 155                 160

Ser Asp Met Glu Val Ser Gly Val Asp Ser Gly Ser Lys Glu Gln Leu
                165                 170                 175

Arg Asp Cys Ser Asn Ser Gly Ile Glu Arg Phe Asn Phe Leu Glu Lys
            180                 185                 190

Ser Ile Gln Asn Leu Glu Glu Val Leu Ser Ser Gln Asp Ser Phe
        195                 200                 205

Asp Pro Ala Ile Phe Gln Ser Cys Gly Arg Val Gly Ser Cys Ser
210                 215                 220

Ser Lys Ser Asp Ala Glu Phe Pro Thr Thr Arg Cys Glu Thr Lys Thr
225                 230                 235                 240

Val Ser Gly Thr Ser Gln Ser Val Gln Thr Gly Ser Pro Asn Leu Ser
                245                 250                 255
```

```
Asp Glu Ile Cys Leu Gln Gly Asn Glu Arg Pro His Leu Tyr Glu Gly
        260                 265                 270

Ser Gly Asp Val Gln Lys Gln Glu Thr Thr Asn Val Ala Gln Lys Lys
            275                 280                 285

Pro Asp Leu Glu Lys Thr Met Asn Trp Lys Asp Ser Val Cys Phe Gly
290                 295                 300

Gln Pro Arg Asn Asp Thr Asn Trp Gln Thr Thr Pro Ser Ser Ser Tyr
305                 310                 315                 320

Glu Gln Cys Ala Thr Arg Gln Pro His Val Leu Asp Ile Glu Asp Phe
                325                 330                 335

Gly Met Gln Gly Glu Gly Leu Gly Tyr Ser Trp Met Ser Ile Ser Pro
            340                 345                 350

Arg Val Asp Arg Val Lys Asn Lys Asn Val Pro Arg Arg Phe Phe Arg
        355                 360                 365

Gln Gly Gly Ser Val Pro Arg Glu Phe Thr Gly Gln Ile Ile Pro Ser
    370                 375                 380

Thr Pro His Glu Leu Pro Gly Met Gly Leu Ser Gly Ser Ser Ser Ala
385                 390                 395                 400

Val Gln Glu His Gln Asp Asp Thr Gln His Asn Gln Gln Asp Glu Met
                405                 410                 415

Asn Lys Ala Ser His Leu Gln Lys Thr Phe Leu Asp Leu Leu Asn Ser
            420                 425                 430

Ser Glu Glu Cys Leu Thr Arg Gln Ser Ser Thr Lys Gln Asn Ile Thr
        435                 440                 445

Asp Gly Cys Leu Pro Arg Asp Arg Thr Ala Glu Asp Val Val Asp Pro
    450                 455                 460

Leu Ser Asn Asn Ser Ser Leu Gln Asn Ile Leu Val Glu Ser Asn Ser
465                 470                 475                 480

Ser Asn Lys Glu Gln Thr Ala Val Glu Tyr Lys Glu Thr Asn Ala Thr
                485                 490                 495

Ile Leu Arg Glu Met Lys Gly Thr Leu Ala Asp Gly Lys Lys Pro Thr
            500                 505                 510

Ser Gln Trp Asp Ser Leu Arg Lys Asp Val Glu Gly Asn Glu Gly Arg
        515                 520                 525

Gln Glu Arg Asn Lys Asn Asn Met Asp Ser Ile Asp Tyr Glu Ala Ile
    530                 535                 540

Arg Arg Ala Ser Ile Ser Glu Ile Ser Glu Ala Ile Lys Glu Arg Gly
545                 550                 555                 560

Met Asn Asn Met Leu Ala Val Arg Ile Lys Asp Phe Leu Glu Arg Ile
                565                 570                 575

Val Lys Asp His Gly Gly Ile Asp Leu Glu Trp Leu Arg Glu Ser Pro
            580                 585                 590

Pro Asp Lys Ala Lys Asp Tyr Leu Leu Ser Ile Arg Gly Leu Gly Leu
        595                 600                 605

Lys Ser Val Glu Cys Val Arg Leu Leu Thr Leu His Asn Leu Ala Phe
    610                 615                 620

Pro Val Asp Thr Asn Val Gly Arg Ile Ala Val Arg Met Gly Trp Val
625                 630                 635                 640

Pro Leu Gln Pro Leu Pro Glu Ser Leu Gln Leu His Leu Leu Glu Leu
                645                 650                 655

Tyr Pro Val Leu Glu Ser Ile Gln Lys Phe Leu Trp Pro Arg Leu Cys
            660                 665                 670
```

```
Lys Leu Asp Gln Arg Thr Leu Tyr Glu Leu His Tyr Gln Leu Ile Thr
            675                 680                 685

Phe Gly Lys Val Phe Cys Thr Lys Ser Arg Pro Asn Cys Asn Ala Cys
        690                 695                 700

Pro Met Arg Gly Glu Cys Arg His Phe Ala Ser Ala Tyr Ala Ser Ala
705                 710                 715                 720

Arg Leu Ala Leu Pro Ala Pro Glu Glu Arg Ser Leu Thr Ser Ala Thr
                725                 730                 735

Ile Pro Val Pro Pro Glu Ser Phe Pro Val Ala Ile Pro Met Ile
            740                 745                 750

Glu Leu Pro Leu Pro Leu Glu Lys Ser Leu Ala Ser Gly Ala Pro Ser
            755                 760                 765

Asn Arg Glu Asn Cys Glu Pro Ile Ile Glu Glu Pro Ala Ser Pro Gly
770                 775                 780

Gln Glu Cys Thr Glu Ile Thr Glu Ser Asp Ile Glu Asp Ala Tyr Tyr
785                 790                 795                 800

Asn Glu Asp Pro Asp Glu Ile Pro Thr Ile Lys Leu Asn Ile Glu Gln
                805                 810                 815

Phe Gly Met Thr Leu Arg Glu His Met Glu Arg Asn Met Glu Leu Gln
            820                 825                 830

Glu Gly Asp Met Ser Lys Ala Leu Val Ala Leu His Pro Thr Thr Thr
        835                 840                 845

Ser Ile Pro Thr Pro Lys Leu Lys Asn Ile Ser Arg Leu Arg Thr Glu
    850                 855                 860

His Gln Val Tyr Glu Leu Pro Asp Ser His Arg Leu Leu Asp Gly Met
865                 870                 875                 880

Asp Lys Arg Glu Pro Asp Asp Pro Ser Pro Tyr Leu Leu Ala Ile Trp
                885                 890                 895

Thr Pro Gly Glu Thr Ala Asn Ser Ala Gln Pro Pro Glu Gln Lys Cys
            900                 905                 910

Gly Gly Lys Ala Ser Gly Lys Met Cys Phe Asp Glu Thr Cys Ser Glu
        915                 920                 925

Cys Asn Ser Leu Arg Glu Ala Asn Ser Gln Thr Val Arg Gly Thr Leu
930                 935                 940

Leu Ile Pro Cys Arg Thr Ala Met Arg Gly Ser Phe Pro Leu Asn Gly
945                 950                 955                 960

Thr Tyr Phe Gln Val Asn Glu Leu Phe Ala Asp His Glu Ser Ser Leu
                965                 970                 975

Lys Pro Ile Asp Val Pro Arg Asp Trp Ile Trp Asp Leu Pro Arg Arg
            980                 985                 990

Thr Val Tyr Phe Gly Thr Ser Val Thr Ser Ile Phe Arg Gly Leu Ser
        995                 1000                1005

Thr Glu Gln Ile Gln Phe Cys Phe Trp Lys Gly Phe Val Cys Val Arg
    1010                1015                1020

Gly Phe Glu Gln Lys Thr Arg Ala Pro Arg Pro Leu Met Ala Arg Leu
1025                1030                1035                1040

His Phe Pro Ala Ser Lys Leu Lys Asn Asn Lys Thr
                1045                1050

<210> SEQ ID NO 4
<211> LENGTH: 1191
<212> TYPE: PRT
<213> ORGANISM: Artificial Sequence
<220> FEATURE:
<223> OTHER INFORMATION: Description of Artificial Sequence:amino
``` terminus deletion DME delta538, DME delta538 truncation

<400> SEQUENCE: 4

```
Val Ile Glu Ile Glu Asp Asp Pro Thr Asp Gly Ala Arg Lys Gly Lys
 1               5                  10                  15

Asn Thr Ala Ser Ile Ser Lys Gly Ala Ser Lys Gly Asn Ser Ser Pro
             20                  25                  30

Val Lys Lys Thr Ala Glu Lys Glu Lys Cys Ile Val Pro Lys Thr Pro
         35                  40                  45

Ala Lys Lys Gly Arg Ala Gly Arg Lys Lys Ser Val Pro Pro Pro Ala
     50                  55                  60

His Ala Ser Glu Ile Gln Leu Trp Gln Pro Thr Pro Lys Thr Pro
 65                  70                  75                  80

Leu Ser Arg Ser Lys Pro Lys Gly Lys Gly Arg Lys Ser Ile Gln Asp
                 85                  90                  95

Ser Gly Lys Ala Arg Gly Pro Ser Gly Glu Leu Leu Cys Gln Asp Ser
            100                 105                 110

Ile Ala Glu Ile Ile Tyr Arg Met Gln Asn Leu Tyr Leu Gly Asp Lys
        115                 120                 125

Glu Arg Glu Gln Glu Gln Asn Ala Met Val Leu Tyr Lys Gly Asp Gly
    130                 135                 140

Ala Leu Val Pro Tyr Glu Ser Lys Lys Arg Lys Pro Arg Pro Lys Val
145                 150                 155                 160

Asp Ile Asp Asp Glu Thr Thr Arg Ile Trp Asn Leu Leu Met Gly Lys
                165                 170                 175

Gly Asp Glu Lys Glu Gly Asp Glu Glu Lys Asp Lys Lys Glu Lys
            180                 185                 190

Trp Trp Glu Glu Glu Arg Arg Val Phe Arg Gly Arg Ala Asp Ser Phe
        195                 200                 205

Ile Ala Arg Met His Leu Val Gln Gly Asp Arg Arg Phe Ser Pro Trp
    210                 215                 220

Lys Gly Ser Val Val Asp Ser Val Ile Gly Val Phe Leu Thr Gln Asn
225                 230                 235                 240

Val Ser Asp His Leu Ser Ser Ser Ala Phe Met Ser Leu Ala Ala Arg
                245                 250                 255

Phe Pro Pro Lys Leu Ser Ser Ser Arg Glu Asp Glu Arg Asn Val Arg
            260                 265                 270

Ser Val Val Val Glu Asp Pro Glu Gly Cys Ile Leu Asn Leu Asn Glu
        275                 280                 285

Ile Pro Ser Trp Gln Glu Lys Val Gln His Pro Ser Asp Met Glu Val
    290                 295                 300

Ser Gly Val Asp Ser Gly Ser Lys Glu Gln Leu Arg Asp Cys Ser Asn
305                 310                 315                 320

Ser Gly Ile Glu Arg Phe Asn Phe Leu Glu Lys Ser Ile Gln Asn Leu
                325                 330                 335

Glu Glu Glu Val Leu Ser Ser Gln Asp Ser Phe Asp Pro Ala Ile Phe
            340                 345                 350

Gln Ser Cys Gly Arg Val Gly Ser Cys Ser Cys Ser Lys Ser Asp Ala
        355                 360                 365

Glu Phe Pro Thr Thr Arg Cys Glu Thr Lys Thr Val Ser Gly Thr Ser
    370                 375                 380

Gln Ser Val Gln Thr Gly Ser Pro Asn Leu Ser Asp Glu Ile Cys Leu
385                 390                 395                 400
```

```
Gln Gly Asn Glu Arg Pro His Leu Tyr Glu Gly Ser Gly Asp Val Gln
                405                 410                 415
Lys Gln Glu Thr Thr Asn Val Ala Gln Lys Lys Pro Asp Leu Glu Lys
            420                 425                 430
Thr Met Asn Trp Lys Asp Ser Val Cys Phe Gly Gln Pro Arg Asn Asp
        435                 440                 445
Thr Asn Trp Gln Thr Thr Pro Ser Ser Ser Tyr Glu Gln Cys Ala Thr
    450                 455                 460
Arg Gln Pro His Val Leu Asp Ile Glu Asp Phe Gly Met Gln Gly Glu
465                 470                 475                 480
Gly Leu Gly Tyr Ser Trp Met Ser Ile Ser Pro Arg Val Asp Arg Val
                485                 490                 495
Lys Asn Lys Asn Val Pro Arg Arg Phe Phe Arg Gln Gly Gly Ser Val
            500                 505                 510
Pro Arg Glu Phe Thr Gly Gln Ile Ile Pro Ser Thr Pro His Glu Leu
        515                 520                 525
Pro Gly Met Gly Leu Ser Gly Ser Ser Ser Ala Val Gln Glu His Gln
    530                 535                 540
Asp Asp Thr Gln His Asn Gln Gln Asp Glu Met Asn Lys Ala Ser His
545                 550                 555                 560
Leu Gln Lys Thr Phe Leu Asp Leu Leu Asn Ser Ser Glu Glu Cys Leu
                565                 570                 575
Thr Arg Gln Ser Ser Thr Lys Gln Asn Ile Thr Asp Gly Cys Leu Pro
            580                 585                 590
Arg Asp Arg Thr Ala Glu Asp Val Val Asp Pro Leu Ser Asn Asn Ser
        595                 600                 605
Ser Leu Gln Asn Ile Leu Val Glu Ser Asn Ser Ser Asn Lys Glu Gln
    610                 615                 620
Thr Ala Val Glu Tyr Lys Glu Thr Asn Ala Thr Ile Leu Arg Glu Met
625                 630                 635                 640
Lys Gly Thr Leu Ala Asp Gly Lys Lys Pro Thr Ser Gln Trp Asp Ser
                645                 650                 655
Leu Arg Lys Asp Val Glu Gly Asn Glu Gly Arg Gln Glu Arg Asn Lys
            660                 665                 670
Asn Asn Met Asp Ser Ile Asp Tyr Glu Ala Ile Arg Arg Ala Ser Ile
        675                 680                 685
Ser Glu Ile Ser Glu Ala Ile Lys Glu Arg Gly Met Asn Asn Met Leu
    690                 695                 700
Ala Val Arg Ile Lys Asp Phe Leu Glu Arg Ile Val Lys Asp His Gly
705                 710                 715                 720
Gly Ile Asp Leu Glu Trp Leu Arg Glu Ser Pro Asp Lys Ala Lys
                725                 730                 735
Asp Tyr Leu Leu Ser Ile Arg Gly Leu Gly Leu Lys Ser Val Glu Cys
            740                 745                 750
Val Arg Leu Leu Thr Leu His Asn Leu Ala Phe Pro Val Asp Thr Asn
        755                 760                 765
Val Gly Arg Ile Ala Val Arg Met Gly Trp Val Pro Leu Gln Pro Leu
    770                 775                 780
Pro Glu Ser Leu Gln Leu His Leu Leu Glu Leu Tyr Pro Val Leu Glu
785                 790                 795                 800
Ser Ile Gln Lys Phe Leu Trp Pro Arg Leu Cys Lys Leu Asp Gln Arg
                805                 810                 815
Thr Leu Tyr Glu Leu His Tyr Gln Leu Ile Thr Phe Gly Lys Val Phe
```

```
                820             825             830
Cys Thr Lys Ser Arg Pro Asn Cys Asn Ala Cys Pro Met Arg Gly Glu
            835             840             845
Cys Arg His Phe Ala Ser Ala Tyr Ala Ser Arg Leu Ala Leu Pro
        850             855             860
Ala Pro Glu Glu Arg Ser Leu Thr Ser Ala Thr Ile Pro Val Pro Pro
865             870             875             880
Glu Ser Phe Pro Pro Val Ala Ile Pro Met Ile Glu Leu Pro Leu Pro
                885             890             895
Leu Glu Lys Ser Leu Ala Ser Gly Ala Pro Ser Asn Arg Glu Asn Cys
            900             905             910
Glu Pro Ile Ile Glu Glu Pro Ala Ser Pro Gly Gln Glu Cys Thr Glu
            915             920             925
Ile Thr Glu Ser Asp Ile Glu Asp Ala Tyr Tyr Asn Glu Asp Pro Asp
        930             935             940
Glu Ile Pro Thr Ile Lys Leu Asn Ile Glu Gln Phe Gly Met Thr Leu
945             950             955             960
Arg Glu His Met Glu Arg Asn Met Glu Leu Gln Gly Asp Met Ser
                965             970             975
Lys Ala Leu Val Ala Leu His Pro Thr Thr Ser Ile Pro Thr Pro
            980             985             990
Lys Leu Lys Asn Ile Ser Arg Leu Arg Thr Glu His Gln Val Tyr Glu
            995             1000            1005
Leu Pro Asp Ser His Arg Leu Leu Asp Gly Met Asp Lys Arg Glu Pro
        1010            1015            1020
Asp Asp Pro Ser Pro Tyr Leu Leu Ala Ile Trp Thr Pro Gly Glu Thr
1025            1030            1035            1040
Ala Asn Ser Ala Gln Pro Pro Glu Gln Lys Cys Gly Gly Lys Ala Ser
                1045            1050            1055
Gly Lys Met Cys Phe Asp Glu Thr Cys Ser Glu Cys Asn Ser Leu Arg
            1060            1065            1070
Glu Ala Asn Ser Gln Thr Val Arg Gly Thr Leu Leu Ile Pro Cys Arg
            1075            1080            1085
Thr Ala Met Arg Gly Ser Phe Pro Leu Asn Gly Thr Tyr Phe Gln Val
            1090            1095            1100
Asn Glu Leu Phe Ala Asp His Glu Ser Ser Leu Lys Pro Ile Asp Val
1105            1110            1115            1120
Pro Arg Asp Trp Ile Trp Asp Leu Pro Arg Arg Thr Val Tyr Phe Gly
            1125            1130            1135
Thr Ser Val Thr Ser Ile Phe Arg Gly Leu Ser Thr Glu Gln Ile Gln
            1140            1145            1150
Phe Cys Phe Trp Lys Gly Phe Val Cys Val Arg Gly Phe Glu Gln Lys
            1155            1160            1165
Thr Arg Ala Pro Arg Pro Leu Met Ala Arg Leu His Phe Pro Ala Ser
            1170            1175            1180
Lys Leu Lys Asn Asn Lys Thr
1185            1190

<210> SEQ ID NO 5
<211> LENGTH: 4182
<212> TYPE: DNA
<213> ORGANISM: Arabidopsis sp.
<220> FEATURE:
<223> OTHER INFORMATION: DNA demethylase ROS1 coding sequence
```

```
<400> SEQUENCE: 5
atggagaaac agaggagaga agaaagcagc tttcaacaac ctccatggat tcctcagaca      60
cccatgaagc cattttcacc gatctgccca tacacggtgg aggatcaata tcatagcagt     120
caattggagg aaaggagatt tgttgggaac aaggatatga gtggtcttga tcacttgtct     180
tttggggatt tgcttgctct agctaacact gcatccctca tattctctgg tcagactcca     240
atacctacaa gaaacacaga ggttatgcaa aaggtactg aagaagtgga gagtttgagc      300
tcagtgagta acaatgttgc tgaacagatc ctcaagactc ctgaaaaacc taagaggaag     360
aagcatcggc caaggttcg tagagaagct aaacccaaga gggagcctaa accacgagct      420
ccgaggaagt ctgttgtcac cgatggtcaa gaaagcaaaa caccaaagag gaaatatgtg     480
cggaagaagt tgaagtcag taaggatcaa gacgctactc cggttgaatc atcagcagct      540
gttgaaactt caactcgtcc taagaggctc tgtagacgag tcttggattt tgaagccgaa     600
aatggagaaa accagaccaa cggtgacatt agagaagcag gtgagatgga atcagctctt     660
caagagaagc agttagattc tgggaatcaa gagttaaaag attgccttct ttcggctcct     720
agcacgccca agagaaagcg cagccaaggt aaagaaaagg gagttcaacc aaagaaaaat     780
ggcagtaatc tagaagaagt cgatatttcg atggcgcaag ctgcaaagag aagacaagga     840
ccaacttgtt gcgacatgaa tctatcaggg attcagtatg atgagcaatg tgactaccag     900
aaaatgcatt ggttgtattc cccaaacttg caacagggag ggatgagata tgatgccatt     960
tgcagcaaag tattctctgg acaacagcac aattatgttt ctgcctttca cgctacgtgc    1020
tacagttcca catctcagct cagtgctaat agagtcctaa ccgttgaaga agacgagaa     1080
ggtatctttc aaggaaggca agagtctgag ctaaatgttc tctcggataa gatagacacg    1140
ccgatcaaga agaaaacaac aggccatgct cgattccgga atttgtcttc aatgaataaa    1200
cttgtggaag ttcctgagca tttaacctca ggatattgta gcaagccaca gcaaaataat    1260
aagattcttg ttgatacgcg ggtgactgtg agcaaaaaga agccaaccaa gtctgagaaa    1320
tcacaaaacca acagaaaaa tcttcttccg aatctttgcc gttttccacc ttcatttact    1380
ggtctttctc cagatgaact ttggaaacga cgtaactcga tcgaaacaat cagtgagcta    1440
ttgcgtctat tagacatcaa cagggagcat tctgaaactg ctctcgttcc ttacacaatg    1500
aatagccaga ttgtactctt tggtggtggc gctggagcaa ttgtgcctgt aactcctgtt    1560
aaaaaaccac gcccacgacc aaaggttgat ctagacgatg agacagacag agtgtggaaa    1620
ctgctattgg agaatattaa tagcgaaggt gttgacggat cagacgagca gaaggcgaaa    1680
tggtgggagg aagaacgtaa tgtgtttcga ggacgagctg actcatttat tgcaaggatg    1740
caccttgtac aaggggatcg acgttttacg cccttggaagg atccgtcgt ggattctgtt    1800
gttggagtat ttctcactca aaatgtttca gaccatctct caagttcggc tttcatgtcg    1860
ttggcttccc agttccctgt ccctttttgta ccgagcagta actttgacgc tggaacaagc    1920
tcgatgcctt ctattcaaat aacgtacttg gactcagagg aaacgatgtc aagcccaccc    1980
gatcacaatc acagttctgt tactttgaaa aatacacagc ctgatgagga aaggattat     2040
gtacctagca atgaaacctc cagaagcagt agtgagattg ccatctcagc ccatgaatca    2100
gttgacaaaa ccacggattc aaaggagtat gttgattcag atcgaaaagg ctcaagtgta    2160
gaggttgata gacggatga gaagtgtcgt gtcctgaacc tgtttccatc tgaagattct    2220
gcacttacat gtcaacattc gatggtgtct gatgctcctc aaaatacaga gagagcagga    2280
tcaagctcag agatcgactt agaaggagag tatcgtactt cctttatgaa gctcctacag    2340
```

```
ggggtacaag tctctctaga agattccaat caagtatcac caaatatgtc tccgggtgat    2400
tgtagctcag aaattaaggg tttccagtca atgaaagagc ccacaaaatc ctctgttgat    2460
agtagtgaac ctggttgttg ctctcagcaa gatggggatg ttttgagttg tcagaaacct    2520
accttaaaag aaaaagggaa aaaggttttg aaggaggaaa aaaaagcgtt tgactgggat    2580
tgtttaagaa gagaagccca agctagagca ggaattagag aaaaaacaag aagtacaatg    2640
gacaccgtgg attggaaggc aatacgagca gcagatgtta aggaagttgc tgaaacaatc    2700
aagagtcgcg ggatgaacca taaacttgca gaacgtatac agggcttcct tgatcgactg    2760
gtaaatgacc atgaagtat cgatcttgaa tggttgagag atgttccacc agataaagca    2820
aaagaatatc ttctgagctt taacggattg ggactgaaaa gtgtggagtg tgtgcggctt    2880
ctaacacttc accatcttgc ctttccagtt gatacaaatg ttgggcgcat agccgtcaga    2940
cttggatggg tgccccttca gccgctccca gagtcacttc agttgcatct tctggaaatg    3000
tatcctatgc ttgaatctat tcaaaagtat ctttggcccc gtctctgcaa actcgaccaa    3060
aaaacattgt atgagttgca ctaccagatg attacttttg gaaaggtctt ttgcacaaag    3120
agcaaaccta attgcaatgc atgtccgatg aaaggagaat gcagacattt tgccagtgcg    3180
tttgcaagtg caaggcttgc tttaccaagt acagagaaag gtatggggac acctgataaa    3240
aacccttttgc ctctacacct gccagagcca ttccagagag agcaagggtc tgaagtagta    3300
cagcactcag aaccagcaaa aaaggtcaca tgttgtgaac caatcatcga agagcctgct    3360
tcaccggagc cagaaaccgc agaagtatca atagctgaca tagaggaggc gtttttttgag    3420
gatccagaag aaattcctac catcaggcta aacatggatg catttaccag taacttgaag    3480
aagataatgg aacacaacaa ggaacttcaa gacggaaaca tgtccagcgc tttagttgca    3540
cttactgctg aaactgcttc tcttccaatg cctaagctca gaatatcag ccagttaagg    3600
acagaacacc gagtttacga acttccagac gagcatcctc ttctagctca gttggaaaag    3660
agagaacctg atgatccatg ttcttatttg cttgctatat ggacgccagg tgagacggct    3720
gattctattc aaccgtctgt tagtacgtgc atattccaag caaatggtat gctttgtgac    3780
gaggagactt gtttctcctg caacagcatc aaggagacta gatctcaaat tgtgagaggg    3840
acaattttga ttccttgtag aacagcgatg aggggtagtt ttcctctaaa tggaacgtac    3900
tttcaagtaa atgaggtgtt tgcggatcat gcatccagcc taaacccaat caatgtccca    3960
agggaattga tatgggaatt acctcgaaga acggtctatt tggtacctc tgttcctacg    4020
atattcaaag gtttatcaac tgagaagata caggcttgct tttggaaagg gtacgtatgt    4080
gtacgtggat ttgatcgaaa gacgagggga ccgaagcctt tgattgcaag attgcacttc    4140
ccggcgagca aactgaaggg acaacaagct aacctcgcct aa    4182
```

<210> SEQ ID NO 6
<211> LENGTH: 1393
<212> TYPE: PRT
<213> ORGANISM: Arabidopsis sp.
<220> FEATURE:
<223> OTHER INFORMATION: DNA demethylase ROS1

<400> SEQUENCE: 6

Met Glu Lys Gln Arg Arg Glu Glu Ser Ser Phe Gln Gln Pro Pro Trp
1               5                   10                  15

Ile Pro Gln Thr Pro Met Lys Pro Phe Ser Pro Ile Cys Pro Tyr Thr
            20                  25                  30

```
Val Glu Asp Gln Tyr His Ser Ser Gln Leu Glu Arg Arg Phe Val
             35                  40                  45
Gly Asn Lys Asp Met Ser Gly Leu Asp His Leu Ser Phe Gly Asp Leu
 50                  55                  60
Leu Ala Leu Ala Asn Thr Ala Ser Leu Ile Phe Ser Gly Gln Thr Pro
 65                  70                  75                  80
Ile Pro Thr Arg Asn Thr Glu Val Met Gln Lys Gly Thr Glu Glu Val
                 85                  90                  95
Glu Ser Leu Ser Ser Val Ser Asn Asn Val Ala Glu Gln Ile Leu Lys
                100                 105                 110
Thr Pro Glu Lys Pro Lys Arg Lys Lys His Arg Pro Lys Val Arg Arg
                115                 120                 125
Glu Ala Lys Pro Lys Arg Glu Pro Lys Pro Arg Ala Pro Arg Lys Ser
130                 135                 140
Val Val Thr Asp Gly Gln Glu Ser Lys Thr Pro Lys Arg Lys Tyr Val
145                 150                 155                 160
Arg Lys Lys Val Glu Val Ser Lys Asp Gln Asp Ala Thr Pro Val Glu
                165                 170                 175
Ser Ser Ala Ala Val Glu Thr Ser Thr Arg Pro Lys Arg Leu Cys Arg
                180                 185                 190
Arg Val Leu Asp Phe Glu Ala Glu Asn Gly Glu Asn Gln Thr Asn Gly
                195                 200                 205
Asp Ile Arg Glu Ala Gly Glu Met Glu Ser Ala Leu Gln Glu Lys Gln
                210                 215                 220
Leu Asp Ser Gly Asn Gln Glu Leu Lys Asp Cys Leu Leu Ser Ala Pro
225                 230                 235                 240
Ser Thr Pro Lys Arg Lys Arg Ser Gln Gly Lys Arg Lys Gly Val Gln
                245                 250                 255
Pro Lys Lys Asn Gly Ser Asn Leu Glu Glu Val Asp Ile Ser Met Ala
                260                 265                 270
Gln Ala Ala Lys Arg Arg Gln Gly Pro Thr Cys Cys Asp Met Asn Leu
                275                 280                 285
Ser Gly Ile Gln Tyr Asp Glu Gln Cys Asp Tyr Gln Lys Met His Trp
                290                 295                 300
Leu Tyr Ser Pro Asn Leu Gln Gln Gly Gly Met Arg Tyr Asp Ala Ile
305                 310                 315                 320
Cys Ser Lys Val Phe Ser Gly Gln Gln His Asn Tyr Val Ser Ala Phe
                325                 330                 335
His Ala Thr Cys Tyr Ser Ser Thr Ser Gln Leu Ser Ala Asn Arg Val
                340                 345                 350
Leu Thr Val Glu Glu Arg Arg Glu Gly Ile Phe Gln Gly Arg Gln Glu
                355                 360                 365
Ser Glu Leu Asn Val Leu Ser Asp Lys Ile Asp Thr Pro Ile Lys Lys
                370                 375                 380
Lys Thr Thr Gly His Ala Arg Phe Arg Asn Leu Ser Ser Met Asn Lys
385                 390                 395                 400
Leu Val Glu Val Pro Glu His Leu Thr Ser Gly Tyr Cys Ser Lys Pro
                405                 410                 415
Gln Gln Asn Asn Lys Ile Leu Val Asp Thr Arg Val Thr Val Ser Lys
                420                 425                 430
Lys Lys Pro Thr Lys Ser Glu Lys Ser Gln Thr Lys Gln Lys Asn Leu
                435                 440                 445
Leu Pro Asn Leu Cys Arg Phe Pro Pro Ser Phe Thr Gly Leu Ser Pro
```

```
                450             455             460
Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
                485                 490                 495

Pro Tyr Thr Met Asn Ser Gln Ile Val Leu Phe Gly Gly Gly Ala Gly
                500                 505                 510

Ala Ile Val Pro Val Thr Pro Val Lys Lys Pro Arg Pro Arg Pro Lys
                515                 520                 525

Val Asp Leu Asp Asp Glu Thr Asp Arg Val Trp Lys Leu Leu Leu Glu
                530                 535                 540

Asn Ile Asn Ser Glu Gly Val Asp Gly Ser Asp Glu Gln Lys Ala Lys
545                 550                 555                 560

Trp Trp Glu Glu Glu Arg Asn Val Phe Arg Gly Arg Ala Asp Ser Phe
                565                 570                 575

Ile Ala Arg Met His Leu Val Gln Gly Asp Arg Arg Phe Thr Pro Trp
                580                 585                 590

Lys Gly Ser Val Val Asp Ser Val Val Gly Val Phe Leu Thr Gln Asn
                595                 600                 605

Val Ser Asp His Leu Ser Ser Ser Ala Phe Met Ser Leu Ala Ser Gln
                610                 615                 620

Phe Pro Val Pro Phe Val Pro Ser Ser Asn Phe Asp Ala Gly Thr Ser
625                 630                 635                 640

Ser Met Pro Ser Ile Gln Ile Thr Tyr Leu Asp Ser Glu Glu Thr Met
                645                 650                 655

Ser Ser Pro Pro Asp His Asn His Ser Ser Val Thr Leu Lys Asn Thr
                660                 665                 670

Gln Pro Asp Glu Glu Lys Asp Tyr Val Pro Ser Asn Glu Thr Ser Arg
                675                 680                 685

Ser Ser Ser Glu Ile Ala Ile Ser Ala His Glu Ser Val Asp Lys Thr
                690                 695                 700

Thr Asp Ser Lys Glu Tyr Val Asp Ser Asp Arg Lys Gly Ser Ser Val
705                 710                 715                 720

Glu Val Asp Lys Thr Asp Glu Lys Cys Arg Val Leu Asn Leu Phe Pro
                725                 730                 735

Ser Glu Asp Ser Ala Leu Thr Cys Gln His Ser Met Val Ser Asp Ala
                740                 745                 750

Pro Gln Asn Thr Glu Arg Ala Gly Ser Ser Ser Glu Ile Asp Leu Glu
                755                 760                 765

Gly Glu Tyr Arg Thr Ser Phe Met Lys Leu Leu Gln Gly Val Gln Val
                770                 775                 780

Ser Leu Glu Asp Ser Asn Gln Val Ser Pro Asn Met Ser Pro Gly Asp
785                 790                 795                 800

Cys Ser Ser Glu Ile Lys Gly Phe Gln Ser Met Lys Glu Pro Thr Lys
                805                 810                 815

Ser Ser Val Asp Ser Ser Glu Pro Gly Cys Cys Ser Gln Gln Asp Gly
                820                 825                 830

Asp Val Leu Ser Cys Gln Lys Pro Thr Leu Lys Glu Lys Gly Lys Lys
                835                 840                 845

Val Leu Lys Glu Glu Lys Lys Ala Phe Asp Trp Asp Cys Leu Arg Arg
850                 855                 860

Glu Ala Gln Ala Arg Ala Gly Ile Arg Glu Lys Thr Arg Ser Thr Met
865                 870                 875                 880
```

-continued

```
Asp Thr Val Asp Trp Lys Ala Ile Arg Ala Ala Asp Val Lys Glu Val
            885                 890                 895

Ala Glu Thr Ile Lys Ser Arg Gly Met Asn His Lys Leu Ala Glu Arg
        900                 905                 910

Ile Gln Gly Phe Leu Asp Arg Leu Val Asn Asp His Gly Ser Ile Asp
            915                 920                 925

Leu Glu Trp Leu Arg Asp Val Pro Pro Asp Lys Ala Lys Glu Tyr Leu
        930                 935                 940

Leu Ser Phe Asn Gly Leu Gly Leu Lys Ser Val Glu Cys Val Arg Leu
945                 950                 955                 960

Leu Thr Leu His His Leu Ala Phe Pro Val Asp Thr Asn Val Gly Arg
            965                 970                 975

Ile Ala Val Arg Leu Gly Trp Val Pro Leu Gln Pro Leu Pro Glu Ser
            980                 985                 990

Leu Gln Leu His Leu Leu Glu Met Tyr Pro Met Leu Glu Ser Ile Gln
            995                 1000                1005

Lys Tyr Leu Trp Pro Arg Leu Cys Lys Leu Asp Gln Lys Thr Leu Tyr
        1010                1015                1020

Glu Leu His Tyr Gln Met Ile Thr Phe Gly Lys Val Phe Cys Thr Lys
1025                1030                1035                1040

Ser Lys Pro Asn Cys Asn Ala Cys Pro Met Lys Gly Glu Cys Arg His
            1045                1050                1055

Phe Ala Ser Ala Phe Ala Ser Ala Arg Leu Ala Leu Pro Ser Thr Glu
            1060                1065                1070

Lys Gly Met Gly Thr Pro Asp Lys Asn Pro Leu Pro Leu His Leu Pro
            1075                1080                1085

Glu Pro Phe Gln Arg Glu Gln Gly Ser Glu Val Val Gln His Ser Glu
            1090                1095                1100

Pro Ala Lys Lys Val Thr Cys Cys Glu Pro Ile Ile Glu Glu Pro Ala
1105                1110                1115                1120

Ser Pro Glu Pro Glu Thr Ala Glu Val Ser Ile Ala Asp Ile Glu Glu
            1125                1130                1135

Ala Phe Phe Glu Asp Pro Glu Glu Ile Pro Thr Ile Arg Leu Asn Met
            1140                1145                1150

Asp Ala Phe Thr Ser Asn Leu Lys Lys Ile Met Glu His Asn Lys Glu
            1155                1160                1165

Leu Gln Asp Gly Asn Met Ser Ser Ala Leu Val Ala Leu Thr Ala Glu
        1170                1175                1180

Thr Ala Ser Leu Pro Met Pro Lys Leu Lys Asn Ile Ser Gln Leu Arg
1185                1190                1195                1200

Thr Glu His Arg Val Tyr Glu Leu Pro Asp Glu His Pro Leu Leu Ala
            1205                1210                1215

Gln Leu Glu Lys Arg Glu Pro Asp Asp Pro Cys Ser Tyr Leu Leu Ala
        1220                1225                1230

Ile Trp Thr Pro Gly Glu Thr Ala Asp Ser Ile Gln Pro Ser Val Ser
            1235                1240                1245

Thr Cys Ile Phe Gln Ala Asn Gly Met Leu Cys Asp Glu Glu Thr Cys
1250                1255                1260

Phe Ser Cys Asn Ser Ile Lys Glu Thr Arg Ser Gln Ile Val Arg Gly
1265                1270                1275                1280

Thr Ile Leu Ile Pro Cys Arg Thr Ala Met Arg Gly Ser Phe Pro Leu
            1285                1290                1295
```

```
Asn Gly Thr Tyr Phe Gln Val Asn Glu Val Phe Ala Asp His Ala Ser
            1300                1305                1310
Ser Leu Asn Pro Ile Asn Val Pro Arg Glu Leu Ile Trp Glu Leu Pro
        1315                1320                1325
Arg Arg Thr Val Tyr Phe Gly Thr Ser Val Pro Thr Ile Phe Lys Gly
    1330                1335                1340
Leu Ser Thr Glu Lys Ile Gln Ala Cys Phe Trp Lys Gly Tyr Val Cys
1345                1350                1355                1360
Val Arg Gly Phe Asp Arg Lys Thr Arg Gly Pro Lys Pro Leu Ile Ala
                1365                1370                1375
Arg Leu His Phe Pro Ala Ser Lys Leu Lys Gly Gln Gln Ala Asn Leu
            1380                1385                1390
Ala

<210> SEQ ID NO 7
<211> LENGTH: 3999
<212> TYPE: DNA
<213> ORGANISM: Arabidopsis sp.
<220> FEATURE:
<223> OTHER INFORMATION: DNA demethylase DML2 coding sequence

<400> SEQUENCE: 7
atggaagtgg aaggtgaagt gagagagaaa gaagctaggg ttaaagggag acaaccagag      60
acagaagttc tacatggtct gccacaagaa cagtcaatat ttaataacat gcaacacaac     120
catcagcctg actcagacag gaggaggctt agtcttgaaa acttacctgg actatacaac     180
atgtcttgta cacaactctt ggctctggcc aatgccacag tcgccacagg ttcatcaatt     240
ggtgcatcat catcatcgtt aagctctcag catccaacgg attcttggat taatagctgg     300
aagatggact ctaatccgtg gactttgagt aaaatgcaaa acaacaata tgatgtgtca      360 actccgcaga agtttctttg tgaccttaat cttacacctg aagagttggt gagcaccagt     420
acgcaacgaa cagaacctga gtctcctcaa ataactttaa agacaccagg aaaaagtctg     480
tctgaaactg atcatgagcc tcacgaccgt atcaagaagt ctgttcttgg aactggatct     540
cctgcagcag taaagaaaag aaagatagca agaaatgatg agaaatctca gctggaaaca     600
ccaacactaa agagaaaaaa gatcaggcca aaggttgtcc gtgaaggcaa acaaaaaaa      660 gcatcatcta aagcagggat taaaaaatcc tctattgctg ctactgctac taaaacttct     720
gaagagagca attatgttcg gccaaaaaga ttaacgagaa gatctatacg attcgacttt     780
gaccttcaag aagaagatga ggaattttgt ggaatcgatt tcacatcagc aggtcacgta     840
gagggttctt caggtgaaga aaatctaacc gatacaacac tgggaatgtt tggtcacgtc     900
ccaaagggaa gaagagggca agaagatcc aatggcttta aaaaaaccga caatgattgc      960
ctcagttcta tgttgtctct tgtcaatacc ggaccaggaa gtttcatgga atcagaagaa    1020
gatcgtccga gtgattcaca aatttctctg ggaagacaga gatccattat ggcaaccaga    1080
ccgcgtaact tccgatcgtt aaagaaactt ttacaaagga ttataccaag caaacgtgat    1140
agaaaaggat gtaagcttcc tcgtggactt ccgaagctta ccgtcgcatc caagttgcaa    1200
ctaaaagtgt ttagaaagaa gcggagtcaa agaaaccgtg tagcaagcca gttcaatgca    1260
aggatattgg acttgcagtg gcgacgccaa atccaacag gtacatcgct agctgatata    1320
tgggaaagaa gtttgactat tgatgctatc actaagttgt ttgaagaatt agacatcaac    1380
aaagagggtc tttgccttcc acataataga gaaactgcac ttattctata caaaagtcg    1440 tatgaagagc aaaaggcaat agtgaagtat agcaagaagc agaaaccgaa agtacaattg    1500
```

```
gatcctgaaa cgagtcgagt gtggaaactc ttaatgtcaa gtatcgactg tgacggtgtt    1560
gatggatcag atgaggaaaa acgtaaatgg tgggaagagg agaggaacat gttccatgga    1620
cgtgcaaact cgttcattgc gcgaatgcgt gttgtccaag gcaatagaac tttctcacct    1680
tggaaagggt cagtagtgga ttcagtagtg ggagttttcc taacccagaa tgtcgcagac    1740
cattcatcaa gttctgcata tatggattta gctgctgagt ttcctgtcga gtggaacttc    1800
aacaagggat catgtcatga agagtgggga agttcagtaa ctcaagaaac aatactgaat    1860
ttggatccaa gaactggagt ttcaactcca agaattcgca atccaactcg cgtcatcata    1920
gaggagattg atgatgatga gaacgacatt gatgctgttt gtagtcagga atcctctaaa    1980
acaagtgaca gttccataac ttctgcagac caatcaaaaa cgatgctgct ggatccattt    2040
aacacagttt tgatgaacga gcaagttgat tcccaaatgg taaaaggcaa aggtcatata    2100
ccatacacgg atgatcttaa tgacttgtcc caggggattt cgatggtctc atctgcttct    2160
actcattgtg agttgaacct aaatgaagta ccacctgaag tagagttgtg cagccatcaa    2220
caagacccgg agagtaccat tcagacacaa gaccagcaag agagcacaag aacggaggat    2280
gtgaagaaga ataggaaaaa accaactacc tccaaaccaa agaaaaagtc aaaggaatca    2340
gcaaagagca cgcaaaagaa aagcgttgac tgggatagtt tgagaaagga agcagaaagt    2400
ggtggccgaa agagagagag aacagaaaga acaatggaca cagttgattg ggatgcactt    2460
cgatgtacag acgtacacaa gatcgctaat ataatcatca acgagggat gaacaacatg    2520 cttgccgaaa gaatcaaggc cttcttaaac agactagtta aaaaacatgg aagcattgac    2580
ttagagtggc taagagatgt tcctcctgat aaagccaagg agtatctact aagcataaac    2640
ggattaggat tgaagagtgt ggagtgtgtt agacttttgt cactacatca gattgcattc    2700
cctgttgaca cgaatgtcgg acgcatagct gtaagactag gatgggttcc cttacagcca    2760
ttgcccgacg agctgcaaat gcatctttta gagttgtacc cagttctaga gtcagttcaa    2820
aagtacctct ggccacgcct ctgcaagctt gaccaaaaaa ccttgtacga gctgcattac    2880
cacatgataa catttggaaa ggtcttttgc acaaaagtaa aacccaattg caatgcatgt    2940
ccaatgaagg cggagtgtcg acattactct agtgcacgtg caagcgcacg gcttgcttta    3000
ccagaaccag aggagagtga cagaacaagt gtaatgatcc atgagaggag atctaaacgc    3060
aagcctgttg tggttaattt tcgaccatcc ttatttcttt atcaagaaaa agagcaagaa    3120
gcacaaagat cccaaaactg tgaaccaatc attgaggaac cagcatcacc agaaccagag    3180
tatatagaac atgatattga agactatcct cgggacaaaa acaacgttgg aacatcagag    3240
gatccttggg aaaataagga cgtaattcct accatcatcc tcaacaagga agctggtaca    3300
tcacatgatt tggtggtcaa caaggaagct ggtacgtcac atgatttggt ggtactaagc    3360
acatatgcag cagcaatacc tagacgtaaa ctcaagatca aggaaaagct acgcacagag    3420
caccacgtat ttgagctccc tgatcaccat tccattctag aagggtttga gaggcgagaa    3480
gctgaggata tagtccctta cttgttagcc atttggacgc aggtgaaaac cgtgaattcc    3540
attcaaccgc caaaacaaag atgtgcttta tttgaaagca ataatacatt atgcaacgaa    3600
aacaaatgtt ttcaatgcaa caagacacgg aagaggaat cacagactgt acgaggaact    3660
atattgatac cttgcagaac agcaatgaga ggtggattcc ctttgaatgg cacatacttc    3720
caaactaatg aggtttttgc tgaccatgac tctagcataa accctatcga cgtcccaaca    3780
gaactgatat gggatctaaa aagaagagtc gcatacttag gatcctctgt atcctcgatt    3840
```

```
tgtaaaggtt tatcagtgga agccataaaa tacaatttcc aggaaggata tgtctgtgta    3900 agggattcg  acagggagaa tcgtaagcca aagagtctag tgaaaagact gcattgttct    3960
cacgtagcaa tcagaactaa agagaagaca gaggaatga                           3999
```

<210> SEQ ID NO 8
<211> LENGTH: 1332
<212> TYPE: PRT
<213> ORGANISM: Arabidopsis sp.
<220> FEATURE:
<223> OTHER INFORMATION: DNA demethylase DML2

<400> SEQUENCE: 8

```
Met Glu Val Glu Gly Glu Val Arg Glu Lys Glu Ala Arg Val Lys Gly
 1               5                  10                  15

Arg Gln Pro Glu Thr Glu Val Leu His Gly Leu Pro Gln Glu Gln Ser
             20                  25                  30

Ile Phe Asn Asn Met Gln His Asn His Gln Pro Asp Ser Asp Arg Arg
         35                  40                  45

Arg Leu Ser Leu Glu Asn Leu Pro Gly Leu Tyr Asn Met Ser Cys Thr
     50                  55                  60

Gln Leu Leu Ala Leu Ala Asn Ala Thr Val Ala Thr Gly Ser Ser Ile
 65                  70                  75                  80

Gly Ala Ser Ser Ser Leu Ser Ser Gln His Pro Thr Asp Ser Trp
                 85                  90                  95

Ile Asn Ser Trp Lys Met Asp Ser Asn Pro Trp Thr Leu Ser Lys Met
            100                 105                 110

Gln Lys Gln Gln Tyr Asp Val Ser Thr Pro Gln Lys Phe Leu Cys Asp
        115                 120                 125

Leu Asn Leu Thr Pro Glu Glu Leu Val Ser Thr Ser Thr Gln Arg Thr
    130                 135                 140

Glu Pro Glu Ser Pro Gln Ile Thr Leu Lys Thr Pro Gly Lys Ser Leu
145                 150                 155                 160

Ser Glu Thr Asp His Glu Pro His Asp Arg Ile Lys Lys Ser Val Leu
                165                 170                 175

Gly Thr Gly Ser Pro Ala Ala Val Lys Lys Arg Lys Ile Ala Arg Asn
            180                 185                 190

Asp Glu Lys Ser Gln Leu Glu Thr Pro Thr Leu Lys Arg Lys Lys Ile
        195                 200                 205

Arg Pro Lys Val Val Arg Glu Gly Lys Thr Lys Ala Ser Ser Lys
    210                 215                 220

Ala Gly Ile Lys Lys Ser Ser Ile Ala Ala Thr Ala Thr Lys Thr Ser
225                 230                 235                 240

Glu Glu Ser Asn Tyr Val Arg Pro Lys Arg Leu Thr Arg Arg Ser Ile
                245                 250                 255

Arg Phe Asp Phe Asp Leu Gln Glu Glu Asp Glu Glu Phe Cys Gly Ile
            260                 265                 270

Asp Phe Thr Ser Ala Gly His Val Glu Gly Ser Ser Gly Glu Glu Asn
        275                 280                 285

Leu Thr Asp Thr Thr Leu Gly Met Phe Gly His Val Pro Lys Gly Arg
    290                 295                 300

Arg Gly Gln Arg Arg Ser Asn Gly Phe Lys Lys Thr Asp Asn Asp Cys
305                 310                 315                 320

Leu Ser Ser Met Leu Ser Leu Val Asn Thr Gly Pro Gly Ser Phe Met
                325                 330                 335
```

```
Glu Ser Glu Glu Asp Arg Pro Ser Asp Ser Gln Ile Ser Leu Gly Arg
                340                 345                 350

Gln Arg Ser Ile Met Ala Thr Arg Pro Arg Asn Phe Arg Ser Leu Lys
            355                 360                 365

Lys Leu Leu Gln Arg Ile Ile Pro Ser Lys Arg Asp Arg Lys Gly Cys
        370                 375                 380

Lys Leu Pro Arg Gly Leu Pro Lys Leu Thr Val Ala Ser Lys Leu Gln
385                 390                 395                 400

Leu Lys Val Phe Arg Lys Arg Ser Gln Arg Asn Arg Val Ala Ser
                405                 410                 415

Gln Phe Asn Ala Arg Ile Leu Asp Leu Gln Trp Arg Arg Gln Asn Pro
            420                 425                 430

Thr Gly Thr Ser Leu Ala Asp Ile Trp Glu Arg Ser Leu Thr Ile Asp
        435                 440                 445

Ala Ile Thr Lys Leu Phe Glu Glu Leu Asp Ile Asn Lys Glu Gly Leu
    450                 455                 460

Cys Leu Pro His Asn Arg Glu Thr Ala Leu Ile Leu Tyr Lys Lys Ser
465                 470                 475                 480

Tyr Glu Glu Gln Lys Ala Ile Val Lys Tyr Ser Lys Lys Gln Lys Pro
                485                 490                 495

Lys Val Gln Leu Asp Pro Glu Thr Ser Arg Val Trp Lys Leu Leu Met
            500                 505                 510

Ser Ser Ile Asp Cys Asp Gly Val Asp Gly Ser Asp Glu Glu Lys Arg
        515                 520                 525

Lys Trp Trp Glu Glu Arg Asn Met Phe His Gly Arg Ala Asn Ser
530                 535                 540

Phe Ile Ala Arg Met Arg Val Val Gln Gly Asn Arg Thr Phe Ser Pro
545                 550                 555                 560

Trp Lys Gly Ser Val Val Asp Ser Val Val Gly Val Phe Leu Thr Gln
                565                 570                 575

Asn Val Ala Asp His Ser Ser Ser Ala Tyr Met Asp Leu Ala Ala
            580                 585                 590

Glu Phe Pro Val Glu Trp Asn Phe Asn Lys Gly Ser Cys His Glu Glu
        595                 600                 605

Trp Gly Ser Ser Val Thr Gln Glu Thr Ile Leu Asn Leu Asp Pro Arg
    610                 615                 620

Thr Gly Val Ser Thr Pro Arg Ile Arg Asn Pro Thr Arg Val Ile Ile
625                 630                 635                 640

Glu Glu Ile Asp Asp Glu Asn Asp Ile Asp Ala Val Cys Ser Gln
                645                 650                 655

Glu Ser Ser Lys Thr Ser Asp Ser Ser Ile Thr Ser Ala Asp Gln Ser
            660                 665                 670

Lys Thr Met Leu Leu Asp Pro Phe Asn Thr Val Leu Met Asn Glu Gln
        675                 680                 685

Val Asp Ser Gln Met Val Lys Gly Lys Gly His Ile Pro Tyr Thr Asp
    690                 695                 700

Asp Leu Asn Asp Leu Ser Gln Gly Ile Ser Met Val Ser Ser Ala Ser
705                 710                 715                 720

Thr His Cys Glu Leu Asn Leu Asn Glu Val Pro Pro Glu Val Glu Leu
                725                 730                 735

Cys Ser His Gln Gln Asp Pro Glu Ser Thr Ile Gln Thr Gln Asp Gln
            740                 745                 750

Gln Glu Ser Thr Arg Thr Glu Asp Val Lys Lys Asn Arg Lys Lys Pro
```

-continued

```
                755                 760                 765
Thr Thr Ser Lys Pro Lys Lys Ser Lys Glu Ser Ala Lys Ser Thr
770                 775                 780

Gln Lys Lys Ser Val Asp Trp Asp Ser Leu Arg Lys Glu Ala Glu Ser
785                 790                 795                 800

Gly Gly Arg Lys Arg Glu Thr Glu Arg Thr Met Asp Thr Val Asp
            805                 810                 815

Trp Asp Ala Leu Arg Cys Thr Asp Val His Lys Ile Ala Asn Ile Ile
            820                 825                 830

Ile Lys Arg Gly Met Asn Asn Met Leu Ala Glu Arg Ile Lys Ala Phe
            835                 840                 845

Leu Asn Arg Leu Val Lys Lys His Gly Ser Ile Asp Leu Glu Trp Leu
850                 855                 860

Arg Asp Val Pro Pro Asp Lys Ala Lys Glu Tyr Leu Leu Ser Ile Asn
865                 870                 875                 880

Gly Leu Gly Leu Lys Ser Val Glu Cys Val Arg Leu Leu Ser Leu His
            885                 890                 895

Gln Ile Ala Phe Pro Val Asp Thr Asn Val Gly Arg Ile Ala Val Arg
            900                 905                 910

Leu Gly Trp Val Pro Leu Gln Pro Leu Pro Asp Glu Leu Gln Met His
            915                 920                 925

Leu Leu Glu Leu Tyr Pro Val Leu Glu Ser Val Gln Lys Tyr Leu Trp
930                 935                 940

Pro Arg Leu Cys Lys Leu Asp Gln Lys Thr Leu Tyr Glu Leu His Tyr
945                 950                 955                 960

His Met Ile Thr Phe Gly Lys Val Phe Cys Thr Lys Val Lys Pro Asn
            965                 970                 975

Cys Asn Ala Cys Pro Met Lys Ala Glu Cys Arg His Tyr Ser Ser Ala
            980                 985                 990

Arg Ala Ser Ala Arg Leu Ala Leu Pro Glu Pro Glu Glu Ser Asp Arg
            995                 1000                1005

Thr Ser Val Met Ile His Glu Arg Arg Ser Lys Arg Lys Pro Val Val
1010                1015                1020

Val Asn Phe Arg Pro Ser Leu Phe Leu Tyr Gln Glu Lys Glu Gln Glu
1025                1030                1035                1040

Ala Gln Arg Ser Gln Asn Cys Glu Pro Ile Ile Glu Glu Pro Ala Ser
            1045                1050                1055

Pro Glu Pro Glu Tyr Ile Glu His Asp Ile Glu Asp Tyr Pro Arg Asp
            1060                1065                1070

Lys Asn Asn Val Gly Thr Ser Glu Asp Pro Trp Glu Asn Lys Asp Val
            1075                1080                1085

Ile Pro Thr Ile Ile Leu Asn Lys Glu Ala Gly Thr Ser His Asp Leu
            1090                1095                1100

Val Val Asn Lys Glu Ala Gly Thr Ser His Asp Leu Val Val Leu Ser
1105                1110                1115                1120

Thr Tyr Ala Ala Ala Ile Pro Arg Arg Lys Leu Lys Ile Lys Glu Lys
            1125                1130                1135

Leu Arg Thr Glu His His Val Phe Glu Leu Pro Asp His His Ser Ile
            1140                1145                1150

Leu Glu Gly Phe Glu Arg Arg Glu Ala Glu Asp Ile Val Pro Tyr Leu
            1155                1160                1165

Leu Ala Ile Trp Thr Pro Gly Glu Thr Val Asn Ser Ile Gln Pro Pro
            1170                1175                1180
```

Lys Gln Arg Cys Ala Leu Phe Glu Ser Asn Asn Thr Leu Cys Asn Glu
1185                1190                1195                1200

Asn Lys Cys Phe Gln Cys Asn Lys Thr Arg Glu Glu Ser Gln Thr
            1205                1210                1215

Val Arg Gly Thr Ile Leu Ile Pro Cys Arg Thr Ala Met Arg Gly Gly
        1220                1225                1230

Phe Pro Leu Asn Gly Thr Tyr Phe Gln Thr Asn Glu Val Phe Ala Asp
            1235                1240                1245

His Asp Ser Ser Ile Asn Pro Ile Asp Val Pro Thr Glu Leu Ile Trp
        1250                1255                1260

Asp Leu Lys Arg Arg Val Ala Tyr Leu Gly Ser Ser Val Ser Ser Ile
1265                1270                1275                1280

Cys Lys Gly Leu Ser Val Glu Ala Ile Lys Tyr Asn Phe Gln Glu Gly
            1285                1290                1295

Tyr Val Cys Val Arg Gly Phe Asp Arg Glu Asn Arg Lys Pro Lys Ser
            1300                1305                1310

Leu Val Lys Arg Leu His Cys Ser His Val Ala Ile Arg Thr Lys Glu
        1315                1320                1325

Lys Thr Glu Glu
    1330

<210> SEQ ID NO 9
<211> LENGTH: 3318
<212> TYPE: DNA
<213> ORGANISM: Arabidopsis sp.
<220> FEATURE:
<223> OTHER INFORMATION: DNA demethylase DML3 coding sequence

<400> SEQUENCE: 9

```
atggagtttt caatagatcg agacaaaaat cttctcatgg ttgttccaga gacacgtatc      60
aaaacaaaac aatttgaaaa agtttatgtg agaagaaaat ctattaagct tccacaaaat     120
tcggtaattt ttccacatga aatcaaagat cgtggtgaag aagagagtaa ggagaaggaa     180
tttttccatc aagatggttc acaacacact tatcaaaatg gcgagacaaa gaattcaaaa     240
gagcatgaaa gaaagtgtga tgaatcagca catcttcaag ataattcaca aaccacccat     300
aaaaaaaagg agaagaagaa ttcaaaagaa aagcatggaa taaagcattc tgaatcagaa     360
catcttcaag atgatatttc gcaacgtgtt accggaaaag gaaggagaag gaattcaaaa     420
gggacaccaa aaaaactgag gtttaatagg cctcggatct tggaagacgg aaagaaacca     480
agaaatcccg ccaccactcg actgagaact atatccaaca agaggaggaa aaaggacata     540
gacagtgaag atgaagttat accagagctt gcaactccaa caaggaaag ctttccaaag     600 agaagaaaga acgagaagat taagagatcc gtggctcgga ctttaaattt taagcaagaa     660
attgttctga gttgtcttga gttcgacaag atttgtggac aattttttcc aagagggaaa     720
aagaggacca ccacacgacg cagatatgat ttcctttgtt ttttacttcc gatgcctgtt     780
tggaaaaaac aatcaagaag gtctaagcgt aggaaaaata tggtcagatg ggctagaatt     840
gcttcttctt caaaactgct agaagaaact ttgcctttaa tagtaagtca tccgactatt     900
aatggacaag cagatgcttc tttacacatt gatgacacac tcgtgagaca tgtagtctca     960
aagcaaacca gaaaagtgc taacaatgtc attgagcatt taaatcgaca aataacttat    1020
cagaaagatc acggtctctc atctctggca gatgttcctt tgcacattga agatacacta    1080
ataaaatcgg ctagttctgt actttcagaa cgacccatca gaaaactaa ggatattgct    1140
```

```
aagttaatca aagatatggg aagattaaag atcaataaaa aggtaacaac gatgatcaaa    1200
gctgacaaga aactcgttac ggcaaaggtt aatcttgatc cagagaccat taaagagtgg    1260
gatgtcttaa tggtgaatga ttcaccaagc cgatcatatg acgataagga gacggaggcc    1320
aaatggaaaa aagaaagaga gattttcaa acccggatag atcttttcat taaccgatg     1380 catcgcttac aaggcaatag aaagtttaaa cagtggaaag gctcagttgt tgactcagtg    1440
gttggagttt ttttgacaca aaatactacc gactatcttt caagcaacgc gtttatgagc    1500
gtggctgcaa aatttcctgt tgatgcaaga gaaggtctat catactatat tgaggaacct    1560
caagatgcta aaagttctga atgtatcatt ttatctgatg agtcaatatc aaaggtggaa    1620
gatcatgaga atactgcaaa aaggaaaaac gagaaaaccg gtattataga agatgagata    1680
gttgactgga acaatcttag aaggatgtac acgaaagaag gatctcgtcc cgaaaatgcat   1740 atggactctg ttaattggag tgacgtgaga ttatctggcc aaaatgtttt ggaaaccacc    1800
attaaaaaac gtggacaatt caggattctt tcagaaagaa tattgaaatt tcttaacgat    1860
gaagttaacc aaaatggaaa tattgatctg gaatggcttc gaaatgctcc atcacattta    1920
gtgaagagat atctgttgga aatcgaaggg atagggctga aaagtgctga gtgcgtacga    1980
ctgttaggac ttaaacatca tgcgtttccg gttgacacaa atgttggtcg tatagcagtt    2040
cgactaggtc tggttcctct tgaaccttta ccaaatggag ttcaaatgca tcaactattc    2100 gagtacccctt caatggattc gattcaaaag taccttttggc cacgattgtg taaacttccc   2160
caagaaactt tatatgaact acattatcaa atgataacat ttggaaaggt tttctgcaca    2220
aaaactattc ctaattgtaa tgcatgtcca atgaagtcag aatgcaaata ttttgcaagt    2280
gcatatgtca gttctaaagt tcttctcgag agtccagaag aaaagatgca tgagcctaat    2340 actttatga atgcacattc tcaagacgtt gctgtagata tgacatcaaa tataaatttg     2400
gtagaagaat gtgtttcttc tggatgtagc gatcaagcta tatgttataa gccactagtt    2460
gagtttcctt cgtccccaag agcggaaatt cccgagtcaa cagacattga agatgttcca    2520
ttcatgaatc tttatcagtc atatgctagt gttcctaaaa ttgattttga cttggatgca    2580
ttgaagaaaa gtgtagaaga tgcacttgta ataagtggca ggatgagcag ttctgatgaa    2640
gaaatatcaa aagcattagt gattcccact cctgaaaatg catgcattcc tatcaaacca    2700
cctcggaaaa tgaagtatta aatcgacta agaactgaac atgtggttta tgtgcttcct     2760
gataatcatg agctgctaca cgattttgag agaagaaaac ttgatgatcc aagtccttac    2820
cttcttgcga tttggcaacc aggtgaaaca tcatcctcgt tcgttccacc aaagaaaaag    2880
tgtagttctg atggatcaaa gctttgcaag ataaagaatt gttcatattg ttggactata    2940
cgagaacaaa actccaacat ttttcgcgga acaattttga ttccatgtag aacagcaatg    3000 cgagggggcct ttccacttaa tggaacatac ttccaaacca atgaggtttt tgctgatcat   3060
gagacaagct taaccccat tgtctttcgt agggagttgt gtaagggact agaaaaacgt     3120
gcactatatt gtggttcaac agtgacatct attttaaac ttttagacac aagacggatt     3180
gaactttgct tttggacagg gtttttatgt ttgagagcat tgatcgaaa gcaacgagat     3240 ccaaaagagc ttgtccgacg tctacacact ccacctgatg agagagggcc aaagtttatg    3300
agtgatgatg atatatag                                                  3318
```

<210> SEQ ID NO 10
<211> LENGTH: 1099
<212> TYPE: PRT
<213> ORGANISM: Arabidopsis sp.

<220> FEATURE:
<223> OTHER INFORMATION: DNA demethylase DML3

<400> SEQUENCE: 10

```
Met Glu Phe Ser Ile Asp Arg Asp Lys Asn Leu Leu Met Val Val Pro
  1               5                  10                  15

Glu Thr Arg Ile Lys Thr Lys Gln Phe Glu Lys Val Tyr Val Arg Arg
                 20                  25                  30

Lys Ser Ile Lys Leu Pro Gln Asn Ser Met Val His Asn Thr Leu Ile
             35                  40                  45

Lys Met Ala Arg Gln Arg Ile Gln Lys Ser Met Lys Glu Ser Val Met
         50                  55                  60

Asn Gln His Ile Phe Lys Asn Phe Asp Ser Tyr Leu Ser Val Ile Tyr
 65                  70                  75                  80

His Pro Cys Cys Phe Val Ile Asn Asn Ser Gln Thr Thr His Lys Lys
                 85                  90                  95

Lys Glu Lys Lys Asn Ser Lys Glu Lys His Gly Ile Lys His Ser Glu
            100                 105                 110

Ser Glu His Leu Gln Asp Asp Ile Ser Gln Arg Val Thr Gly Lys Gly
            115                 120                 125

Arg Arg Arg Asn Ser Lys Gly Thr Pro Lys Lys Leu Arg Phe Asn Arg
        130                 135                 140

Pro Arg Ile Leu Glu Asp Gly Lys Lys Pro Arg Asn Pro Ala Thr Thr
145                 150                 155                 160

Arg Leu Arg Thr Ile Ser Asn Lys Arg Arg Lys Lys Asp Ile Asp Ser
                165                 170                 175

Glu Asp Glu Val Ile Pro Glu Leu Ala Thr Pro Thr Lys Glu Ser Phe
            180                 185                 190

Pro Lys Arg Arg Lys Asn Glu Lys Ile Lys Arg Ser Val Ala Arg Thr
        195                 200                 205

Leu Asn Phe Lys Gln Glu Ile Val Leu Ser Cys Leu Glu Phe Asp Lys
    210                 215                 220

Ile Cys Gly Pro Ile Phe Pro Arg Gly Lys Lys Arg Thr Thr Thr Arg
225                 230                 235                 240

Arg Arg Tyr Asp Phe Leu Cys Phe Leu Leu Pro Met Pro Val Trp Lys
                245                 250                 255

Lys Gln Ser Arg Arg Ser Lys Arg Arg Lys Asn Met Val Arg Trp Ala
            260                 265                 270

Arg Ile Ala Ser Ser Ser Lys Leu Leu Glu Glu Thr Leu Pro Leu Ile
        275                 280                 285

Val Ser His Pro Thr Ile Asn Gly Gln Ala Asp Ala Ser Leu His Ile
    290                 295                 300

Asp Asp Thr Leu Val Arg His Val Val Ser Lys Gln Thr Lys Lys Ser
305                 310                 315                 320

Ala Asn Asn Val Ile Glu His Leu Asn Arg Gln Ile Thr Tyr Gln Lys
                325                 330                 335

Asp His Gly Leu Ser Ser Leu Ala Asp Val Pro Leu His Ile Glu Asp
            340                 345                 350

Thr Leu Ile Lys Ser Ala Ser Ser Val Leu Ser Glu Arg Pro Ile Lys
        355                 360                 365

Lys Thr Lys Asp Ile Ala Lys Leu Ile Lys Asp Met Gly Arg Leu Lys
    370                 375                 380

Ile Asn Lys Lys Val Thr Thr Met Ile Lys Ala Asp Lys Lys Leu Val
385                 390                 395                 400
```

-continued

```
Thr Ala Lys Val Asn Leu Asp Pro Glu Thr Ile Lys Glu Trp Asp Val
                405                 410                 415
Leu Met Val Asn Asp Ser Pro Ser Arg Ser Tyr Asp Lys Glu Thr
            420                 425                 430
Glu Ala Lys Trp Lys Lys Glu Arg Glu Ile Phe Gln Thr Arg Ile Asp
            435                 440                 445
Leu Phe Ile Asn Arg Met His Arg Leu Gln Gly Asn Arg Lys Phe Lys
450                 455                 460
Gln Trp Lys Gly Ser Val Val Asp Ser Val Val Gly Val Phe Leu Thr
465                 470                 475                 480
Gln Asn Thr Thr Asp Tyr Leu Ser Ser Asn Ala Phe Met Ser Val Ala
                485                 490                 495
Ala Lys Phe Pro Val Asp Ala Arg Glu Gly Leu Ser Tyr Tyr Ile Glu
                500                 505                 510
Glu Pro Gln Asp Ala Lys Ser Ser Glu Cys Ile Ile Leu Ser Asp Glu
            515                 520                 525
Ser Ile Ser Lys Val Glu Asp His Glu Asn Thr Ala Lys Arg Lys Asn
            530                 535                 540
Glu Lys Thr Gly Ile Ile Glu Asp Glu Ile Val Asp Trp Asn Asn Leu
545                 550                 555                 560
Arg Arg Met Tyr Thr Lys Glu Gly Ser Arg Pro Glu Met His Met Asp
                565                 570                 575
Ser Val Asn Trp Ser Asp Val Arg Leu Ser Gly Gln Asn Val Leu Glu
                580                 585                 590
Thr Thr Ile Lys Lys Arg Gly Gln Phe Arg Ile Leu Ser Glu Arg Ile
            595                 600                 605
Leu Lys Phe Leu Asn Asp Glu Val Asn Gln Asn Gly Asn Ile Asp Leu
            610                 615                 620
Glu Trp Leu Arg Asn Ala Pro Ser His Leu Val Lys Arg Tyr Leu Leu
625                 630                 635                 640
Glu Ile Glu Gly Ile Gly Leu Lys Ser Ala Glu Cys Val Arg Leu Leu
                645                 650                 655
Gly Leu Lys His His Ala Phe Pro Val Asp Thr Asn Val Gly Arg Ile
                660                 665                 670
Ala Val Arg Leu Gly Leu Val Pro Leu Glu Pro Leu Pro Asn Gly Val
            675                 680                 685
Gln Met His Gln Leu Phe Glu Tyr Pro Ser Met Asp Ser Ile Gln Lys
            690                 695                 700
Tyr Leu Trp Pro Arg Leu Cys Lys Leu Pro Gln Glu Thr Leu Tyr Glu
705                 710                 715                 720
Leu His Tyr Gln Met Ile Thr Phe Gly Lys Val Phe Cys Thr Lys Thr
                725                 730                 735
Ile Pro Asn Cys Asn Ala Cys Pro Met Lys Ser Glu Cys Lys Tyr Phe
                740                 745                 750
Ala Ser Ala Tyr Val Ser Ser Lys Val Leu Leu Glu Ser Pro Glu Glu
            755                 760                 765
Lys Met His Glu Pro Asn Thr Phe Met Asn Ala His Ser Gln Asp Val
            770                 775                 780
Ala Val Asp Met Thr Ser Asn Ile Asn Leu Val Glu Glu Cys Val Ser
785                 790                 795                 800
Ser Gly Cys Ser Asp Gln Ala Ile Cys Tyr Lys Pro Leu Val Glu Phe
                805                 810                 815
```

-continued

```
Pro Ser Ser Pro Arg Ala Glu Ile Pro Glu Ser Thr Asp Ile Glu Asp
            820                 825                 830

Val Pro Phe Met Asn Leu Tyr Gln Ser Tyr Ala Ser Val Pro Lys Ile
        835                 840                 845

Asp Phe Asp Leu Asp Ala Leu Lys Lys Ser Val Glu Asp Ala Leu Val
    850                 855                 860

Ile Ser Gly Arg Met Ser Ser Asp Glu Glu Ile Ser Lys Ala Leu
865                 870                 875                 880

Val Ile Pro Thr Pro Glu Asn Ala Cys Ile Pro Ile Lys Pro Pro Arg
                885                 890                 895

Lys Met Lys Tyr Tyr Asn Arg Leu Arg Thr Glu His Val Val Tyr Val
            900                 905                 910

Leu Pro Asp Asn His Glu Leu Leu His Asp Phe Glu Arg Arg Lys Leu
        915                 920                 925

Asp Asp Pro Ser Pro Tyr Leu Leu Ala Ile Trp Gln Pro Gly Glu Thr
    930                 935                 940

Ser Ser Ser Phe Val Pro Pro Lys Lys Cys Ser Ser Asp Gly Ser
945                 950                 955                 960

Lys Leu Cys Lys Ile Lys Asn Cys Ser Tyr Cys Trp Thr Ile Arg Glu
                965                 970                 975

Gln Asn Ser Asn Ile Phe Arg Gly Thr Ile Leu Ile Pro Cys Arg Thr
            980                 985                 990

Ala Met Arg Gly Ala Phe Pro Leu Asn Gly Thr Tyr Phe Gln Thr Asn
        995                 1000                1005

Glu Val Phe Ala Asp His Glu Thr Ser Leu Asn Pro Ile Val Phe Arg
    1010                1015                1020

Arg Glu Leu Cys Lys Gly Leu Glu Lys Arg Ala Leu Tyr Cys Gly Ser
1025                1030                1035                1040

Thr Val Thr Ser Ile Phe Lys Leu Leu Asp Thr Arg Arg Ile Glu Leu
                1045                1050                1055

Cys Phe Trp Thr Gly Phe Leu Cys Leu Arg Ala Phe Arg Lys Gln
            1060                1065                1070

Arg Asp Pro Lys Glu Leu Val Arg Arg Leu His Thr Pro Pro Asp Glu
        1075                1080                1085

Arg Gly Pro Lys Phe Met Ser Asp Asp Ile
    1090                1095
```

<210> SEQ ID NO 11
<211> LENGTH: 5190
<212> TYPE: DNA
<213> ORGANISM: Artificial Sequence
<220> FEATURE:
<223> OTHER INFORMATION: Description of Artificial Sequence:synthetic
      ROS1-DME chimera, construct with DME amino acids
      1,192-1,402 deleted and ROS1 amino acids 859-1,069
      inserted, DME containing ROS1 DNA glycolase domain

<400> SEQUENCE: 11

```
atgcagagca ttatggactc gtctgctgtt aatgcgacgg aagctactga acaaaatgat      60
ggcagcagac aagatgttct ggagttcgac cttaacaaaa ctcctcagca gaaaccctcc     120
aaaaggaaaa ggaagttcat gcccaaggtg gtcgtggaag caaacctaa agaaagcca      180 cgcaaacctg cagaacttcc caaagtggtc gtggaaggca acctaaaag gaagccacgc     240 aaagctgcaa ctcaggaaaa agtgaaatct aagaaaccg ggagtgccaa aagaaaaat      300 ttgaaagaat cagcaactaa aaagccagcc aatgttggag atatgagcaa caaaagccct     360
```

```
gaagtcacac tcaaaagttg cagaaaagct ttgaattttg acttggagaa tcctggagat    420
gcgaggcaag gtgactctga gtctgaaatt gtccagaaca gtagtggcgc aaactcgttt    480
tctgagatca gagatgccat tggtggaact aatggtagtt tcctggattc agtgtcacaa    540
atagacaaga ccaatggatt gggggctatg aaccagccac ttgaagtgtc aatgggaaac    600
cagccagata aactatctac aggagcgaaa ctggccagag accaacaacc tgatttattg    660
actagaaacc agcaatgcca gttcccagtg caacccagag acacccagtt cccaatggaa    720
aaccaacaag cttggcttca gatgaaaaac caacttattg gctttccatt tggtaaccag    780
caacctcgca tgaccataag aaaccagcag ccttgcttgg ccatgggtaa tcaacaacct    840
atgtatctga taggaactcc acggcctgca ttagtaagtg gaaaccagca actaggaggt    900
ccccaaggaa acaagcggcc tatatttttg aatcaccaga cttgtttacc tgctggaaat    960
cagctatatg gatcacctac agacatgcat caacttgtta tgtcaaccgg agggcaacaa   1020
catggactac tgataaaaaa ccagcaacct ggatcattaa taagaggcca gcagccttgc   1080
gtacctttga ttgaccagca acctgcaact ccaaaaggtt ttactcactt gaatcagatg   1140
gtagctacca gcatgtcatc gcctgggctt cgacctcatt ctcagtcaca agttcctaca   1200
acatatctac atgtggaatc tgtttccagg attttgaatg ggactacagg tacatgccag   1260
agaagcaggg ctcctgcata cgattcttta cagcaagata tccatcaagg aaataagtac   1320
atactttctc atgagatatc caatggtaat gggtgcaaga aagcgttacc tcaaaactct   1380
tctctgccaa ctccaattat ggctaaactt gaggaagcca ggggctcgaa gagacagtat   1440
catcgtgcaa tgggacagac ggaaaagcat gatctaaact tagctcaaca gattgctcaa   1500
tcacaagatg tggagagaca taacagcagc acgtgtgtgg aatatttaga tgctgcaaag   1560
aaaacgaaaa tccagaaagt agtccaagaa aatttgcatg gcatgccacc tgaggttata   1620
gaaatcgagg atgatccaac tgatggggca agaaaaggta aaaatactgc cagcatcagt   1680
aaaggtgcat ctaaaggaaa ctcgtctcca gttaaaaaga cagcagaaaa ggagaaatgt   1740
attgtcccaa aaacgcctgc aaaaaagggt cgagcaggta gaaaaaaatc agtacctccg   1800
cctgctcatg cctcagagat ccagcttttg gcaacctactc ctccaaagac acctttatca   1860
agaagcaagc ctaaaggaaa agggagaaag tccatacaag attcaggaaa agcaagaggt   1920
ccatcaggag aacttctgtg tcaggattct attgcggaaa taatttacag gatgcaaaat   1980
ctgtatctag gagacaaaga aagagaacaa gagcaaaatg caatggtctt gtacaaagga   2040
gatggtgcac ttgttcccta tgagagcaag aagcgaaaac caagacccaa agttgacatt   2100
gacgatgaaa caactcgcat atggaactta ctgatgggga aggagatgaa aaagaaggg    2160 gatgaagaga aggataaaaa aaagagaag tggtgggaag aagaaagaag agtcttccga   2220
ggaagggctg attccttcat cgctcgcatg cacctggtac aaggagatag acgtttttcg   2280
ccatggaagg gatcggtggt tgattcggtc attggagttt ccttacaca gaatgtctcg    2340 gatcaccttt caagctctgc gttcatgtct ctagctgctc gattccctcc aaaattaagc   2400
agcagccgag aagatgaaag gaatgttaga agcgtagttg ttgaagatcc agaaggatgc   2460
attctgaact taaatgaaat tccttcgtgg caggaaaagg ttcaacatcc atctgacatg   2520
gaagtttctg gggttgatag tggatcaaaa gagcagctaa gggactgttc aaactctgga   2580
attgaaagat ttaatttctt agagaagagt attcaaaatt tagaagagga agtattatca   2640
tcacaagatt cttttgatcc ggcgatattt cagtcgtgtg ggagagttgg atcctgttca   2700
tgttccaaat cagacgcaga gtttcctaca accaggtgtg aaacaaaaac tgtcagtgga   2760
```

```
acatcacaat cagtgcaaac tgggagccca aacttgtctg atgaaatttg tcttcaaggg    2820
aatgagagac cgcatctata tgaaggatct ggtgatgttc agaaacaaga aactacaaat    2880
gtcgctcaga agaaacctga tcttgaaaaa acaatgaatt ggaaagactc tgtctgtttt    2940
ggtcagccaa gaaatgatac taattggcaa acaactcctt ccagcagcta tgagcagtgt    3000
gcgactcgac agccacatgt actagacata gaggattttg aatgcaagg tgaaggcctt    3060 ggttattctt ggatgtccat ctcaccaaga gttgacagag taaagaacaa aaatgtacca    3120
cgcaggtttt tcagacaagg tggaagtgtt ccaagagaat tcacaggtca gatcatacca    3180
tcaacgcctc atgaattacc aggaatggga ttgtccggtt cctcaagcgc cgtccaagaa    3240
caccaggacg atacccaaca taatcaacaa gatgagatga ataaagcatc ccatttacaa    3300
aaaacatttt tggatctgct caactcctct gaagaatgcc ttacaagaca gtccagtacc    3360
aaacagaaca tcacggatgg ctgtctaccg agagatagaa ctgctgaaga cgtggttgat    3420
ccgctcagta acaattcaag cttacagaac atattggtcg aatcaaattc cagcaataaa    3480
gagcagacgg cagttgaata caaggagaca aatgccacta ttttacgaga gatgaaaggg    3540
acgcttgctg atgggaaaaa gcctacaagc cagtgggatt gtttaagaag agaagcccaa    3600
gctagagcag gaattagaga aaaaacaaga agtacaatgg acaccgtgga ttggaaggca    3660
atacgagcag cagatgttaa ggaagttgct gaaacaatca agagtcgcgg gatgaaccat    3720
aaacttgcag aacgtataca gggcttcctt gatcgactgg taaatgacca tggaagtatc    3780
gatcttgaat ggttgagaga tgttccacca gataaagcaa aagaatatct tctgagcttt    3840
aacggattgg gactgaaaag tgtggagtgt gtgcggcttc taacacttca ccatcttgcc    3900
tttccagttg atacaaatgt tgggcgcata gccgtcagac ttggatgggt gccccttcag    3960
ccgctcccag agtcacttca gttgcatctt ctggaaatgt atcctatgct tgaatctatt    4020
caaaagtatc tttggccccg tctctgcaaa ctcgaccaaa aaacattgta tgagttgcac    4080
taccagatga ttacttttgg aaaggtcttt tgcacaaaga gcaaacctaa ttgcaatgca    4140
tgtccgatga aggagaatg cagacatttt gccagtgcgt ttgcaagtgc aaggcttgct    4200
ttaccagcac cagaggagag gagcttaaca agtgcaacta ttccggtccc tcccgagtcc    4260
tttcctcctg tagccatccc gatgatagaa ctacctcttc cgttggagaa atccctagca    4320
agtggagcac catcgaatag agaaaactgt gaaccaataa ttgaagagcc ggcctcgccc    4380
gggcaagagt gcactgaaat aaccgagagt gatattgaag atgcttacta caatgaggac    4440
cctgacgaga tcccaacaat aaaactcaac attgaacagt ttggaatgac tctacgggaa    4500
cacatggaaa gaaacatgga gctccaagaa ggtgacatgt ccaaggcttt ggttgctttg    4560
catccaacaa ctacttctat tccaactccc aaactaaaga acattagccg tctcaggaca    4620
gagcaccaag tgtacgagct cccagattca catcgtctcc ttgatggtat ggataaaaga    4680
gaaccagatg atccaagtcc ttatctctta gctatatgga caccaggtga acagcgaat    4740 tcggcacaac cgcctgaaca gaagtgtgga gggaaagcgt ctggcaaaat gtgctttgac    4800
gagacttgtt ctgagtgtaa cagtctgagg gaagcaaact cacagacagt tcgaggaact    4860
cttctgatac cttgtcggac tgccatgaga ggaagttttc cgctcaacgg gacatatttc    4920
caagtcaacg agttatttgc agaccacgag tccagtctca aacccatcga tgttcctaga    4980
gattggatat gggatctccc aagaaggact gtttacttcg gaacatcagt aacatcaata    5040
ttcagaggtc tttcaacgga gcagatacag ttctgctttt ggaaaggatt cgtatgtgtc    5100
```

```
cgtggattcg aacagaagac aagagcaccg cgtccattaa tggcaaggtt gcattttcct    5160
gcgagcaaat tgaagaacaa caaaacctaa                                     5190
```

<210> SEQ ID NO 12
<211> LENGTH: 1729
<212> TYPE: PRT
<213> ORGANISM: Artificial Sequence
<220> FEATURE:
<223> OTHER INFORMATION: Description of Artificial Sequence:synthetic
      ROS1-DME chimera, construct with DME amino acids
      1,192-1,402 deleted and ROS1 amino acids 859-1,069
      inserted, DME containing ROS1 DNA glycolase domain

<400> SEQUENCE: 12

```
Met Gln Ser Ile Met Asp Ser Ala Val Asn Ala Thr Glu Ala Thr
 1               5                  10                  15

Glu Gln Asn Asp Gly Ser Arg Gln Asp Val Leu Glu Phe Asp Leu Asn
                20                  25                  30

Lys Thr Pro Gln Gln Lys Pro Ser Lys Arg Lys Arg Lys Phe Met Pro
            35                  40                  45

Lys Val Val Glu Gly Lys Pro Arg Lys Pro Arg Lys Pro Ala
        50                  55                  60

Glu Leu Pro Lys Val Val Glu Gly Lys Pro Lys Arg Lys Pro Arg
 65                  70                  75                  80

Lys Ala Ala Thr Gln Glu Lys Val Lys Ser Lys Glu Thr Gly Ser Ala
                85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
    130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190

Pro Leu Glu Val Ser Met Gly Asn Gln Pro Asp Lys Leu Ser Thr Gly
        195                 200                 205

Ala Lys Leu Ala Arg Asp Gln Gln Pro Asp Leu Leu Thr Arg Asn Gln
    210                 215                 220

Gln Cys Gln Phe Pro Val Ala Thr Gln Asn Thr Gln Phe Pro Met Glu
225                 230                 235                 240

Asn Gln Gln Ala Trp Leu Gln Met Lys Asn Gln Leu Ile Gly Phe Pro
                245                 250                 255

Phe Gly Asn Gln Gln Pro Arg Met Thr Ile Arg Asn Gln Gln Pro Cys
            260                 265                 270

Leu Ala Met Gly Asn Gln Gln Pro Met Tyr Leu Ile Gly Thr Pro Arg
        275                 280                 285

Pro Ala Leu Val Ser Gly Asn Gln Gln Leu Gly Gly Pro Gln Gly Asn
    290                 295                 300

Lys Arg Pro Ile Phe Leu Asn His Gln Thr Cys Leu Pro Ala Gly Asn
305                 310                 315                 320

Gln Leu Tyr Gly Ser Pro Thr Asp Met His Gln Leu Val Met Ser Thr
                325                 330                 335
```

```
Gly Gly Gln Gln His Gly Leu Leu Ile Lys Asn Gln Gln Pro Gly Ser
            340                 345                 350

Leu Ile Arg Gly Gln Gln Pro Cys Val Pro Leu Ile Asp Gln Gln Pro
            355                 360                 365

Ala Thr Pro Lys Gly Phe Thr His Leu Asn Gln Met Val Ala Thr Ser
370                 375                 380

Met Ser Ser Pro Gly Leu Arg Pro His Ser Gln Ser Gln Val Pro Thr
385                 390                 395                 400

Thr Tyr Leu His Val Glu Ser Val Ser Arg Ile Leu Asn Gly Thr Thr
            405                 410                 415

Gly Thr Cys Gln Arg Ser Arg Ala Pro Ala Tyr Asp Ser Leu Gln Gln
            420                 425                 430

Asp Ile His Gln Gly Asn Lys Tyr Ile Leu Ser His Glu Ile Ser Asn
            435                 440                 445

Gly Asn Gly Cys Lys Lys Ala Leu Pro Gln Asn Ser Ser Leu Pro Thr
450                 455                 460

Pro Ile Met Ala Lys Leu Glu Glu Ala Arg Gly Ser Lys Arg Gln Tyr
465                 470                 475                 480

His Arg Ala Met Gly Gln Thr Glu Lys His Asp Leu Asn Leu Ala Gln
            485                 490                 495

Gln Ile Ala Gln Ser Gln Asp Val Glu Arg His Asn Ser Ser Thr Cys
            500                 505                 510

Val Glu Tyr Leu Asp Ala Ala Lys Lys Thr Lys Ile Gln Lys Val Val
            515                 520                 525

Gln Glu Asn Leu His Gly Met Pro Pro Glu Val Ile Glu Ile Glu Asp
            530                 535                 540

Asp Pro Thr Asp Gly Ala Arg Lys Gly Lys Asn Thr Ala Ser Ile Ser
545                 550                 555                 560

Lys Gly Ala Ser Lys Gly Asn Ser Ser Pro Val Lys Lys Thr Ala Glu
            565                 570                 575

Lys Glu Lys Cys Ile Val Pro Lys Thr Pro Ala Lys Lys Gly Arg Ala
            580                 585                 590

Gly Arg Lys Lys Ser Val Pro Pro Ala His Ala Ser Glu Ile Gln
            595                 600                 605

Leu Trp Gln Pro Thr Pro Pro Lys Thr Pro Leu Ser Arg Ser Lys Pro
            610                 615                 620

Lys Gly Lys Gly Arg Lys Ser Ile Gln Asp Ser Gly Lys Ala Arg Gly
625                 630                 635                 640

Pro Ser Gly Glu Leu Leu Cys Gln Asp Ser Ile Ala Glu Ile Ile Tyr
            645                 650                 655

Arg Met Gln Asn Leu Tyr Leu Gly Asp Lys Glu Arg Glu Gln Glu Gln
            660                 665                 670

Asn Ala Met Val Leu Tyr Lys Gly Asp Gly Ala Leu Val Pro Tyr Glu
            675                 680                 685

Ser Lys Lys Arg Lys Pro Arg Pro Lys Val Asp Ile Asp Asp Glu Thr
            690                 695                 700

Thr Arg Ile Trp Asn Leu Leu Met Gly Lys Gly Asp Glu Lys Glu Gly
705                 710                 715                 720

Asp Glu Glu Lys Asp Lys Lys Glu Lys Trp Trp Glu Glu Arg
            725                 730                 735

Arg Val Phe Arg Gly Arg Ala Asp Ser Phe Ile Ala Arg Met His Leu
            740                 745                 750
```

```
Val Gln Gly Asp Arg Arg Phe Ser Pro Trp Lys Gly Ser Val Val Asp
            755                 760                 765

Ser Val Ile Gly Val Phe Leu Thr Gln Asn Val Ser Asp His Leu Ser
        770                 775                 780

Ser Ser Ala Phe Met Ser Leu Ala Ala Arg Phe Pro Pro Lys Leu Ser
785                 790                 795                 800

Ser Ser Arg Glu Asp Glu Arg Asn Val Arg Ser Val Val Glu Asp
                805                 810                 815

Pro Glu Gly Cys Ile Leu Asn Leu Asn Glu Ile Pro Ser Trp Gln Glu
                820                 825                 830

Lys Val Gln His Pro Ser Asp Met Glu Val Ser Gly Val Asp Ser Gly
                835                 840                 845

Ser Lys Glu Gln Leu Arg Asp Cys Ser Asn Ser Gly Ile Glu Arg Phe
850                 855                 860

Asn Phe Leu Glu Lys Ser Ile Gln Asn Leu Glu Glu Val Leu Ser
865                 870                 875                 880

Ser Gln Asp Ser Phe Asp Pro Ala Ile Phe Gln Ser Cys Gly Arg Val
                885                 890                 895

Gly Ser Cys Ser Cys Ser Lys Ser Asp Ala Glu Phe Pro Thr Thr Arg
                900                 905                 910

Cys Glu Thr Lys Thr Val Ser Gly Thr Ser Gln Ser Val Gln Thr Gly
                915                 920                 925

Ser Pro Asn Leu Ser Asp Glu Ile Cys Leu Gln Gly Asn Glu Arg Pro
                930                 935                 940

His Leu Tyr Glu Gly Ser Gly Asp Val Gln Lys Gln Glu Thr Thr Asn
945                 950                 955                 960

Val Ala Gln Lys Lys Pro Asp Leu Glu Lys Thr Met Asn Trp Lys Asp
                965                 970                 975

Ser Val Cys Phe Gly Gln Pro Arg Asn Asp Thr Asn Trp Gln Thr Thr
                980                 985                 990

Pro Ser Ser Ser Tyr Glu Gln Cys Ala Thr Arg Gln Pro His Val Leu
                995                 1000                1005

Asp Ile Glu Asp Phe Gly Met Gln Gly Glu Gly Leu Gly Tyr Ser Trp
1010                1015                1020

Met Ser Ile Ser Pro Arg Val Asp Arg Val Lys Asn Lys Asn Val Pro
1025                1030                1035                1040

Arg Arg Phe Phe Arg Gln Gly Gly Ser Val Pro Arg Glu Phe Thr Gly
                1045                1050                1055

Gln Ile Ile Pro Ser Thr Pro His Glu Leu Pro Gly Met Gly Leu Ser
                1060                1065                1070

Gly Ser Ser Ser Ala Val Gln Glu His Gln Asp Asp Thr Gln His Asn
                1075                1080                1085

Gln Gln Asp Glu Met Asn Lys Ala Ser His Leu Gln Lys Thr Phe Leu
                1090                1095                1100

Asp Leu Leu Asn Ser Ser Glu Cys Leu Thr Arg Gln Ser Ser Thr
1105                1110                1115                1120

Lys Gln Asn Ile Thr Asp Gly Cys Leu Pro Arg Asp Arg Thr Ala Glu
                1125                1130                1135

Asp Val Val Asp Pro Leu Ser Asn Asn Ser Ser Leu Gln Asn Ile Leu
                1140                1145                1150

Val Glu Ser Asn Ser Ser Asn Lys Glu Gln Thr Ala Val Glu Tyr Lys
                1155                1160                1165

Glu Thr Asn Ala Thr Ile Leu Arg Glu Met Lys Gly Thr Leu Ala Asp
```

-continued

```
            1170                1175                1180
Gly Lys Lys Pro Thr Ser Gln Trp Asp Cys Leu Arg Arg Glu Ala Gln
1185                1190                1195                1200
Ala Arg Ala Gly Ile Arg Glu Lys Thr Arg Ser Thr Met Asp Thr Val
            1205                1210                1215
Asp Trp Lys Ala Ile Arg Ala Ala Asp Val Lys Glu Val Ala Glu Thr
            1220                1225                1230
Ile Lys Ser Arg Gly Met Asn His Lys Leu Ala Glu Arg Ile Gln Gly
            1235                1240                1245
Phe Leu Asp Arg Leu Val Asn Asp His Gly Ser Ile Asp Leu Glu Trp
            1250                1255                1260
Leu Arg Asp Val Pro Pro Asp Lys Ala Lys Glu Tyr Leu Leu Ser Phe
1265                1270                1275                1280
Asn Gly Leu Gly Leu Lys Ser Val Glu Cys Val Arg Leu Leu Thr Leu
            1285                1290                1295
His His Leu Ala Phe Pro Val Asp Thr Asn Val Gly Arg Ile Ala Val
            1300                1305                1310
Arg Leu Gly Trp Val Pro Leu Gln Pro Leu Pro Glu Ser Leu Gln Leu
            1315                1320                1325
His Leu Leu Glu Met Tyr Pro Met Leu Glu Ser Ile Gln Lys Tyr Leu
            1330                1335                1340
Trp Pro Arg Leu Cys Lys Leu Asp Gln Lys Thr Leu Tyr Glu Leu His
1345                1350                1355                1360
Tyr Gln Met Ile Thr Phe Gly Lys Val Phe Cys Thr Lys Ser Lys Pro
            1365                1370                1375
Asn Cys Asn Ala Cys Pro Met Lys Gly Glu Cys Arg His Phe Ala Ser
            1380                1385                1390
Ala Phe Ala Ser Ala Arg Leu Ala Leu Pro Ala Pro Glu Glu Arg Ser
            1395                1400                1405
Leu Thr Ser Ala Thr Ile Pro Val Pro Pro Glu Ser Phe Pro Pro Val
            1410                1415                1420
Ala Ile Pro Met Ile Glu Leu Pro Leu Pro Leu Glu Lys Ser Leu Ala
1425                1430                1435                1440
Ser Gly Ala Pro Ser Asn Arg Glu Asn Cys Glu Pro Ile Ile Glu Glu
            1445                1450                1455
Pro Ala Ser Pro Gly Gln Glu Cys Thr Glu Ile Thr Glu Ser Asp Ile
            1460                1465                1470
Glu Asp Ala Tyr Tyr Asn Glu Asp Pro Asp Glu Ile Pro Thr Ile Lys
            1475                1480                1485
Leu Asn Ile Glu Gln Phe Gly Met Thr Leu Arg Glu His Met Glu Arg
            1490                1495                1500
Asn Met Glu Leu Gln Glu Gly Asp Met Ser Lys Ala Leu Val Ala Leu
1505                1510                1515                1520
His Pro Thr Thr Thr Ser Ile Pro Thr Pro Lys Leu Lys Asn Ile Ser
            1525                1530                1535
Arg Leu Arg Thr Glu His Gln Val Tyr Glu Leu Pro Asp Ser His Arg
            1540                1545                1550
Leu Leu Asp Gly Met Asp Lys Arg Glu Pro Asp Asp Pro Ser Pro Tyr
            1555                1560                1565
Leu Leu Ala Ile Trp Thr Pro Gly Glu Thr Ala Asn Ser Ala Gln Pro
            1570                1575                1580
Pro Glu Gln Lys Cys Gly Gly Lys Ala Ser Gly Lys Met Cys Phe Asp
1585                1590                1595                1600
```

```
Glu Thr Cys Ser Glu Cys Asn Ser Leu Arg Glu Ala Asn Ser Gln Thr
            1605                1610                1615

Val Arg Gly Thr Leu Leu Ile Pro Cys Arg Thr Ala Met Arg Gly Ser
        1620                1625                1630

Phe Pro Leu Asn Gly Thr Tyr Phe Gln Val Asn Glu Leu Phe Ala Asp
        1635                1640                1645

His Glu Ser Ser Leu Lys Pro Ile Asp Val Pro Arg Asp Trp Ile Trp
    1650                1655                1660

Asp Leu Pro Arg Arg Thr Val Tyr Phe Gly Thr Ser Val Thr Ser Ile
1665                1670                1675                1680

Phe Arg Gly Leu Ser Thr Glu Gln Ile Gln Phe Cys Phe Trp Lys Gly
            1685                1690                1695

Phe Val Cys Val Arg Gly Phe Glu Gln Lys Thr Arg Ala Pro Arg Pro
        1700                1705                1710

Leu Met Ala Arg Leu His Phe Pro Ala Ser Lys Leu Lys Asn Asn Lys
        1715                1720                1725

Thr
```

<210> SEQ ID NO 13
<211> LENGTH: 4182
<212> TYPE: DNA
<213> ORGANISM: Artificial Sequence
<220> FEATURE:
<223> OTHER INFORMATION: Description of Artificial Sequence:synthetic
ROS1-DME chimera, construct with ROS1 amino acids
859-1069 deleted and DME amino acids 1,192-1,402
inserted, ROS1 containing DME DNA glycolase domain

<400> SEQUENCE: 13

```
atggagaaac agaggagaga agaaagcagc tttcaacaac ctccatggat tcctcagaca    60
cccatgaagc cattttcacc gatctgccca tacacggtgg aggatcaata tcatagcagt   120
caattggagg aaaggagatt tgttgggaac aaggatatga gtggtcttga tcacttgtct   180
tttggggatt tgcttgctct agctaacact gcatccctca tattctctgg tcagactcca   240
atacctacaa gaaacacaga ggttatgcaa aaaggtactg aagaagtgga gagtttgagc   300
tcagtgagta acaatgttgc tgaacagatc ctcaagactc ctgaaaaacc taagaggaag   360
aagcatcggc caaggttcg tagagaagct aaacccaaga gggagcctaa accacgagct   420
ccgaggaagt ctgttgtcac cgatggtcaa gaaagcaaaa caccaaagag gaaatatgtg   480
cggaagaagg ttgaagtcag taaggatcaa gacgctactc cggttgaatc atcagcagct   540
gttgaaactt caactcgtcc taagaggctc tgtagacgag tcttggattt tgaagccgaa   600
aatggagaaa accagaccaa cggtgacatt agagaagcag gtgagatgga atcagctctt   660
caagagaagc agttagattc tgggaatcaa gagttaaaag attgccttct ttcggctcct   720
agcacgccca agagaaagcg cagccaaggt aaaagaaagg gagttcaacc aaagaaaaat   780
ggcagtaatc tagaagaagt cgatatttcg atggcgcaag ctgcaaagag aagacaagga   840
ccaacttgtt gcgacatgaa tctatcaggg attcagtatg atgagcaatg tgactaccag   900
aaaatgcatt ggttgtattc cccaaacttg caacagggag ggatgagata tgatgccatt   960
tgcagcaaag tattctctgg acaacagcac aattatgttt ctgcctttca cgctacgtgc  1020
tacagttcca catctcagct cagtgctaat agagtcctaa ccgttgaaga agacgagaa   1080
ggtatctttc aaggaaggca agagtctgag ctaaatgttc tctcggataa gatagacacg  1140
ccgatcaaga gaaaacaac aggccatgct cgattccgga atttgtcttc aatgaataaa  1200
```

```
cttgtggaag ttcctgagca tttaacctca ggatattgta gcaagccaca gcaaaataat   1260
aagattcttg ttgatacgcg ggtgactgtg agcaaaaaga agccaaccaa gtctgagaaa   1320
tcacaaacca aacagaaaaa tcttcttccg aatctttgcc gttttccacc ttcatttact   1380
ggtctttctc cagatgaact ttggaaacga cgtaactcga tcgaaacaat cagtgagcta   1440
ttgcgtctat tagacatcaa cagggagcat tctgaaactg ctctcgttcc ttacacaatg   1500
aatagccaga ttgtactctt tggtggtggc gctggagcaa ttgtgcctgt aactcctgtt   1560
aaaaaaccac gcccacgacc aaaggttgat ctagacgatg agacagacag agtgtggaaa   1620
ctgctattgg agaatattaa tagcgaaggt gttgacggat cagacgagca gaaggcgaaa   1680
tggtgggagg aagaacgtaa tgtgtttcga ggacgagctg actcatttat tgcaaggatg   1740
caccttgtac aaggggatcg acgttttacg ccttggaagg gatccgtcgt ggattctgtt   1800
gttggagtat ttctcactca aaatgtttca gaccatctct caagttcggc tttcatgtcg   1860
ttggcttccc agttccctgt ccctttttgta ccgagcagta actttgacgc tggaacaagc   1920
tcgatgcctt ctattcaaat aacgtacttg gactcagagg aaacgatgtc aagcccaccc   1980
gatcacaatc acagttctgt tactttgaaa aatacacagc ctgatgagga aaggattat    2040 gtacctagca atgaaacctc cagaagcagt agtgagattg ccatctcagc ccatgaatca   2100
gttgacaaaa ccacggattc aaaggagtat gttgattcag atcgaaaagg ctcaagtgta   2160
gaggttgata agacggatga agtgtcgt gtcctgaacc tgtttccatc tgaagattct    2220
gcacttacat gtcaacattc gatggtgtct gatgctcctc aaaatacaga gagagcagga   2280
tcaagctcag agatcgactt agaaggagag tatcgtactt cctttatgaa gctcctacag   2340
ggggtacaag tctctctaga agattccaat caagtatcac caaatatgtc tccgggtgat   2400
tgtagctcag aaattaaggg tttccagtca atgaaagagc ccacaaaatc ctctgttgat   2460
agtagtgaac ctggttgttg ctctcagcaa gatggggatg ttttgagttg tcagaaacct   2520
accttaaaag aaaaagggaa aaaggttttg aaggaggaaa aaaagcgtt tgactgggat    2580 agtctcagaa aagatgtgga ggggaatgaa gggagacagg aacgaaacaa aaacaatatg   2640
gattccatag actatgaagc aataagacgt gctagtatca gcgagatttc tgaggctatc   2700
aaggaaagag ggatgaataa catgttggcc gtacgaatta aggatttcct agaacggata   2760
gttaaagatc atggtggtat cgaccttgaa tggttgagag aatctcctcc tgataaagcc   2820
aaggactatc tcttgagcat aagaggtctg ggtttgaaaa gtgttgaatg cgtgcgactc   2880
ttaacactcc acaatcttgc tttccctgtt gacacgaatt ttggaaggat agcagttagg   2940
atgggatggg tgcctctaca acccctacct gaatcacttc agttacacct cctggagcta   3000
tacccagtgc tcgagtccat ccaaaaattt ctttggccaa gactttgcaa actcgatcaa   3060
cgaacactgt atgaattaca ctaccaactg attacgtttg gaaaggtatt ttgcacaaag   3120
agtagaccaa attgtaatgc atgtccaatg agaggagagt gcagacactt tgccagtgct   3180
tatgctagtg caagacttgc tttaccgagt acagagaaag gtatgggac acctgataaa     3240 aacccctttgc ctctacacct gccagagcca ttccagagag agcaagggtc tgaagtagta   3300
cagcactcag aaccagcaaa aaaggtcaca tgttgtgaac caatcatcga agagcctgct   3360
tcaccggagc cagaaaccgc agaagtatca atagctgaca tagaggaggc gttttttgag   3420
gatccagaag aaattcctac catcaggcta aacatggatg catttaccag taacttgaag   3480
aagataatgg aacacaacaa ggaacttcaa gacggaaaca tgtccagcgc tttagttgca   3540
```

-continued

```
cttactgctg aaactgcttc tcttccaatg cctaagctca agaatatcag ccagttaagg    3600
acagaacacc gagtttacga acttccagac gagcatcctc ttctagctca gttggaaaag    3660
agagaacctg atgatccatg ttcttatttg cttgctatat ggacgccagg tgagacggct    3720
gattctattc aaccgtctgt tagtacgtgc atattccaag caaatggtat gctttgtgac    3780
gaggagactt gtttctcctg caacagcatc aaggagacta gatctcaaat tgtgagaggg    3840
acaattttga ttccttgtag aacagcgatg aggggtagtt ttcctctaaa tggaacgtac    3900
tttcaagtaa atgaggtgtt tgcggatcat gcatccagcc taaacccaat caatgtccca    3960
agggaattga tatgggaatt acctcgaaga acggtctatt ttggtacctc tgttcctacg    4020
atattcaaag gtttatcaac tgagaagata caggcttgct tttggaaagg gtacgtatgt    4080
gtacgtggat ttgatcgaaa gacgagggga ccgaagcctt tgattgcaag attgcacttc    4140
ccggcgagca aactgaaggg acaacaagct aacctcgcct aa                       4182
```

<210> SEQ ID NO 14
<211> LENGTH: 1393
<212> TYPE: PRT
<213> ORGANISM: Artificial Sequence
<220> FEATURE:
<223> OTHER INFORMATION: Description of Artificial Sequence:synthetic
ROS1-DME chimera, construct with ROS1 amino acids
859-1069 deleted and DME amino acids 1,192-1,402
inserted, ROS1 containing DME DNA glycolase domain

<400> SEQUENCE: 14

```
Met Glu Lys Gln Arg Arg Glu Glu Ser Ser Phe Gln Gln Pro Pro Trp
  1               5                  10                  15

Ile Pro Gln Thr Pro Met Lys Pro Phe Ser Pro Ile Cys Pro Tyr Thr
                 20                  25                  30

Val Glu Asp Gln Tyr His Ser Ser Gln Leu Glu Glu Arg Arg Phe Val
             35                  40                  45

Gly Asn Lys Asp Met Ser Gly Leu Asp His Leu Ser Phe Gly Asp Leu
         50                  55                  60

Leu Ala Leu Ala Asn Thr Ala Ser Leu Ile Phe Ser Gly Gln Thr Pro
 65                  70                  75                  80

Ile Pro Thr Arg Asn Thr Glu Val Met Gln Lys Gly Thr Glu Glu Val
                 85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240
```

```
Ser Thr Pro Lys Arg Lys Arg Ser Gln Gly Lys Arg Lys Gly Val Gln
            245                 250                 255

Pro Lys Lys Asn Gly Ser Asn Leu Glu Val Asp Ile Ser Met Ala
        260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
        290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
            355                 360                 365

Ser Glu Leu Asn Val Leu Ser Asp Lys Ile Asp Thr Pro Ile Lys Lys
            370                 375                 380

Lys Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
            435                 440                 445

Leu Pro Asn Leu Cys Arg Phe Pro Pro Ser Phe Thr Gly Leu Ser Pro
        450                 455                 460

Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
                485                 490                 495

Pro Tyr Thr Met Asn Ser Gln Ile Val Leu Phe Gly Gly Ala Gly
            500                 505                 510

Ala Ile Val Pro Val Thr Pro Val Lys Lys Pro Arg Pro Arg Pro Lys
        515                 520                 525

Val Asp Leu Asp Asp Glu Thr Asp Arg Val Trp Lys Leu Leu Leu Glu
        530                 535                 540

Asn Ile Asn Ser Glu Gly Val Asp Gly Ser Asp Glu Gln Lys Ala Lys
545                 550                 555                 560

Trp Trp Glu Glu Glu Arg Asn Val Phe Arg Gly Arg Ala Asp Ser Phe
                565                 570                 575

Ile Ala Arg Met His Leu Val Gln Gly Asp Arg Arg Phe Thr Pro Trp
            580                 585                 590

Lys Gly Ser Val Val Asp Ser Val Gly Val Phe Leu Thr Gln Asn
            595                 600                 605

Val Ser Asp His Leu Ser Ser Ser Ala Phe Met Ser Leu Ala Ser Gln
        610                 615                 620

Phe Pro Val Pro Phe Val Pro Ser Ser Asn Phe Asp Ala Gly Thr Ser
625                 630                 635                 640

Ser Met Pro Ser Ile Gln Ile Thr Tyr Leu Asp Ser Glu Glu Thr Met
                645                 650                 655
```

-continued

Ser Ser Pro Pro Asp His Asn His Ser Ser Val Thr Leu Lys Asn Thr
            660                 665                 670

Gln Pro Asp Glu Glu Lys Asp Tyr Val Pro Ser Asn Glu Thr Ser Arg
    675                 680                 685

Ser Ser Ser Glu Ile Ala Ile Ser Ala His Glu Ser Val Asp Lys Thr
690                 695                 700

Thr Asp Ser Lys Glu Tyr Val Asp Ser Asp Arg Lys Gly Ser Ser Val
705                 710                 715                 720

Glu Val Asp Lys Thr Asp Glu Lys Cys Arg Val Leu Asn Leu Phe Pro
                725                 730                 735

Ser Glu Asp Ser Ala Leu Thr Cys Gln His Ser Met Val Ser Asp Ala
            740                 745                 750

Pro Gln Asn Thr Glu Arg Ala Gly Ser Ser Ser Glu Ile Asp Leu Glu
        755                 760                 765

Gly Glu Tyr Arg Thr Ser Phe Met Lys Leu Leu Gln Gly Val Gln Val
    770                 775                 780

Ser Leu Glu Asp Ser Asn Gln Val Ser Pro Asn Met Ser Pro Gly Asp
785                 790                 795                 800

Cys Ser Ser Glu Ile Lys Gly Phe Gln Ser Met Lys Glu Pro Thr Lys
                805                 810                 815

Ser Ser Val Asp Ser Ser Glu Pro Gly Cys Cys Ser Gln Gln Asp Gly
            820                 825                 830

Asp Val Leu Ser Cys Gln Lys Pro Thr Leu Lys Glu Lys Gly Lys Lys
        835                 840                 845

Val Leu Lys Glu Lys Lys Ala Phe Asp Trp Asp Ser Leu Arg Lys
850                 855                 860

Asp Val Glu Gly Asn Glu Gly Arg Gln Glu Arg Asn Lys Asn Asn Met
865                 870                 875                 880

Asp Ser Ile Asp Tyr Glu Ala Ile Arg Arg Ala Ser Ile Ser Glu Ile
                885                 890                 895

Ser Glu Ala Ile Lys Glu Arg Gly Met Asn Asn Met Leu Ala Val Arg
            900                 905                 910

Ile Lys Asp Phe Leu Glu Arg Ile Val Lys Asp His Gly Gly Ile Asp
        915                 920                 925

Leu Glu Trp Leu Arg Glu Ser Pro Pro Asp Lys Ala Lys Asp Tyr Leu
    930                 935                 940

Leu Ser Ile Arg Gly Leu Gly Leu Lys Ser Val Glu Cys Val Arg Leu
945                 950                 955                 960

Leu Thr Leu His Asn Leu Ala Phe Pro Val Asp Thr Asn Val Gly Arg
                965                 970                 975

Ile Ala Val Arg Met Gly Trp Val Pro Leu Gln Pro Leu Pro Glu Ser
            980                 985                 990

Leu Gln Leu His Leu Leu Glu Leu Tyr Pro Val Leu Glu Ser Ile Gln
        995                 1000                1005

Lys Phe Leu Trp Pro Arg Leu Cys Lys Leu Asp Gln Arg Thr Leu Tyr
    1010                1015                1020

Glu Leu His Tyr Gln Leu Ile Thr Phe Gly Lys Val Phe Cys Thr Lys
1025                1030                1035                1040

Ser Arg Pro Asn Cys Asn Ala Cys Pro Met Arg Gly Glu Cys Arg His
                1045                1050                1055

Phe Ala Ser Ala Tyr Ala Ser Ala Arg Leu Ala Leu Pro Ser Thr Glu
            1060                1065                1070

Lys Gly Met Gly Thr Pro Asp Lys Asn Pro Leu Pro Leu His Leu Pro

-continued

```
                1075                1080                1085
Glu Pro Phe Gln Arg Glu Gln Gly Ser Glu Val Val Gln His Ser Glu
        1090                1095                1100
Pro Ala Lys Lys Val Thr Cys Cys Glu Pro Ile Ile Glu Glu Pro Ala
1105                1110                1115                1120
Ser Pro Glu Pro Glu Thr Ala Glu Val Ser Ile Ala Asp Ile Glu Glu
                1125                1130                1135
Ala Phe Phe Glu Asp Pro Glu Glu Ile Pro Thr Ile Arg Leu Asn Met
            1140                1145                1150
Asp Ala Phe Thr Ser Asn Leu Lys Lys Ile Met Glu His Asn Lys Glu
        1155                1160                1165
Leu Gln Asp Gly Asn Met Ser Ser Ala Leu Val Ala Leu Thr Ala Glu
    1170                1175                1180
Thr Ala Ser Leu Pro Met Pro Lys Leu Lys Asn Ile Ser Gln Leu Arg
1185                1190                1195                1200
Thr Glu His Arg Val Tyr Glu Leu Pro Asp Glu His Pro Leu Leu Ala
                1205                1210                1215
Gln Leu Glu Lys Arg Glu Pro Asp Asp Pro Cys Ser Tyr Leu Leu Ala
            1220                1225                1230
Ile Trp Thr Pro Gly Glu Thr Ala Asp Ser Ile Gln Pro Ser Val Ser
        1235                1240                1245
Thr Cys Ile Phe Gln Ala Asn Gly Met Leu Cys Asp Glu Glu Thr Cys
    1250                1255                1260
Phe Ser Cys Asn Ser Ile Lys Glu Thr Arg Ser Gln Ile Val Arg Gly
1265                1270                1275                1280
Thr Ile Leu Ile Pro Cys Arg Thr Ala Met Arg Gly Ser Phe Pro Leu
                1285                1290                1295
Asn Gly Thr Tyr Phe Gln Val Asn Glu Val Phe Ala Asp His Ala Ser
            1300                1305                1310
Ser Leu Asn Pro Ile Asn Val Pro Arg Glu Leu Ile Trp Glu Leu Pro
        1315                1320                1325
Arg Arg Thr Val Tyr Phe Gly Thr Ser Val Pro Thr Ile Phe Lys Gly
    1330                1335                1340
Leu Ser Thr Glu Lys Ile Gln Ala Cys Phe Trp Lys Gly Tyr Val Cys
1345                1350                1355                1360
Val Arg Gly Phe Asp Arg Lys Thr Arg Gly Pro Lys Pro Leu Ile Ala
                1365                1370                1375
Arg Leu His Phe Pro Ala Ser Lys Leu Lys Gly Gln Gln Ala Asn Leu
            1380                1385                1390
Ala
```

<210> SEQ ID NO 15
<211> LENGTH: 4191
<212> TYPE: DNA
<213> ORGANISM: Artificial Sequence
<220> FEATURE:
<223> OTHER INFORMATION: Description of Artificial Sequence:synthetic
    ROS1-DME chimera, construct with ROS1 amino acids 859-1,394
    deleted and DME amino acids 1,192-1,730 inserted, ROS1 N-terminus
    and DME DNA glycolase domain and C-terminus

<400> SEQUENCE: 15
atggagaaac agaggagaga agaaagcagc tttcaacaac ctccatggat tcctcagaca    60
cccatgaagc cattttcacc gatctgccca tacacggtgg aggatcaata tcatagcagt   120
caattggagg aaaggagatt tgttgggaac aaggatatga gtggtcttga tcacttgtct   180

```
tttgggatt tgcttgctct agctaacact gcatccctca tattctctgg tcagactcca    240
atacctacaa gaaacacaga ggttatgcaa aaaggtactg aagaagtgga gagtttgagc    300
tcagtgagta acaatgttgc tgaacagatc ctcaagactc ctgaaaaacc taagaggaag    360
aagcatcggc caaggttcg tagagaagct aaacccaaga gggagcctaa accacgagct    420
ccgaggaagt ctgttgtcac cgatggtcaa gaaagcaaaa caccaaagag gaaatatgtg    480
cggaagaagg ttgaagtcag taaggatcaa gacgctactc cggttgaatc atcagcagct    540
gttgaaactt caactcgtcc taagaggctc tgtagacgag tcttggattt tgaagccgaa    600 aatgagaaa accagaccaa cggtgacatt agagaagcag gtgagatgga atcagctctt    660
caagagaagc agttagattc tgggaatcaa gagttaaaag attgccttct ttcggctcct    720
agcacgccca agagaaagcg cagccaaggt aaagaaagg gagttcaacc aaagaaaaat    780
ggcagtaatc tagaagaagt cgatatttcg atggcgcaag ctgcaaagag aagacaagga    840
ccaacttgtt gcgacatgaa tctatcaggg attcagtatg atgagcaatg tgactaccag    900
aaaatgcatt ggttgtattc cccaaacttg caacagggag ggatgagata tgatgccatt    960
tgcagcaaag tattctctgg acaacagcac aattatgttt ctgcctttca cgctacgtgc    1020
tacagttcca catctcagct cagtgctaat agagtcctaa ccgttaaga aagacgagaa    1080 ggtatctttc aaggaaggca agagtctgag ctaaatgttc tctcggataa gatagacacg    1140
ccgatcaaga agaaaacaac aggccatgct cgattccgga atttgtcttc aatgaataaa    1200 cttgtgaag ttcctgagca tttaacctca ggatattgta gcaagccaca gcaaaataat    1260
aagattcttg ttgatacgcg ggtgactgtg agcaaaaaga agccaaccaa gtctgagaaa    1320
tcacaaacca aacagaaaaa tcttcttccg aatctttgcc gttttccacc ttcatttact    1380
ggtctttctc cagatgaact ttggaaacga cgtaactcga tcgaaacaat cagtgagcta    1440
ttgcgtctat tagacatcaa cagggagcat tctgaaactg ctctcgttcc ttacacaatg    1500
aatagccaga ttgtactctt tggtggtggc gctggagcaa ttgtgcctgt aactcctgtt    1560 aaaaaccac gcccacgacc aaaggttgat ctagacgatg agacagacag agtgtggaaa    1620
ctgctattgg agaatattaa tagcgaaggt gttgacggat cagacgagca gaaggcgaaa    1680
tggtgggagg aagaacgtaa tgtgtttcga ggacgagctg actcatttat tgcaaggatg    1740
caccttgtac aaggggatcg acgttttacg ccttggaagg gatccgtcgt ggattctgtt    1800
gttggagtat ttctcactca aaatgtttca gaccatctct caagttcggc tttcatgtcg    1860
ttggcttccc agttccctgt ccctttgta ccgagcagta actttgacgc tggaacaagc    1920
tcgatgcctt ctattcaaat aacgtacttg gactcagagg aaacgatgtc aagcccaccc    1980
gatcacaatc acagttctgt tactttgaaa aatacacagc ctgatgagga aaggattat    2040 gtacctagca atgaaacctc cagaagcagt agtgagattg ccatctcagc ccatgaatca    2100
gttgacaaaa ccacggattc aaaggagtat gttgattcag atcgaaaagg ctcaagtgta    2160
gaggttgata agacggatga aagtgtcgt gtcctgaacc tgtttccatc tgaagattct    2220
gcacttacat gtcaacattc gatggtgtct gatgctcctc aaaatacaga gagagcagga    2280
tcaagctcag agatcgactt agaaggagag tatcgtactt cctttatgaa gctcctacag    2340
ggggtacaag tctctctaga agattccaat caagtatcac caaatatgtc tccgggtgat    2400
tgtagctcag aaattaaggg tttccagtca atgaaagagc ccacaaaatc ctctgttgat    2460
agtagtgaac ctggttgttg ctctcagcaa gatggggatg ttttgagttg tcagaaacct    2520
```

-continued

| | |
|---|---|
| accttaaaag aaaaagggaa aaaggttttg aaggaggaaa aaaaagcgtt tgactgggat | 2580 |
| agtctcagaa aagatgtgga gggaatgaa gggagacagg aacgaaacaa aaacaatatg | 2640 |
| gattccatag actatgaagc aataagacgt gctagtatca gcgagatttc tgaggctatc | 2700 |
| aaggaaagag ggatgaataa catgttggcc gtacgaatta aggatttcct agaacggata | 2760 |
| gttaaagatc atggtggtat cgaccttgaa tggttgagag aatctcctcc tgataaagcc | 2820 |
| aaggactatc tcttgagcat aagaggtctg ggtttgaaaa gtgttgaatg cgtgcgactc | 2880 |
| ttaacactcc acaatcttgc tttccctgtt gacacgaatg ttggaaggat agcagttagg | 2940 |
| atgggatggg tgcctctaca acccctacct gaatcacttc agttacacct cctggagcta | 3000 |
| tacccagtgc tcgagtccat ccaaaaattt ctttggccaa gactttgcaa actcgatcaa | 3060 |
| cgaacactgt atgaattaca ctaccaactg attacgtttg gaaaggtatt ttgcacaaag | 3120 |
| agtagaccaa attgtaatgc atgtccaatg agaggagagt gcagacactt tgccagtgct | 3180 |
| tatgctagtg caagacttgc tttaccggca ccagaggaga ggagcttaac aagtgcaact | 3240 |
| attccggtcc ctcccgagtc ctttcctcct gtagccatcc cgatgataga actacctctt | 3300 |
| ccgttggaga aatccctagc aagtggagca ccatcgaata gagaaaactg tgaaccaata | 3360 |
| attgaagagc cggcctcgcc cgggcaagag tgcactgaaa taaccgagag tgatattgaa | 3420 |
| gatgcttact acaatgagga ccctgacgag atcccaacaa taaaactcaa cattgaacag | 3480 |
| tttgaaatga ctctacggga acacatgaa agaaacatgg agctccaaga aggtgacatg | 3540 |
| tccaaggctt tggttgcttt gcatccaaca actacttcta ttccaactcc caaactaaag | 3600 |
| aacattagcc gtctcaggac agagcaccaa gtgtacgagc tcccagattc acatcgtctc | 3660 |
| cttgatggta tggataaaag agaaccagat gatccaagtc cttatctctt agctatatgg | 3720 |
| acaccaggtg aaacagcgaa ttcggcacaa ccgcctgaac agaagtgtgg agggaaagcg | 3780 |
| tctggcaaaa tgtgctttga cgagacttgt tctgagtgta acagtctgag ggaagcaaac | 3840 |
| tcacagacag ttcgaggaac tcttctgata ccttgtcgga ctgccatgag aggaagtttt | 3900 |
| ccgctcaacg ggacatattt ccaagtcaac gagttatttg cagaccacga gtccagtctc | 3960 |
| aaacccatcg atgttcctag agattggata tgggatctcc caagaaggac tgtttacttc | 4020 |
| ggaacatcag taacatcaat attcagaggt cttcaacgg agcagataca gttctgcttt | 4080 |
| tggaaaggat tcgtatgtgt ccgtggattc gaacagaaga caagagcacc gcgtccatta | 4140 |
| atggcaaggt tgcatttcc tgcgagcaaa ttgaagaaca acaaaaccta a | 4191 |

<210> SEQ ID NO 16
<211> LENGTH: 1396
<212> TYPE: PRT
<213> ORGANISM: Artificial Sequence
<220> FEATURE:
<223> OTHER INFORMATION: Description of Artificial Sequence:synthetic
    ROS1-DME chimera, construct with ROS1 amino acids 859-1,394
    deleted and DME amino acids 1,192-1,730 inserted, ROS1 N-terminus
    and DME DNA glycolase domain and C-terminus

<400> SEQUENCE: 16

Met Glu Lys Gln Arg Arg Glu Glu Ser Ser Phe Gln Gln Pro Pro Trp
1               5                   10                  15

Ile Pro Gln Thr Pro Met Lys Pro Phe Ser Pro Ile Cys Pro Tyr Thr
            20                  25                  30

Val Glu Asp Gln Tyr His Ser Ser Gln Leu Glu Glu Arg Arg Phe Val
        35                  40                  45

Gly Asn Lys Asp Met Ser Gly Leu Asp His Leu Ser Phe Gly Asp Leu

```
            50                  55                  60
Leu Ala Leu Ala Asn Thr Ala Ser Leu Ile Phe Ser Gly Gln Thr Pro
 65                  70                  75                  80

Ile Pro Thr Arg Asn Thr Glu Val Met Gln Lys Gly Thr Glu Glu Val
                 85                  90                  95

Glu Ser Leu Ser Ser Val Ser Asn Asn Val Ala Glu Gln Ile Leu Lys
                100                 105                 110

Thr Pro Glu Lys Pro Lys Arg Lys Lys His Arg Pro Lys Val Arg Arg
            115                 120                 125

Glu Ala Lys Pro Lys Arg Glu Pro Lys Pro Arg Ala Pro Arg Lys Ser
            130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
                180                 185                 190

Arg Val Leu Asp Phe Glu Ala Glu Asn Gly Glu Asn Gln Thr Asn Gly
            195                 200                 205

Asp Ile Arg Glu Ala Gly Glu Met Glu Ser Ala Leu Gln Glu Lys Gln
210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
                260                 265                 270

Gln Ala Ala Lys Arg Arg Gln Gly Pro Thr Cys Cys Asp Met Asn Leu
            275                 280                 285

Ser Gly Ile Gln Tyr Asp Glu Gln Cys Asp Tyr Gln Lys Met His Trp
            290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
            355                 360                 365

Ser Glu Leu Asn Val Leu Ser Asp Lys Ile Asp Thr Pro Ile Lys Lys
            370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
            435                 440                 445

Leu Pro Asn Leu Cys Arg Phe Pro Pro Ser Phe Thr Gly Leu Ser Pro
450                 455                 460

Asp Glu Leu Trp Lys Arg Arg Asn Ser Ile Glu Thr Ile Ser Glu Leu
465                 470                 475                 480
```

```
Leu Arg Leu Leu Asp Ile Asn Arg Glu His Ser Glu Thr Ala Leu Val
            485                 490                 495

Pro Tyr Thr Met Asn Ser Gln Ile Val Leu Phe Gly Gly Ala Gly
            500                 505                 510

Ala Ile Val Pro Val Thr Pro Val Lys Lys Pro Arg Pro Arg Pro Lys
            515                 520                 525

Val Asp Leu Asp Asp Glu Thr Asp Arg Val Trp Lys Leu Leu Leu Glu
    530                 535                 540

Asn Ile Asn Ser Glu Gly Val Asp Gly Ser Asp Gln Lys Ala Lys
545                 550                 555                 560

Trp Trp Glu Glu Glu Arg Asn Val Phe Arg Gly Arg Ala Asp Ser Phe
                565                 570                 575

Ile Ala Arg Met His Leu Val Gln Gly Asp Arg Arg Phe Thr Pro Trp
            580                 585                 590

Lys Gly Ser Val Val Asp Ser Val Gly Val Phe Leu Thr Gln Asn
            595                 600                 605

Val Ser Asp His Leu Ser Ser Ser Ala Phe Met Ser Leu Ala Ser Gln
    610                 615                 620

Phe Pro Val Pro Phe Val Pro Ser Ser Asn Phe Asp Ala Gly Thr Ser
625                 630                 635                 640

Ser Met Pro Ser Ile Gln Ile Thr Tyr Leu Asp Ser Glu Glu Thr Met
                645                 650                 655

Ser Ser Pro Pro Asp His Asn His Ser Ser Val Thr Leu Lys Asn Thr
                660                 665                 670

Gln Pro Asp Glu Glu Lys Asp Tyr Val Pro Ser Asn Glu Thr Ser Arg
            675                 680                 685

Ser Ser Ser Glu Ile Ala Ile Ser Ala His Glu Ser Val Asp Lys Thr
            690                 695                 700

Thr Asp Ser Lys Glu Tyr Val Asp Ser Asp Arg Lys Gly Ser Ser Val
705                 710                 715                 720

Glu Val Asp Lys Thr Asp Glu Lys Cys Arg Val Leu Asn Leu Phe Pro
                725                 730                 735

Ser Glu Asp Ser Ala Leu Thr Cys Gln His Ser Met Val Ser Asp Ala
            740                 745                 750

Pro Gln Asn Thr Glu Arg Ala Gly Ser Ser Ser Glu Ile Asp Leu Glu
            755                 760                 765

Gly Glu Tyr Arg Thr Ser Phe Met Lys Leu Leu Gln Gly Val Gln Val
    770                 775                 780

Ser Leu Glu Asp Ser Asn Gln Val Ser Pro Asn Met Ser Pro Gly Asp
785                 790                 795                 800

Cys Ser Ser Glu Ile Lys Gly Phe Gln Ser Met Lys Glu Pro Thr Lys
                805                 810                 815

Ser Ser Val Asp Ser Ser Glu Pro Gly Cys Cys Ser Gln Gln Asp Gly
            820                 825                 830

Asp Val Leu Ser Cys Gln Lys Pro Thr Leu Lys Glu Lys Gly Lys Lys
            835                 840                 845

Val Leu Lys Glu Glu Lys Lys Ala Phe Asp Trp Asp Ser Leu Arg Lys
850                 855                 860

Asp Val Glu Gly Asn Glu Gly Arg Gln Glu Arg Asn Lys Asn Asn Met
865                 870                 875                 880

Asp Ser Ile Asp Tyr Glu Ala Ile Arg Arg Ala Ser Ile Ser Glu Ile
                885                 890                 895
```

```
Ser Glu Ala Ile Lys Glu Arg Gly Met Asn Asn Met Leu Ala Val Arg
            900                 905                 910
Ile Lys Asp Phe Leu Glu Arg Ile Val Lys Asp His Gly Gly Ile Asp
            915                 920                 925
Leu Glu Trp Leu Arg Glu Ser Pro Pro Asp Lys Ala Lys Asp Tyr Leu
            930                 935                 940
Leu Ser Ile Arg Gly Leu Gly Leu Lys Ser Val Glu Cys Val Arg Leu
945                 950                 955                 960
Leu Thr Leu His Asn Leu Ala Phe Pro Val Asp Thr Asn Val Gly Arg
            965                 970                 975
Ile Ala Val Arg Met Gly Trp Val Pro Leu Gln Pro Leu Pro Glu Ser
            980                 985                 990
Leu Gln Leu His Leu Leu Glu Leu Tyr Pro Val Leu Glu Ser Ile Gln
            995                 1000                1005
Lys Phe Leu Trp Pro Arg Leu Cys Lys Leu Asp Gln Arg Thr Leu Tyr
            1010                1015                1020
Glu Leu His Tyr Gln Leu Ile Thr Phe Gly Lys Val Phe Cys Thr Lys
1025                1030                1035                1040
Ser Arg Pro Asn Cys Asn Ala Cys Pro Met Arg Gly Glu Cys Arg His
            1045                1050                1055
Phe Ala Ser Ala Tyr Ala Ser Ala Arg Leu Ala Leu Pro Ala Pro Glu
            1060                1065                1070
Glu Arg Ser Leu Thr Ser Ala Thr Ile Pro Val Pro Pro Glu Ser Phe
            1075                1080                1085
Pro Pro Val Ala Ile Pro Met Ile Glu Leu Pro Leu Pro Leu Glu Lys
            1090                1095                1100
Ser Leu Ala Ser Gly Ala Pro Ser Asn Arg Glu Asn Cys Glu Pro Ile
1105                1110                1115                1120
Ile Glu Glu Pro Ala Ser Pro Gly Gln Glu Cys Thr Glu Ile Thr Glu
            1125                1130                1135
Ser Asp Ile Glu Asp Ala Tyr Tyr Asn Glu Asp Pro Ser Glu Ile Pro
            1140                1145                1150
Thr Ile Lys Leu Asn Ile Glu Gln Phe Gly Met Thr Leu Arg Glu His
            1155                1160                1165
Met Glu Arg Asn Met Glu Leu Gln Glu Gly Asp Met Ser Lys Ala Leu
            1170                1175                1180
Val Ala Leu His Pro Thr Thr Thr Ser Ile Pro Thr Pro Lys Leu Lys
1185                1190                1195                1200
Asn Ile Ser Arg Leu Arg Thr Glu His Gln Val Tyr Glu Leu Pro Asp
            1205                1210                1215
Ser His Arg Leu Leu Asp Gly Met Asp Lys Arg Glu Pro Asp Asp Pro
            1220                1225                1230
Ser Pro Tyr Leu Leu Ala Ile Trp Thr Pro Gly Glu Thr Ala Asn Ser
            1235                1240                1245
Ala Gln Pro Pro Glu Gln Lys Cys Gly Gly Lys Ala Ser Gly Lys Met
            1250                1255                1260
Cys Phe Asp Glu Thr Cys Ser Glu Cys Asn Ser Leu Arg Glu Ala Asn
1265                1270                1275                1280
Ser Gln Thr Val Arg Gly Thr Leu Leu Ile Pro Cys Arg Thr Ala Met
            1285                1290                1295
Arg Gly Ser Phe Pro Leu Asn Gly Thr Tyr Phe Gln Val Asn Glu Leu
            1300                1305                1310
Phe Ala Asp His Glu Ser Ser Leu Lys Pro Ile Asp Val Pro Arg Asp
```

```
                    1315                1320                1325

Trp Ile Trp Asp Leu Pro Arg Arg Thr Val Tyr Phe Gly Thr Ser Val
    1330                1335                1340

Thr Ser Ile Phe Arg Gly Leu Ser Thr Glu Gln Ile Gln Phe Cys Phe
1345                1350                1355                1360

Trp Lys Gly Phe Val Cys Val Arg Gly Phe Glu Gln Lys Thr Arg Ala
                1365                1370                1375

Pro Arg Pro Leu Met Ala Arg Leu His Phe Pro Ala Ser Lys Leu Lys
        1380                1385                1390

Asn Asn Lys Thr
        1395

<210> SEQ ID NO 17
<211> LENGTH: 5181
<212> TYPE: DNA
<213> ORGANISM: Artificial Sequence
<220> FEATURE:
<223> OTHER INFORMATION: Description of Artificial Sequence:synthetic
      ROS1-DME chimera, construct with DME amino acids 1,192-1,730
      deleted and ROS1 amino acids 859-1,394 inserted, DME N-terminus
      and ROS1 DNA glycolase domain and C-terminus

<400> SEQUENCE: 17
atgcagagca ttatggactc gtctgctgtt aatgcgacgg aagctactga acaaaatgat      60
ggcagcagac aagatgttct ggagttcgac cttaacaaaa ctcctcagca gaaaccctcc    120
aaaaggaaaa ggaagttcat gcccaaggtg gtcgtggaag gcaaacctaa agaaagcca     180 cgcaaacctg cagaacttcc caagtggtc gtggaaggca acctaaaag gaagccacgc      240 aaagctgcaa ctcaggaaaa agtgaaatct aaagaaaccg ggagtgccaa aagaaaaat    300 ttgaaagaat cagcaactaa aaagccagcc aatgttggag atatgagcaa caaaagccct    360
gaagtcacac tcaaaagttg cagaaaagct ttgaattttg acttggagaa tcctggagat    420
gcgaggcaag tgactctga gtctgaaatt gtccagaaca gtagtggcgc aaactcgttt     480
tctgagatca gagatgccat ggtggaact aatggtagtt tcctggattc agtgtcacaa     540
atagacaaga ccaatggatt gggggctatg aaccagccac ttgaagtgtc aatgggaaac    600
cagccagata aactatctac aggagcgaaa ctggccagag accaacaacc tgatttattg    660
actagaaacc agcaatgcca gttcccagtg gcaacccaga cacccagtt cccaatggaa     720 aaccaacaag cttggcttca gatgaaaaac caacttattg gctttccatt tggtaaccag    780
caacctcgca tgaccataag aaaccagcag ccttgcttgg ccatgggtaa tcaacaacct    840
atgtatctga taggaactcc acggcctgca ttagtaagtg gaaaccagca actaggaggt    900
ccccaaggaa acaagcggcc tatatttttg aatcaccaga cttgtttacc tgctggaaat    960
cagctatatg gatcacctac agacatgcat caacttgtta tgtcaaccgg agggcaacaa   1020
catggactac tgataaaaaa ccagcaacct ggatcattaa taagaggcca gcagccttgc   1080
gtacctttga ttgaccagca acctgcaact ccaaaaggtt ttactcactt gaatcagatg   1140
gtagctacca gcatgtcatc gcctgggctt cgacctcatt ctcagtcaca agttcctaca   1200
acatatctac atgtggaatc tgtttccagg attttgaatg ggactacagg tacatgccag   1260
agaagcaggg ctcctgcata cgattcttta cagcaagata tccatcaagg aaataagtac   1320
atactttctc atgagatatc caatggtaat gggtgcaaga aagcgttacc tcaaaactct   1380
tctctgccaa ctccaattat ggctaaactt gaggaagcca ggggctcgaa gagacagtat   1440
catcgtgcaa tgggacagac ggaaaagcat gatctaaact tagctcaaca gattgctcaa   1500
```

```
tcacaagatg tggagagaca taacagcagc acgtgtgtgg aatatttaga tgctgcaaag   1560
aaaacgaaaa tccagaaagt agtccaagaa aatttgcatg gcatgccacc tgaggttata   1620
gaaatcgagg atgatccaac tgatggggca agaaaaggta aaaatactgc cagcatcagt   1680
aaaggtgcat ctaaaggaaa ctcgtctcca gttaaaaaga cagcagaaaa ggagaaatgt   1740
attgtcccaa aaacgcctgc aaaaaagggt cgagcaggta gaaaaaaatc agtacctccg   1800
cctgctcatg cctcagagat ccagcttttgg caacctactc ctccaaagac accttttatca  1860
agaagcaagc ctaaaggaaa agggagaaag tccatacaag attcaggaaa agcaagaggt   1920
ccatcaggag aacttctgtg tcaggattct attgcggaaa taatttacag gatgcaaaat   1980
ctgtatctag agacaaaga aagagaacaa gagcaaaatg caatggtctt gtacaaagga   2040
gatggtgcac ttgttcccta tgagagcaag aagcgaaaac caagacccaa agttgacatt   2100
gacgatgaaa caactcgcat atggaactta ctgatgggga aggagatga aaaagaaggg   2160
gatgaagaga aggataaaaa gaaagagaag tggtgggaag aagaaagaag agtcttccga   2220
ggaagggctg attccttcat cgctcgcatg cacctggtac aaggagatag acgttttttcg  2280
ccatggaagg gatcggtggt tgattcggtc attggagttt tccttacaca gaatgtctcg   2340
gatcaccttt caagctctgc gttcatgtct ctagctgctc gattccctcc aaaattaagc   2400
agcagccgag aagatgaaag gaatgttaga agcgtagttg ttgaagatcc agaaggatgc   2460
attctgaact aaatgaaat tccttcgtgg caggaaaagg ttcaacatcc atctgacatg   2520
gaagtttctg gggttgatag tggatcaaaa gagcagctaa gggactgttc aaactctgga   2580
attgaaagat ttaatttctt agagaagagt attcaaaatt tagaagagga agtattatca   2640
tcacaagatt cttttgatcc ggcgatattt cagtcgtgtg ggagagttgg atcctgttca   2700
tgttccaaat cagacgcaga gtttcctaca accaggtgtg aaacaaaaac tgtcagtgga   2760
acatcacaat cagtgcaaac tgggagccca aacttgtctg atgaaatttg tcttcaaggg   2820
aatgagagac cgcatctata tgaaggatct ggtgatgttc agaaacaaga aactacaaat   2880
gtcgctcaga agaaacctga tcttgaaaaa acaatgaatt ggaaagactc tgtctgttt   2940
ggtcagccaa gaaatgatac taattggcaa acaactcctt ccagcagcta tgagcagtgt   3000
gcgactcgac agccacatgt actagacata gaggattttg gaatgcaagg tgaaggcctt   3060
ggttattctt ggatgtccat ctcaccaaga gttgacagag taaagaacaa aaatgtacca   3120
cgcaggtttt tcagacaagg tggaagtgtt ccaagagaat tcacaggtca gatcatacca   3180
tcaacgcctc atgaattacc aggaatggga ttgtccggtt cctcaagcgc cgtccaagaa   3240
caccaggacg atacccaaca taatcaacaa gatgagatga ataaagcatc ccatttacaa   3300
aaaacatttt tggatctgct caactcctct gaagaatgcc ttacaagaca gtccagtacc   3360
aaacagaaca tcacggatgg ctgtctaccg agagataaa ctgctgaaga cgtggttgat   3420
ccgctcagta acaattcaag cttacagaac atattggtcg aatcaaattc cagcaataaa   3480
gagcagacgg cagttgaata caaggagaca aatgccacta ttttacgaga gatgaagggg   3540
acgcttgctg atgggaaaaa gcctacaagc cagtgggatt gtttaagaag agaagcccaa   3600
gctagagcag gaattagaga aaaaacaaga agtacaatgg acaccgtgga ttggaaggca   3660
atacgagcag cagatgttaa ggaagttgct gaaacaatca gagtcgcgg gatgaaccat   3720
aaacttgcag aacgtataca gggcttcctt gatcgactgg taaatgacca tggaagtatc   3780
gatcttgaat ggttgagaga tgttccacca gataaagcaa aagaatatct tctgagcttt   3840
```

| | | |
|---|---|---|
| aacggattgg gactgaaaag tgtggagtgt gtgcggcttc taacacttca ccatcttgcc | | 3900 |
| tttccagttg atacaaatgt tgggcgcata gccgtcagac ttggatgggt gccccttcag | | 3960 |
| ccgctcccag agtcacttca gttgcatctt ctggaaatgt atcctatgct tgaatctatt | | 4020 |
| caaaagtatc tttggccccg tctctgcaaa ctcgaccaaa aaacattgta tgagttgcac | | 4080 |
| taccagatga ttacttttgg aaaggtcttt tgcacaaaga gcaaacctaa ttgcaatgca | | 4140 |
| tgtccgatga aggagaatg cagacatttt gccagtgcgt ttgcaagtgc aaggcttgct | | 4200 |
| ttaccaagta cagagaaagg tatggggaca cctgataaaa acccttttgcc tctacacctg | | 4260 |
| ccagagccat tccagagaga gcaagggtct gaagtagtac agcactcaga accagcaaaa | | 4320 |
| aaggtcacat gttgtgaacc aatcatcgaa gagcctgctt caccggagcc agaaaccgca | | 4380 |
| gaagtatcaa tagctgacat agaggaggcg ttttttgagg atccagaaga aattcctacc | | 4440 |
| atcaggctaa acatggatgc atttaccagt aacttgaaga agataatgga acacaacaag | | 4500 |
| gaacttcaag acggaaacat gtccagcgct ttagttgcac ttactgctga aactgcttct | | 4560 |
| cttccaatgc ctaagctcaa gaatatcagc cagttaagga cagaacaccg agtttacgaa | | 4620 |
| cttccagacg agcatcctct tctagctcag ttggaaaaga gagaacctga tgatccatgt | | 4680 |
| tcttatttgc ttgctatatg gacgccaggt gagacggctg attctattca accgtctgtt | | 4740 |
| agtacgtgca tattccaagc aaatggtatg ctttgtgacg aggagacttg tttctcctgc | | 4800 |
| aacagcatca aggagactag atctcaaatt gtgagaggga caattttgat tccttgtaga | | 4860 |
| acagcgatga ggggtagttt tcctctaaat ggaacgtact ttcaagtaaa tgaggtgttt | | 4920 |
| gcggatcatg catccagcct aaacccaatc aatgtcccaa gggaattgat atgggaatta | | 4980 |
| cctcgaagaa cggtctattt tggtacctct gttcctacga tattcaaagg tttatcaact | | 5040 |
| gagaagatac aggcttgctt ttggaaaggg tacgtatgtg tacgtggatt tgatcgaaag | | 5100 |
| acgaggggac cgaagccttt gattgcaaga ttgcacttcc cggcgagcaa actgaaggga | | 5160 |
| caacaagcta acctcgccta a | | 5181 |

<210> SEQ ID NO 18
<211> LENGTH: 1726
<212> TYPE: PRT
<213> ORGANISM: Artificial Sequence
<220> FEATURE:
<223> OTHER INFORMATION: Description of Artificial Sequence:synthetic
ROS1-DME chimera, construct with DME amino acids 1,192-1,730
deleted and ROS1 amino acids 859-1,394 inserted, DME N-terminus
and ROS1 DNA glycolase domain and C-terminus

<400> SEQUENCE: 18

Met Gln Ser Ile Met Asp Ser Ser Ala Val Asn Ala Thr Glu Ala Thr
1               5                   10                  15

Glu Gln Asn Asp Gly Ser Arg Gln Asp Val Leu Glu Phe Asp Leu Asn
            20                  25                  30

Lys Thr Pro Gln Gln Lys Pro Ser Lys Arg Lys Arg Lys Phe Met Pro
        35                  40                  45

Lys Val Val Val Glu Gly Lys Pro Lys Arg Lys Pro Arg Lys Pro Ala
    50                  55                  60

Glu Leu Pro Lys Val Val Val Glu Gly Lys Pro Lys Arg Lys Pro Arg
65                  70                  75                  80

Lys Ala Ala Thr Gln Glu Lys Val Lys Ser Lys Glu Thr Gly Ser Ala
                85                  90                  95

Lys Lys Lys Asn Leu Lys Glu Ser Ala Thr Lys Lys Pro Ala Asn Val
            100                 105                 110

-continued

```
Gly Asp Met Ser Asn Lys Ser Pro Glu Val Thr Leu Lys Ser Cys Arg
            115                 120                 125
Lys Ala Leu Asn Phe Asp Leu Glu Asn Pro Gly Asp Ala Arg Gln Gly
        130                 135                 140
Asp Ser Glu Ser Glu Ile Val Gln Asn Ser Ser Gly Ala Asn Ser Phe
145                 150                 155                 160
Ser Glu Ile Arg Asp Ala Ile Gly Gly Thr Asn Gly Ser Phe Leu Asp
                165                 170                 175
Ser Val Ser Gln Ile Asp Lys Thr Asn Gly Leu Gly Ala Met Asn Gln
            180                 185                 190
Pro Leu Glu Val Ser Met Gly Asn Gln Pro Asp Lys Leu Ser Thr Gly
        195                 200                 205
Ala Lys Leu Ala Arg Asp Gln Gln Pro Asp Leu Leu Thr Arg Asn Gln
    210                 215                 220
Gln Cys Gln Phe Pro Val Ala Thr Gln Asn Thr Gln Phe Pro Met Glu
225                 230                 235                 240
Asn Gln Gln Ala Trp Leu Gln Met Lys Asn Gln Leu Ile Gly Phe Pro
                245                 250                 255
Phe Gly Asn Gln Gln Pro Arg Met Thr Ile Arg Asn Gln Gln Pro Cys
            260                 265                 270
Leu Ala Met Gly Asn Gln Gln Pro Met Tyr Leu Ile Gly Thr Pro Arg
        275                 280                 285
Pro Ala Leu Val Ser Gly Asn Gln Gln Leu Gly Gly Pro Gln Gly Asn
    290                 295                 300
Lys Arg Pro Ile Phe Leu Asn His Gln Thr Cys Leu Pro Ala Gly Asn
305                 310                 315                 320
Gln Leu Tyr Gly Ser Pro Thr Asp Met His Gln Leu Val Met Ser Thr
                325                 330                 335
Gly Gly Gln Gln His Gly Leu Leu Ile Lys Asn Gln Gln Pro Gly Ser
            340                 345                 350
Leu Ile Arg Gly Gln Gln Pro Cys Val Pro Leu Ile Asp Gln Gln Pro
        355                 360                 365
Ala Thr Pro Lys Gly Phe Thr His Leu Asn Gln Met Val Ala Thr Ser
    370                 375                 380
Met Ser Ser Pro Gly Leu Arg Pro His Ser Gln Ser Gln Val Pro Thr
385                 390                 395                 400
Thr Tyr Leu His Val Glu Ser Val Ser Arg Ile Leu Asn Gly Thr Thr
                405                 410                 415
Gly Thr Cys Gln Arg Ser Arg Ala Pro Ala Tyr Asp Ser Leu Gln Gln
            420                 425                 430
Asp Ile His Gln Gly Asn Lys Tyr Ile Leu Ser His Glu Ile Ser Asn
        435                 440                 445
Gly Asn Gly Cys Lys Lys Ala Leu Pro Gln Asn Ser Ser Leu Pro Thr
    450                 455                 460
Pro Ile Met Ala Lys Leu Glu Glu Ala Arg Gly Ser Lys Arg Gln Tyr
465                 470                 475                 480
His Arg Ala Met Gly Gln Thr Glu Lys His Asp Leu Asn Leu Ala Gln
                485                 490                 495
Gln Ile Ala Gln Ser Gln Asp Val Glu Arg His Asn Ser Ser Thr Cys
            500                 505                 510
Val Glu Tyr Leu Asp Ala Ala Lys Lys Thr Lys Ile Gln Lys Val Val
        515                 520                 525
```

```
Gln Glu Asn Leu His Gly Met Pro Pro Glu Val Ile Glu Ile Glu Asp
        530                 535                 540
Asp Pro Thr Asp Gly Ala Arg Lys Gly Lys Asn Thr Ala Ser Ile Ser
545                 550                 555                 560
Lys Gly Ala Ser Lys Gly Asn Ser Ser Pro Val Lys Lys Thr Ala Glu
                565                 570                 575
Lys Glu Lys Cys Ile Val Pro Lys Thr Pro Ala Lys Lys Gly Arg Ala
                580                 585                 590
Gly Arg Lys Lys Ser Val Pro Pro Ala His Ala Ser Glu Ile Gln
            595                 600                 605
Leu Trp Gln Pro Thr Pro Pro Lys Thr Pro Leu Ser Arg Ser Lys Pro
610                 615                 620
Lys Gly Lys Gly Arg Lys Ser Ile Gln Asp Ser Gly Lys Ala Arg Gly
625                 630                 635                 640
Pro Ser Gly Glu Leu Leu Cys Gln Asp Ser Ile Ala Glu Ile Ile Tyr
                645                 650                 655
Arg Met Gln Asn Leu Tyr Leu Gly Asp Lys Glu Arg Glu Gln Glu Gln
                660                 665                 670
Asn Ala Met Val Leu Tyr Lys Gly Asp Gly Ala Leu Val Pro Tyr Glu
                675                 680                 685
Ser Lys Lys Arg Lys Pro Arg Pro Lys Val Asp Ile Asp Asp Glu Thr
            690                 695                 700
Thr Arg Ile Trp Asn Leu Leu Met Gly Lys Gly Asp Glu Lys Glu Gly
705                 710                 715                 720
Asp Glu Glu Lys Asp Lys Lys Glu Lys Trp Trp Glu Glu Glu Arg
                725                 730                 735
Arg Val Phe Arg Gly Arg Ala Asp Ser Phe Ile Ala Arg Met His Leu
                740                 745                 750
Val Gln Gly Asp Arg Arg Phe Ser Pro Trp Lys Gly Ser Val Val Asp
            755                 760                 765
Ser Val Ile Gly Val Phe Leu Thr Gln Asn Val Ser Asp His Leu Ser
770                 775                 780
Ser Ser Ala Phe Met Ser Leu Ala Ala Arg Phe Pro Pro Lys Leu Ser
785                 790                 795                 800
Ser Ser Arg Glu Asp Glu Arg Asn Val Arg Ser Val Val Glu Asp
                805                 810                 815
Pro Glu Gly Cys Ile Leu Asn Leu Asn Glu Ile Pro Ser Trp Gln Glu
            820                 825                 830
Lys Val Gln His Pro Ser Asp Met Glu Val Ser Gly Val Asp Ser Gly
                835                 840                 845
Ser Lys Glu Gln Leu Arg Asp Cys Ser Asn Ser Gly Ile Glu Arg Phe
850                 855                 860
Asn Phe Leu Glu Lys Ser Ile Gln Asn Leu Glu Glu Val Leu Ser
865                 870                 875                 880
Ser Gln Asp Ser Phe Asp Pro Ala Ile Phe Gln Ser Cys Gly Arg Val
                885                 890                 895
Gly Ser Cys Ser Cys Ser Lys Ser Asp Ala Glu Phe Pro Thr Thr Arg
                900                 905                 910
Cys Glu Thr Lys Thr Val Ser Gly Thr Ser Gln Ser Val Gln Thr Gly
            915                 920                 925
Ser Pro Asn Leu Ser Asp Glu Ile Cys Leu Gln Gly Asn Glu Arg Pro
930                 935                 940
His Leu Tyr Glu Gly Ser Gly Asp Val Gln Lys Gln Glu Thr Thr Asn
```

```
            945                 950                 955                 960
Val Ala Gln Lys Lys Pro Asp Leu Glu Lys Thr Met Asn Trp Lys Asp
                        965                 970                 975
Ser Val Cys Phe Gly Gln Pro Arg Asn Asp Thr Asn Trp Gln Thr Thr
                980                 985                 990
Pro Ser Ser Ser Tyr Glu Gln Cys Ala Thr Arg Gln Pro His Val Leu
                995                 1000                1005
Asp Ile Glu Asp Phe Gly Met Gln Gly Glu Gly Leu Gly Tyr Ser Trp
            1010                1015                1020
Met Ser Ile Ser Pro Arg Val Asp Arg Val Lys Asn Lys Asn Val Pro
1025                1030                1035                1040
Arg Arg Phe Phe Arg Gln Gly Gly Ser Val Pro Arg Glu Phe Thr Gly
                    1045                1050                1055
Gln Ile Ile Pro Ser Thr Pro His Glu Leu Pro Gly Met Gly Leu Ser
                1060                1065                1070
Gly Ser Ser Ser Ala Val Gln Glu His Gln Asp Asp Thr Gln His Asn
            1075                1080                1085
Gln Gln Asp Glu Met Asn Lys Ala Ser His Leu Gln Lys Thr Phe Leu
    1090                1095                1100
Asp Leu Leu Asn Ser Ser Glu Glu Cys Leu Thr Arg Gln Ser Ser Thr
1105                1110                1115                1120
Lys Gln Asn Ile Thr Asp Gly Cys Leu Pro Arg Asp Arg Thr Ala Glu
                    1125                1130                1135
Asp Val Val Asp Pro Leu Ser Asn Asn Ser Ser Leu Gln Asn Ile Leu
                1140                1145                1150
Val Glu Ser Asn Ser Ser Asn Lys Glu Gln Thr Ala Val Glu Tyr Lys
            1155                1160                1165
Glu Thr Asn Ala Thr Ile Leu Arg Glu Met Lys Gly Thr Leu Ala Asp
        1170                1175                1180
Gly Lys Lys Pro Thr Ser Gln Trp Asp Cys Leu Arg Arg Glu Ala Gln
1185                1190                1195                1200
Ala Arg Ala Gly Ile Arg Glu Lys Thr Arg Ser Thr Met Asp Thr Val
                    1205                1210                1215
Asp Trp Lys Ala Ile Arg Ala Ala Asp Val Lys Glu Val Ala Glu Thr
                1220                1225                1230
Ile Lys Ser Arg Gly Met Asn His Lys Leu Ala Glu Arg Ile Gln Gly
            1235                1240                1245
Phe Leu Asp Arg Leu Val Asn Asp His Gly Ser Ile Asp Leu Glu Trp
    1250                1255                1260
Leu Arg Asp Val Pro Pro Asp Lys Ala Lys Glu Tyr Leu Leu Ser Phe
1265                1270                1275                1280
Asn Gly Leu Gly Leu Lys Ser Val Glu Cys Val Arg Leu Leu Thr Leu
                    1285                1290                1295
His His Leu Ala Phe Pro Val Asp Thr Asn Val Gly Arg Ile Ala Val
                1300                1305                1310
Arg Leu Gly Trp Val Pro Leu Gln Pro Leu Pro Glu Ser Leu Gln Leu
            1315                1320                1325
His Leu Leu Glu Met Tyr Pro Met Leu Glu Ser Ile Gln Lys Tyr Leu
    1330                1335                1340
Trp Pro Arg Leu Cys Lys Leu Asp Gln Lys Thr Leu Tyr Glu Leu His
1345                1350                1355                1360
Tyr Gln Met Ile Thr Phe Gly Lys Val Phe Cys Thr Lys Ser Lys Pro
                    1365                1370                1375
```

Asn Cys Asn Ala Cys Pro Met Lys Gly Glu Cys Arg His Phe Ala Ser
             1380                1385                1390

Ala Phe Ala Ser Ala Arg Leu Ala Leu Pro Ser Thr Glu Lys Gly Met
        1395                1400                1405

Gly Thr Pro Asp Lys Asn Pro Leu Pro Leu His Leu Pro Glu Pro Phe
    1410                1415                1420

Gln Arg Glu Gln Gly Ser Glu Val Val Gln His Ser Glu Pro Ala Lys
1425                1430                1435                1440

Lys Val Thr Cys Cys Glu Pro Ile Ile Glu Glu Pro Ala Ser Pro Glu
                1445                1450                1455

Pro Glu Thr Ala Glu Val Ser Ile Ala Asp Ile Glu Glu Ala Phe Phe
            1460                1465                1470

Glu Asp Pro Glu Glu Ile Pro Thr Ile Arg Leu Asn Met Asp Ala Phe
        1475                1480                1485

Thr Ser Asn Leu Lys Lys Ile Met Glu His Asn Lys Glu Leu Gln Asp
    1490                1495                1500

Gly Asn Met Ser Ser Ala Leu Val Ala Leu Thr Ala Glu Thr Ala Ser
1505                1510                1515                1520

Leu Pro Met Pro Lys Leu Lys Asn Ile Ser Gln Leu Arg Thr Glu His
                1525                1530                1535

Arg Val Tyr Glu Leu Pro Asp Glu His Pro Leu Leu Ala Gln Leu Glu
            1540                1545                1550

Lys Arg Glu Pro Asp Asp Pro Cys Ser Tyr Leu Leu Ala Ile Trp Thr
        1555                1560                1565

Pro Gly Glu Thr Ala Asp Ser Ile Gln Pro Ser Val Ser Thr Cys Ile
    1570                1575                1580

Phe Gln Ala Asn Gly Met Leu Cys Asp Glu Glu Thr Cys Phe Ser Cys
1585                1590                1595                1600

Asn Ser Ile Lys Glu Thr Arg Ser Gln Ile Val Arg Gly Thr Ile Leu
                1605                1610                1615

Ile Pro Cys Arg Thr Ala Met Arg Gly Ser Phe Pro Leu Asn Gly Thr
            1620                1625                1630

Tyr Phe Gln Val Asn Glu Val Phe Ala Asp His Ala Ser Ser Leu Asn
        1635                1640                1645

Pro Ile Asn Val Pro Arg Glu Leu Ile Trp Glu Leu Pro Arg Arg Thr
    1650                1655                1660

Val Tyr Phe Gly Thr Ser Val Pro Thr Ile Phe Lys Gly Leu Ser Thr
1665                1670                1675                1680

Glu Lys Ile Gln Ala Cys Phe Trp Lys Gly Tyr Val Cys Val Arg Gly
                1685                1690                1695

Phe Asp Arg Lys Thr Arg Gly Pro Lys Pro Leu Ile Ala Arg Leu His
            1700                1705                1710

Phe Pro Ala Ser Lys Leu Lys Gly Gln Gln Ala Asn Leu Ala
        1715                1720                1725

<210> SEQ ID NO 19
<211> LENGTH: 5187
<212> TYPE: DNA
<213> ORGANISM: Artificial Sequence
<220> FEATURE:
<223> OTHER INFORMATION: Description of Artificial Sequence:synthetic
      ROS1-DME chimera, construct with DME amino acids
      690-797 deleted and ROS1 amino acids 521-627
      inserted, DME containing ROS1 Domain A

<400> SEQUENCE: 19

-continued

```
atgcagagca ttatggactc gtctgctgtt aatgcgacgg aagctactga acaaaatgat    60
ggcagcagac aagatgttct ggagttcgac cttaacaaaa ctcctcagca gaaaccctcc   120
aaaaggaaaa ggaagttcat gcccaaggtg gtcgtggaag gcaaacctaa agaaagcca   180
cgcaaacctg cagaacttcc caaagtggtc gtggaaggca aacctaaaag gaagccacgc   240
aaagctgcaa ctcaggaaaa agtgaaatct aagaaaccg ggagtgccaa aagaaaaat   300
ttgaaagaat cagcaactaa aaagccagcc aatgttggag atatgagcaa caaaagccct   360
gaagtcacac tcaaaagttg cagaaaagct ttgaattttg acttggagaa tcctggagat   420
gcgaggcaag gtgactctga gtctgaaatt gtccagaaca gtagtggcgc aaactcgttt   480
tctgagatca gagatgccat tggtggaact aatggtagtt tcctggattc agtgtcacaa   540
atagacaaga ccaatggatt gggggctatg aaccagccac ttgaagtgtc aatgggaaac   600
cagccagata aactatctac aggagcgaaa ctggccagag accaacaacc tgatttattg   660
actagaaacc agcaatgcca gttcccagtg gcaacccaga cacccagtt cccaatggaa   720
aaccaacaag cttggcttca gatgaaaaac caacttattg gctttccatt tggtaaccag   780
caacctcgca tgaccataag aaaccagcag ccttgcttgg ccatgggtaa tcaacaacct   840
atgtatctga taggaactcc acggcctgca ttagtaagtg gaaaccagca actaggaggt   900
ccccaaggaa acaagcggcc tatattttg aatcaccaga cttgtttacc tgctggaaat   960
cagctatatg gatcacctac agacatgcat caacttgtta tgtcaaccgg agggcaacaa  1020
catggactac tgataaaaa ccagcaacct ggatcattaa taagaggcca gcagccttgc  1080
gtacctttga ttgaccagca acctgcaact ccaaaaggtt ttactcactt gaatcagatg  1140
gtagctacca gcatgtcatc gcctgggctt cgacctcatt ctcagtcaca gttcctaca   1200
acatatctac atgtggaatc tgtttccagg attttgaatg ggactacagg tacatgccag  1260
agaagcaggg ctcctgcata cgattcttta cagcaagata tccatcaagg aaataagtac  1320
atactttctc atgagatatc caatggtaat gggtgcaaga aagcgttacc tcaaaactct  1380
tctctgccaa ctccaattat ggctaaactt gaggaagcca ggggctcgaa gagacagtat  1440
catcgtgcaa tgggacagac ggaaaagcat gatctaaact tagctcaaca gattgctcaa  1500
tcacaagatg tggagagaca taacagcagc acgtgtgtgg aatatttaga tgctgcaaag  1560
aaaacgaaaa tccagaaagt agtccaagaa aatttgcatg gcatgccacc tgaggttata  1620
gaaatcgagg atgatccaac tgatggggca agaaaaggta aaaatactgc cagcatcagt  1680
aaaggtgcat ctaaaggaaa ctcgtctcca gttaaaaaga cagcagaaaa ggagaaatgt  1740
attgtcccaa aaacgcctgc aaaaaagggt cgagcaggta gaaaaaaatc agtacctccg  1800
cctgctcatg cctcagagat ccagcttttgg caacctactc ctccaaagac acctttatca  1860
agaagcaagc ctaaaggaaa agggagaaag tccatacaag attcaggaaa agcaagaggt  1920
ccatcaggag aacttctgtg tcaggattct attgcggaaa taatttacag gatgcaaat   1980
ctgtatctag agacaaaga aagagaacaa gagcaaatg caatggtctt gtacaaagga  2040
gatggtgcac ttgttcccta tgagagcaaa aaaccacgcc cacgaccaaa ggttgatcta  2100
gacgatgaga cagacagagt gtggaaactg ctattggaga atattaatag cgaaggtgtt  2160
gacggatcag acgagcagaa ggcgaaatgg tgggaggaag aacgtaatgt gtttcgagga  2220
cgagctgact catttattgc aaggatgcac cttgtacaag gggatcgacg ttttacgcct  2280
tggaagggat ccgtcgtgga ttctgttgtt ggagtatttc tcactcaaaa tgtttcagac  2340
```

```
catctctcaa gttcggcttt catgtcgttg gcttcccagt tccctgtcaa attaagcagc    2400
agccgagaag atgaaaggaa tgttagaagc gtagttgttg aagatccaga aggatgcatt    2460
ctgaacttaa atgaaattcc ttcgtggcag gaaaaggttc aacatccatc tgacatggaa    2520
gtttctgggg ttgatagtgg atcaaaagag cagctaaggg actgttcaaa ctctggaatt    2580
gaaagattta atttcttaga gaagagtatt caaaatttag aagaggaagt attatcatca    2640
caagattctt ttgatccggc gatatttcag tcgtgtggga gagttggatc ctgttcatgt    2700
tccaaatcag acgcagagtt tcctacaacc aggtgtgaaa caaaaactgt cagtggaaca    2760
tcacaatcag tgcaaactgg gagcccaaac ttgtctgatg aaatttgtct tcaagggaat    2820
gagagaccgc atctatatga aggatctggt gatgttcaga acaagaaac tacaaatgtc     2880 gctcagaaga aacctgatct tgaaaaaaca atgaattgga aagactctgt ctgttttggt    2940
cagccaagaa atgatactaa ttggcaaaca actccttcca gcagctatga gcagtgtgcg    3000
actcgacagc cacatgtact agacatagag gattttggaa tgcaaggtga aggccttggt    3060
tattcttgga tgtccatctc accaagagtt gacagagtaa agaacaaaaa tgtaccacgc    3120
aggtttttca gacaaggtgg aagtgttcca agagaattca caggtcagat cataccatca    3180
acgcctcatg aattaccagg aatgggattg tccggttcct caagcgccgt ccaagaacac    3240
caggacgata cccaacataa tcaacaagat gagatgaata agcatccca tttacaaaaa    3300 acattttggg atctgctcaa ctcctctgaa gaatgcctta caagacagtc cagtaccaaa    3360
cagaacatca cggatggctg tctaccgaga gatagaactg ctgaagacgt ggttgatccg    3420
ctcagtaaca attcaagctt acagaacata ttggtcgaat caaattccag caataaagag    3480
cagacggcag ttgaatacaa ggagacaaat gccactattt tacgagagat gaagggacg    3540 cttgctgatg ggaaaaagcc tacaagccag tgggatagtc tcagaaaaga tgtggagggg    3600
aatgaaggga gacaggaacg aaacaaaaac aatatggatt ccatagacta tgaagcaata    3660
agacgtgcta gtatcagcga gatttctgag gctatcaagg aaagagggat gaataacatg    3720
ttggccgtac gaattaagga tttcctagaa cggatagtta agatcatgg tggtatcgac    3780 cttgaatggt tgagagaatc tcctcctgat aaagccaagg actatctctt gagcataaga    3840 ggtctggggtt tgaaaagtgt tgaatgcgtg cgactcttaa cactccacaa tcttgctttc    3900
cctgttgaca cgaatgttgg aaggatagca gttaggatgg gatgggtgcc tctacaaccc    3960
ctacctgaat cacttcagtt acacctcctg gagctatacc cagtgctcga gtccatccaa    4020
aaatttcttt ggccaagact ttgcaaactc gatcaacgaa cactgtatga attacactac    4080
caactgatta cgtttggaaa ggtattttgc acaaagagta gaccaaattg taatgcatgt    4140
ccaatgagag gagagtgcag acactttgcc agtgctatg ctagtgcaag acttgcttta    4200
ccggcaccag aggagaggag cttaacaagt gcaactattc cggtccctcc cgagtccttt    4260
cctcctgtag ccatcccgat gatagaacta cctcttccgt tggagaaatc cctagcaagt    4320
ggagcaccat cgaatagaga aaactgtgaa ccaataattg aagagccggc ctcgcccggg    4380
caagagtgca ctgaaataac cgagagtgat attgaagatg cttactacaa tgaggaccct    4440
gacgagatcc aacaataaa actcaacatt gaacagtttg gaatgactct acgggaacac    4500
atggaaagaa acatggagct ccaagaaggt gacatgtcca aggctttggt tgctttgcat    4560
ccaacaacta cttctattcc aactcccaaa ctaaagaaca ttagccgtct caggacagag    4620
caccaagtgt acgagctccc agattcacat cgtctccttg atggtatgga taaaagagaa    4680
ccagatgatc caagtcctta tctcttagct atatggacac caggtgaaac agcgaattcg    4740
```

```
gcacaaccgc ctgaacagaa gtgtggaggg aaagcgtctg gcaaaatgtg ctttgacgag    4800
acttgttctg agtgtaacag tctgaggaa gcaaactcac agacagttcg aggaactctt    4860 ctgataccttt gtcggactgc catgagagga agttttccgc tcaacgggac atatttccaa   4920
gtcaacgagt tatttgcaga ccacgagtcc agtctcaaac ccatcgatgt tcctagagat    4980
tggatatggg atctcccaag aaggactgtt tacttcggaa catcagtaac atcaatattc    5040
agaggtcttt caacggagca gatacagttc tgcttttgga aaggattcgt atgtgtccgt    5100
ggattcgaac agaagacaag agcaccgcgt ccattaatgg caaggttgca ttttcctgcg    5160
agcaaattga agaacaacaa aacctaa                                        5187
```

<210> SEQ ID NO 20
<211> LENGTH: 1728
<212> TYPE: PRT
<213> ORGANISM: Artificial Sequence
<220> FEATURE:
<223> OTHER INFORMATION: Description of Artificial Sequence:synthetic
      ROS1-DME chimera, construct with DME amino acids
      690-797 deleted and ROS1 amino acids 521-627
      inserted, DME containing ROS1 Domain A

<400> SEQUENCE: 20

```
Met Gln Ser Ile Met Asp Ser Ser Ala Val Asn Ala Thr Glu Ala Thr
1               5                   10                  15

Glu Gln Asn Asp Gly Ser Arg Gln Asp Val Leu Glu Phe Asp Leu Asn
            20                  25                  30

Lys Thr Pro Gln Gln Lys Pro Ser Lys Arg Lys Arg Lys Phe Met Pro
        35                  40                  45

Lys Val Val Glu Gly Lys Pro Lys Arg Lys Pro Arg Lys Pro Ala
    50                  55                  60

Glu Leu Pro Lys Val Val Glu Gly Lys Pro Lys Arg Lys Pro Arg
65                  70                  75                  80

Lys Ala Ala Thr Gln Glu Lys Val Lys Ser Lys Glu Thr Gly Ser Ala
                85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
    130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190

Pro Leu Glu Val Ser Met Gly Asn Gln Pro Lys Leu Ser Thr Gly
        195                 200                 205

Ala Lys Leu Ala Arg Asp Gln Gln Pro Asp Leu Leu Thr Arg Asn Gln
    210                 215                 220

Gln Cys Gln Phe Pro Val Ala Thr Gln Asn Thr Gln Phe Pro Met Glu
225                 230                 235                 240

Asn Gln Gln Ala Trp Leu Gln Met Lys Asn Gln Leu Ile Gly Phe Pro
                245                 250                 255

Phe Gly Asn Gln Gln Pro Arg Met Thr Ile Arg Asn Gln Gln Pro Cys
```

```
              260                 265                 270
Leu Ala Met Gly Asn Gln Gln Pro Met Tyr Leu Ile Gly Thr Pro Arg
            275                 280                 285
Pro Ala Leu Val Ser Gly Asn Gln Gln Leu Gly Gly Pro Gln Gly Asn
        290                 295                 300
Lys Arg Pro Ile Phe Leu Asn His Gln Thr Cys Leu Pro Ala Gly Asn
305                 310                 315                 320
Gln Leu Tyr Gly Ser Pro Thr Asp Met His Gln Leu Val Met Ser Thr
                325                 330                 335
Gly Gly Gln Gln His Gly Leu Leu Ile Lys Asn Gln Gln Pro Gly Ser
            340                 345                 350
Leu Ile Arg Gly Gln Gln Pro Cys Val Pro Leu Ile Asp Gln Gln Pro
        355                 360                 365
Ala Thr Pro Lys Gly Phe Thr His Leu Asn Gln Met Val Ala Thr Ser
    370                 375                 380
Met Ser Ser Pro Gly Leu Arg Pro His Ser Gln Ser Gln Val Pro Thr
385                 390                 395                 400
Thr Tyr Leu His Val Glu Ser Val Ser Arg Ile Leu Asn Gly Thr Thr
                405                 410                 415
Gly Thr Cys Gln Arg Ser Arg Ala Pro Ala Tyr Asp Ser Leu Gln Gln
            420                 425                 430
Asp Ile His Gln Gly Asn Lys Tyr Ile Leu Ser His Glu Ile Ser Asn
        435                 440                 445
Gly Asn Gly Cys Lys Lys Ala Leu Pro Gln Asn Ser Ser Leu Pro Thr
    450                 455                 460
Pro Ile Met Ala Lys Leu Glu Glu Ala Arg Gly Ser Lys Arg Gln Tyr
465                 470                 475                 480
His Arg Ala Met Gly Gln Thr Glu Lys His Asp Leu Asn Leu Ala Gln
                485                 490                 495
Gln Ile Ala Gln Ser Gln Asp Val Glu Arg His Asn Ser Ser Thr Cys
            500                 505                 510
Val Glu Tyr Leu Asp Ala Ala Lys Lys Thr Lys Ile Gln Lys Val Val
        515                 520                 525
Gln Glu Asn Leu His Gly Met Pro Pro Glu Val Ile Glu Ile Glu Asp
    530                 535                 540
Asp Pro Thr Asp Gly Ala Arg Lys Gly Lys Asn Thr Ala Ser Ile Ser
545                 550                 555                 560
Lys Gly Ala Ser Lys Gly Asn Ser Ser Pro Val Lys Lys Thr Ala Glu
                565                 570                 575
Lys Glu Lys Cys Ile Val Pro Lys Thr Pro Ala Lys Lys Gly Arg Ala
            580                 585                 590
Gly Arg Lys Lys Ser Val Pro Pro Ala His Ala Ser Glu Ile Gln
        595                 600                 605
Leu Trp Gln Pro Thr Pro Pro Lys Thr Pro Leu Ser Arg Ser Lys Pro
    610                 615                 620
Lys Gly Lys Gly Arg Lys Ser Ile Gln Asp Ser Gly Lys Ala Arg Gly
625                 630                 635                 640
Pro Ser Gly Glu Leu Leu Cys Gln Asp Ser Ile Ala Glu Ile Ile Tyr
                645                 650                 655
Arg Met Gln Asn Leu Tyr Leu Gly Asp Lys Glu Arg Glu Gln Glu Gln
            660                 665                 670
Asn Ala Met Val Leu Tyr Lys Gly Asp Gly Ala Leu Val Pro Tyr Glu
        675                 680                 685
```

-continued

```
Ser Lys Lys Pro Arg Pro Arg Pro Lys Val Asp Leu Asp Asp Glu Thr
    690                 695                 700
Asp Arg Val Trp Lys Leu Leu Glu Asn Ile Asn Ser Glu Gly Val
705                 710                 715                 720
Asp Gly Ser Asp Glu Gln Lys Ala Lys Trp Trp Glu Glu Arg Asn
                725                 730                 735
Val Phe Arg Gly Arg Ala Asp Ser Phe Ile Ala Arg Met His Leu Val
                740                 745                 750
Gln Gly Asp Arg Arg Phe Thr Pro Trp Lys Gly Ser Val Val Asp Ser
            755                 760                 765
Val Val Gly Val Phe Leu Thr Gln Asn Val Ser Asp His Leu Ser Ser
    770                 775                 780
Ser Ala Phe Met Ser Leu Ala Ser Gln Phe Pro Val Lys Leu Ser Ser
785                 790                 795                 800
Ser Arg Glu Asp Glu Arg Asn Val Arg Ser Val Val Glu Asp Pro
                805                 810                 815
Glu Gly Cys Ile Leu Asn Leu Asn Glu Ile Pro Ser Trp Gln Glu Lys
                820                 825                 830
Val Gln His Pro Ser Asp Met Glu Val Ser Gly Val Asp Ser Gly Ser
    835                 840                 845
Lys Glu Gln Leu Arg Asp Cys Ser Asn Ser Gly Ile Glu Arg Phe Asn
850                 855                 860
Phe Leu Glu Lys Ser Ile Gln Asn Leu Glu Glu Val Leu Ser Ser
865                 870                 875                 880
Gln Asp Ser Phe Asp Pro Ala Ile Phe Gln Ser Cys Gly Arg Val Gly
                885                 890                 895
Ser Cys Ser Cys Ser Lys Ser Asp Ala Glu Phe Pro Thr Thr Arg Cys
                900                 905                 910
Glu Thr Lys Thr Val Ser Gly Thr Ser Gln Ser Val Gln Thr Gly Ser
            915                 920                 925
Pro Asn Leu Ser Asp Glu Ile Cys Leu Gln Gly Asn Glu Arg Pro His
    930                 935                 940
Leu Tyr Glu Gly Ser Gly Asp Val Gln Lys Gln Glu Thr Thr Asn Val
945                 950                 955                 960
Ala Gln Lys Lys Pro Asp Leu Glu Lys Thr Met Asn Trp Lys Asp Ser
                965                 970                 975
Val Cys Phe Gly Gln Pro Arg Asn Asp Thr Asn Trp Gln Thr Thr Pro
                980                 985                 990
Ser Ser Ser Tyr Glu Gln Cys Ala Thr Arg Gln Pro His Val Leu Asp
            995                 1000                1005
Ile Glu Asp Phe Gly Met Gln Gly Glu Gly Leu Gly Tyr Ser Trp Met
    1010                1015                1020
Ser Ile Ser Pro Arg Val Asp Arg Val Lys Asn Lys Asn Val Pro Arg
1025                1030                1035                1040
Arg Phe Phe Arg Gln Gly Gly Ser Val Pro Arg Glu Phe Thr Gly Gln
                1045                1050                1055
Ile Ile Pro Ser Thr Pro His Glu Leu Pro Gly Met Gly Leu Ser Gly
                1060                1065                1070
Ser Ser Ser Ala Val Gln Glu His Gln Asp Asp Thr Gln His Asn Gln
            1075                1080                1085
Gln Asp Glu Met Asn Lys Ala Ser His Leu Gln Lys Thr Phe Leu Asp
    1090                1095                1100
```

```
Leu Leu Asn Ser Ser Glu Glu Cys Leu Thr Arg Gln Ser Ser Thr Lys
1105                1110                1115                1120

Gln Asn Ile Thr Asp Gly Cys Leu Pro Arg Asp Arg Thr Ala Glu Asp
            1125                1130                1135

Val Val Asp Pro Leu Ser Asn Asn Ser Ser Leu Gln Asn Ile Leu Val
        1140                1145                1150

Glu Ser Asn Ser Ser Asn Lys Glu Gln Thr Ala Val Glu Tyr Lys Glu
    1155                1160                1165

Thr Asn Ala Thr Ile Leu Arg Glu Met Lys Gly Thr Leu Ala Asp Gly
1170                1175                1180

Lys Lys Pro Thr Ser Gln Trp Asp Ser Leu Arg Lys Asp Val Glu Gly
1185                1190                1195                1200

Asn Glu Gly Arg Gln Glu Arg Asn Lys Asn Asn Met Asp Ser Ile Asp
            1205                1210                1215

Tyr Glu Ala Ile Arg Arg Ala Ser Ile Ser Glu Ile Ser Glu Ala Ile
        1220                1225                1230

Lys Glu Arg Gly Met Asn Asn Met Leu Ala Val Arg Ile Lys Asp Phe
    1235                1240                1245

Leu Glu Arg Ile Val Lys Asp His Gly Gly Ile Asp Leu Glu Trp Leu
1250                1255                1260

Arg Glu Ser Pro Pro Asp Lys Ala Lys Asp Tyr Leu Leu Ser Ile Arg
1265                1270                1275                1280

Gly Leu Gly Leu Lys Ser Val Glu Cys Val Arg Leu Leu Thr Leu His
            1285                1290                1295

Asn Leu Ala Phe Pro Val Asp Thr Asn Val Gly Arg Ile Ala Val Arg
        1300                1305                1310

Met Gly Trp Val Pro Leu Gln Pro Leu Pro Glu Ser Leu Gln Leu His
    1315                1320                1325

Leu Leu Glu Leu Tyr Pro Val Leu Glu Ser Ile Gln Lys Phe Leu Trp
1330                1335                1340

Pro Arg Leu Cys Lys Leu Asp Gln Arg Thr Leu Tyr Glu Leu His Tyr
1345                1350                1355                1360

Gln Leu Ile Thr Phe Gly Lys Val Phe Cys Thr Lys Ser Arg Pro Asn
            1365                1370                1375

Cys Asn Ala Cys Pro Met Arg Gly Glu Cys Arg His Phe Ala Ser Ala
        1380                1385                1390

Tyr Ala Ser Ala Arg Leu Ala Leu Pro Ala Pro Glu Glu Arg Ser Leu
    1395                1400                1405

Thr Ser Ala Thr Ile Pro Val Pro Pro Glu Ser Phe Pro Pro Val Ala
1410                1415                1420

Ile Pro Met Ile Glu Leu Pro Leu Pro Leu Glu Lys Ser Leu Ala Ser
1425                1430                1435                1440

Gly Ala Pro Ser Asn Arg Glu Asn Cys Glu Pro Ile Ile Glu Glu Pro
            1445                1450                1455

Ala Ser Pro Gly Gln Glu Cys Thr Glu Ile Thr Glu Ser Asp Ile Glu
        1460                1465                1470

Asp Ala Tyr Tyr Asn Glu Asp Pro Asp Glu Ile Pro Thr Ile Lys Leu
    1475                1480                1485

Asn Ile Glu Gln Phe Gly Met Thr Leu Arg Glu His Met Glu Arg Asn
1490                1495                1500

Met Glu Leu Gln Glu Gly Asp Met Ser Lys Ala Leu Val Ala Leu His
1505                1510                1515                1520

Pro Thr Thr Thr Ser Ile Pro Thr Pro Lys Leu Lys Asn Ile Ser Arg
```

```
              1525                1530                1535
Leu Arg Thr Glu His Gln Val Tyr Glu Leu Pro Asp Ser His Arg Leu
            1540                1545                1550

Leu Asp Gly Met Asp Lys Arg Glu Pro Asp Pro Ser Pro Tyr Leu
        1555                1560                1565

Leu Ala Ile Trp Thr Pro Gly Glu Thr Ala Asn Ser Ala Gln Pro Pro
    1570                1575                1580

Glu Gln Lys Cys Gly Gly Lys Ala Ser Gly Lys Met Cys Phe Asp Glu
1585                1590                1595                1600

Thr Cys Ser Glu Cys Asn Ser Leu Arg Glu Ala Asn Ser Gln Thr Val
                1605                1610                1615

Arg Gly Thr Leu Leu Ile Pro Cys Arg Thr Ala Met Arg Gly Ser Phe
                1620                1625                1630

Pro Leu Asn Gly Thr Tyr Phe Gln Val Asn Glu Leu Phe Ala Asp His
            1635                1640                1645

Glu Ser Ser Leu Lys Pro Ile Asp Val Pro Arg Asp Trp Ile Trp Asp
        1650                1655                1660

Leu Pro Arg Arg Thr Val Tyr Phe Gly Thr Ser Val Thr Ser Ile Phe
1665                1670                1675                1680

Arg Gly Leu Ser Thr Glu Gln Ile Gln Phe Cys Phe Trp Lys Gly Phe
                1685                1690                1695

Val Cys Val Arg Gly Phe Glu Gln Lys Thr Arg Ala Pro Arg Pro Leu
            1700                1705                1710

Met Ala Arg Leu His Phe Pro Ala Ser Lys Leu Lys Asn Asn Lys Thr
        1715                1720                1725

<210> SEQ ID NO 21
<211> LENGTH: 4185
<212> TYPE: DNA
<213> ORGANISM: Artificial Sequence
<220> FEATURE:
<223> OTHER INFORMATION: Description of Artificial Sequence:synthetic
      ROS1-DME chimera, construct with ROS1 amino acids
      521-627 deleted and DME amino acids 690-797
      inserted, ROS1 containing DME Domain A

<400> SEQUENCE: 21
atggagaaac agaggagaga agaaagcagc tttcaacaac ctccatggat tcctcagaca     60
cccatgaagc cattttcacc gatctgccca tacacggtgg aggatcaata tcatagcagt    120
caattggagg aaaggagatt tgttgggaac aaggatatga gtggtcttga tcacttgtct    180
tttggggatt tgcttgctct agctaacact gcatccctca tattctctgg tcagactcca    240
atacctacaa gaaacacaga ggttatgcaa aaaggtactg aagaagtgga gagtttgagc    300
tcagtgagta acaatgttgc tgaacagatc ctcaagactc tgaaaaaacc taagaggaag    360
aagcatcggc caaaggttcg tagaaagct aaacccaaga gggagcctaa accacgagct    420
ccgaggaagt ctgttgtcac cgatggtcaa gaaagcaaaa caccaaagag gaaatatgtg    480
cggaagaagg ttgaagtcag taaggatcaa gacgctactc cggttgaatc atcagcagct    540
gttgaaactt caactcgtcc taagaggctc tgtagacgag tcttggattt tgaagccgaa    600
aatggagaaa accagaccaa cggtgacatt agagaagcag gtgagatgga atcagctctc    660
caagagaagc agttagattc tgggaatcaa gagttaaaag attgccttct ttcggctcct    720
agcacgccca agaaaagcg cagccaaggt aaaagaaagg gagttcaacc aaagaaaaat    780
ggcagtaatc tagaagaagt cgatatttcg atggcgcaag ctgcaaagag aagacaagga    840
```

```
ccaacttgtt gcgacatgaa tctatcaggg attcagtatg atgagcaatg tgactaccag    900
aaaatgcatt ggttgtattc cccaaacttg caacagggag ggatgagata tgatgccatt    960
tgcagcaaag tattctctgg acaacagcac aattatgttt ctgcctttca cgctacgtgc   1020
tacagttcca catctcagct cagtgctaat agagtcctaa ccgttgaaga aagacgagaa   1080
ggtatctttc aaggaaggca agagtctgag ctaaatgttc tctcggataa gatagacacg   1140
ccgatcaaga agaaaacaac aggccatgct cgattccgga atttgtcttc aatgaataaa   1200
cttgtggaag ttcctgagca tttaacctca ggatattgta gcaagccaca gcaaaataat   1260
aagattcttg ttgatacgcg ggtgactgtg agcaaaaaga agccaaccaa gtctgagaaa   1320
tcacaaacca aacagaaaaa tcttcttccg aatctttgcc gttttccacc ttcatttact   1380
ggtctttctc cagatgaact ttggaaacga cgtaactcga tcgaaacaat cagtgagcta   1440
ttgcgtctat tagacatcaa cagggagcat tctgaaactg ctctcgttcc ttacacaatg   1500
aatagccaga ttgtactctt tggtggtggc gctggagcaa ttgtgcctgt aactcctgtt   1560
aagaagcgaa aaccaagacc caaagttgac attgacgatg aaacaactcg catatggaac   1620
ttactgatgg ggaaaggaga tgaaaaagaa ggggatgaag agaaggataa aaagaaagag   1680
aagtggtggg aagaagaaag aagagtcttc cgaggaaggg ctgattcctt catcgctcgc   1740
atgcacctgg tacaaggaga tagacgtttt tcgccatgga agggatcggt ggttgattcg   1800
gtcattgagt ttttccttac acagaatgtc tcggatcacc tttcaagctc tgcgttcatg   1860
tctctagctg ctcgattccc tccaccttt gtaccgagca gtaactttga cgctggaaca   1920
agctcgatgc cttctattca ataacgtac ttggactcag aggaaacgat gtcaagccca   1980
cccgatcaca atcacagttc tgttactttg aaaaatacac agcctgatga ggagaaggat   2040
tatgtaccta gcaatgaaac ctccagaagc agtagtgaga ttgccatctc agcccatgaa   2100
tcagttgaca aaaccacgga ttcaaaggag tatgttgatt cagatcgaaa aggctcaagt   2160
gtagaggttg ataagacgga tgagaagtgt cgtgtcctga acctgttttcc atctgaagat   2220
tctgcactta catgtcaaca ttcgatggtg tctgatgctc ctcaaaatac agagagagca   2280
ggatcaagct cagagatcga cttagaagga gagtatcgta cttcctttat gaagctccta   2340
caggggtac aagtctctct agaagattcc aatcaagtat caccaaatat gtctccgggt   2400
gattgtagct cagaaattaa gggttttccag tcaatgaaag agcccacaaa atcctctgtt   2460
gatagtagtg aacctggttg ttgctctcag caagatgggg atgttttgag ttgtcagaaa   2520
cctaccttaa aagaaaaagg gaaaaaggtt ttgaaggagg aaaaaaaagc gtttgactgg   2580
gattgtttaa gaagagaagc ccaagctaga gcaggaatta gagaaaaaac aagaagtaca   2640
atggacaccg tggattggaa ggcaatacga gcagcagatg ttaaggaagt tgctgaaaca   2700
atcaagagtc gcgggatgaa ccataaactt gcagaacgta tacagggctt ccttgatcga   2760
ctggtaaatg accatggaag tatcgatctt gaatggttga gagatgttcc accagataaa   2820
gcaaaagaat atcttctgag cttttaacgga ttgggactga aaagtgtgga gtgtgtgcgg   2880
cttctaacac ttcaccatct tgcctttcca gttgatacaa atgttgggcg catagccgtc   2940
agacttggat gggtgcccct tcagccgctc ccagagtcac ttcagttgca tcttctggaa   3000
atgtatccta tgcttgaatc tattcaaaag tatctttggc cccgtctctg caaactcgac   3060
caaaaaacat tgtatgagtt gcactaccag atgattactt ttggaaaggt cttttgcaca   3120
aagagcaaac ctaattgcaa tgcatgtccg atgaaaggaa aatgcagaca ttttgccagt   3180
gcgtttgcaa gtgcaaggct tgctttacca agtacagaga aaggtatggg gacacctgat   3240
```

```
aaaaacccctt tgcctctaca cctgccagag ccattccaga gagagcaagg gtctgaagta    3300
gtacagcact cagaaccagc aaaaaaggtc acatgttgtg aaccaatcat cgaagagcct    3360
gcttcaccgg agccagaaac cgcagaagta tcaatagctg acatagagga ggcgttttt     3420 gaggatccag aagaaattcc taccatcagg ctaaacatgg atgcatttac cagtaacttg    3480
aagaagataa tggaacacaa caaggaactt caagacggaa acatgtccag cgctttagtt    3540
gcacttactg ctgaaactgc ttctcttcca atgcctaagc tcaagaatat cagccagtta    3600
aggacagaac accgagttta cgaacttcca gacgagcatc ctcttctagc tcagttggaa    3660
aagagagaac ctgatgatcc atgttcttat ttgcttgcta tatggacgcc aggtgagacg    3720
gctgattcta ttcaaccgtc tgttagtacg tgcatattcc aagcaaatgg tatgctttgt    3780
gacgaggaga cttgtttctc ctgcaacagc atcaaggaga ctagatctca aattgtgaga    3840
gggacaattt tgattccttg tagaacagcg atgagggta gttttcctct aaatggaacg     3900
tactttcaag taaatgaggt gtttgcggat catgcatcca gcctaaaccc aatcaatgtc    3960
ccaagggaat tgatatggga attacctcga agaacggtct attttggtac ctctgttcct    4020
acgatattca aggtttatc aactgagaag atacaggctt gcttttggaa agggtacgta     4080
tgtgtacgtg gatttgatcg aaagacgagg ggaccgaagc ctttgattgc aagattgcac    4140
ttcccggcga gcaaactgaa gggacaacaa gctaacctcg cctaa                    4185
```

<210> SEQ ID NO 22
<211> LENGTH: 1394
<212> TYPE: PRT
<213> ORGANISM: Artificial Sequence
<220> FEATURE:
<223> OTHER INFORMATION: Description of Artificial Sequence:synthetic
     ROS1-DME chimera, construct with ROS1 amino acids
     521-627 deleted and DME amino acids 690-797
     inserted, ROS1 containing DME Domain A

<400> SEQUENCE: 22

```
Met Glu Lys Gln Arg Arg Glu Glu Ser Ser Phe Gln Gln Pro Pro Trp
 1               5                  10                  15

Ile Pro Gln Thr Pro Met Lys Pro Phe Ser Pro Ile Cys Pro Tyr Thr
            20                  25                  30

Val Glu Asp Gln Tyr His Ser Ser Gln Leu Glu Glu Arg Arg Phe Val
        35                  40                  45

Gly Asn Lys Asp Met Ser Gly Leu Asp His Leu Ser Phe Gly Asp Leu
    50                  55                  60

Leu Ala Leu Ala Asn Thr Ala Ser Leu Ile Phe Ser Gly Gln Thr Pro
65                  70                  75                  80

Ile Pro Thr Arg Asn Thr Glu Val Met Gln Lys Gly Thr Glu Glu Val
                85                  90                  95

Glu Ser Leu Ser Ser Val Ser Asn Asn Val Ala Glu Gln Ile Leu Lys
            100                 105                 110

Thr Pro Glu Lys Pro Lys Arg Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175
```

```
Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
    290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
    370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
    450                 455                 460

Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
                485                 490                 495

Pro Tyr Thr Met Asn Ser Gln Ile Val Leu Phe Gly Gly Ala Gly
            500                 505                 510

Ala Ile Val Pro Val Thr Pro Val Lys Lys Arg Lys Pro Arg Pro Lys
        515                 520                 525

Val Asp Ile Asp Asp Glu Thr Thr Arg Ile Trp Asn Leu Leu Met Gly
    530                 535                 540

Lys Gly Asp Glu Lys Glu Gly Asp Glu Lys Asp Lys Lys Glu
545                 550                 555                 560

Lys Trp Trp Glu Glu Glu Arg Val Phe Arg Gly Arg Ala Asp Ser
                565                 570                 575

Phe Ile Ala Arg Met His Leu Val Gln Gly Asp Arg Arg Phe Ser Pro
            580                 585                 590

Trp Lys Gly Ser Val Val Asp Ser Val Ile Gly Val Phe Leu Thr Gln
```

```
            595                 600                 605
Asn Val Ser Asp His Leu Ser Ser Ala Phe Met Ser Leu Ala Ala
610                 615                 620

Arg Phe Pro Pro Phe Val Pro Ser Ser Asn Phe Asp Ala Gly Thr
625                 630                 635                 640

Ser Ser Met Pro Ser Ile Gln Ile Thr Tyr Leu Asp Ser Glu Glu Thr
                645                 650                 655

Met Ser Ser Pro Pro Asp His Asn His Ser Ser Val Thr Leu Lys Asn
                660                 665                 670

Thr Gln Pro Asp Glu Glu Lys Asp Tyr Val Pro Ser Asn Glu Thr Ser
                675                 680                 685

Arg Ser Ser Ser Glu Ile Ala Ile Ser Ala His Glu Ser Val Asp Lys
690                 695                 700

Thr Thr Asp Ser Lys Glu Tyr Val Asp Ser Asp Arg Lys Gly Ser Ser
705                 710                 715                 720

Val Glu Val Asp Lys Thr Asp Glu Lys Cys Arg Val Leu Asn Leu Phe
                725                 730                 735

Pro Ser Glu Asp Ser Ala Leu Thr Cys Gln His Ser Met Val Ser Asp
                740                 745                 750

Ala Pro Gln Asn Thr Glu Arg Ala Gly Ser Ser Ser Glu Ile Asp Leu
                755                 760                 765

Glu Gly Glu Tyr Arg Thr Ser Phe Met Lys Leu Leu Gln Gly Val Gln
770                 775                 780

Val Ser Leu Glu Asp Ser Asn Gln Val Ser Pro Asn Met Ser Pro Gly
785                 790                 795                 800

Asp Cys Ser Ser Glu Ile Lys Gly Phe Gln Ser Met Lys Glu Pro Thr
                805                 810                 815

Lys Ser Ser Val Asp Ser Ser Glu Pro Gly Cys Cys Ser Gln Gln Asp
                820                 825                 830

Gly Asp Val Leu Ser Cys Gln Lys Pro Thr Leu Lys Glu Lys Gly Lys
                835                 840                 845

Lys Val Leu Lys Glu Glu Lys Lys Ala Phe Asp Trp Asp Cys Leu Arg
850                 855                 860

Arg Glu Ala Gln Ala Arg Ala Gly Ile Arg Glu Lys Thr Arg Ser Thr
865                 870                 875                 880

Met Asp Thr Val Asp Trp Lys Ala Ile Arg Ala Asp Val Lys Glu
                885                 890                 895

Val Ala Glu Thr Ile Lys Ser Arg Gly Met Asn His Lys Leu Ala Glu
                900                 905                 910

Arg Ile Gln Gly Phe Leu Asp Arg Leu Val Asn Asp His Gly Ser Ile
                915                 920                 925

Asp Leu Glu Trp Leu Arg Asp Val Pro Pro Asp Lys Ala Lys Glu Tyr
                930                 935                 940

Leu Leu Ser Phe Asn Gly Leu Gly Leu Lys Ser Val Glu Cys Val Arg
945                 950                 955                 960

Leu Leu Thr Leu His His Leu Ala Phe Pro Val Asp Thr Asn Val Gly
                965                 970                 975

Arg Ile Ala Val Arg Leu Gly Trp Val Pro Leu Gln Pro Leu Pro Glu
                980                 985                 990

Ser Leu Gln Leu His Leu Leu Glu Met Tyr Pro Met Leu Glu Ser Ile
                995                 1000                1005

Gln Lys Tyr Leu Trp Pro Arg Leu Cys Lys Leu Asp Gln Lys Thr Leu
                1010                1015                1020
```

Tyr Glu Leu His Tyr Gln Met Ile Thr Phe Gly Lys Val Phe Cys Thr
1025                1030                1035                1040

Lys Ser Lys Pro Asn Cys Asn Ala Cys Pro Met Lys Gly Glu Cys Arg
            1045                1050                1055

His Phe Ala Ser Ala Phe Ala Ser Ala Arg Leu Ala Leu Pro Ser Thr
        1060                1065                1070

Glu Lys Gly Met Gly Thr Pro Asp Lys Asn Pro Leu Pro Leu His Leu
    1075                1080                1085

Pro Glu Pro Phe Gln Arg Glu Gln Gly Ser Glu Val Val Gln His Ser
1090                1095                1100

Glu Pro Ala Lys Lys Val Thr Cys Cys Glu Pro Ile Ile Glu Glu Pro
1105                1110                1115                1120

Ala Ser Pro Glu Pro Glu Thr Ala Glu Val Ser Ile Ala Asp Ile Glu
            1125                1130                1135

Glu Ala Phe Phe Glu Asp Pro Glu Ile Pro Thr Ile Arg Leu Asn
        1140                1145                1150

Met Asp Ala Phe Thr Ser Asn Leu Lys Lys Ile Met Glu His Asn Lys
    1155                1160                1165

Glu Leu Gln Asp Gly Asn Met Ser Ser Ala Leu Val Ala Leu Thr Ala
    1170                1175                1180

Glu Thr Ala Ser Leu Pro Met Pro Lys Leu Lys Asn Ile Ser Gln Leu
1185                1190                1195                1200

Arg Thr Glu His Arg Val Tyr Glu Leu Pro Asp Glu His Pro Leu Leu
            1205                1210                1215

Ala Gln Leu Glu Lys Arg Glu Pro Asp Asp Pro Cys Ser Tyr Leu Leu
        1220                1225                1230

Ala Ile Trp Thr Pro Gly Glu Thr Ala Asp Ser Ile Gln Pro Ser Val
    1235                1240                1245

Ser Thr Cys Ile Phe Gln Ala Asn Gly Met Leu Cys Asp Glu Glu Thr
    1250                1255                1260

Cys Phe Ser Cys Asn Ser Ile Lys Glu Thr Arg Ser Gln Ile Val Arg
1265                1270                1275                1280

Gly Thr Ile Leu Ile Pro Cys Arg Thr Ala Met Arg Gly Ser Phe Pro
            1285                1290                1295

Leu Asn Gly Thr Tyr Phe Gln Val Asn Glu Val Phe Ala Asp His Ala
        1300                1305                1310

Ser Ser Leu Asn Pro Ile Asn Val Pro Arg Glu Leu Ile Trp Glu Leu
    1315                1320                1325

Pro Arg Arg Thr Val Tyr Phe Gly Thr Ser Val Pro Thr Ile Phe Lys
    1330                1335                1340

Gly Leu Ser Thr Glu Lys Ile Gln Ala Cys Phe Trp Lys Gly Tyr Val
1345                1350                1355                1360

Cys Val Arg Gly Phe Asp Arg Lys Thr Arg Gly Pro Lys Pro Leu Ile
            1365                1370                1375

Ala Arg Leu His Phe Pro Ala Ser Lys Leu Lys Gly Gln Gln Ala Asn
        1380                1385                1390

Leu Ala

<210> SEQ ID NO 23
<211> LENGTH: 4683
<212> TYPE: DNA
<213> ORGANISM: Artificial Sequence
<220> FEATURE:
<223> OTHER INFORMATION: Description of Artificial Sequence:synthetic -continued ROS1-DME chimera, construct with DME amino acids
1-689 deleted and ROS1 amino acids 1-520 inserted,
DME containing ROS1 N-terminus

<400> SEQUENCE: 23

| | |
|---|---|
| atggagaaac agaggagaga agaaagcagc tttcaacaac ctccatggat tcctcagaca | 60 |
| cccatgaagc cattttcacc gatctgccca tacacggtgg aggatcaata tcatagcagt | 120 |
| caattggagg aaaggagatt tgttgggaac aaggatatga gtggtcttga tcacttgtct | 180 |
| tttggggatt tgcttgctct agctaacact gcatccctca tattctctgg tcagactcca | 240 |
| atacctacaa gaaacacaga ggttatgcaa aaaggtactg aagaagtgga gagtttgagc | 300 |
| tcagtgagta acaatgttgc tgaacagatc ctcaagactc ctgaaaaacc taagaggaag | 360 |
| aagcatcggc caaggttcg tagagaagct aaacccaaga gggagcctaa accacgagct | 420 |
| ccgaggaagt ctgttgtcac cgatggtcaa gaaagcaaaa caccaaagag gaaatatgtg | 480 |
| cggaagaagt tgaagtcag taaggatcaa gacgctactc cggttgaatc atcagcagct | 540 |
| gttgaaactt caactcgtcc taagaggctc tgtagacgag tcttggattt tgaagccgaa | 600 |
| aatggagaaa accagaccaa cggtgacatt agagaagcag gtgagatgga atcagctctt | 660 |
| caagagaagc agttagattc tgggaatcaa gagttaaaag attgccttct ttcggctcct | 720 |
| agcacgccca agagaaagcg cagccaaggt aaaagaaagg gagttcaacc aaagaaaaat | 780 |
| ggcagtaatc tagaagaagt cgatatttcg atggcgcaag ctgcaaagag aagacaagga | 840 |
| ccaacttgtt gcgacatgaa tctatcaggg attcagtatg atgagcaatg tgactaccag | 900 |
| aaaatgcatt ggttgtattc cccaaacttg caacagggag ggatgagata tgatgccatt | 960 |
| tgcagcaaag tattctctgg acaacagcac aattatgttt ctgcctttca cgctacgtgc | 1020 |
| tacagttcca catctcagct cagtgctaat agagtcctaa ccgttgaaga aagacgagaa | 1080 |
| ggtatctttc aaggaaggca agagtctgag ctaaatgttc tctcggataa gatagacacg | 1140 |
| ccgatcaaga agaaaacaac aggccatgct cgattccgga atttgtcttc aatgaataaa | 1200 |
| cttgtggaag ttcctgagca tttaacctca ggatattgta gcaagccaca gcaaataat | 1260 |
| aagattcttg ttgatacgcg ggtgactgtg agcaaaaaga agccaaccaa gtctgagaaa | 1320 |
| tcacaaaacca aacagaaaaa tcttcttccg aatctttgcc gttttccacc ttcatttact | 1380 |
| ggtctttctc cagatgaact ttggaaacga cgtaactcga tcgaaacaat cagtgagcta | 1440 |
| ttgcgtctat tagacatcaa cagggagcat tctgaaactg ctctcgttcc ttacacaatg | 1500 |
| aatagccaga ttgtactctt tggtggtggc gctggagcaa ttgtgcctgt aactcctgtt | 1560 |
| aagaagcgaa aaccaagacc caaagttgac attgacgatg aaacaactcg catatggaac | 1620 |
| ttactgatgg ggaaaggaga tgaaaaagaa gggatgaag agaaggataa aaagaaagag | 1680 |
| aagtggtggg aagaagaaag aagagtcttc cgaggaaggg ctgattcctt catcgctcgc | 1740 |
| atgcacctgg tacaaggaga tagacgtttt tcgccatgga agggatcggt ggttgattcg | 1800 |
| gtcattggag ttttccttac acagaatgtc tcggatcacc tttcaagctc tgcgttcatg | 1860 |
| tctctagctg ctcgattccc tccaaaatta agcagcagcc gagaagatga aggaatgtt | 1920 |
| agaagcgtag ttgttgaaga tccagaagga tgcattctga acttaaatga aattccttcg | 1980 |
| tggcaggaaa aggttcaaca tccatctgac atggaagttt ctggggttga tagtggatca | 2040 |
| aaagagcagc taagggactg ttcaaactct ggaattgaaa gatttaattt cttagagaag | 2100 |
| agtattcaaa atttagaaga ggaagtatta tcatcacaag attcttttga tccggcgata | 2160 |
| tttcagtcgt gtgggagagt tggatcctgt tcatgttcca aatcagacgc agagtttcct | 2220 |

```
acaaccaggt gtgaaacaaa aactgtcagt ggaacatcac aatcagtgca aactgggagc   2280
ccaaacttgt ctgatgaaat ttgtcttcaa gggaatgaga gaccgcatct atatgaagga   2340
tctggtgatg ttcagaaaca agaaactaca aatgtcgctc agaagaaacc tgatcttgaa   2400
aaaacaatga attggaaaga ctctgtctgt tttggtcagc caagaaatga tactaattgg   2460
caaacaactc cttccagcag ctatgagcag tgtgcgactc gacagccaca tgtactagac   2520
atagaggatt ttggaatgca aggtgaaggc cttggttatt cttggatgtc catctcacca   2580
agagttgaca gagtaaagaa caaaaatgta ccacgcaggt ttttcagaca aggtggaagt   2640
gttccaagag aattcacagg tcagatcata ccatcaacgc ctcatgaatt accaggaatg   2700
ggattgtccg gttcctcaag cgccgtccaa gaacaccagg acgataccca acataatcaa   2760
caagatgaga tgaataaagc atcccattta caaaaaacat ttttggatct gctcaactcc   2820
tctgaagaat gccttacaag acagtccagt accaaacaga acatcacgga tggctgtcta   2880
ccgagagata gaactgctga agacgtggtt gatccgctca gtaacaattc aagcttacag   2940
aacatattgg tcgaatcaaa ttccagcaat aaagagcaga cggcagttga atacaaggag   3000
acaaatgcca ctattttacg agagatgaaa gggacgcttg ctgatgggaa aaagcctaca   3060
agccagtggg atagtctcag aaaagatgtg gaggggaatg aagggagaca ggaacgaaac   3120
aaaaacaata tggattccat agactatgaa gcaataagac gtgctagtat cagcgagatt   3180
tctgaggcta tcaaggaaag agggatgaat aacatgttgg ccgtacgaat taaggatttc   3240
ctagaacgga tagttaaaga tcatggtggt atcgaccttg aatggttgag agaatctcct   3300
cctgataaag ccaaggacta tctcttgagc ataagaggtc tgggtttgaa aagtgttgaa   3360
tgcgtgcgac tcttaacact ccacaatctt gctttccctg ttgacacgaa tgttggaagg   3420
atagcagtta ggatgggatg ggtgcctcta caaccccctac ctgaatcact tcagttacac   3480
ctcctggagc tatacccagt gctcgagtcc atccaaaaat ttctttggcc aagactttgc   3540
aaactcgatc aacgaacact gtatgaatta cactaccaac tgattacgtt tggaaaggta   3600
ttttgcacaa agagtagacc aaattgtaat gcatgtccaa tgagaggaga gtgcagacac   3660
tttgccagtg cttatgctag tgcaagactt gctttaccgg caccagagga gaggagctta   3720
acaagtgcaa ctattccggt ccctcccgag tcctttcctc ctgtagccat cccgatgata   3780
gaactacctc ttccgttgga gaatccctta gcaagtggag caccatcgaa tagagaaaac   3840
tgtgaaccaa taattgaaga gccggcctcg cccgggcaag agtgcactga ataaccgag   3900 agtgatattg aagatgctta ctacaatgag gaccctgacg agatcccaac aataaaactc   3960
aacattgaac agtttggaat gactctacgg gaacacatgg aaagaaacat ggagctccaa   4020
gaaggtgaca tgtccaaggc tttggttgct ttgcatccaa caactacttc tattccaact   4080
cccaaactaa agaacattag ccgtctcagg acagagcacc aagtgtacga gctcccagat   4140
tcacatcgtc tccttgatgg tatggataaa agagaaccag atgatccaag tccttatctc   4200
ttagctatat ggacaccagg tgaaacagcg aattcggcac aaccgcctga acagaagtgt   4260
ggagggaaag cgtctggcaa aatgtgcttt gacgagactt gttctgagtg taacagtctg   4320
agggaagcaa actcacagac agttcgagga actcttctga taccttgtcg gactgccatg   4380
agaggaagtt ttccgctcaa cgggacatat ttccaagtca acgagttatt tgcagaccac   4440
gagtccagtc tcaaacccat cgatgttcct agagattgga tatgggatct cccaagaagg   4500
actgtttact tcggaacatc agtaacatca atattcagag gtctttcaac ggagcagata   4560
```

-continued

```
cagttctgct tttggaaagg attcgtatgt gtccgtggat tcgaacagaa gacaagagca    4620
ccgcgtccat taatggcaag gttgcatttt cctgcgagca aattgaagaa caacaaaacc    4680
taa                                                                  4683
```

<210> SEQ ID NO 24
<211> LENGTH: 1560
<212> TYPE: PRT
<213> ORGANISM: Artificial Sequence
<220> FEATURE:
<223> OTHER INFORMATION: Description of Artificial Sequence:synthetic
      ROS1-DME chimera, construct with DME amino acids
      1-689 deleted and ROS1 amino acids 1-520 inserted,
      DME containing ROS1 N-terminus

<400> SEQUENCE: 24

```
Met Glu Lys Gln Arg Arg Glu Glu Ser Ser Phe Gln Gln Pro Pro Trp
 1               5                  10                  15

Ile Pro Gln Thr Pro Met Lys Pro Phe Ser Pro Ile Cys Pro Tyr Thr
             20                  25                  30

Val Glu Asp Gln Tyr His Ser Gln Leu Glu Glu Arg Arg Phe Val
         35                  40                  45

Gly Asn Lys Asp Met Ser Gly Leu Asp His Leu Ser Phe Gly Asp Leu
     50                  55                  60

Leu Ala Leu Ala Asn Thr Ala Ser Leu Ile Phe Ser Gly Gln Thr Pro
 65                  70                  75                  80

Ile Pro Thr Arg Asn Thr Glu Val Met Gln Lys Gly Thr Glu Glu Val
             85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
    290                 295                 300

Leu Tyr Ser Pro Asn Leu Gln Gln Gly Gly Met Arg Tyr Asp Ala Ile
305                 310                 315                 320
```

```
Cys Ser Lys Val Phe Ser Gly Gln Gln His Asn Tyr Val Ser Ala Phe
            325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
            355                 360                 365

Ser Glu Leu Asn Val Leu Ser Asp Lys Ile Asp Thr Pro Ile Lys Lys
        370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
            405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
        450                 455                 460

Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
            485                 490                 495

Pro Tyr Thr Met Asn Ser Gln Ile Val Leu Phe Gly Gly Ala Gly
            500                 505                 510

Ala Ile Val Pro Val Thr Pro Val Lys Lys Arg Lys Pro Arg Pro Lys
            515                 520                 525

Val Asp Ile Asp Asp Glu Thr Thr Arg Ile Trp Asn Leu Leu Met Gly
        530                 535                 540

Lys Gly Asp Glu Lys Glu Gly Asp Glu Lys Asp Lys Lys Lys Glu
545                 550                 555                 560

Lys Trp Trp Glu Glu Arg Arg Val Phe Arg Gly Arg Ala Asp Ser
            565                 570                 575

Phe Ile Ala Arg Met His Leu Val Gln Gly Asp Arg Arg Phe Ser Pro
            580                 585                 590

Trp Lys Gly Ser Val Val Asp Ser Val Ile Gly Val Phe Leu Thr Gln
            595                 600                 605

Asn Val Ser Asp His Leu Ser Ser Ser Ala Phe Met Ser Leu Ala Ala
            610                 615                 620

Arg Phe Pro Pro Lys Leu Ser Ser Arg Glu Asp Glu Arg Asn Val
625                 630                 635                 640

Arg Ser Val Val Glu Asp Pro Glu Gly Cys Ile Leu Asn Leu Asn
            645                 650                 655

Glu Ile Pro Ser Trp Gln Glu Lys Val Gln His Pro Ser Asp Met Glu
            660                 665                 670

Val Ser Gly Val Asp Ser Gly Ser Lys Glu Gln Leu Arg Asp Cys Ser
            675                 680                 685

Asn Ser Gly Ile Glu Arg Phe Asn Phe Leu Glu Lys Ser Ile Gln Asn
            690                 695                 700

Leu Glu Glu Glu Val Leu Ser Ser Gln Asp Ser Phe Asp Pro Ala Ile
705                 710                 715                 720

Phe Gln Ser Cys Gly Arg Val Gly Ser Cys Cys Ser Lys Ser Asp
            725                 730                 735

Ala Glu Phe Pro Thr Thr Arg Cys Glu Thr Lys Thr Val Ser Gly Thr
```

-continued

```
                740                 745                 750
Ser Gln Ser Val Gln Thr Gly Ser Pro Asn Leu Ser Asp Glu Ile Cys
            755                 760                 765

Leu Gln Gly Asn Glu Arg Pro His Leu Tyr Glu Gly Ser Gly Asp Val
        770                 775                 780

Gln Lys Gln Glu Thr Thr Asn Val Ala Gln Lys Lys Pro Asp Leu Glu
785                 790                 795                 800

Lys Thr Met Asn Trp Lys Asp Ser Val Cys Phe Gly Gln Pro Arg Asn
                805                 810                 815

Asp Thr Asn Trp Gln Thr Thr Pro Ser Ser Tyr Glu Gln Cys Ala
            820                 825                 830

Thr Arg Gln Pro His Val Leu Asp Ile Glu Asp Phe Gly Met Gln Gly
        835                 840                 845

Glu Gly Leu Gly Tyr Ser Trp Met Ser Ile Ser Pro Arg Val Asp Arg
    850                 855                 860

Val Lys Asn Lys Asn Val Pro Arg Arg Phe Phe Arg Gln Gly Gly Ser
865                 870                 875                 880

Val Pro Arg Glu Phe Thr Gly Gln Ile Ile Pro Ser Thr Pro His Glu
                885                 890                 895

Leu Pro Gly Met Gly Leu Ser Gly Ser Ser Ser Ala Val Gln Glu His
            900                 905                 910

Gln Asp Asp Thr Gln His Asn Gln Gln Asp Glu Met Asn Lys Ala Ser
        915                 920                 925

His Leu Gln Lys Thr Phe Leu Asp Leu Leu Asn Ser Ser Glu Glu Cys
    930                 935                 940

Leu Thr Arg Gln Ser Ser Thr Lys Gln Asn Ile Thr Asp Gly Cys Leu
945                 950                 955                 960

Pro Arg Asp Arg Thr Ala Glu Asp Val Val Asp Pro Leu Ser Asn Asn
                965                 970                 975

Ser Ser Leu Gln Asn Ile Leu Val Glu Ser Asn Ser Asn Lys Glu
            980                 985                 990

Gln Thr Ala Val Glu Tyr Lys Glu Thr Asn Ala Thr Ile Leu Arg Glu
        995                 1000                1005

Met Lys Gly Thr Leu Ala Asp Gly Lys Lys Pro Thr Ser Gln Trp Asp
    1010                1015                1020

Ser Leu Arg Lys Asp Val Glu Gly Asn Glu Gly Arg Gln Glu Arg Asn
1025                1030                1035                1040

Lys Asn Asn Met Asp Ser Ile Asp Tyr Glu Ala Ile Arg Arg Ala Ser
                1045                1050                1055

Ile Ser Glu Ile Ser Glu Ala Ile Lys Glu Arg Gly Met Asn Asn Met
            1060                1065                1070

Leu Ala Val Arg Ile Lys Asp Phe Leu Glu Arg Ile Val Lys Asp His
        1075                1080                1085

Gly Gly Ile Asp Leu Glu Trp Leu Arg Glu Ser Pro Pro Asp Lys Ala
    1090                1095                1100

Lys Asp Tyr Leu Leu Ser Ile Arg Gly Leu Gly Leu Lys Ser Val Glu
1105                1110                1115                1120

Cys Val Arg Leu Leu Thr Leu His Asn Leu Ala Phe Pro Val Asp Thr
                1125                1130                1135

Asn Val Gly Arg Ile Ala Val Arg Met Gly Trp Val Pro Leu Gln Pro
            1140                1145                1150

Leu Pro Glu Ser Leu Gln Leu His Leu Leu Glu Leu Tyr Pro Val Leu
        1155                1160                1165
```

Glu Ser Ile Gln Lys Phe Leu Trp Pro Arg Leu Cys Lys Leu Asp Gln
    1170                1175                1180

Arg Thr Leu Tyr Glu Leu His Tyr Gln Leu Ile Thr Phe Gly Lys Val
1185                1190                1195                1200

Phe Cys Thr Lys Ser Arg Pro Asn Cys Asn Ala Cys Pro Met Arg Gly
                1205                1210                1215

Glu Cys Arg His Phe Ala Ser Ala Tyr Ala Ser Ala Arg Leu Ala Leu
                1220                1225                1230

Pro Ala Pro Glu Glu Arg Ser Leu Thr Ser Ala Thr Ile Pro Val Pro
                1235                1240                1245

Pro Glu Ser Phe Pro Pro Val Ala Ile Pro Met Ile Glu Leu Pro Leu
                1250                1255                1260

Pro Leu Glu Lys Ser Leu Ala Ser Gly Ala Pro Ser Asn Arg Glu Asn
1265                1270                1275                1280

Cys Glu Pro Ile Ile Glu Pro Ala Ser Pro Gly Gln Glu Cys Thr
                1285                1290                1295

Glu Ile Thr Glu Ser Asp Ile Glu Asp Ala Tyr Tyr Asn Glu Asp Pro
                1300                1305                1310

Asp Glu Ile Pro Thr Ile Lys Leu Asn Ile Glu Gln Phe Gly Met Thr
                1315                1320                1325

Leu Arg Glu His Met Glu Arg Asn Met Glu Leu Gln Glu Gly Asp Met
                1330                1335                1340

Ser Lys Ala Leu Val Ala Leu His Pro Thr Thr Thr Ser Ile Pro Thr
1345                1350                1355                1360

Pro Lys Leu Lys Asn Ile Ser Arg Leu Arg Thr Glu His Gln Val Tyr
                1365                1370                1375

Glu Leu Pro Asp Ser His Arg Leu Leu Asp Gly Met Asp Lys Arg Glu
                1380                1385                1390

Pro Asp Asp Pro Ser Pro Tyr Leu Leu Ala Ile Trp Thr Pro Gly Glu
                1395                1400                1405

Thr Ala Asn Ser Ala Gln Pro Pro Glu Gln Lys Cys Gly Gly Lys Ala
                1410                1415                1420

Ser Gly Lys Met Cys Phe Asp Glu Thr Cys Ser Glu Cys Asn Ser Leu
1425                1430                1435                1440

Arg Glu Ala Asn Ser Gln Thr Val Arg Gly Thr Leu Leu Ile Pro Cys
                1445                1450                1455

Arg Thr Ala Met Arg Gly Ser Phe Pro Leu Asn Gly Thr Tyr Phe Gln
                1460                1465                1470

Val Asn Glu Leu Phe Ala Asp His Glu Ser Ser Leu Lys Pro Ile Asp
                1475                1480                1485

Val Pro Arg Asp Trp Ile Trp Asp Leu Pro Arg Arg Thr Val Tyr Phe
                1490                1495                1500

Gly Thr Ser Val Thr Ser Ile Phe Arg Gly Leu Ser Thr Glu Gln Ile
1505                1510                1515                1520

Gln Phe Cys Phe Trp Lys Gly Phe Val Cys Val Arg Gly Phe Glu Gln
                1525                1530                1535

Lys Thr Arg Ala Pro Arg Pro Leu Met Ala Arg Leu His Phe Pro Ala
                1540                1545                1550

Ser Lys Leu Lys Asn Asn Lys Thr
                1555                1560

<210> SEQ ID NO 25
<211> LENGTH: 5181

<212> TYPE: DNA
<213> ORGANISM: Artificial Sequence
<220> FEATURE:
<223> OTHER INFORMATION: Description of Artificial Sequence:synthetic
ROS1-DME chimera, construct with DME amino acids 1,403-1,730
deleted and ROS1 amino acids 1,070-1,394 inserted,
DME containing ROS1 C-terminus

<400> SEQUENCE: 25

| | | | | | |
|---|---|---|---|---|---|
| atgcagagca | ttatggactc | gtctgctgtt | aatgcgacgg | aagctactga | acaaaatgat | 60 |
| ggcagcagac | aagatgttct | ggagttcgac | cttaacaaaa | ctcctcagca | gaaaccctcc | 120 |
| aaaaggaaaa | ggaagttcat | gcccaaggtg | gtcgtggaag | gcaaacctaa | agaaagcca | 180 |
| cgcaaacctg | cagaacttcc | caaagtggtc | gtggaaggca | aacctaaaag | gaagccacgc | 240 |
| aaagctgcaa | ctcaggaaaa | agtgaaatct | aaagaaaccg | ggagtgccaa | aagaaaaat | 300 |
| ttgaaagaat | cagcaactaa | aaagccagcc | aatgttggag | atatgagcaa | caaaagccct | 360 |
| gaagtcacac | tcaaaagttg | cagaaaagct | ttgaattttg | acttggagaa | tcctggagat | 420 |
| gcgaggcaag | gtgactctga | gtctgaaatt | gtccagaaca | gtagtggcgc | aaactcgttt | 480 |
| tctgagatca | gagatgccat | tggtggaact | aatggtagtt | tcctggattc | agtgtcacaa | 540 |
| atagacaaga | ccaatggatt | gggggctatg | aaccagccac | ttgaagtgtc | aatgggaaac | 600 |
| cagccagata | aactatctac | aggagcgaaa | ctggccagag | accaacaacc | tgatttattg | 660 |
| actagaaacc | agcaatgcca | gttcccagtg | gcaacccaga | acaccccagtt | cccaatggaa | 720 |
| aaccaacaag | cttggcttca | gatgaaaaac | caacttattg | gctttccatt | tggtaaccag | 780 |
| caacctcgca | tgaccataag | aaaccagcag | ccttgcttgg | ccatgggtaa | tcaacaacct | 840 |
| atgtatctga | taggaactcc | acggcctgca | ttagtaagtg | gaaaccagca | actaggaggt | 900 |
| ccccaaggaa | acaagcggcc | tatattttg | aatcaccaga | cttgtttacc | tgctggaaat | 960 |
| cagctatatg | gatcacctac | agacatgcat | caacttgtta | tgtcaaccgg | agggcaacaa | 1020 |
| catggactac | tgataaaaaa | ccagcaacct | ggatcattaa | taagaggcca | gcagccttgc | 1080 |
| gtacctttga | ttgaccagca | acctgcaact | ccaaaaggtt | ttactcactt | gaatcagatg | 1140 |
| gtagctacca | gcatgtcatc | gcctgggctt | cgacctcatt | ctcagtcaca | agttcctaca | 1200 |
| acatatctac | atgtggaatc | tgtttccagg | attttgaatg | ggactacagg | tacatgccag | 1260 |
| agaagcaggg | ctcctgcata | cgattctta | cagcaagata | tccatcaagg | aaataagtac | 1320 |
| atactttctc | atgagatatc | caatggtaat | gggtgcaaga | aagcgttacc | tcaaaactct | 1380 |
| tctctgccaa | ctccaattat | ggctaaactt | gaggaagcca | ggggctcgaa | gagacagtat | 1440 |
| catcgtgcaa | tgggacagac | ggaaaagcat | gatctaaact | tagctcaaca | gattgctcaa | 1500 |
| tcacaagatg | tggagagaca | taacagcagc | acgtgtgtgg | aatatttaga | tgctgcaaag | 1560 |
| aaaacgaaaa | tccagaaagt | agtccaagaa | aatttgcatg | gcatgccacc | tgaggttata | 1620 |
| gaaatcgagg | atgatccaac | tgatggggca | agaaaaggta | aaatactgc | cagcatcagt | 1680 |
| aaaggtgcat | ctaaaggaaa | ctcgtctcca | gttaaaaaga | cagcagaaaa | ggagaaatgt | 1740 |
| attgtcccaa | aaacgcctgc | aaaaaagggt | cgagcaggta | gaaaaaaatc | agtacctccg | 1800 |
| cctgctcatg | cctcagagat | ccagctttgg | caacctactc | ctccaaagac | acctttatca | 1860 |
| agaagcaagc | ctaaaggaaa | agggagaaag | tccatacaag | attcaggaaa | agcaagaggt | 1920 |
| ccatcaggag | aacttctgtg | tcaggattct | attgcgaaa | taattacag | gatgcaaaat | 1980 |
| ctgtatctag | gagacaaaga | aagagaacaa | gagcaaaatg | caatggtctt | gtacaaagga | 2040 |
| gatggtgcac | ttgttcccta | tgagagcaag | aagcgaaaac | caagacccaa | agttgacatt | 2100 |

```
gacgatgaaa caactcgcat atggaactta ctgatgggga aaggagatga aaaagaaggg    2160
gatgaagaga aggataaaaa gaaagagaag tggtgggaag aagaaagaag agtcttccga    2220
ggaagggctg attccttcat cgctcgcatg cacctggtac aaggagatag acgtttttcg    2280
ccatggaagg gatcggtggt tgattcggtc attggagttt tccttacaca gaatgtctcg    2340
gatcaccttt caagctctgc gttcatgtct ctagctgctc gattccctcc aaaattaagc    2400
agcagccgag aagatgaaag gaatgttaga agcgtagttg ttgaagatcc agaaggatgc    2460
attctgaact taaatgaaat tccttcgtgg caggaaaagg ttcaacatcc atctgacatg    2520
gaagtttctg gggttgatag tggatcaaaa gagcagctaa gggactgttc aaactctgga    2580
attgaaagat ttaatttctt agagaagagt attcaaaatt tagaagagga agtattatca    2640
tcacaagatt cttttgatcc ggcgatattt cagtcgtgtg ggagagttgg atcctgttca    2700
tgttccaaat cagacgcaga gtttcctaca accaggtgtg aaacaaaaac tgtcagtgga    2760
acatcacaat cagtgcaaac tgggagccca aacttgtctg atgaaatttg tcttcaaggg    2820
aatgagagac cgcatctata tgaaggatct ggtgatgttc agaaacaaga aactacaaat    2880
gtcgctcaga agaaacctga tcttgaaaaa acaatgaatt ggaaagactc tgtctgtttt    2940
ggtcagccaa gaaatgatac taattggcaa acaactcctt ccagcagcta tgagcagtgt    3000
gcgactcgac agccacatgt actagacata gaggattttg gaatgcaagg tgaaggcctt    3060
ggttattctt ggatgtccat ctcaccaaga gttgacagag taaagaacaa aaatgtacca    3120
cgcaggtttt tcagacaagg tggaagtgtt ccaagagaat tcacaggtca gatcatacca    3180
tcaacgcctc atgaattacc aggaatggga ttgtccggtt cctcaagcgc cgtccaagaa    3240
caccaggacg atacccaaca taatcaacaa gatgagatga ataaagcatc ccatttacaa    3300
aaaacatttt tggatctgct caactcctct gaagaatgcc ttacaagaca gtccagtacc    3360
aaacagaaca tcacggatgg ctgtctaccg agagatagaa ctgctgaaga cgtggttgat    3420
ccgctcagta acaattcaag cttacagaac atattggtcg aatcaaattc cagcaataaa    3480
gagcagacgg cagttgaata caaggagaca aatgccacta ttttacgaga gatgaaaggg    3540
acgcttgctg atgggaaaaa gcctacaagc cagtgggata gtctcagaaa agatgtggag    3600
gggaatgaag ggagacagga acgaaacaaa aacaatatgg attccataga ctatgaagca    3660
ataagacgtg ctagtatcag cgagatttct gaggctatca aggaaagagg gatgaataac    3720
atgttggccg tacgaattaa ggatttccta gaacggatag ttaaagatca tggtggtatc    3780
gaccttgaat ggttgagaga atctcctcct gataaagcca aggactatct cttgagcata    3840
agaggtctgg gtttgaaaag tgttgaatgc gtgcgactct aacactcca caatcttgct    3900
ttccctgttg acacgaatgt tggaaggata gcagttagga tgggatgggt gcctctacaa    3960
cccctacctg aatcacttca gttacacctc ctggagctat acccagtgct cgagtccatc    4020
caaaaatttc tttggccaag actttgcaaa ctcgatcaac gaacactgta tgaattacac    4080
taccaactga ttacgtttgg aaaggtattt tgcacaaaga gtagaccaaa ttgtaatgca    4140
tgtccaatga gaggagagtg cagacacttt gccagtgctt atgctagtgc aagacttgct    4200
ttaccgagta cagagaaagg tatggggaca cctgataaaa acccttttgcc tctacacctg    4260
ccagagccat tccagagaga gcaagggtct gaagtagtac agcactcaga accagcaaaa    4320
aaggtcacat gttgtgaacc aatcatcgaa gagcctgctt caccggagcc agaaaccgca    4380
gaagtatcaa tagctgacat agaggaggcg ttttttgagg atccagaaga aattcctacc    4440
```

```
atcaggctaa acatggatgc atttaccagt aacttgaaga agataatgga acacaacaag    4500
gaacttcaag acggaaacat gtccagcgct ttagttgcac ttactgctga aactgcttct    4560
cttccaatgc ctaagctcaa gaatatcagc cagttaagga cagaacaccg agtttacgaa    4620
cttccagacg agcatcctct tctagctcag ttggaaaaga gagaacctga tgatccatgt    4680
tcttatttgc ttgctatatg gacgccaggt gagacggctg attctattca accgtctgtt    4740
agtacgtgca tattccaagc aaatggtatg ctttgtgacg aggagacttg tttctcctgc    4800
aacagcatca aggagactag atctcaaatt gtgagaggga caattttgat tccttgtaga    4860
acagcgatga ggggtagttt tcctctaaat ggaacgtact ttcaagtaaa tgaggtgttt    4920
gcggatcatg catccagcct aaacccaatc aatgtcccaa gggaattgat atgggaatta    4980
cctcgaagaa cggtctattt tggtacctct gttcctacga tattcaaagg tttatcaact    5040
gagaagatac aggcttgctt ttggaaaggg tacgtatgtg tacgtggatt tgatcgaaag    5100
acgaggggac cgaagccttt gattgcaaga ttgcacttcc cggcgagcaa actgaaggga    5160
caacaagcta acctcgccta a                                              5181
```

<210> SEQ ID NO 26
<211> LENGTH: 1726
<212> TYPE: PRT
<213> ORGANISM: Artificial Sequence
<220> FEATURE:
<223> OTHER INFORMATION: Description of Artificial Sequence:synthetic
    ROS1-DME chimera, construct with DME amino acids 1,403-1,730
    deleted and ROS1 amino acids 1,070-1,394 inserted,
    DME containing ROS1 C-terminus

<400> SEQUENCE: 26

```
Met Gln Ser Ile Met Asp Ser Ser Ala Val Asn Ala Thr Glu Ala Thr
  1               5                  10                  15

Glu Gln Asn Asp Gly Ser Arg Gln Asp Val Leu Glu Phe Asp Leu Asn
                 20                  25                  30

Lys Thr Pro Gln Gln Lys Pro Ser Lys Arg Lys Arg Lys Phe Met Pro
         35                  40                  45

Lys Val Val Glu Gly Lys Pro Lys Arg Lys Pro Arg Lys Pro Ala
     50                  55                  60

Glu Leu Pro Lys Val Val Glu Gly Lys Pro Lys Arg Lys Pro Arg
 65                  70                  75                  80

Lys Ala Ala Thr Gln Glu Lys Val Lys Ser Glu Thr Gly Ser Ala
                 85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
    130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190

Pro Leu Glu Val Ser Met Gly Asn Gln Pro Asp Lys Leu Ser Thr Gly
        195                 200                 205

Ala Lys Leu Ala Arg Asp Gln Gln Pro Asp Leu Leu Thr Arg Asn Gln
```

```
                210                 215                 220
Gln Cys Gln Phe Pro Val Ala Thr Gln Asn Thr Gln Phe Pro Met Glu
225                 230                 235                 240

Asn Gln Gln Ala Trp Leu Gln Met Lys Asn Gln Leu Ile Gly Phe Pro
                245                 250                 255

Phe Gly Asn Gln Gln Pro Arg Met Thr Ile Arg Asn Gln Gln Pro Cys
                260                 265                 270

Leu Ala Met Gly Asn Gln Gln Pro Met Tyr Leu Ile Gly Thr Pro Arg
                275                 280                 285

Pro Ala Leu Val Ser Gly Asn Gln Gln Leu Gly Gly Pro Gln Gly Asn
                290                 295                 300

Lys Arg Pro Ile Phe Leu Asn His Gln Thr Cys Leu Pro Ala Gly Asn
305                 310                 315                 320

Gln Leu Tyr Gly Ser Pro Thr Asp Met His Gln Leu Val Met Ser Thr
                325                 330                 335

Gly Gly Gln Gln His Gly Leu Leu Ile Lys Asn Gln Gln Pro Gly Ser
                340                 345                 350

Leu Ile Arg Gly Gln Gln Pro Cys Val Pro Leu Ile Asp Gln Gln Pro
                355                 360                 365

Ala Thr Pro Lys Gly Phe Thr His Leu Asn Gln Met Val Ala Thr Ser
370                 375                 380

Met Ser Pro Gly Leu Arg Pro His Ser Gln Ser Gln Val Pro Thr
385                 390                 395                 400

Thr Tyr Leu His Val Glu Ser Val Ser Arg Ile Leu Asn Gly Thr Thr
                405                 410                 415

Gly Thr Cys Gln Arg Ser Arg Ala Pro Ala Tyr Asp Ser Leu Gln Gln
                420                 425                 430

Asp Ile His Gln Gly Asn Lys Tyr Ile Leu Ser His Glu Ile Ser Asn
                435                 440                 445

Gly Asn Gly Cys Lys Lys Ala Leu Pro Gln Asn Ser Ser Leu Pro Thr
                450                 455                 460

Pro Ile Met Ala Lys Leu Glu Glu Ala Arg Gly Ser Lys Arg Gln Tyr
465                 470                 475                 480

His Arg Ala Met Gly Gln Thr Glu Lys His Asp Leu Asn Leu Ala Gln
                485                 490                 495

Gln Ile Ala Gln Ser Gln Asp Val Glu Arg His Asn Ser Ser Thr Cys
                500                 505                 510

Val Glu Tyr Leu Asp Ala Ala Lys Lys Thr Lys Ile Gln Lys Val Val
                515                 520                 525

Gln Glu Asn Leu His Gly Met Pro Pro Glu Val Ile Glu Ile Glu Asp
530                 535                 540

Asp Pro Thr Asp Gly Ala Arg Lys Gly Lys Asn Thr Ala Ser Ile Ser
545                 550                 555                 560

Lys Gly Ala Ser Lys Gly Asn Ser Ser Pro Val Lys Lys Thr Ala Glu
                565                 570                 575

Lys Glu Lys Cys Ile Val Pro Lys Thr Pro Ala Lys Gly Arg Ala
                580                 585                 590

Gly Arg Lys Lys Ser Val Pro Pro Ala His Ala Ser Glu Ile Gln
                595                 600                 605

Leu Trp Gln Pro Thr Pro Pro Lys Thr Pro Leu Ser Arg Ser Lys Pro
                610                 615                 620

Lys Gly Lys Gly Arg Lys Ser Ile Gln Asp Ser Gly Lys Ala Arg Gly
625                 630                 635                 640
```

```
Pro Ser Gly Glu Leu Leu Cys Gln Asp Ser Ile Ala Glu Ile Ile Tyr
                645                 650                 655

Arg Met Gln Asn Leu Tyr Leu Gly Asp Lys Glu Arg Glu Gln Glu Gln
                660                 665                 670

Asn Ala Met Val Leu Tyr Lys Gly Asp Gly Ala Leu Val Pro Tyr Glu
                675                 680                 685

Ser Lys Lys Arg Lys Pro Arg Pro Lys Val Asp Ile Asp Asp Glu Thr
                690                 695                 700

Thr Arg Ile Trp Asn Leu Leu Met Gly Lys Gly Asp Glu Lys Glu Gly
705                 710                 715                 720

Asp Glu Glu Lys Asp Lys Lys Glu Lys Trp Trp Glu Glu Glu Arg
                725                 730                 735

Arg Val Phe Arg Gly Arg Ala Asp Ser Phe Ile Ala Arg Met His Leu
                740                 745                 750

Val Gln Gly Asp Arg Arg Phe Ser Pro Trp Lys Gly Ser Val Val Asp
                755                 760                 765

Ser Val Ile Gly Val Phe Leu Thr Gln Asn Val Ser Asp His Leu Ser
                770                 775                 780

Ser Ser Ala Phe Met Ser Leu Ala Ala Arg Phe Pro Pro Lys Leu Ser
785                 790                 795                 800

Ser Ser Arg Glu Asp Glu Arg Asn Val Arg Ser Val Val Glu Asp
                805                 810                 815

Pro Glu Gly Cys Ile Leu Asn Leu Asn Glu Ile Pro Ser Trp Gln Glu
                820                 825                 830

Lys Val Gln His Pro Ser Asp Met Glu Val Ser Gly Val Asp Ser Gly
                835                 840                 845

Ser Lys Glu Gln Leu Arg Asp Cys Ser Asn Ser Gly Ile Glu Arg Phe
                850                 855                 860

Asn Phe Leu Glu Lys Ser Ile Gln Asn Leu Glu Glu Val Leu Ser
865                 870                 875                 880

Ser Gln Asp Ser Phe Asp Pro Ala Ile Phe Gln Ser Cys Gly Arg Val
                885                 890                 895

Gly Ser Cys Ser Cys Ser Lys Ser Asp Ala Glu Phe Pro Thr Thr Arg
                900                 905                 910

Cys Glu Thr Lys Thr Val Ser Gly Thr Ser Gln Ser Val Gln Thr Gly
                915                 920                 925

Ser Pro Asn Leu Ser Asp Glu Ile Cys Leu Gln Gly Asn Glu Arg Pro
930                 935                 940

His Leu Tyr Glu Gly Ser Gly Asp Val Gln Lys Gln Glu Thr Thr Asn
945                 950                 955                 960

Val Ala Gln Lys Lys Pro Asp Leu Glu Lys Thr Met Asn Trp Lys Asp
                965                 970                 975

Ser Val Cys Phe Gly Gln Pro Arg Asn Asp Thr Asn Trp Gln Thr Thr
                980                 985                 990

Pro Ser Ser Ser Tyr Glu Gln Cys Ala Thr Arg Gln Pro His Val Leu
                995                 1000                1005

Asp Ile Glu Asp Phe Gly Met Gln Gly Glu Gly Leu Gly Tyr Ser Trp
    1010                1015                1020

Met Ser Ile Ser Pro Arg Val Asp Arg Val Lys Asn Lys Asn Val Pro
1025                1030                1035                1040

Arg Arg Phe Phe Arg Gln Gly Gly Ser Val Pro Arg Glu Phe Thr Gly
                1045                1050                1055
```

```
Gln Ile Ile Pro Ser Thr Pro His Glu Leu Pro Gly Met Gly Leu Ser
            1060                1065                1070

Gly Ser Ser Ser Ala Val Gln Glu His Gln Asp Asp Thr Gln His Asn
        1075                1080                1085

Gln Gln Asp Glu Met Asn Lys Ala Ser His Leu Gln Lys Thr Phe Leu
    1090                1095                1100

Asp Leu Leu Asn Ser Ser Glu Glu Cys Leu Thr Arg Gln Ser Ser Thr
1105                1110                1115                1120

Lys Gln Asn Ile Thr Asp Gly Cys Leu Pro Arg Asp Arg Thr Ala Glu
            1125                1130                1135

Asp Val Val Asp Pro Leu Ser Asn Asn Ser Ser Leu Gln Asn Ile Leu
        1140                1145                1150

Val Glu Ser Asn Ser Ser Asn Lys Glu Gln Thr Ala Val Glu Tyr Lys
            1155                1160                1165

Glu Thr Asn Ala Thr Ile Leu Arg Glu Met Lys Gly Thr Leu Ala Asp
    1170                1175                1180

Gly Lys Lys Pro Thr Ser Gln Trp Asp Ser Leu Arg Lys Asp Val Glu
1185                1190                1195                1200

Gly Asn Glu Gly Arg Gln Glu Arg Asn Lys Asn Asn Met Asp Ser Ile
            1205                1210                1215

Asp Tyr Glu Ala Ile Arg Arg Ala Ser Ile Ser Glu Ile Ser Glu Ala
        1220                1225                1230

Ile Lys Glu Arg Gly Met Asn Asn Met Leu Ala Val Arg Ile Lys Asp
            1235                1240                1245

Phe Leu Glu Arg Ile Val Lys Asp His Gly Ile Asp Leu Glu Trp
    1250                1255                1260

Leu Arg Glu Ser Pro Pro Asp Lys Ala Lys Asp Tyr Leu Leu Ser Ile
1265                1270                1275                1280

Arg Gly Leu Gly Leu Lys Ser Val Glu Cys Val Arg Leu Leu Thr Leu
            1285                1290                1295

His Asn Leu Ala Phe Pro Val Asp Thr Asn Val Gly Arg Ile Ala Val
        1300                1305                1310

Arg Met Gly Trp Val Pro Leu Gln Pro Leu Pro Glu Ser Leu Gln Leu
        1315                1320                1325

His Leu Leu Glu Leu Tyr Pro Val Leu Glu Ser Ile Gln Lys Phe Leu
        1330                1335                1340

Trp Pro Arg Leu Cys Lys Leu Asp Gln Arg Thr Leu Tyr Glu Leu His
1345                1350                1355                1360

Tyr Gln Leu Ile Thr Phe Gly Lys Val Phe Cys Thr Lys Ser Arg Pro
            1365                1370                1375

Asn Cys Asn Ala Cys Pro Met Arg Gly Glu Cys Arg His Phe Ala Ser
        1380                1385                1390

Ala Tyr Ala Ser Ala Arg Leu Ala Leu Pro Ser Thr Glu Lys Gly Met
        1395                1400                1405

Gly Thr Pro Asp Lys Asn Pro Leu Pro Leu His Leu Pro Glu Pro Phe
    1410                1415                1420

Gln Arg Glu Gln Gly Ser Glu Val Val Gln His Ser Glu Pro Ala Lys
1425                1430                1435                1440

Lys Val Thr Cys Cys Glu Pro Ile Ile Glu Glu Pro Ala Ser Pro Glu
            1445                1450                1455

Pro Glu Thr Ala Glu Val Ser Ile Ala Asp Ile Glu Glu Ala Phe Phe
        1460                1465                1470

Glu Asp Pro Glu Glu Ile Pro Thr Ile Arg Leu Asn Met Asp Ala Phe
```

-continued

```
                      1475                1480                1485

Thr Ser Asn Leu Lys Lys Ile Met Glu His Asn Lys Glu Leu Gln Asp
                1490                1495                1500

Gly Asn Met Ser Ser Ala Leu Val Ala Leu Thr Ala Glu Thr Ala Ser
1505                1510                1515                1520

Leu Pro Met Pro Lys Leu Lys Asn Ile Ser Gln Leu Arg Thr Glu His
                    1525                1530                1535

Arg Val Tyr Glu Leu Pro Asp Glu His Pro Leu Leu Ala Gln Leu Glu
                1540                1545                1550

Lys Arg Glu Pro Asp Asp Pro Cys Ser Tyr Leu Leu Ala Ile Trp Thr
            1555                1560                1565

Pro Gly Glu Thr Ala Asp Ser Ile Gln Pro Ser Val Ser Thr Cys Ile
        1570                1575                1580

Phe Gln Ala Asn Gly Met Leu Cys Asp Glu Glu Thr Cys Phe Ser Cys
1585                1590                1595                1600

Asn Ser Ile Lys Glu Thr Arg Ser Gln Ile Val Arg Gly Thr Ile Leu
                1605                1610                1615

Ile Pro Cys Arg Thr Ala Met Arg Gly Ser Phe Pro Leu Asn Gly Thr
            1620                1625                1630

Tyr Phe Gln Val Asn Glu Val Phe Ala Asp His Ala Ser Ser Leu Asn
        1635                1640                1645

Pro Ile Asn Val Pro Arg Glu Leu Ile Trp Glu Leu Pro Arg Arg Thr
    1650                1655                1660

Val Tyr Phe Gly Thr Ser Val Pro Thr Ile Phe Lys Gly Leu Ser Thr
1665                1670                1675                1680

Glu Lys Ile Gln Ala Cys Phe Trp Lys Gly Tyr Val Cys Val Arg Gly
                1685                1690                1695

Phe Asp Arg Lys Thr Arg Gly Pro Lys Pro Leu Ile Ala Arg Leu His
            1700                1705                1710

Phe Pro Ala Ser Lys Leu Lys Gly Gln Gln Ala Asn Leu Ala
        1715                1720                1725

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence:synthetic
      DNA oligonucleotide substrate sequence

<400> SEQUENCE: 27
ctatacctcc tcaactccgg tcaccgtctc cggcg                               35

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence:synthetic
      region of cysteines that form the Fe-S cluster

<400> SEQUENCE: 28

Thr Phe Gly Lys Val Phe Cys Thr Lys Ser Arg Pro Asn Cys Asn Ala
  1               5                  10                  15

Cys Pro Met Arg Gly Glu Cys Arg His Phe Ala Ser Ala
                20                  25

<210> SEQ ID NO 29
```

```
<211> LENGTH: 130
<212> TYPE: PRT
<213> ORGANISM: Artificial Sequence
<220> FEATURE:
<223> OTHER INFORMATION: Description of Artificial Sequence:synthetic
      DME DNA glycosylase domain region to undergo
      site-directed mutagenesis, conserved DME
      demethylase DNA glycosylase domain intron location

<400> SEQUENCE: 29

Asp Lys Ala Lys Asp Tyr Leu Leu Ser Ile Arg Gly Leu Gly Leu Lys
  1               5                  10                  15

Ser Val Glu Cys Val Arg Leu Leu Thr Leu His Asn Leu Ala Phe Pro
                 20                  25                  30

Val Asp Thr Asn Val Gly Arg Ile Ala Val Arg Met Gly Trp Val Pro
             35                  40                  45

Leu Gln Pro Leu Pro Glu Ser Leu Gln Leu His Leu Leu Glu Leu Tyr
         50                  55                  60

Pro Val Leu Glu Ser Ile Gln Lys Phe Leu Trp Pro Arg Leu Cys Lys
 65                  70                  75                  80

Leu Asp Gln Arg Thr Leu Tyr Glu Leu His Tyr Gln Leu Ile Thr Phe
                 85                  90                  95

Gly Lys Val Phe Cys Thr Lys Ser Arg Pro Asn Cys Asn Ala Cys Pro
            100                 105                 110

Met Arg Gly Glu Cys Arg His Phe Ala Ser Ala Tyr Ala Ser Ala Arg
        115                 120                 125

Leu Ala
    130

<210> SEQ ID NO 30
<211> LENGTH: 116
<212> TYPE: PRT
<213> ORGANISM: Artificial Sequence
<220> FEATURE:
<223> OTHER INFORMATION: Description of Artificial Sequence:synthetic E.
      coli MutY region to undergo site-directed
      mutagenesis

<400> SEQUENCE: 30

Pro Glu Thr Phe Glu Glu Val Ala Ala Leu Pro Gly Val Gly Arg Ser
  1               5                  10                  15

Thr Ala Gly Ala Ile Leu Ser Leu Ser Leu Gly Lys His Phe Pro Ile
                 20                  25                  30

Leu Asp Gly Asn Val Lys Arg Val Leu Ala Arg Cys Tyr Ala Val Ser
             35                  40                  45

Gly Trp Pro Gly Lys Lys Glu Val Glu Asn Lys Leu Trp Ser Leu Ser
         50                  55                  60

Glu Gln Val Thr Pro Ala Val Gly Val Glu Arg Phe Asn Gln Ala Met
 65                  70                  75                  80

Met Asp Leu Gly Ala Met Ile Cys Thr Arg Ser Lys Pro Lys Cys Ser
                 85                  90                  95

Leu Cys Pro Leu Gln Asn Gly Cys Ile Ala Ala Ala Asn Asn Ser Trp
            100                 105                 110

Ala Leu Tyr Pro
        115

<210> SEQ ID NO 31
<211> LENGTH: 107
<212> TYPE: PRT
<213> ORGANISM: Artificial Sequence
```

```
<220> FEATURE:
<223> OTHER INFORMATION: Description of Artificial Sequence:synthetic E.
      coli endonuclease III (EndoIII) region to undergo
      site-directed mutagenesis

<400> SEQUENCE: 31

Pro Glu Asp Arg Ala Ala Leu Glu Ala Leu Pro Gly Val Gly Arg Lys
 1               5                  10                  15

Thr Ala Asn Val Val Leu Asn Thr Ala Phe Gly Trp Pro Thr Ile Ala
            20                  25                  30

Val Asp Thr His Ile Phe Arg Val Cys Asn Arg Thr Gln Phe Ala Pro
        35                  40                  45

Gly Lys Asn Val Glu Gln Val Glu Glu Lys Leu Leu Lys Val Val Pro
    50                  55                  60

Ala Glu Phe Lys Val Asp Cys His His Trp Leu Ile Leu His Gly Arg
65                  70                  75                  80

Tyr Thr Cys Ile Ala Arg Lys Pro Arg Cys Gly Ser Cys Ile Ile Glu
                85                  90                  95

Asp Leu Cys Glu Tyr Lys Glu Lys Val Asp Ile
            100                 105

<210> SEQ ID NO 32
<211> LENGTH: 130
<212> TYPE: PRT
<213> ORGANISM: Artificial Sequence
<220> FEATURE:
<223> OTHER INFORMATION: Description of Artificial Sequence:synthetic
      conserved ROS1 demethylase DNA glycosylase domain
      intron location

<400> SEQUENCE: 32

Asp Lys Ala Lys Glu Tyr Leu Leu Ser Phe Asn Gly Leu Gly Leu Lys
 1               5                  10                  15

Ser Val Glu Cys Val Arg Leu Leu Thr Leu His His Leu Ala Phe Pro
            20                  25                  30

Val Asp Thr Asn Val Gly Arg Ile Ala Val Arg Leu Gly Trp Val Pro
        35                  40                  45

Leu Gln Pro Leu Pro Glu Ser Leu Gln Leu His Leu Leu Glu Met Tyr
    50                  55                  60

Pro Met Leu Glu Ser Ile Gln Lys Tyr Leu Trp Pro Arg Leu Cys Lys
65                  70                  75                  80

Leu Asp Gln Lys Thr Leu Tyr Glu Leu His Tyr Gln Met Ile Thr Phe
                85                  90                  95

Gly Lys Val Phe Cys Thr Lys Ser Lys Pro Asn Cys Asn Ala Cys Pro
            100                 105                 110

Met Lys Gly Glu Cys Arg His Phe Ala Ser Ala Phe Ala Ser Ala Arg
        115                 120                 125

Leu Ala
    130

<210> SEQ ID NO 33
<211> LENGTH: 130
<212> TYPE: PRT
<213> ORGANISM: Artificial Sequence
<220> FEATURE:
<223> OTHER INFORMATION: Description of Artificial Sequence:synthetic
      conserved DML2 demethylase DNA glycosylase domain
      intron location

<400> SEQUENCE: 33
```

```
Asp Lys Ala Lys Glu Tyr Leu Leu Ser Ile Asn Gly Leu Gly Leu Lys
 1               5                  10                  15

Ser Val Glu Cys Val Arg Leu Leu Ser Leu His Gln Ile Ala Phe Pro
            20                  25                  30

Val Asp Thr Asn Val Gly Arg Ile Ala Val Arg Leu Gly Trp Val Pro
        35                  40                  45

Leu Gln Pro Leu Pro Asp Glu Leu Gln Met His Leu Leu Glu Leu Tyr
    50                  55                  60

Pro Val Leu Glu Ser Val Gln Lys Tyr Leu Trp Pro Arg Leu Cys Lys
65                  70                  75                  80

Leu Asp Gln Lys Thr Leu Tyr Glu Leu His Tyr His Met Ile Thr Phe
                85                  90                  95

Gly Lys Val Phe Cys Thr Lys Val Lys Pro Asn Cys Asn Ala Cys Pro
            100                 105                 110

Met Lys Ala Glu Cys Arg His Tyr Ser Ser Ala Arg Ala Ser Ala Arg
        115                 120                 125

Leu Ala
    130

<210> SEQ ID NO 34
<211> LENGTH: 130
<212> TYPE: PRT
<213> ORGANISM: Artificial Sequence
<220> FEATURE:
<223> OTHER INFORMATION: Description of Artificial Sequence:synthetic
      conserved DML3 demethylase DNA glycosylase domain
      intron location

<400> SEQUENCE: 34

His Leu Val Lys Arg Tyr Leu Leu Glu Ile Glu Gly Ile Gly Leu Lys
 1               5                  10                  15

Ser Ala Glu Cys Val Arg Leu Leu Gly Leu Lys His His Ala Phe Pro
            20                  25                  30

Val Asp Thr Asn Val Gly Arg Ile Ala Val Arg Leu Gly Leu Val Pro
        35                  40                  45

Leu Glu Pro Leu Pro Asn Gly Val Gln Met His Gln Leu Phe Glu Tyr
    50                  55                  60

Pro Ser Met Asp Ser Ile Gln Lys Tyr Leu Trp Pro Arg Leu Cys Lys
65                  70                  75                  80

Leu Pro Gln Glu Thr Leu Tyr Glu Leu His Tyr Gln Met Ile Thr Phe
                85                  90                  95

Gly Lys Val Phe Cys Thr Lys Thr Ile Pro Asn Cys Asn Ala Cys Pro
            100                 105                 110

Met Lys Ser Glu Cys Lys Tyr Phe Ala Ser Ala Tyr Val Ser Ser Lys
        115                 120                 125

Val Leu
    130

<210> SEQ ID NO 35
<211> LENGTH: 400
<212> TYPE: PRT
<213> ORGANISM: Artificial Sequence
<220> FEATURE:
<223> OTHER INFORMATION: Description of Artificial Sequence:synthetic
      DME demethylase DNA glycosylase domain mutations
<220> FEATURE:
<221> NAME/KEY: VARIANT
<222> LOCATION: (185)
<223> OTHER INFORMATION: Xaa =  Gly or Arg
<220> FEATURE:
```

```
<221> NAME/KEY: VARIANT
<222> LOCATION: (210)
<223> OTHER INFORMATION: Xaa = Lys or Thr
<220> FEATURE:
<221> NAME/KEY: VARIANT
<222> LOCATION: (216)
<223> OTHER INFORMATION: Xaa = Ile or Lys
<220> FEATURE:
<221> NAME/KEY: VARIANT
<222> LOCATION: (225)
<223> OTHER INFORMATION: Xaa = Ser or Ile
<220> FEATURE:
<221> NAME/KEY: VARIANT
<222> LOCATION: (230)
<223> OTHER INFORMATION: Xaa = Ser or Pro
<220> FEATURE:
<221> NAME/KEY: VARIANT
<222> LOCATION: (238)
<223> OTHER INFORMATION: Xaa = Met, Ile or Thr
<220> FEATURE:
<221> NAME/KEY: VARIANT
<222> LOCATION: (246)
<223> OTHER INFORMATION: Xaa = Ile or Met
<220> FEATURE:
<221> NAME/KEY: VARIANT
<222> LOCATION: (277)
<223> OTHER INFORMATION: Xaa = Leu or Pro
<220> FEATURE:
<221> NAME/KEY: VARIANT
<222> LOCATION: (286)
<223> OTHER INFORMATION: Xaa = Lys, Gln, Asn, Arg or Glu
<220> FEATURE:
<221> NAME/KEY: VARIANT
<222> LOCATION: (289)
<223> OTHER INFORMATION: Xaa = Glu or Val
<220> FEATURE:
<221> NAME/KEY: VARIANT
<222> LOCATION: (291)
<223> OTHER INFORMATION: Xaa = Val or Glu
<220> FEATURE:
<221> NAME/KEY: VARIANT
<222> LOCATION: (293)
<223> OTHER INFORMATION: Xaa = Leu or Phe
<220> FEATURE:
<221> NAME/KEY: VARIANT
<222> LOCATION: (300)
<223> OTHER INFORMATION: Xaa = Ala or Val
<220> FEATURE:
<221> NAME/KEY: VARIANT
<222> LOCATION: (308)
<223> OTHER INFORMATION: Xaa = Gly or Glu
<220> FEATURE:
<221> NAME/KEY: VARIANT
<222> LOCATION: (309)
<223> OTHER INFORMATION: Xaa = Arg or Ala
<220> FEATURE:
<221> NAME/KEY: VARIANT
<222> LOCATION: (310)
<223> OTHER INFORMATION: Xaa = Ile or Met
<220> FEATURE:
<221> NAME/KEY: VARIANT
<222> LOCATION: (313)
<223> OTHER INFORMATION: Xaa = Arg, Ala or Gly
<220> FEATURE:
<221> NAME/KEY: VARIANT
<222> LOCATION: (315)
<223> OTHER INFORMATION: Xaa = Gly or Arg
<220> FEATURE:
<221> NAME/KEY: VARIANT
<222> LOCATION: (344)
<223> OTHER INFORMATION: Xaa = Leu or His
<220> FEATURE:
<221> NAME/KEY: VARIANT
<222> LOCATION: (359)
<223> OTHER INFORMATION: Xaa = Leu or Val
<220> FEATURE:
<221> NAME/KEY: VARIANT
<222> LOCATION: (360)
<223> OTHER INFORMATION: Xaa = His or Arg
```

-continued

```
<220> FEATURE:
<221> NAME/KEY: VARIANT
<222> LOCATION: (362)
<223> OTHER INFORMATION: Xaa = Gln, Pro or Arg
<220> FEATURE:
<221> NAME/KEY: VARIANT
<222> LOCATION: (363)
<223> OTHER INFORMATION: Xaa = Leu or Arg
<220> FEATURE:
<221> NAME/KEY: VARIANT
<222> LOCATION: (366)
<223> OTHER INFORMATION: Xaa = Phe or Leu
<220> FEATURE:
<221> NAME/KEY: VARIANT
<222> LOCATION: (369)
<223> OTHER INFORMATION: Xaa = Val or Gly
<220> FEATURE:
<221> NAME/KEY: VARIANT
<222> LOCATION: (371)
<223> OTHER INFORMATION: Xaa = Cys or Ser
<220> FEATURE:
<221> NAME/KEY: VARIANT
<222> LOCATION: (375)
<223> OTHER INFORMATION: Xaa = Arg or Ala
<220> FEATURE:
<221> NAME/KEY: VARIANT
<222> LOCATION: (376)
<223> OTHER INFORMATION: Xaa = Pro or Leu
<220> FEATURE:
<221> NAME/KEY: VARIANT
<222> LOCATION: (377)
<223> OTHER INFORMATION: Xaa = Asn, Asp or Thr
<220> FEATURE:
<221> NAME/KEY: VARIANT
<222> LOCATION: (378)
<223> OTHER INFORMATION: Xaa = Cys or Ser
<220> FEATURE:
<221> NAME/KEY: VARIANT
<222> LOCATION: (381)
<223> OTHER INFORMATION: Xaa = Cys, Ser or Arg
<220> FEATURE:
<221> NAME/KEY: VARIANT
<222> LOCATION: (382)
<223> OTHER INFORMATION: Xaa = Pro or Gln
<220> FEATURE:
<221> NAME/KEY: VARIANT
<222> LOCATION: (387)
<223> OTHER INFORMATION: Xaa = Cys, Ser or Arg
<220> FEATURE:
<221> NAME/KEY: VARIANT
<222> LOCATION: (389)
<223> OTHER INFORMATION: Xaa = His or Gln
<220> FEATURE:
<221> NAME/KEY: VARIANT
<222> LOCATION: (390)
<223> OTHER INFORMATION: Xaa = Phe or Ala

<400> SEQUENCE: 35

Ala Thr Arg Gln Pro His Val Leu Asp Ile Glu Asp Phe Gly Met Gln
  1               5                  10                  15

Gly Glu Gly Leu Gly Tyr Ser Trp Met Ser Ile Ser Pro Arg Val Asp
             20                  25                  30

Arg Val Lys Asn Lys Asn Val Pro Arg Arg Phe Phe Arg Gln Gly Gly
         35                  40                  45

Ser Val Pro Arg Glu Phe Thr Gly Gln Ile Ile Pro Ser Thr Pro His
     50                  55                  60

Glu Leu Pro Gly Met Gly Leu Ser Gly Ser Ser Ala Val Gln Glu
 65                  70                  75                  80

His Gln Asp Asp Thr Gln His Asn Gln Gln Asp Glu Met Asn Lys Ala
                 85                  90                  95

Ser His Leu Gln Lys Thr Phe Leu Asp Leu Leu Asn Ser Ser Glu Glu
            100                 105                 110
```

```
Cys Leu Thr Arg Gln Ser Ser Thr Lys Gln Asn Ile Thr Asp Gly Cys
        115                 120                 125

Leu Pro Arg Asp Arg Thr Ala Glu Asp Val Val Asp Pro Leu Ser Asn
    130                 135                 140

Asn Ser Ser Leu Gln Asn Ile Leu Val Glu Ser Asn Ser Ser Asn Lys
145                 150                 155                 160

Glu Gln Thr Ala Val Glu Tyr Lys Gly Thr Asn Ala Thr Ile Leu Arg
                165                 170                 175

Glu Met Lys Gly Thr Leu Ala Asp Xaa Lys Lys Pro Thr Ser Gln Trp
            180                 185                 190

Asp Ser Leu Arg Lys Asp Val Glu Gly Asn Gly Arg Gln Glu Arg
        195                 200                 205

Asn Xaa Asn Asn Met Asp Ser Xaa Asp Tyr Glu Ala Ile Arg Arg Ala
    210                 215                 220

Xaa Ile Ser Glu Ile Xaa Glu Ala Ile Lys Glu Arg Gly Xaa Asn Asn
225                 230                 235                 240

Met Leu Ala Val Arg Xaa Lys Asp Phe Leu Glu Arg Ile Val Lys Asp
                245                 250                 255

His Gly Gly Ile Asp Leu Glu Trp Leu Arg Glu Ser Pro Pro Asp Lys
            260                 265                 270

Ala Lys Asp Tyr Xaa Leu Ser Ile Arg Gly Leu Gly Leu Xaa Ser Val
        275                 280                 285

Xaa Cys Xaa Arg Xaa Leu Thr Leu His Asn Leu Xaa Phe Pro Val Asx
    290                 295                 300

Thr Asn Val Xaa Xaa Xaa Ala Val Xaa Met Xaa Trp Val Pro Leu Gln
305                 310                 315                 320

Pro Leu Pro Glu Ser Leu Gln Leu His Leu Leu Glu Leu Tyr Pro Val
                325                 330                 335

Leu Glu Ser Ile Gln Lys Phe Xaa Trp Pro Arg Leu Cys Lys Leu Asp
            340                 345                 350

Gln Arg Thr Leu Tyr Glu Xaa Xaa Tyr Xaa Xaa Ile Thr Xaa Gly Lys
        355                 360                 365

Xaa Phe Xaa Thr Lys Ser Xaa Xaa Xaa Xaa Asn Ala Xaa Xaa Met Arg
    370                 375                 380

Gly Glu Xaa Arg Xaa Xaa Ala Ser Ala Tyr Ala Ser Ala Arg Leu Ala
385                 390                 395                 400

<210> SEQ ID NO 36
<211> LENGTH: 329
<212> TYPE: PRT
<213> ORGANISM: Artificial Sequence
<220> FEATURE:
<223> OTHER INFORMATION: Description of Artificial Sequence:synthetic
      DME demethylase C-terminal mutations
<220> FEATURE:
<221> NAME/KEY: VARIANT
<222> LOCATION: (23)
<223> OTHER INFORMATION: Xaa = Pro or Ser
<220> FEATURE:
<221> NAME/KEY: VARIANT
<222> LOCATION: (103)
<223> OTHER INFORMATION: Xaa = Glu or Gly
<220> FEATURE:
<221> NAME/KEY: VARIANT
<222> LOCATION: (144)
<223> OTHER INFORMATION: Xaa = Val or Glu
<220> FEATURE:
<221> NAME/KEY: VARIANT
<222> LOCATION: (146)
<223> OTHER INFORMATION: Xaa = Glu or Lys
```

```
<220> FEATURE:
<221> NAME/KEY: VARIANT
<222> LOCATION: (147)
<223> OTHER INFORMATION: Xaa = Leu or Pro
<220> FEATURE:
<221> NAME/KEY: VARIANT
<222> LOCATION: (148)
<223> OTHER INFORMATION: Xaa = Pro or Ser
<220> FEATURE:
<221> NAME/KEY: VARIANT
<222> LOCATION: (149)
<223> OTHER INFORMATION: Xaa = Asp or Val
<220> FEATURE:
<221> NAME/KEY: VARIANT
<222> LOCATION: (164)
<223> OTHER INFORMATION: Xaa = Asp or Val
<220> FEATURE:
<221> NAME/KEY: VARIANT
<222> LOCATION: (172)
<223> OTHER INFORMATION: Xaa = Ile or Met
<220> FEATURE:
<221> NAME/KEY: VARIANT
<222> LOCATION: (173)
<223> OTHER INFORMATION: Xaa = Trp or Arg
<220> FEATURE:
<221> NAME/KEY: VARIANT
<222> LOCATION: (220)
<223> OTHER INFORMATION: Xaa = Thr or Ala
<220> FEATURE:
<221> NAME/KEY: VARIANT
<222> LOCATION: (221)
<223> OTHER INFORMATION: Xaa = Leu or His
<220> FEATURE:
<221> NAME/KEY: VARIANT
<222> LOCATION: (222)
<223> OTHER INFORMATION: Xaa = Leu, Pro or Gln
<220> FEATURE:
<221> NAME/KEY: VARIANT
<222> LOCATION: (225)
<223> OTHER INFORMATION: Xaa = Cys or Arg
<220> FEATURE:
<221> NAME/KEY: VARIANT
<222> LOCATION: (226)
<223> OTHER INFORMATION: Xaa = Arg, Gln or Leu
<220> FEATURE:
<221> NAME/KEY: VARIANT
<222> LOCATION: (235)
<223> OTHER INFORMATION: Xaa = Leu or Pro
<220> FEATURE:
<221> NAME/KEY: VARIANT
<222> LOCATION: (237)
<223> OTHER INFORMATION: Xaa = Gly or Val
<220> FEATURE:
<221> NAME/KEY: VARIANT
<222> LOCATION: (245)
<223> OTHER INFORMATION: Xaa = Leu or Phe
<220> FEATURE:
<221> NAME/KEY: VARIANT
<222> LOCATION: (252)
<223> OTHER INFORMATION: Xaa = Ser or Asn
<220> FEATURE:
<221> NAME/KEY: VARIANT
<222> LOCATION: (253)
<223> OTHER INFORMATION: Xaa = Leu or Pro
<220> FEATURE:
<221> NAME/KEY: VARIANT
<222> LOCATION: (255)
<223> OTHER INFORMATION: Xaa = Pro, Ser or Thr
<220> FEATURE:
<221> NAME/KEY: VARIANT
<222> LOCATION: (262)
<223> OTHER INFORMATION: Xaa = Trp or Arg
<220> FEATURE:
<221> NAME/KEY: VARIANT
<222> LOCATION: (271)
<223> OTHER INFORMATION: Xaa = Val, Asp or Phe
<220> FEATURE:
<221> NAME/KEY: VARIANT
<222> LOCATION: (274)
```

<223> OTHER INFORMATION: Xaa = Gly or Val
<220> FEATURE:
<221> NAME/KEY: VARIANT
<222> LOCATION: (301)
<223> OTHER INFORMATION: Xaa = Arg or Leu
<220> FEATURE:
<221> NAME/KEY: VARIANT
<222> LOCATION: (308)
<223> OTHER INFORMATION: Xaa = Arg or Ser

<400> SEQUENCE: 36

Leu Pro Ala Pro Glu Glu Arg Ser Leu Thr Ser Ala Thr Ile Pro Val
 1               5                  10                  15

Pro Pro Glu Ser Phe Pro Xaa Val Ala Ile Pro Met Ile Glu Leu Pro
             20                  25                  30

Leu Pro Leu Glu Lys Ser Leu Ala Ser Gly Ala Pro Ser Asn Arg Glu
         35                  40                  45

Asn Cys Glu Pro Ile Ile Glu Glu Pro Ala Ser Pro Gly Gln Glu Cys
     50                  55                  60

Thr Glu Ile Thr Glu Ser Asp Ile Glu Asp Ala Tyr Tyr Asn Glu Asp
 65                  70                  75                  80

Pro Asp Glu Ile Pro Thr Ile Lys Leu Asn Ile Glu Gln Phe Gly Met
             85                  90                  95

Thr Leu Arg Glu His Met Xaa Arg Asn Met Glu Leu Gln Glu Gly Asp
        100                 105                 110

Met Ser Lys Ala Leu Val Ala Leu His Pro Thr Thr Thr Ser Ile Pro
    115                 120                 125

Thr Pro Lys Leu Lys Asn Ile Ser Arg Leu Arg Thr Glu His Gln Xaa
130                 135                 140

Tyr Xaa Xaa Xaa Xaa Ser His Arg Leu Leu Asp Gly Met Asp Lys Arg
145                 150                 155                 160

Glu Pro Asp Xaa Pro Ser Pro Tyr Leu Leu Ala Xaa Xaa Thr Pro Gly
                165                 170                 175

Glu Thr Ala Asn Ser Ala Gln Pro Pro Glu Gln Lys Cys Gly Gly Lys
            180                 185                 190

Ala Ser Gly Lys Met Cys Phe Asp Glu Thr Cys Ser Glu Cys Asn Ser
        195                 200                 205

Leu Arg Glu Ala Asn Ser Gln Thr Val Arg Gly Xaa Xaa Xaa Ile Pro
    210                 215                 220

Xaa Xaa Thr Ala Met Arg Gly Ser Phe Pro Xaa Asn Xaa Thr Tyr Phe
225                 230                 235                 240

Gln Val Asn Glu Xaa Phe Ala Asx His Glu Ser Xaa Xaa Lys Xaa Ile
                245                 250                 255

Asp Val Pro Arg Asp Xaa Ile Trp Asp Leu Pro Arg Arg Thr Xaa Tyr
            260                 265                 270

Phe Xaa Thr Ser Val Thr Ser Ile Phe Arg Gly Leu Ser Thr Glu Gln
        275                 280                 285

Ile Gln Phe Cys Phe Trp Lys Gly Phe Val Cys Val Xaa Gly Phe Glu
    290                 295                 300

Gln Lys Thr Xaa Ala Pro Arg Pro Leu Met Ala Arg Leu His Phe Pro
305                 310                 315                 320

Ala Ser Lys Leu Lys Asn Asn Lys Thr
                325

<210> SEQ ID NO 37
<211> LENGTH: 110
<212> TYPE: PRT

-continued

<213> ORGANISM: Artificial Sequence
<220> FEATURE:
<223> OTHER INFORMATION: Description of Artificial Sequence:synthetic
      DME demethylase Domain A

<400> SEQUENCE: 37

Glu Ser Lys Lys Arg Lys Pro Arg Pro Lys Val Asp Ile Asp Glu
 1               5                  10                  15

Thr Thr Arg Ile Trp Asn Leu Leu Met Gly Lys Gly Asp Lys Glu
                20                  25                  30

Gly Asp Glu Glu Lys Asp Lys Lys Glu Lys Trp Trp Glu Glu Glu
            35                  40                  45

Arg Arg Val Phe Arg Gly Arg Ala Asp Ser Phe Ile Ala Arg Met His
 50                  55                  60

Leu Val Gln Gly Asp Arg Arg Phe Ser Pro Trp Lys Gly Ser Val Val
 65                  70                  75                  80

Asp Ser Val Ile Gly Val Phe Leu Thr Gln Asn Val Ser Asp His Leu
                85                  90                  95

Ser Ser Ser Ala Phe Met Ser Leu Ala Ala Arg Phe Pro Pro
            100                 105                 110

<210> SEQ ID NO 38
<211> LENGTH: 109
<212> TYPE: PRT
<213> ORGANISM: Artificial Sequence
<220> FEATURE:
<223> OTHER INFORMATION: Description of Artificial Sequence:synthetic
      ROS1 demethylase Domain A

<400> SEQUENCE: 38

Pro Val Lys Lys Pro Arg Pro Arg Pro Lys Val Asp Leu Asp Glu
 1               5                  10                  15

Thr Asp Arg Val Trp Lys Leu Leu Leu Glu Asn Ile Asn Ser Glu Gly
                20                  25                  30

Val Asp Gly Ser Asp Glu Gln Lys Ala Lys Trp Trp Glu Glu Glu Arg
            35                  40                  45

Asn Val Phe Arg Gly Arg Ala Asp Ser Phe Ile Ala Arg Met His Leu
 50                  55                  60

Val Gln Gly Asp Arg Arg Phe Thr Pro Trp Lys Gly Ser Val Val Asp
 65                  70                  75                  80

Ser Val Val Gly Val Phe Leu Thr Gln Asn Val Ser Asp His Leu Ser
                85                  90                  95

Ser Ser Ala Phe Met Ser Leu Ala Ser Gln Phe Pro Val
            100                 105

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence:synthetic
      DML2 demethylase Domain A

<400> SEQUENCE: 39

Tyr Ser Lys Lys Gln Lys Pro Val Gln Leu Asp Pro Glu Thr Ser
 1               5                  10                  15

Arg Val Trp Lys Leu Leu Met Ser Ser Ile Asp Cys Asp Gly Val Asp
                20                  25                  30

Gly Ser Asp Glu Glu Lys Arg Lys Trp Trp Glu Glu Glu Arg Asn Met
            35                  40                  45

```
Phe His Gly Arg Ala Asn Ser Phe Ile Ala Arg Met Arg Val Val Gln
         50                  55                  60

Gly Asn Arg Thr Phe Ser Pro Trp Lys Gly Ser Val Val Asp Ser Val
 65                  70                  75                  80

Val Gly Val Phe Leu Thr Gln Asn Val Ala Asp His Ser Ser Ser Ser
                 85                  90                  95

Ala Tyr Met Asp Leu Ala Ala Glu Phe Pro Val
            100                 105

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence:synthetic
      DML3 demethylase Domain A

<400> SEQUENCE: 40

Lys Ala Asp Lys Lys Leu Val Thr Ala Lys Val Asn Leu Asp Pro Glu
  1               5                  10                  15

Thr Ile Lys Glu Trp Asp Val Leu Met Val Asn Asp Ser Pro Ser Arg
             20                  25                  30

Ser Tyr Asp Asp Lys Glu Thr Glu Ala Lys Trp Lys Lys Glu Arg Glu
         35                  40                  45

Ile Phe Gln Thr Arg Ile Asp Leu Phe Ile Asn Arg Met His Arg Leu
     50                  55                  60

Gln Gly Asn Arg Lys Phe Lys Gln Trp Lys Gly Ser Val Val Asp Ser
 65                  70                  75                  80

Val Val Gly Val Phe Leu Thr Gln Asn Thr Thr Asp Tyr Leu Ser Ser
                 85                  90                  95

Asn Ala Phe Met Ser Val Ala Ala Lys Phe Pro Val
            100                 105

<210> SEQ ID NO 41
<211> LENGTH: 202
<212> TYPE: PRT
<213> ORGANISM: Artificial Sequence
<220> FEATURE:
<223> OTHER INFORMATION: Description of Artificial Sequence:synthetic
      DME demethylase glycosylase domain

<400> SEQUENCE: 41

Gly Arg Gln Glu Arg Asn Lys Asn Asn Met Asp Ser Ile Asp Tyr Glu
  1               5                  10                  15

Ala Ile Arg Arg Ala Ser Ile Ser Glu Ile Ser Glu Ala Ile Lys Glu
             20                  25                  30

Arg Gly Met Asn Asn Met Leu Ala Val Arg Ile Lys Asp Phe Leu Glu
         35                  40                  45

Arg Ile Val Lys Asp His Gly Gly Ile Asp Leu Glu Trp Leu Arg Glu
     50                  55                  60

Ser Pro Pro Asp Lys Ala Lys Asp Tyr Leu Leu Ser Ile Arg Gly Leu
 65                  70                  75                  80

Gly Leu Lys Ser Val Glu Cys Val Arg Leu Leu Thr Leu His Asn Leu
                 85                  90                  95

Ala Phe Pro Val Asp Thr Asn Val Gly Arg Ile Ala Val Arg Met Gly
            100                 105                 110

Trp Val Pro Leu Gln Pro Leu Pro Glu Ser Leu Gln Leu His Leu Leu
            115                 120                 125
```

```
Glu Leu Tyr Pro Val Leu Glu Ser Ile Gln Lys Phe Leu Trp Pro Arg
    130                 135                 140

Leu Cys Lys Leu Asp Gln Arg Thr Leu Tyr Glu Leu His Tyr Gln Leu
145                 150                 155                 160

Ile Thr Phe Gly Lys Val Phe Cys Thr Lys Ser Arg Pro Asn Cys Asn
                165                 170                 175

Ala Cys Pro Met Arg Gly Glu Cys Arg His Phe Ala Ser Ala Tyr Ala
                180                 185                 190

Ser Ala Arg Leu Ala Leu Pro Ala Pro Glu
            195                 200

<210> SEQ ID NO 42
<211> LENGTH: 202
<212> TYPE: PRT
<213> ORGANISM: Artificial Sequence
<220> FEATURE:
<223> OTHER INFORMATION: Description of Artificial Sequence:synthetic
      ROS1 demethylase glycosylase domain

<400> SEQUENCE: 42

Gly Ile Arg Glu Lys Thr Arg Ser Thr Met Asp Thr Val Asp Trp Lys
1               5                   10                  15

Ala Ile Arg Ala Ala Asp Val Lys Glu Val Ala Glu Thr Ile Lys Ser
                20                  25                  30

Arg Gly Met Asn His Lys Leu Ala Glu Arg Ile Gln Gly Phe Leu Asp
            35                  40                  45

Arg Leu Val Asn Asp His Gly Ser Ile Asp Leu Glu Trp Leu Arg Asp
50                  55                  60

Val Pro Pro Asp Lys Ala Lys Glu Tyr Leu Leu Ser Phe Asn Gly Leu
65                  70                  75                  80

Gly Leu Lys Ser Val Glu Cys Val Arg Leu Leu Thr Leu His His Leu
                85                  90                  95

Ala Phe Pro Val Asp Thr Asn Val Gly Arg Ile Ala Val Arg Leu Gly
                100                 105                 110

Trp Val Pro Leu Gln Pro Leu Pro Glu Ser Leu Gln Leu His Leu Leu
            115                 120                 125

Glu Met Tyr Pro Met Leu Glu Ser Ile Gln Lys Tyr Leu Trp Pro Arg
    130                 135                 140

Leu Cys Lys Leu Asp Gln Lys Thr Leu Tyr Glu Leu His Tyr Gln Met
145                 150                 155                 160

Ile Thr Phe Gly Lys Val Phe Cys Thr Lys Ser Lys Pro Asn Cys Asn
                165                 170                 175

Ala Cys Pro Met Lys Gly Glu Cys Arg His Phe Ala Ser Ala Phe Ala
                180                 185                 190

Ser Ala Arg Leu Ala Leu Pro Ser Thr Glu
            195                 200

<210> SEQ ID NO 43
<211> LENGTH: 202
<212> TYPE: PRT
<213> ORGANISM: Artificial Sequence
<220> FEATURE:
<223> OTHER INFORMATION: Description of Artificial Sequence:synthetic
      DML2 demethylase glycosylase domain

<400> SEQUENCE: 43

Arg Lys Arg Glu Arg Thr Glu Arg Thr Met Asp Thr Val Asp Trp Asp
1               5                   10                  15
```

```
Ala Leu Arg Cys Thr Asp Val His Lys Ile Ala Asn Ile Ile Ile Lys
            20                  25                  30

Arg Gly Met Asn Asn Met Leu Ala Glu Arg Ile Lys Ala Phe Leu Asn
        35                  40                  45

Arg Leu Val Lys Lys His Gly Ser Ile Asp Leu Glu Trp Leu Arg Asp
    50                  55                  60

Val Pro Pro Asp Lys Ala Lys Glu Tyr Leu Leu Ser Ile Asn Gly Leu
65                  70                  75                  80

Gly Leu Lys Ser Val Glu Cys Val Arg Leu Leu Ser Leu His Gln Ile
                85                  90                  95

Ala Phe Pro Val Asp Thr Asn Val Gly Arg Ile Ala Val Arg Leu Gly
            100                 105                 110

Trp Val Pro Leu Gln Pro Leu Pro Asp Glu Leu Gln Met His Leu Leu
        115                 120                 125

Glu Leu Tyr Pro Val Leu Glu Ser Val Gln Lys Tyr Leu Trp Pro Arg
    130                 135                 140

Leu Cys Lys Leu Asp Gln Lys Thr Leu Tyr Glu Leu His Tyr His Met
145                 150                 155                 160

Ile Thr Phe Gly Lys Val Phe Cys Thr Lys Val Lys Pro Asn Cys Asn
                165                 170                 175

Ala Cys Pro Met Lys Ala Glu Cys Arg His Tyr Ser Ser Ala Arg Ala
            180                 185                 190

Ser Ala Arg Leu Ala Leu Pro Glu Pro Glu
        195                 200

<210> SEQ ID NO 44
<211> LENGTH: 202
<212> TYPE: PRT
<213> ORGANISM: Artificial Sequence
<220> FEATURE:
<223> OTHER INFORMATION: Description of Artificial Sequence:synthetic
      DML3 demethylase glycosylase domain

<400> SEQUENCE: 44

Lys Glu Gly Ser Arg Pro Glu Met His Met Asp Ser Val Asn Trp Ser
1               5                   10                  15

Asp Val Arg Leu Ser Gly Gln Asn Val Leu Glu Thr Thr Ile Lys Lys
            20                  25                  30

Arg Gly Gln Phe Arg Ile Leu Ser Glu Arg Ile Leu Lys Phe Leu Asn
        35                  40                  45

Asp Glu Val Asn Gln Asn Gly Asn Ile Asp Leu Glu Trp Leu Arg Asn
    50                  55                  60

Ala Pro Ser His Leu Val Lys Arg Tyr Leu Leu Glu Ile Glu Gly Ile
65                  70                  75                  80

Gly Leu Lys Ser Ala Glu Cys Val Arg Leu Leu Gly Leu Lys His His
                85                  90                  95

Ala Phe Pro Val Asp Thr Asn Val Gly Arg Ile Ala Val Arg Leu Gly
            100                 105                 110

Leu Val Pro Leu Glu Pro Leu Pro Asn Gly Val Gln Met His Gln Leu
        115                 120                 125

Phe Glu Tyr Pro Ser Met Asp Ser Ile Gln Lys Tyr Leu Trp Pro Arg
    130                 135                 140

Leu Cys Lys Leu Pro Gln Glu Thr Leu Tyr Glu Leu His Tyr Gln Met
145                 150                 155                 160

Ile Thr Phe Gly Lys Val Phe Cys Thr Lys Thr Ile Pro Asn Cys Asn
```

```
                      165                 170                 175

Ala Cys Pro Met Lys Ser Glu Cys Lys Tyr Phe Ala Ser Ala Tyr Val
            180                 185                 190

Ser Ser Lys Val Leu Leu Glu Ser Pro Glu
        195                 200

<210> SEQ ID NO 45
<211> LENGTH: 217
<212> TYPE: PRT
<213> ORGANISM: Artificial Sequence
<220> FEATURE:
<223> OTHER INFORMATION: Description of Artificial Sequence:synthetic
      DME demethylase Domain B

<400> SEQUENCE: 45

Met Ser Lys Ala Leu Val Ala Leu His Pro Thr Thr Ser Ile Pro
 1               5                  10                  15

Thr Pro Lys Leu Lys Asn Ile Ser Arg Leu Arg Thr Glu His Gln Val
            20                  25                  30

Tyr Glu Leu Pro Asp Ser His Arg Leu Leu Asp Gly Met Asp Lys Arg
        35                  40                  45

Glu Pro Asp Asp Pro Ser Pro Tyr Leu Leu Ala Ile Trp Thr Pro Gly
    50                  55                  60

Glu Thr Ala Asn Ser Ala Gln Pro Pro Glu Gln Lys Cys Gly Gly Lys
65                  70                  75                  80

Ala Ser Gly Lys Met Cys Phe Asp Glu Thr Cys Ser Glu Cys Asn Ser
                85                  90                  95

Leu Arg Glu Ala Asn Ser Gln Thr Val Arg Gly Thr Leu Leu Ile Pro
            100                 105                 110

Cys Arg Thr Ala Met Arg Gly Ser Phe Pro Leu Asn Gly Thr Tyr Phe
        115                 120                 125

Gln Val Asn Glu Leu Phe Ala Asp His Glu Ser Ser Leu Lys Pro Ile
    130                 135                 140

Asp Val Pro Arg Asp Trp Ile Trp Asp Leu Pro Arg Arg Thr Val Tyr
145                 150                 155                 160

Phe Gly Thr Ser Val Thr Ser Ile Phe Arg Gly Leu Ser Thr Glu Gln
                165                 170                 175

Ile Gln Phe Cys Phe Trp Lys Gly Phe Val Cys Val Arg Gly Phe Glu
            180                 185                 190

Gln Lys Thr Arg Ala Pro Arg Pro Leu Met Ala Arg Leu His Phe Pro
        195                 200                 205

Ala Ser Lys Leu Lys Asn Asn Lys Thr
    210                 215

<210> SEQ ID NO 46
<211> LENGTH: 220
<212> TYPE: PRT
<213> ORGANISM: Artificial Sequence
<220> FEATURE:
<223> OTHER INFORMATION: Description of Artificial Sequence:synthetic
      ROS1 demethylase Domain B

<400> SEQUENCE: 46

Met Ser Ser Ala Leu Val Ala Leu Thr Ala Glu Thr Ala Ser Leu Pro
 1               5                  10                  15

Met Pro Lys Leu Lys Asn Ile Ser Gln Leu Arg Thr Glu His Arg Val
            20                  25                  30

Tyr Glu Leu Pro Asp Glu His Pro Leu Leu Ala Gln Leu Glu Lys Arg
```

```
           35                  40                  45
Glu Pro Asp Pro Cys Ser Tyr Leu Leu Ala Ile Trp Thr Pro Gly
 50                  55                  60
Glu Thr Ala Asp Ser Ile Gln Pro Ser Val Ser Thr Cys Ile Phe Gln
 65                  70                  75                  80
Ala Asn Gly Met Leu Cys Asp Glu Glu Thr Cys Phe Ser Cys Asn Ser
                 85                  90                  95
Ile Lys Glu Thr Arg Ser Gln Ile Val Arg Gly Thr Ile Leu Ile Pro
            100                 105                 110
Cys Arg Thr Ala Met Arg Gly Ser Phe Pro Leu Asn Gly Thr Tyr Phe
            115                 120                 125
Gln Val Asn Glu Val Phe Ala Asp His Ala Ser Ser Leu Asn Pro Ile
        130                 135                 140
Asn Val Pro Arg Glu Leu Ile Trp Glu Leu Pro Arg Arg Thr Val Tyr
145                 150                 155                 160
Phe Gly Thr Ser Val Pro Thr Ile Phe Lys Gly Leu Ser Thr Glu Lys
                165                 170                 175
Ile Gln Ala Cys Phe Trp Lys Gly Tyr Val Cys Val Arg Gly Phe Asp
            180                 185                 190
Arg Lys Thr Arg Gly Pro Lys Pro Leu Ile Ala Arg Leu His Phe Pro
            195                 200                 205
Ala Ser Lys Leu Lys Gly Gln Gln Ala Asn Leu Ala
        210                 215                 220

<210> SEQ ID NO 47
<211> LENGTH: 221
<212> TYPE: PRT
<213> ORGANISM: Artificial Sequence
<220> FEATURE:
<223> OTHER INFORMATION: Description of Artificial Sequence:synthetic
      DML2 demethylase Domain B

<400> SEQUENCE: 47

Thr Ser His Asp Leu Val Val Leu Ser Thr Tyr Ala Ala Ala Ile Pro
 1               5                  10                  15
Arg Arg Lys Leu Lys Ile Lys Glu Lys Leu Arg Thr Glu His His Val
             20                  25                  30
Phe Glu Leu Pro Asp His His Ser Ile Leu Glu Gly Phe Glu Arg Arg
         35                  40                  45
Glu Ala Glu Asp Ile Val Pro Tyr Leu Leu Ala Ile Trp Thr Pro Gly
 50                  55                  60
Glu Thr Val Asn Ser Ile Gln Pro Pro Lys Gln Arg Cys Ala Leu Phe
 65                  70                  75                  80
Glu Ser Asn Asn Thr Leu Cys Asn Glu Asn Lys Cys Phe Gln Cys Asn
                 85                  90                  95
Lys Thr Arg Glu Glu Ser Gln Thr Val Arg Gly Thr Ile Leu Ile
            100                 105                 110
Pro Cys Arg Thr Ala Met Arg Gly Gly Phe Pro Leu Asn Gly Thr Tyr
            115                 120                 125
Phe Gln Thr Asn Glu Val Phe Ala Asp His Asp Ser Ile Asn Pro
        130                 135                 140
Ile Asp Val Pro Thr Glu Leu Ile Trp Asp Leu Lys Arg Arg Val Ala
145                 150                 155                 160
Tyr Leu Gly Ser Ser Val Ser Ser Ile Cys Lys Gly Leu Ser Val Glu
                165                 170                 175
```

```
Ala Ile Lys Tyr Asn Phe Gln Glu Gly Tyr Val Cys Val Arg Gly Phe
            180                 185                 190

Asp Arg Glu Asn Arg Lys Pro Lys Ser Leu Val Lys Arg Leu His Cys
            195                 200                 205

Ser His Val Ala Ile Arg Thr Lys Glu Lys Thr Glu Glu
    210                 215                 220

<210> SEQ ID NO 48
<211> LENGTH: 224
<212> TYPE: PRT
<213> ORGANISM: Artificial Sequence
<220> FEATURE:
<223> OTHER INFORMATION: Description of Artificial Sequence:synthetic
      DML3 demethylase Domain B

<400> SEQUENCE: 48

Ile Ser Lys Ala Leu Val Ile Pro Thr Pro Glu Asn Ala Cys Ile Pro
  1               5                  10                  15

Ile Lys Pro Pro Arg Lys Met Lys Tyr Tyr Asn Arg Leu Arg Thr Glu
             20                  25                  30

His Val Val Tyr Val Leu Pro Asp Asn His Glu Leu Leu His Asp Phe
         35                  40                  45

Glu Arg Arg Lys Leu Asp Asp Pro Ser Pro Tyr Leu Leu Ala Ile Trp
     50                  55                  60

Gln Pro Gly Glu Thr Ser Ser Phe Val Pro Pro Lys Lys Cys
 65                  70                  75                  80

Ser Ser Asp Gly Ser Lys Leu Cys Lys Ile Lys Asn Cys Ser Tyr Cys
                 85                  90                  95

Trp Thr Ile Arg Glu Gln Asn Ser Asn Ile Phe Arg Gly Thr Ile Leu
            100                 105                 110

Ile Pro Cys Arg Thr Ala Met Arg Gly Ala Phe Pro Leu Asn Gly Thr
            115                 120                 125

Tyr Phe Gln Thr Asn Glu Val Phe Ala Asp His Glu Thr Ser Leu Asn
        130                 135                 140

Pro Ile Val Phe Arg Arg Glu Leu Cys Lys Gly Leu Glu Lys Arg Ala
145                 150                 155                 160

Leu Tyr Cys Gly Ser Thr Val Thr Ser Ile Phe Lys Leu Leu Asp Thr
                165                 170                 175

Arg Arg Ile Glu Leu Cys Phe Trp Thr Gly Phe Leu Cys Leu Arg Ala
            180                 185                 190

Phe Asp Arg Lys Gln Arg Asp Pro Lys Glu Leu Val Arg Arg Leu His
            195                 200                 205

Thr Pro Pro Asp Glu Arg Gly Pro Lys Phe Met Ser Asp Asp Ile
    210                 215                 220

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence:synthetic
      PCR amplification primer SR12 for MEA RNA from exons 3
      to 6

<400> SEQUENCE: 49
cagaggatga taatggagga ga                                          22

<210> SEQ ID NO 50
<211> LENGTH: 23
```

```
<212> TYPE: DNA
<213> ORGANISM: Artificial Sequence
<220> FEATURE:
<223> OTHER INFORMATION: Description of Artificial Sequence:synthetic
      PCR amplification primer UCB3SR8 for MEA RNA from
      exons 3 to 6

<400> SEQUENCE: 50
gcttgagttc attgtatctt tcc                                           23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence:synthetic
      first PCR amplification primer VPE2912 for control alpha
      VPE

<400> SEQUENCE: 51
acaactttcc cacttcctcc t                                             21

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence:synthetic
      first and second PCR amplification primer VPEdSal for
      control alpha VPE

<400> SEQUENCE: 52
tcgccggatc cagcggatac tggaattgtc g                                  31

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:synthetic
      second PCR amplification primer VPE2679 for
      control alpha VPE

<400> SEQUENCE: 53
gattctcctc gttctccgca                                               20

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence:synthetic
      PCR amplification primer MEA3904 for the -4 kb region

<400> SEQUENCE: 54
aactttattc atrtaatrrt craacact                                      28

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence:synthetic
      PCR amplification primer MEA5187BFc for the -3 kb
      region

<400> SEQUENCE: 55
caaaatactc tattctacat tcccatctat                                    30
```

```
<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence:synthetic
      PCR amplification primer and nested amplification
      primer MEA5810BRc for the -3 kb region

<400> SEQUENCE: 56
taaataaatt aaatgagttt gagtataaaa tg                                      32

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence:synthetic
      PCR amplification primer MEA7671 for the -500 bp
      region

<400> SEQUENCE: 57
taaccattaa acattaattt aaatctt                                            27

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence:synthetic
      PCR amplification primer RLDBi for RLD first repeat

<400> SEQUENCE: 58
taatttaaaa taatggtgat gttgttagtt tg                                      32

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence:synthetic
      PCR amplification primer RLDBi4 for RLD first repeat

<400> SEQUENCE: 59
aaaaarrttt tataaatatt aaattaatat ra                                      32

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence:synthetic
      primer MEA8355F for MEA coding region bisulfite
      sequencing

<400> SEQUENCE: 60
tttcactcca aacatatata aattaac                                            27

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA8755R for MEA coding region bisulfite
      sequencing
```

<400> SEQUENCE: 61
gaytaatgta taaytgttta ttagatgtat                                30

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence:synthetic
      primer MEA8646F for MEA coding region bisulfite
      sequencing

<400> SEQUENCE: 62
ctcttctrta trttttctr aaaattaarr a                               31

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA9066R for MEA coding region bisulfite
      sequencing

<400> SEQUENCE: 63
tgyatyaaty ttggyttttt tggytgaatg                                30

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence:synthetic
      primer MEA9294F for MEA coding region bisulfite
      sequencing

<400> SEQUENCE: 64 cactttrtc raraatrcaa aacccactt                                  29

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA9801R for MEA coding region bisulfite
      sequencing

<400> SEQUENCE: 65
taatgyaaaa aytaayyata taaatyggty                                30

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence:synthetic
      primer MEA9810F for MEA coding region bisulfite
      sequencing

<400> SEQUENCE: 66
cttrattatt aatttrtart ccatatttaa taaactr                        37

<210> SEQ ID NO 67
<211> LENGTH: 38
<212> TYPE: DNA
<213> ORGANISM: Artificial Sequence

```
<220> FEATURE:
<223> OTHER INFORMATION: Description of Artificial Sequence:synthetic
      primer MEA10221R for MEA coding region bisulfite
      sequencing

<400> SEQUENCE: 67
gtggytaaat taaaaaagaa agattyaaag ttayyatg                              38

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence:synthetic
      primer MEA10310F for MEA coding region bisulfite
      sequencing

<400> SEQUENCE: 68
cccrartcta ratccrtaar cattaaatc                                        29

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence:synthetic
      primer MEA10650R for MEA coding region bisulfite
      sequencing

<400> SEQUENCE: 69
ggatytgaga yyayaatytt gtttgatata gag                                   33

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence:synthetic
      primer MEA10528F for MEA coding region bisulfite
      sequencing

<400> SEQUENCE: 70
ctattcctta attacrtttta ttarttactr rt                                   32

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence:synthetic
      primer MEA10905R for MEA coding region bisulfite
      sequencing

<400> SEQUENCE: 71
gttttgttaa ggtytaatga yatagtayat tg                                    32

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence:synthetic
      primer MEA10761F for MEA coding region bisulfite
      sequencing

<400> SEQUENCE: 72
tacttacact rtattccttr attatrc                                          27
```

```
<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence:synthetic
      primer MEA11285R for MEA coding region bisulfite
      sequencing

<400> SEQUENCE: 73
tayaaaytya tgttyaaatt aaatytyatg g                              31

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA11131F for MEA coding region bisulfite
      sequencing

<400> SEQUENCE: 74
ataarcacta cacaccatrc acttrcaart                                30

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence:synthetic
      primer MEA11460R for MEA coding region bisulfite
      sequencing

<400> SEQUENCE: 75
caaattctat aatcaaarta attcaaacc                                 29

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence:synthetic
      primer MEA11571F for MEA coding region bisulfite
      sequencing

<400> SEQUENCE: 76
catacaattc ctccttcaaa ccaataa                                   27

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence:synthetic
      primer MEA11987R for MEA coding region bisulfite
      sequencing

<400> SEQUENCE: 77
gatyattyaa ggtaaagagg taggaagaay yaa                            33

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA11906F for MEA coding region bisulfite
      sequencing
```

```
<400> SEQUENCE: 78
ctratcactc atratraarc taatrarcrt                                    30

<210> SEQ ID NO 79
<211> LENGTH: 32
<212> TYPE: DNA
<213> ORGANISM: Artificial Sequence
<220> FEATURE:
<223> OTHER INFORMATION: Description of Artificial Sequence:synthetic
      primer MEA12300R for MEA coding region bisulfite
      sequencing

<400> SEQUENCE: 79
gagtttgagt ttyttggaat atyttyaata tg                                 32

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence:synthetic
      primer MEA12234F for MEA coding region bisulfite
      sequencing

<400> SEQUENCE: 80
tcrtrtatca actttactcr tcrttrattr r                                  31

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA12647R for MEA coding region bisulfite
      sequencing

<400> SEQUENCE: 81
gttttggttt agtaayayaa aatagyatta                                    30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence:synthetic
      primer MEA12740F for MEA coding region bisulfite
      sequencing

<400> SEQUENCE: 82
caatrtttat rttrttartt trcataracc                                    30

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence:synthetic
      primer MEA13093R for MEA coding region bisulfite
      sequencing

<400> SEQUENCE: 83
gtttagatay taaatgttag atgyatyaaa t                                  31

<210> SEQ ID NO 84
<211> LENGTH: 39
<212> TYPE: DNA
<213> ORGANISM: Artificial Sequence
```

-continued

```
<220> FEATURE:
<223> OTHER INFORMATION: Description of Artificial Sequence:synthetic
      PCR amplification primer MEA8323Xba for the -500 bp
      region

<400> SEQUENCE: 84
atattctaga ctttttttct cgtcttctct gatgttggt                          39

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence:synthetic
      PCR amplification primer UCB3SR12R-sac1 for the -500
      bp region

<400> SEQUENCE: 85
gggagctcgt taagcctgtg gttgacaac                                     29

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence:synthetic
      PCR amplification primer B5-7RR for the MEA-ISR repeat
      region

<400> SEQUENCE: 86
ttaggtatta gctcgtttgg tttta                                         25

<210> SEQ ID NO 87
<211> LENGTH: 34
<212> TYPE: DNA
<213> ORGANISM: Artificial Sequence
<220> FEATURE:
<223> OTHER INFORMATION: Description of Artificial Sequence:synthetic
      PCR amplification primer MEA 3 REP for the MEA-ISR
      repeat region

<400> SEQUENCE: 87
cttaaaagat tttcaactca ttttttttaa aagg                               34

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence:synthetic
      PCR oligonucleotide JH021

<400> SEQUENCE: 88
ttaatctaga atgcagagca ttatggactc g                                  31

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence:synthetic
      PCR oligonucleotide JH017

<400> SEQUENCE: 89
cggtcgactt aggttttgtt gttcttcaat ttgc                               34
```

<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence:synthetic
      oligonucleotide MEA-1.6F

<400> SEQUENCE: 90
ctatacctcc tcaactccgg tcaccgtctc cggcg                              35

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F18meC
<220> FEATURE:
<221> NAME/KEY: modified_base
<222> LOCATION: (18)
<223> OTHER INFORMATION: n = m5c

<400> SEQUENCE: 91
ctatacctcc tcaactcngg tcaccgtctc cggcg                              35

<210> SEQ ID NO 92
<211> LENGTH: 35
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F17meC
<220> FEATURE:
<221> NAME/KEY: modified_base
<222> LOCATION: (17)
<223> OTHER INFORMATION: n = m5c

<400> SEQUENCE: 92
ctatacctcc tcaactncgg tcaccgtctc cggcg                              35

<210> SEQ ID NO 93
<211> LENGTH: 35
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F22meC
<220> FEATURE:
<221> NAME/KEY: modified_base
<222> LOCATION: (22)
<223> OTHER INFORMATION: n = m5c

<400> SEQUENCE: 93
ctatacctcc tcaactccgg tnaccgtctc cggcg                              35

<210> SEQ ID NO 94
<211> LENGTH: 17
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F18AP 5' portion
<220> FEATURE:
<221> NAME/KEY: modified_base
<222> LOCATION: (17)
<223> OTHER INFORMATION: n = c 3' modified by an abasic phosphodiester
      bond to SEQ ID NO:95

```
<400> SEQUENCE: 94
ctatacctcc tcaactn                                                17

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F18AP 3' portion
<220> FEATURE:
<221> NAME/KEY: modified_base
<222> LOCATION: (1)
<223> OTHER INFORMATION: n = g 5' modified by an abasic phosphodiester
      bond to SEQ ID NO:94

<400> SEQUENCE: 95
ngtcaccgtc tccggcg                                                17

<210> SEQ ID NO 96
<211> LENGTH: 16
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F17AP 5' portion
<220> FEATURE:
<221> NAME/KEY: modified_base
<222> LOCATION: (16)
<223> OTHER INFORMATION: n = t 3' modified by an abasic phosphodiester
      bond to SEQ ID NO:97

<400> SEQUENCE: 96
ctatacctcc tcaacn                                                 16

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F 3' portion
<220> FEATURE:
<221> NAME/KEY: modified_base
<222> LOCATION: (1)
<223> OTHER INFORMATION: n = c 5' modified by an abasic phosphodiester
      bond to SEQ ID NO:96

<400> SEQUENCE: 97
nggtcaccgt ctccggcg                                               18

<210> SEQ ID NO 98
<211> LENGTH: 14
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F15AP 5' portion
<220> FEATURE:
<221> NAME/KEY: modified_base
<222> LOCATION: (14)
<223> OTHER INFORMATION: n = a 3' modified by an abasic phosphodiester
      bond to SEQ ID NO:99

<400> SEQUENCE: 98
ctatacctcc tcan                                                   14
```

```
<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F15AP 3' portion
<220> FEATURE:
<221> NAME/KEY: modified_base
<222> LOCATION: (1)
<223> OTHER INFORMATION: n = t 5' modified by an abasic phosphodiester
      bond to SEQ ID NO:98

<400> SEQUENCE: 99
nccggtcacc gtctccggcg                                              20

<210> SEQ ID NO 100
<211> LENGTH: 11
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F12AP 5' portion
<220> FEATURE:
<221> NAME/KEY: modified_base
<222> LOCATION: (11)
<223> OTHER INFORMATION: n = t 3' modified by an abasic phosphodiester
      bond to SEQ ID NO:101

<400> SEQUENCE: 100
ctatacctcc n                                                       11

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F12AP 3' portion
<220> FEATURE:
<221> NAME/KEY: modified_base
<222> LOCATION: (1)
<223> OTHER INFORMATION: n = a 5' modified by an abasic phosphodiester
      bond to SEQ ID NO:100

<400> SEQUENCE: 101
nactccggtc accgtctccg gcg                                          23

<210> SEQ ID NO 102
<211> LENGTH: 35
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6F18T

<400> SEQUENCE: 102
ctatacctcc tcaactctgg tcaccgtctc cggcg                             35

<210> SEQ ID NO 103
<211> LENGTH: 35
<212> TYPE: DNA
<213> ORGANISM: Artificial Sequence
<220> FEATURE:
<223> OTHER INFORMATION: Description of Artificial Sequence:synthetic
      oligonucleotide MEA-1.6R

<400> SEQUENCE: 103
cgccggagac ggtgaccgga gttgaggagg tatag                             35
```

```
<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence:synthetic
      modified oligonucleotide MEA-1.6R17meC
<220> FEATURE:
<221> NAME/KEY: modified_base
<222> LOCATION: (17)
<223> OTHER INFORMATION: n = m5c

<400> SEQUENCE: 104
cgccggagac ggtgacngga gttgaggagg tatag                              35

<210> SEQ ID NO 105
<211> LENGTH: 27
<212> TYPE: DNA
<213> ORGANISM: Artificial Sequence
<220> FEATURE:
<223> OTHER INFORMATION: Description of Artificial Sequence:synthetic
      PCR amplification LNA-containing primer MEA-LNA006 for
      MEA region one
<220> FEATURE:
<221> NAME/KEY: modified_base
<222> LOCATION: (27)
<223> OTHER INFORMATION: n = g LNA nucleotide analogue containing
      2'-O,4'-C methylene bridge

<400> SEQUENCE: 105
caccaacatc agagaagacg agaaaan                                       27

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence:synthetic
      PCR amplification LNA-containing primer MEA-LNA004 for
      MEA region one
<220> FEATURE:
<221> NAME/KEY: modified_base
<222> LOCATION: (27)
<223> OTHER INFORMATION: n = c LNA nucleotide analogue containing
      2'-O,4'-C methylene bridge

<400> SEQUENCE: 106
gattatgact aatgtataac tgtttan                                       27

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence:synthetic
      PCR amplification LNA-containing primer MEA-LNA002 for
      MEA region 2
<220> FEATURE:
<221> NAME/KEY: modified_base
<222> LOCATION: (26)
<223> OTHER INFORMATION: n = g LNA nucleotide analogue containing
      2'-O,4'-C methylene bridge

<400> SEQUENCE: 107
gggtctcaat tttgtgaact ggtgtn                                        26

<210> SEQ ID NO 108
<211> LENGTH: 33
<212> TYPE: DNA
<213> ORGANISM: Artificial Sequence
```

-continued

```
<220> FEATURE:
<223> OTHER INFORMATION: Description of Artificial Sequence:synthetic
      PCR amplification LNA-containing primer MEA-LNA003 for
      MEA region 2
<220> FEATURE:
<221> NAME/KEY: modified_base
<222> LOCATION: (33)
<223> OTHER INFORMATION: n = c LNA nucleotide analogue containing
      2'-O,4'-C methylene bridge

<400> SEQUENCE: 108
ccgatatttt ttactattta taacgttaat tan                                    33
```